(12) United States Patent
Jimenez et al.

(10) Patent No.: US 6,599,879 B1
(45) Date of Patent: *Jul. 29, 2003

(54) THERAPEUTIC USES OF KERATINOCYTE GROWTH FACTOR-2

(75) Inventors: Pablo Jimenez, Ellicott, MD (US); Mark A. Rampy, Montgomery Village, MD (US); Donna Mendrick, Mount Airy, MD (US); Deborah Russell, Laytonsville, MD (US); Arthur Louie, Potomac, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/248,998

(22) Filed: Feb. 12, 1999

Related U.S. Application Data

(60) Provisional application No. 60/114,387, filed on Dec. 30, 1998, and provisional application No. 60/074,585, filed on Feb. 13, 1998.

(51) Int. Cl.[7] .................. A61K 38/18; C07K 14/475; C07K 14/50
(52) U.S. Cl. .................. 514/12; 514/2; 530/399
(58) Field of Search .................. 514/2, 12; 530/399

(56) References Cited

U.S. PATENT DOCUMENTS

| 5,773,252 A | 6/1998 | Greene et al. |
|---|---|---|
| 6,077,692 A | 6/2000 | Ruben et al. |
| 6,238,888 B1 | 5/2001 | Gentz et al. |
| 2002/0016295 A1 | 2/2002 | Gentz et al. |

FOREIGN PATENT DOCUMENTS

| EP | 0 619 370 A1 | 10/1994 |
|---|---|---|
| WO | WO 95/24928 A3 | 10/1995 |
| WO | WO 99/32135 | 7/1999 |
| WO | WO 99/41282 | 8/1999 |
| WO | WO 00/72872 | 12/2000 |
| WO | WO 01/02433 | 1/2001 |

OTHER PUBLICATIONS

Robson et al. Introduction to Protein & Protein Engineering. Elsevier, NY. p. 41, 1996.*
Ngo et al. The Protein Folding Problem and Tertiary Structure Prediction. Birkhauser. Boston pp. 492–495, 1994.*
Wells. Biochemistry 29 (37):8509–8517, 1990.*
Bowie et al. Science 247:1306–1310, 1990.*
Bowie, J.U., et al., "Deciphering the Message in Protein Sequences: Tolerance to Amino Acid Substitutions," *Science* 247:1306–1310, American Association for the Advancement of Science (1990).
Jimenez, P.A., and Rampy, M.A., "Keratinocyte Growth Factor–2 Accelerates Wound Healing in Incisional Wounds," *J. Surg. Res. 81*:238–242, Academic Press, Inc. (Feb. 1999).
Ngo, J.T., et al., "Computational Complexity, Protein Structure Prediction, and the Levinthal Paradox," in: *The Protein Folding Problem and Tertiary Structure Prediction*, Merz, Jr., K. and Le Grand, S., eds., Birkhauser, Boston, Massachusetts, pp. 491–495 (1994).
Robson, B., and Garnier, J., "Modern ideas and notations relating to primary structure, in: *Introduction to Proteins and Protein Engineering*," Robson, B. and Garnier, J., eds., Elsevier Science, Amsterdam, The Netherlands, p. 41 (1986).
Wells, J.A., "Additivity of Mutational Effects in Proteins," *Biochem. 29*:8509–8517, American Chemical Society, (1990).
NCBI Entrez, GenBank Report, Accession No. U67918, Jimenez, P.A. et al., National Center for Biotechnology Information (Jul. 1997).

* cited by examiner

*Primary Examiner*—Christine J. Saoud
(74) *Attorney, Agent, or Firm*—Human Genome Sciences, Inc.

(57) ABSTRACT

The present invention relates to the administration of Keratinocyte Growth Factor-2 (KGF-2) to stimulate proliferation of platelets and to increase levels of fibrinogen, albumin, globulin and total serum protein. Further, the present invention relates to administering KGF-2 to protect or treat the bladder and prostate. Moreover, the present invention relates to administering KGF-2 to stimulate growth of nasal, oral, and esophageal mucosa, lacrimal glands, salivary glands and Goblet cells.

8 Claims, 63 Drawing Sheets

```
        ATGTGGAAATGGATACTGACACATTGTGCCTCAGCCTTTCCCCACCTGCCCGGCTGCTGC
  1     ---------+---------+---------+---------+---------+---------+    60
        TACACCTTTACCTATGACTGTGTAACACGGAGTCGGAAAGGGGTGGACGGGCCGACGACG

M  W  K  I  L  T  H  C  A  S  A  F  P  H  L  P  G  C  C

TGCTGCTGCTTTTTGTTGCTGTTCTTGGTGTCTTCCGTCCCTGTCACCTGCCAAGCCCTT
  61    ---------+---------+---------+---------+---------+---------+   120
        ACGACGACGAAAAACAACGACAAGAACCACAGAAGGCAGGGACAGTGGACGGTTCGGGAA

C  C  C  F  L  L  L  F  L  V  S  S  V  P  V  T  C  Q  A  L

GGTCAGGACATGGTGTCACCAGAGGCCACCAACTCTTCTTCCTCCTCCTTCTCCTCTCCT
 121    ---------+---------+---------+---------+---------+---------+   180
        CCAGTCCTGTACCACAGTGGTCTCCGGTGGTTGAGAAGAAGGAGGAGGAAGAGGAGAGGA

G  Q  D  M  V  S  P  E  A  T  N  S  S  S  S  S  F  S  S  P

TCCAGCGCGGGAAGGCATGTgCGGAGCTACAATCACCTTCAAGGAGATGTCCGCTGGAGA
 181    ---------+---------+---------+---------+---------+---------+   240
        AGGTCGCGCCCTTCCGTACAcGCCTCGATGTTAGTGGAAGTTCCTCTACAGGCGACCTCT

S  S  A  G  R  H  V  R  S  Y  N  H  L  Q  G  D  V  R  W  R

MATCH WITH FIG. 1B
```

FIG.1A

MATCH WITH FIG. 1A

```
       AAGCTATTCTCTTTCACCAAGTACTTTCTCAAGATTGAGAAGAACGGGAAGGTCAGCGGG
241    ---------+---------+---------+---------+---------+---------+   300
       TTCGATAAGAGAAAGTGGTTCATGAAAGAGTTCTAACTCTTCTTGCCCTTCCAGTCGCCC

K  L  F  S  F  T  K  Y  F  L  K  I  E  K  N  G  K  V  S  G

ACCAAGAAGGAGAACTGCCCGTACAGCATCCTGGAGATAACATCAGTAGAAATCGGAGTT
301    ---------+---------+---------+---------+---------+---------+   360
       TGGTTCTTCCTCTTGACGGGCATGTCGTAGGACCTCTATTGTAGTCATCTTTAGCCTCAA

T  K  K  E  N  C  P  Y  S  I  L  E  I  T  S  V  E  I  G  V

GTTGCCGTCAAAGCCATTAACAGCAACTATTACTTAGCCATGAACAAGAAGGGGAAACTC
361    ---------+---------+---------+---------+---------+---------+   420
       CAACGGCAGTTTCGGTAATTGTCGTTGATAATGAATCGGTACTTGTTCTTCCCCTTTGAG

V  A  V  K  A  I  N  S  N  Y  Y  L  A  M  N  K  K  G  K  L

TATGGCTCAAAAGAATTTAACAATGACTGTAAGCTGAAGGAGAGGATAGAGGAAAATGGA
421    ---------+---------+---------+---------+---------+---------+   480
       ATACCGAGTTTTCTTAAATTGTTACTGACATTCGACTTCCTCTCCTATCTCCTTTTACCT

Y  G  S  K  E  F  N  N  D  C  K  L  K  E  R  I  E  E  N  G
```

MATCH WITH FIG. 1C

FIG. 1B

MATCH WITH FIG. 1B

```
     TACAATACCTATGCATCATTTAACTGGCAGCATAATGGGAGGCAAATGTATGTGGCATTG
481  ---------+---------+---------+---------+---------+---------+  540
     ATGTTATGGATACGTAGTAAATTGACCGTCGTATTACCCTCCGTTTACATACACCGTAAC

Y  N  T  Y  A  S  F  N  W  Q  H  N  G  R  Q  M  Y  V  A  L

AATGGAAAAGGAGCTCCAAGGAGAGGACAGAAAACACGAAGGAAAAACACCTCTGCTCAC
541  ---------+---------+---------+---------+---------+---------+  600
     TTACCTTTTCCTCGAGGTTCCTCTCCTGTCTTTTGTGCTTCCTTTTTGTGGAGACGAGTG

N  G  K  G  A  P  R  R  G  Q  K  T  R  R  K  N  T  S  A  H

TTTCTTCCAATGGTGGTACACTCATAG
601  ---------+---------+-------  627
     AAAGAAGGTTACCACCATGTGAGTATC

```
        1                                                        50
FGF4    MS.GPGTAAV  ALLPAVLLAL  LA........  .PWAGRGGAA  APTAPNGTLE
FGF6    MSRGAGRLQG  TLWALVFLGI  LV........  .GMVVPSPAG  TR.ANNTLLD
FGF5    .......MSL  SFLLLLFFSH  LILSAWAHGE  KRLAPKGQPG  PAATDRNPIG
FGF1    ..........  ..........  ..........  ..........  ..........
FGF2    ..........  ..........  ..........  ..........  ..........
FGF9    ..........  ..........  ..........  ..MAPLGEVG  NYFGVQDAVP
FGF7    ..........  .....MHKW   ILTWILPTLL  .....YRSCF  HIICLVGTIS
KGF2    ..........  ......MWKW  ILTHCASAFP  HLPGCCCCCF  LLLFLVSSVP
FGF3    ..........  ..........  ..........  .......MGL  IWLLLLSLLE
FGF8    MGSPRSALSC  LLLHLLVLCL  QAQVRSAAQK  RGPGAGNPAD  TLGQGHEDRP 51                                                       100
FGF4    AELERRWESL  VALSLARLPV  AA..QPKEAA  VQSGAGDY..  ...LLGIKRL
FGF6    S...RGWGTL  LSRSRAGLAG  EI......AG  VNWESG.Y..  ...LVGIKRQ
FGF5    SSSRQSSSSA  MSSSSASSSP  AASLGSQGSG  LEQSSFQW..  ...SPSGRRT
FGF1    ......MAEG  EITTFTALTE  KFN...LPPG  .......N..  ...YK...KP
FGF2    ......MAAG  SITTLPALPE  DGGSGAFPPG  .......H..  ...FK...DP
FGF9    FGNVPVLPVD  SPVLLSDHLG  QSEAGGLPRG  PAVTDLDH..  ...LKGILRR
FGF7    LACNDMTPEQ  M...ATNVNC  ......SSPE  RHTRSYDY..  ...MEGGDIR
KGF2    VTCQALGQDM  VSPEATNSSS  SSFSSPSSAG  RHVRSYNH..  ...LQ.GDVR
FGF3    PGWPAAGPGA  ..........  ...RLRRDAG  GRGGVYEH..  ...L.GGAPR
FGF8    FGQRSRAGKN  FTNPAPNYPE  EGSKEQRDSV  LPKVTQRHVR  EQSLVTDQLS
```

MATCH WITH FIG. 2B

FIG. 2A

MATCH WITH FIG. 2A

```
       101                                                                      150
FGF4   RRL.....YC NVGIGFHLQA LPDGRIGGAH ADT.RDSLLE LSPVERGV.V
FGF6   RRL.....YC NVGIGFHLQV LPDGRISGTH EEN.PYSLLE ISTVERGV.V
FGF5   GSL.....YC RVGIGFHLQI YPDGKVNGSH EAN.MLSVLE IFAVSQGI.V
FGF1   KLL.....YC SNG.GHFLRI LPDGTVDGTR DRSDQHIQLQ LSAESVGE.V
FGF2   KRL.....YC KNG.GFFLRI HPDGRVDGVR EKSDPHIKLQ LQAEERGV.V
FGF9   RQL.....YC R.T.GFHLEI FPNGTIQGTR KDHSRFGILE FISIAVGL.V
FGF7   VRR.....LF CRT.QWYLRI DKRGKVKGTQ EMKNNYNIME IRTVAVGI.V
KGF2   WRK.....LF SFT.KYFLKI EKNGKVSGTK KENCPYSILE ITSVEIGV.V
FGF3   RRK.....LY CAT.KYHLQL HPSGRVNGSL .ENSAYSILE ITAVEVGI.V
FGF8   RRLIRTYQLY SRTSGKHVQV LANKRINAMA EDGDPFAKLI VETDTFGSRV 151                                                                      200
FGF4   SIFGVASRFF VAMSSKGKLY G.SPFFTDEC TFKEILLPNN YNAYESYKYP
FGF6   SLFGVRSALF VAMNSKGRLY A.TPSFQEEC KFRETLLPNN YNAYESDLYQ
FGF5   GIRGVFSNKF LAMSKKGKLH A.SAKFTDDC KFRERFQENS YNTYASAIHR
FGF1   YIKSTETGQY LAMDTDGLLY G.SQTPNEEC LFLERLEENH YNTYISKKH.
FGF2   SIKGVCANRY LAMKEDGRLL A.SKCVTDEC FFFERLESNN YNTYRSRKY.
FGF9   SIRGVDSGLY LGMNEKGELY G.SEKLTQEC VFREQFEENW YNTYSSNLYK
FGF7   AIKGVESEFY LAMNKEGKLY A.KKECNEDC NFKELILENH YNTYAS....
KGF2   AVKAINSNYY LAMNKKGKLY G.SKEFNNDC KLKERIEENG YNTYAS....
FGF3   AIRGLFSGRY LAMNKRGRLY A.SEHYSAEC EFVERIHELG YNTYASRLYR
FGF8   RVRGAETGLY ICMNKKGKLI AKSNGKGKDC VFTEIVLENN YTALQNAKY.
```

MATCH WITH FIG. 2C

FIG. 2B

MATCH WITH FIG. 2B

```
           201                                                           250
FGF4       ..........  GM......FI  ALSKNGKTKK  G..NRVSPTM  KVTHFLPRL.
FGF6       ..........  GT......YI  ALSKYGRVKR  G..SKVSPIM  TVTHFLPRI.
FGF5       ..........  TEKTGREWYV  ALNKRGKAKR  GCSPRVKPQH  ISTHFLPRFK
FGF1       ..........  ...AEKNWFV  GLKKNGSCKR  G..PRTHYGQ  KAILFLPLPV
FGF2       ..........  ...T..SWYV  ALKRTGQYKL  G..SKTGPGQ  KAILFLPMSA
FGF9       HV........  ..DTGRRYYV  ALNKDGTPRE  G..TRTKRHQ  KFTHFLPRPV
FGF7       .......AKW  THNGGEM.FV  ALNQKGIPVR  G..KKTKKEQ  KTAHFLPMAI
KGF2       .......FNW  QHNGRQM.YV  ALNGKGAPRR  G..QKTRRKN  TSAHFLPMVV
FGF3       TVSSTPGARR  QPSAERLWYV  SVNGKGRPRR  G..FKTRRTQ  KSSLFLPRVL
FGF8       ..........  .....EGWYM  AFTRKGRPRK  G..SKTRQHQ  REVHFMKRLP 251                                                           300
FGF4       ..........  ..........  ..........  ..........  ..........
FGF6       ..........  ..........  ..........  ..........  ..........
FGF5       QSEQPELSFT  VTVPEKKNPP  SPIKSKIPLS  APRKNTNSVK  YRLKFRFG..
FGF1       SSD.......  ..........  ..........  ..........  ..........
FGF2       KS........  ..........  ..........  ..........  ..........
FGF9       DPDKVPELYK  DILSQS....  ..........  ..........  ..........
FGF7       T.........  ..........  ..........  ..........  ..........
KGF2       HS........  ..........  ..........  ..........  ..........
FGF3       DHRDHEMVRQ  LQSGLPRPPG  KGVQPRRRRQ  KQSPDNLEPS  HVQASRLGSQ
FGF8       RGHHTTEQSL  RFEFLNYPPF  TRSLRGSQRT  WAPEPR....  ..........
```

MATCH WITH FIG. 2D

FIG. 2C

MATCH WITH FIG. 2C

```
              301
FGF4        ......
FGF6        ......
FGF5        ......
FGF1        ......
FGF2        ......
FGF9        ......
FGF7        ......
KGF2        ......
FGF3        LEASAH
FGF8        ......
```

FIG.2D

```
GGAATTCCGG GAAGAGAGGG AAGAAAACAA CGGCGACTGG GCAGCTGCCT CCACTTCTGA    60
CAACTCCAAA GGGATATACT TGTAGAAGTG GCTCGCAGGC TGGGGCTCCG CAGAGAGAGA   120
CCAGAAGGTG CCAACCGCAG AGGGGTGCAG ATATCTCCCC CTATTCCCCA CCCCACCTCC   180
CTTGGGTTTT GTTCACCGTG CTGTCATCTG TTTTTCAGAC CTTTTTGGCA TCTAACATGG   240
TGAAGAAAGG AGTAAAGAAG AGAACAAAGT AACTCCTGGG GGAGCGAAGA GCGCTGGTGA   300
CCAACACCAC CAACGCCACC ACCAGCTCCT GCTGCTGCGG CCACCCACGT CCACCATTTA   360
CCGGGAGGCT CCAGAGGCGT AGGCAGCGGA TCCGAGAAAG GAGCGAGGGG AGTCAGCCGG   420
CTTTTCCGAG GAGTTATGGA TGTTGGTGCA TTCACTTCTG GCCAGATCCG CGCCCAGAGG   480
GAGCTAACCA GCAGCCACCA CCTCGAGCTC TCTCCTTGCC TTGCATCGGG TCTTACCCTT   540
CCAGTATGTT CCTTCTGATG AGACAATTTC CAGTGCCGAG AGTTTCAGTA CA ATG       595
                                                            Met
```

```
TGG AAA TGG ATA CTG ACA CAT TGT GCC TCA GCC TTT CCC CAC CTG CCC    643
Trp Lys Trp Ile Leu Thr His Cys Ala Ser Ala Phe Pro His Leu Pro

GGC TGC TGC TGC TGC TGC TTT TTG TTG CTG TTC TTG GTG TCT TCC GTC    691
Gly Cys Cys Cys Cys Cys Phe Leu Leu Leu Phe Leu Val Ser Ser Val

CCT GTC ACC TGC CAA GCC CTT GGT CAG GAC ATG GTG TCA CCA GAG GCC    739
Pro Val Thr Cys Gln Ala Leu Gly Gln Asp Met Val Ser Pro Glu Ala

ACC AAC TCT TCT TCC TCC TCC TTC TCC TCT CCT TCC AGC GCG GGA AGG    787
Thr Asn Ser Ser Ser Ser Ser Phe Ser Ser Pro Ser Ser Ala Gly Arg

CAT GTG CGG AGC TAC AAT CAC CTT CAA GGA GAT GTC CGC TGG AGA AAG    835
His Val Arg Ser Tyr Asn His Leu Gln Gly Asp Val Arg Trp Arg Lys

CTA TTC TCT TTC ACC AAG TAC TTT CTC AAG ATT GAG AAG AAC GGG AAG    883
Leu Phe Ser Phe Thr Lys Tyr Phe Leu Lys Ile Glu Lys Asn Gly Lys

GTC AGC GGG ACC AAG AAG GAG AAC TGC CCG TAC AGC ATC CTG GAG ATA    931
Val Ser Gly Thr Lys Lys Glu Asn Cys Pro Tyr Ser Ile Leu Glu Ile

ACA TCA GTA GAA ATC GGA GTT GTT GCC GTC AAA GCC ATT AAC AGC AAC    979
Thr Ser Val Glu Ile Gly Val Val Ala Val Lys Ala Ile Asn Ser Asn

TAT TAC TTA GCC ATG AAC AAG AAG GGG AAA CTC TAT GGC TCA AAA GAA   1027
Tyr Tyr Leu Ala Met Asn Lys Lys Gly Lys Leu Tyr Gly Ser Lys Glu

TTT AAC AAT GAC TGT AAG CTG AAG GAG AGG ATA GAG GAA AAT GGA TAC   1075
Phe Asn Asn Asp Cys Lys Leu Lys Glu Arg Ile Glu Glu Asn Gly Tyr
```

FIG.3A

```
AAT ACC TAT GCA TCA TTT AAC TGG CAG CAT AAT GGG AGG CAA ATG TAT        1123
Asn Thr Tyr Ala Ser Phe Asn Trp Gln His Asn Gly Arg Gln Met Tyr
GTG GCA TTG AAT GGA AAA GGA GCT CCA AGG AGA GGA CAG AAA ACA CGA        1171
Val Ala Leu Asn Gly Lys Gly Ala Pro Arg Arg Gly Gln Lys Thr Arg
AGG AAA AAC ACC TCT GCT CAC TTT CTT CCA ATG GTG GTA CAC TCA            1216
Arg Lys Asn Thr Ser Ala His Phe Leu Pro Met Val Val His Ser
TAGAGGAAGG CAACGTTTGT GGATGCAGTA AAACCAATGG CTCTTTTGCC AAGAATAGTG      1276
GATATTCTTC ATGAAGACAG TAGATTGAAA GGCAAAGACA CGTTGCAGAT GTCTGCTTGC      1336
TTAAAAGAAA GCCAGCCTTT GAAGGTTTTT GTATTCACTG CTGACATATG ATGTTCTTTT      1396
AATTAGTTCT GTGTCATGTC TTATAATCAA GATATAGGCA GATCGAATGG GATAGAAGTT      1456
ATTCCCAAGT GAAAAACATT GTGGCTGGGT TTTTTGTTGT TGTTGTCAAG TTTTTGTTTT      1516
TAAACCTCTG AGATAGAACT TAAAGGACAT AGAACAATCT GTTGAAAGAA CGATCTTCGG      1576
GAAAGTTATT TATGGAATAC GAACTCATAT CAAAGACTTC ATTGCTCATT CAAGCCTAAT      1636
GAATCAATGA ACAGTAATAC GTGCAAGCAT TTACTGGAAA GCACTTGGGT CATATCATAT      1696
GCACAACCAA AGGAGTTCTG GATGTGGTCT CATGGAATAA TTGAATAGAA TTTAAAAATA      1756
TAAACATGTT AGTGTGAAAC TGTTCTAACA ATACAAATAG TATGGTATGC TTGTGCATTC      1816
TGCCTTCATC CCTTTCTATT TCTTTCTAAG TTATTTATTT AATAGGATGT TAAATATCTT      1876
TTGGGGTTTT AAAGAGTATC TCAGCAGCTG TCTTCTGATT TATCTTTTCT TTTTATTCAG      1936
CACACCACAT GCATGTTCAC GACAAAGTGT TTTTAAAACT TGGCGAACAC TTCAAAAATA      1996
GGAGTTGGGA TTAGGGAAGC AGTATGAGTG CCCGTGTGCT ATCAGTTGAC TTAATTTGCA      2056
CTTCTGCAGT AATAACCATC AACAATAAAT ATGGCAATGC TGTGCCATGG CTTGAGTGAG      2116
AGATGTCTGC TATCATTTGA AAACATATAT TACTCTCGAG GCTTCCTGTC TCAAGAAATA      2176
GACCAGAAGG CCAAATTCTT CTCTTTCAAT ACATCAGTTT GCCTCCAAGA ATATACTAAA      2236
AAAAGGAAAA TTAATTGCTA AATACATTTA AATAGCCTAG CCTCATTATT TACTCATGAT      2296
TTCTTGCCAA ATGTCATGGC GGTAAAGAGG CTGTCCACAT CTCTAAAAAC CCTCTGTAAA      2356
TTCCACATAA TGCATCTTTC CCAAAGGAAC TATAAAGAAT TTGGTATGAA GCGCAACTCT      2416
```

FIG.3B

```
CCCAGGGGCT TAAACTGAGC AAATCAAATA TATACTGGTA TATGTGTAAC CATATACAAA    2476
AACCTGTTCT AGCTGTATGA TCTAGTCTTT ACAAAACCAA ATAAAACTTG TTTTCTGTAA    2536
ATTTAAAGAG CTTTACAAGG TTCCATAATG TAACCATATC AAAATTCATT TTGTTAGAGC    2596
ACGTATAGAA AAGAGTACAT AAGAGTTTAC CAATCATCAT CACATTGTAT TCCACTAAAT    2656
AAATACATAA GCCTTATTTG CAGTGTCTGT AGTGATTTTA AAAATGTAGA AAAATACTAT    2716
TTGTTCTAAA TACTTTTAAG CAATAACTAT AATAGTATAT TGATGCTGCA GTTTTATCTT    2776
CATATTTCTT GTTTTGAAAA AGCATTTTAT TGTTTGGACA CAGTATTTTG GTACAAAAAA    2836
AAAGACTCAC TAAATGTGTC TTACTAAAGT TTAACCTTTG GAAATGCTGG CGTTCTGTGA    2896
TTCTCCAACA AACTTATTTG TGTCAATACT TAACCAGCAC TTCCAGTTAA TCTGTTATTT    2956
TTAAAAATTG CTTTATTAAG AAATTTTTTG TATAATCCCA TAAAAGGTCA TATTTTTCCC    3016
ATTCTTCAAA AAAACTGTAT TTCAGAAGAA ACACATTTGA GGCACTGTCT TTTGGCTTAT    3076
AGTTTAAATT GCATTTCATC ATACTTTGCT TCCAACTTGC TTTTTGGCAA ATGAGATTAT    3136
AAAAATGTTT AATTTTGTG GTTGGAATCT GGATGTTAAA ATTTAATTGG TAACTCAGTC     3196
TGTGAGCTAT AATGTAATGC ATTCCTATCC AAACTAGGTA TCTTTTTTTC CTTTATGTTG    3256
AAATAATAAT GGCACCTGAC ACATAGACAT AGACCACCCA CAACCTAAAT TAAATGTTTG    3316
GTAAGACAAA TACACATTGG ATGACCACAG TAACAGCAAA CAGGGCACAA ACTGGATTCT    3376
TATTTCACAT AGACATTTAG ATTACTAAAG AGGGCTATGT GTAAACAGTC ATCATTATAG    3436
TACTCAAGAC ACTAAAACAG CTTCTAGCCA AATATATTAA AGCTTGCAGA GGCCAAAAAT    3496
AGAAAACATC TCCCCTGTCT CTCCCACATT TCCCTCACAG AAAGACAAAA AACCTGCCTG    3556
GTGCAGTAGC TCACACCTGT AATCCCAGCA GTTTGGGAGA CTGTGGGAAG ATGGCTTGAG    3616
TCCAGGAGTT CTAGACAGGC CTGAGAAACC TAGTGAGACA TCCTTCTCTT AAACAAAACA    3676
AAACAAAACA AATGTAGCCA TGCGTGGTGG CATATACCTG TGGTCCCAAC TACTCAGGAG    3736
GCTGAAACGG AAGGATCTCT TGGGCCCCAG GAGTTTGAGG CTGCAGTGAG CTATAATCTT    3796
GCCATTGCAC TCCAGCCTGG GTGAAAAAGA GCCAGAAAGA AAGGAAAGAG AGAAAAGAGA    3856
AAAGAAAGAG AGAAAAGACA GAAAGACAGG AAGGAAGGAA GGAAGGAAGG AAGGAAGGAA    3916
GGAAGCAAGG AAAGAAGGAA GGAAGGAAAG AAGGGAGGGA AGGAAGGAGA GAGAAAGAAA    3976
GATTGTTTGG TAAGGAGTAA TGACATTCTC TTGCATTTAA AAGTGGCATA TTTGCTTGAA    4036
```

FIG.3C

```
ATGGAAATAG AATTCTGGTC CCTTTTGCAA CTACTGAAGA AAAAAAAAAG CAGTTTCAGC    4096
CCTGAATGTT GTAGATTTGA AAAAAAAAAA AAAAAAACTC GAGGGGGGGC CCGTACCCAA    4156
TTCGCCCTAT AGTGAGTCGT A                                              4177
```

FIG.3D

ATGAGAGGATCGCATCACCATCACCATCACGGATCCTGCCAGGCTCTGGGTC
AGGACATGGTTTCTCCGGAAGCTACCAACTCTTCCTCTTCCTCTTTCTCTTCCC
CGTCTTCCGCTGGTCGTCACGTTCGTTCTTACAACCACCTGCAGGGTGACGTTC
GTTGGCGTAAACTGTTCTCTTTCACCAAATACTTCCTGAAAATCGAAAAA
AACGGTAAAGTTTCTGGGACCAAGAAGGAGAACTGCCCGTACAGCATCCTG
GAGATAACATCAGTAGAAATCGGAGTTGTTGCCGTCAAAGCCATTAACAG
CAACTATTACTTAGCCATGAACAAGAAGGGGAAACTCTATGGCTCAAAAG
AATTTAACAATGACTGTAAGCTGAAGGAGAGGATAGAGGAAAATGGAT
ACAATACCTATGCATCATTTAACTGGCAGCATAATGGGAGGCAAATGTAT
GTGGCATTGAaTGGAAAAGGAGCTCCAaGGAGAGGACAGAAAACACGAAG
GAAAAACACCTCTGCTCACTTTCTTCCAATGGTGGTACACTCATAG

MRGSHHHHHHGSCQALGQDMVSPEATNSSSSSFSSPSSAGRHVRSYNHLQGD
VRWRKLFSFTKYFLKIEKNGKVSGTKKENCPYSILEITSVEIGVVAVKAINSN
YYLAMNKKGKLYGSKEFNNDCKLKERIEENGYNTYASFNWQHNGRQMYVA
LNGKGAPRRGQKTRRKNTSAHFLPMVVHS kgf-2 synthetic cys37 Bam HI
AAAGGATCCTGCCAGGCTCTGGGTCAGGACATG

FIG.5

```
                                         -35              Operator 1
  1  AAGCTTAAAAAACTGCAAAAAATAGT TTGACT TGTGAGCGGATAAGAAT -10                 Operator 2
 50 TAAGAT GTACCCA ATTGTGAGCGGATAACAATT TCACACATTAA

S/D
 94 A GAGGAG AAATTA CATATG
```

FIG.9

ATGTGGAAATGGATACTGACCCACTGCGCTTCTGCTTTCCCGCACCTGCCGGGTTGCTGC 60
Met Trp Lys Trp Ile Leu Thr His Cys Ala Ser Ala Phe Pro His Leu Pro Gly Cys Cys

TGCTGCTGCTTCCTGCTGCTGTTCCTGGTTTCTTCTGTTCCGGTTACCTGCCAGGCTCTG 120
Cys Cys Cys Phe Leu Leu Leu Phe Leu Val Ser Ser Val Pro Val Thr Cys Gln Ala Leu

GGTCAGGACATGGTTTCTCCGGAAGCTACCAACTCTTCCTCTTCCTCTTTCTCTTCCCCG 180
Gly Gln Asp Met Val Ser Pro Glu Ala Thr Asn Ser Ser Ser Ser Ser Phe Ser Ser Pro

ACTTCCGCTGGTCGTCACGTTCGTTCTTACAACCACCTGCAGGGTGACGTTCGTTGGCGT 240
Thr Ser Ala Gly Arg His Val Arg Ser Tyr Asn His Leu Gln Gly Asp Val Arg Trp Arg

AAACTGTTCTCTTTCACCAAATACTTCCTGAAAATCGAAAAAAACGGTAAAGTTTCTGGG 300
Lys Leu Phe Ser Phe Thr Lys Tyr Phe Leu Lys Ile Glu Lys Asn Gly Lys Val Ser Gly

ACCAAGAAGGAGAACTGCCCGTACAGCATCCTGGAGATAACATCAGTAGAAATCGGAGTT 360
Thr Lys Lys Glu Asn Cys Pro Tyr Ser Ile Leu Glu Ile Thr Ser Val Glu Ile Gly Val

GTTGCCGTCAAAGCCATTAACAGCAACTATTACTTAGCCATGAACAAGAAGGGGAAACTC 420
Val Ala Val Lys Ala Ile Asn Ser Asn Tyr Tyr Leu Ala Met Asn Lys Lys Gly Lys Leu

TATGGCTCAAAAGAATTTAACAATGACTGTAAGCTGAAGGAGAGGATAGAGGAAAATGGA 480
Tyr Gly Ser Lys Glu Phe Asn Asn Asp Cys Lys Leu Lys Glu Arg Ile Glu Glu Asn Gly

TACAATACCTATGCATCATTTAACTGGCAGCATAATGGGAGGCAAATGTATGTGGCATTG 540
Tyr Asn Thr Tyr Ala Ser Phe Asn Trp Gln His Asn Gly Arg Gln Met Tyr Val Ala Leu

AATGGAAAAGGAGCTCCAAGGAGAGGACAGAAAACACGAAGGAAAAACACCTCTGCTCAC 600
Asn Gly Lys Gly Ala Pro Arg Arg Gly Gln Lys Thr Arg Arg Lys Asn Thr Ser Ala His

TTTCTTCCAATGGTGGTACACTCATAG 627
Phe Leu Pro Met Val Val His Ser *

FIG.10

```
ATGACCTGCCAGGCTCTGGGTCAGGACATGGTTTCTCCGGAAGCTACCAACTCTTCCTCT    60
MetThrCysGlnAlaLeuGlyGlnAspMetValSerProGluAlaThrAsnSerSerSer

TCCTCTTTCTCTTCCCCGTCTTCCGCTGGTCGTCACGTTCGTTCTTACAACCACCTGCAG   120
SerSerPheSerSerProSerSerAlaGlyArgHisValArgSerTyrAsnHisLeuGln

GGTGACGTTCGTTGGCGTAAACTGTTCTCTTTCACCAAATACTTCCTGAAAATCGAAAAA   180
GlyAspValArgTrpArgLysLeuPheSerPheThrLysTyrPheLeuLysIleGluLys

AACGGTAAAGTTTCTGGGACCAAGAAGGAGAACTGCCCGTACAGCATCCTGGAGATAACA   240
AsnGlyLysValSerGlyThrLysLysGluAsnCysProTyrSerIleLeuGluIleThr

TCAGTAGAAATCGGAGTTGTTGCCGTCAAAGCCATTAACAGCAACTATTACTTAGCCATG   300
SerValGluIleGlyValValAlaValLysAlaIleAsnSerAsnTyrTyrLeuAlaMet

AACAAGAAGGGGAAACTCTATGGCTCAAAAGAATTTAACAATGACTGTAAGCTGAAGGAG   360
AsnLysLysGlyLysLeuTyrGlySerLysGluPheAsnAsnAspCysLysLeuLysGlu

AGGATAGAGGAAAATGGATACAATACCTATGCATCATTTAACTGGCAGCATAATGGGAGG   420
ArgIleGluGluAsnGlyTyrAsnThrTyrAlaSerPheAsnTrpGlnHisAsnGlyArg

CAAATGTATGTGGCATTGAATGGAAAAGGAGCTCCAAGGAGAGGACAGAAAACACGAAGG   480
GlnMetTyrValAlaLeuAsnGlyLysGlyAlaProArgArgGlyGlnLysThrArgArg

AAAAACACCTCTGCTCACTTTCTTCCAATGGTGGTACACTCATAG   525
LysAsnThrSerAlaHisPheLeuProMetValValHisSer *
```

FIG.11A

```
ATGACTTGCCAGGCACTGGGTCAAGACATGGTTTCCCCGGAAGCTACCAACAGCTCCAGCTCTAGCTTCA
|+++++++++|+++++++++|+++++++++|+++++++++|+++++++++|+++++++++|+++++++++|  70
TACTGAACGGTCCGTGACCCAGTTCTGTACCAAAGGGGCCTTCGATGGTTGTCGAGGTCGAGATCGAAGT
  M  T  C  Q  A  L  G  Q  D  M  V  S  P  E  A  T  N  S  S  S  S  F
```

```
GCAGCCCATCTAGCGCAGGTCGTCACGTTCGCTCTTACAACCACTTACAGGGTGATGTTCGTTGGCGCAA
|+++++++++|+++++++++|+++++++++|+++++++++|+++++++++|+++++++++|+++++++++| 140
CGTCGGGTAGATCGCGTCCAGCAGTGCAAGCGAGAATGTTGGTGAATGTCCCACTACAAGCAACCGCGTT
  S  S  P  S  S  A  G  R  H  V  R  S  Y  N  H  L  Q  G  D  V  R  W  R  K
```

```
ACTGTTCAGCTTTACCAAGTACTTCCTGAAAATCGAAAAAAACGGTAAAGTTTCTGGGACCAAGAAGGAG
|+++++++++|+++++++++|+++++++++|+++++++++|+++++++++|+++++++++|+++++++++| 210
TGACAAGTCGAAATGGTTCATGAAGGACTTTTAGCTTTTTTTGCCATTTCAAAGACCCTGGTTCTTCCTC
  L  F  S  F  T  K  Y  F  L  K  I  E  K  N  G  K  V  S  G  T  K  K  E
```

```
AACTGCCCGTACAGCATCCTGGAGATAACATCAGTAGAAATCGGAGTTGTTGCCGTCAAAGCCATTAACA
|+++++++++|+++++++++|+++++++++|+++++++++|+++++++++|+++++++++|+++++++++| 280
TTGACGGGCATGTCGTAGGACCTCTATTGTAGTCATCTTTAGCCTCAACAACGGCAGTTTCGGTAATTGT
  N  C  P  Y  S  I  L  E  I  T  S  V  E  I  G  V  V  A  V  K  A  I  N
```

```
GCAACTATTACTTAGCCATGAACAAGAAGGGGAAACTCTATGGCTCAAAAGAATTTAACAATGACTGTAA
|+++++++++|+++++++++|+++++++++|+++++++++|+++++++++|+++++++++|+++++++++| 350
CGTTGATAATGAATCGGTACTTGTTCTTCCCCTTTGAGATACCGAGTTTTCTTAAATTGTTACTGACATT
  S  N  Y  Y  L  A  M  N  K  K  G  K  L  Y  G  S  K  E  F  N  N  D  C  K
```

```
GCTGAAGGAGAGGATAGAGGAAAATGGATACAATACCTATGCATCATTTAACTGGCAGCATAATGGGAGG
|+++++++++|+++++++++|+++++++++|+++++++++|+++++++++|+++++++++|+++++++++| 420
CGACTTCCTCTCCTATCTCCTTTTACCTATGTTATGGATACGTAGTAAATTGACCGTCGTATTACCCTCC
  L  K  E  R  I  E  E  N  G  Y  N  T  Y  A  S  F  N  W  Q  H  N  G  R
```

```
CAAATGTATGTGGCATTGAATGGAAAAGGAGCTCCAAGGAGAGGACAGAAAACACGAAGGAAAAACACCT
|+++++++++|+++++++++|+++++++++|+++++++++|+++++++++|+++++++++|+++++++++| 490
GTTTACATACACCGTAACTTACCTTTTCCTCGAGGTTCCTCTCCTGTCTTTTGTGCTTCCTTTTTGTGGA
  Q  M  Y  V  A  L  N  G  K  G  A  P  R  R  G  Q  K  T  R  R  K  N  T
```

```
CTGCTCACTTTCTTCCAATGGTGGTACACTCATAG
|+++++++++|+++++++++|+++++++++|+++++→ 525
GACGAGTGAAAGAAGGTTACCACCATGTGAGTATC
  S  A  H  F  L  P  M  V  V  H  S
                                   →
```

FIG.11B

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

MTCQALGQDMVSPEATNSSSSSFSSPSSAGRHVRSYNHLQGDVRWRKLFSFTKYFLKIE
KNGKVSGTKKENCPYSILEITSVEIGVVAVKAINSNYYLAMNKKGKLYGSKEFNNDCKL
KERIEENGYNTYASFNWQHNGRQMYVALNGKGAPRRGQKTRRKNTSAHFLPMVVHS.

FIG.12

ATGGCTGGTCGTCACGTTCGTTCTTACAACCACCTGCAGGGTGACGTTCGTTGGCGT
AAACTGTTCTCTTTCACCAAATACTTCCTGAAAATCGAAAAAAACGGTAAAGTTTCT
GGGACCAAGAAGGAGAACTGCCCGTACAGCATCCTGGAGATAACATCAGTAGAAATC
GGAGTTGTTGCCGTCAAAGCCATTAACAGCAACTATTACTTAGCCATGAACAAGAAG
GGGAAACTCTATGGCTCAAAAGAATTTAACAATGACTGTAAGCTGAAGGAGAGGATA
GAGGAAAATGGATACAATACCTATGCATCATTTAACTGGCAGCATAATGGGAGGCAA
ATGTATGTGGCATTGAATGGAAAAGGAGCTCCAAGGAGAGGACAGAAAACACGAAGG
AAAAACACCTCTGCTCACTTTCTTCCAATGGTGGTACACTCATAG

MAGRHVRSYNHLQGDVRWRKLFSFTKYFLKIEKNGKVSGTKKENCPYSILEITSVEIGV
VAVKAINSNYYLAMNKKGKLYGSKEFNNDCKLKERIEENGYNTYASFNWQHNGRQMYVA
LNGKGAPRRGQKTRRKNTSAHFLPMVVHS.

FIG.13

ATGGTTCGTTGGCGTAAACTGTTCTCTTTCACCAAATACTTCCTGAAAATCGAAAAA
AACGGTAAAGTTTCTGGGACCAAGAAGGAGAACTGCCCGTACAGCATCCTGGAGATA
ACATCAGTAGAAATCGGAGTTGTTGCCGTCAAAGCCATTAACAGCAACTATTACTTA
GCCATGAACAAGAAGGGGAAACTCTATGGCTCAAAAGAATTTAACAATGACTGTAAG
CTGAAGGAGAGGATAGAGGAAAATGGATACAATACCTATGCATCATTTAACTGGCAG
CATAATGGGAGGCAAATGTATGTGGCATTGAATGGAAAAGGAGCTCCAAGGAGAGGA
CAGAAAACACGAAGGAAAAACACCTCTGCTCACTTTCTTCCAATGGTGGTACACTCA
TAG

MVRWRKLFSFTKYFLKIEKNGKVSGTKKENCPYSILEITSVEIGVVAVKAINSNYYLAM
NKKGKLYGSKEFNNDCKLKERIEENGYNTYASFNWQHNGRQMYVALNGKGAPRRGQKTR
RKNTSAHFLPMVVHS.

FIG.14

ATGGAAAAAAACGGTAAAGTTTCTGGGACCAAGAAGGAGAACTGCCCGTACAGCAT
CCTGGAGATAACATCAGTAGAAATCGGAGTTGTTGCCGTCAAAGCCATTAACAGCA
ACTATTACTTAGCCATGAACAAGAAGGGGAAACTCTATGGCTCAAAAGAATTTAAC
AATGACTGTAAGCTGAAGGAGAGGATAGAGGAAAATGGATACAATACCTATGCATC
ATTTAACTGGCAGCATAATGGGAGGCAAATGTATGTGGCATTGAATGGAAAAGGAG
CTCCAAGGAGAGGACAGAAAACACGAAGGAAAAACACCTCTGCTCACTTTCTTCCA
ATGGTGGTACACTCATAG

MEKNGKVSGTKKENCPYSILEITSVEIGVVAVKAINSNYYLAMNKKGKLYGSKEFNNDC
KLKERIEENGYNTYASFNWQHNGRQMYVALNGKGAPRRGQKTRRKNTSAHFLPMVVH
S.

FIG.15

ATGGAGAACTGCCCGTACAGCATCCTGGAGATAACATCAGTAGAAATCGGAGTTGT
TGCCGTCAAAGCCATTAACAGCAACTATTACTTAGCCATGAACAAGAAGGGGAAAC
TCTATGGCTCAAAAGAATTTAACAATGACTGTAAGCTGAAGGAGAGGATAGAGGAA
AATGGATACAATACCTATGCATCATTTAACTGGCAGCATAATGGGAGGCAAATGTA
TGTGGCATTGAATGGAAAAGGAGCTCCAAGGAGAGGACAGAAAACACGAAGGAAAA
ACACCTCTGCTCACTTTCTTCCAATGGTGGTACACTCATAG

MENCPYSILEITSVEIGVVAVKAINSNYYLAMNKKGKLYGSKEFNNDCKLKERIEENGY
NTYASFNWQHNGRQMYVALNGKGAPRRGQKTRRKNTSAHFLPMVVHS.

FIG.16

ATGGTCAAAGCCATTAACAGCAACTATTACTTAGCCATGAACAAGAAGGGGAAACT
CTATGGCTCAAAAGAATTTAACAATGACTGTAAGCTGAAGGAGAGGATAGAGGAAA
ATGGATACAATACCTATGCATCATTTAACTGGCAGCATAATGGGAGGCAAATGTAT
GTGGCATTGAATGGAAAAGGAGCTCCAAGGAGAGGACAGAAAACACGAAGGAAAAA
CACCTCTGCTCACTTTCTTCCAATGGTGGTACACTCATAG

MVKAINSNYYLAMNKKGKLYGSKEFNNDCKLKERIEENGYNTYASFNWQHNGRQMY
VALNGKGAPRRGQKTRRKNTSAHFLPMVVHS.

FIG.17

ATGGGGAAACTCTATGGCTCAAAAGAATTTAACAATGACTGTAAGCTGAAGGAGAG
GATAGAGGAAAATGGATACAATACCTATGCATCATTTAACTGGCAGCATAATGGGA
GGCAAATGTATGTGGCATTGAATGGAAAAGGAGCTCCAAGGAGAGGACAGAAAACA
CGAAGGAAAAACACCTCTGCTCACTTTCTTCCAATGGTGGTACACTCATAG

MGKLYGSKEFNNDCKLKERIEENGYNTYASFNWQHNGRQMYVALNGKGAPRRGQKT
RRKNTSAHFLPMVVHS.

FIG.18

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAG

MTCQALGQDMVSPEATNSSSSSFSSPSSAGRHVRSYNHLQGDVRWRKLFSFTKYFLKIE
KNGKVSGTKKENCPYSILEITSVEIGVVAVKAINSNYYLAMNKKGKLYGSKEFNNDCKL
K

FIG.19

ATGGCTGGTCGTCACGTTCGTTCTTACAACCACCTGCAGGGTGACGTTCGTTGGCGT
AAACTGTTCTCTTTCACCAAATACTTCCTGAAAATCGAAAAAAACGGTAAAGTTTCT
GGGACCAAGAAGGAGAACTGCCCGTACAGCATCCTGGAGATAACATCAGTAGAAATC
GGAGTTGTTGCCGTCAAAGCCATTAACAGCAACTATTACTTAGCCATGAACAAGAAG
GGGAAACTCTATGGCTCAAAAGAATTTAACAATGACTGTAAGCTGAAG

MAGRHVRSYNHLQGDVRWRKLFSFTKYFLKIEKNGKVSGTKKENCPYSILEITSVEIGV
VAVKAINSNYYLAMNKKGKLYGSKEFNNDCKLK

FIG.20

C-37 To Ser

ATGACCTCTCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

FIG.21

C-106 To Ser

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTCTCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

FIG.22

| DAYS | KGF-2 | | | BUFFER | |
|---|---|---|---|---|---|
| | MEAN | SEM | | MEAN | SEM |
| 1 | 21.95 | 5.55 | | 10.99 | 1.45 |
| 2 | 18.25 | 1.86 | | 7.49 | 2.31 |
| 3 | 13.33 | 2.59 | | 9.8 | 1.8 |
| 7 | 8.05 | 1.11 | | 9.56 | 2.85 |
| 14 | 10.27 | 0.93 | | 11.51 | 0.78 |

| DAYS | KGF-2 | | | BUFFER | |
|---|---|---|---|---|---|
| | MEAN | SEM | | MEAN | SEM |
| 1 | 37.42 | 4.55 | | 15.03 | 2.15 |
| 2 | 57.59 | 5.39 | | 11.19 | 3.21 |
| 3 | 31.25 | 6.05 | | 13.52 | 1.57 |
| 7 | 23.64 | 5.77 | | 15.56 | 2.95 |
| 14 | 26.35 | 6.02 | | 20.56 | 2.95 |

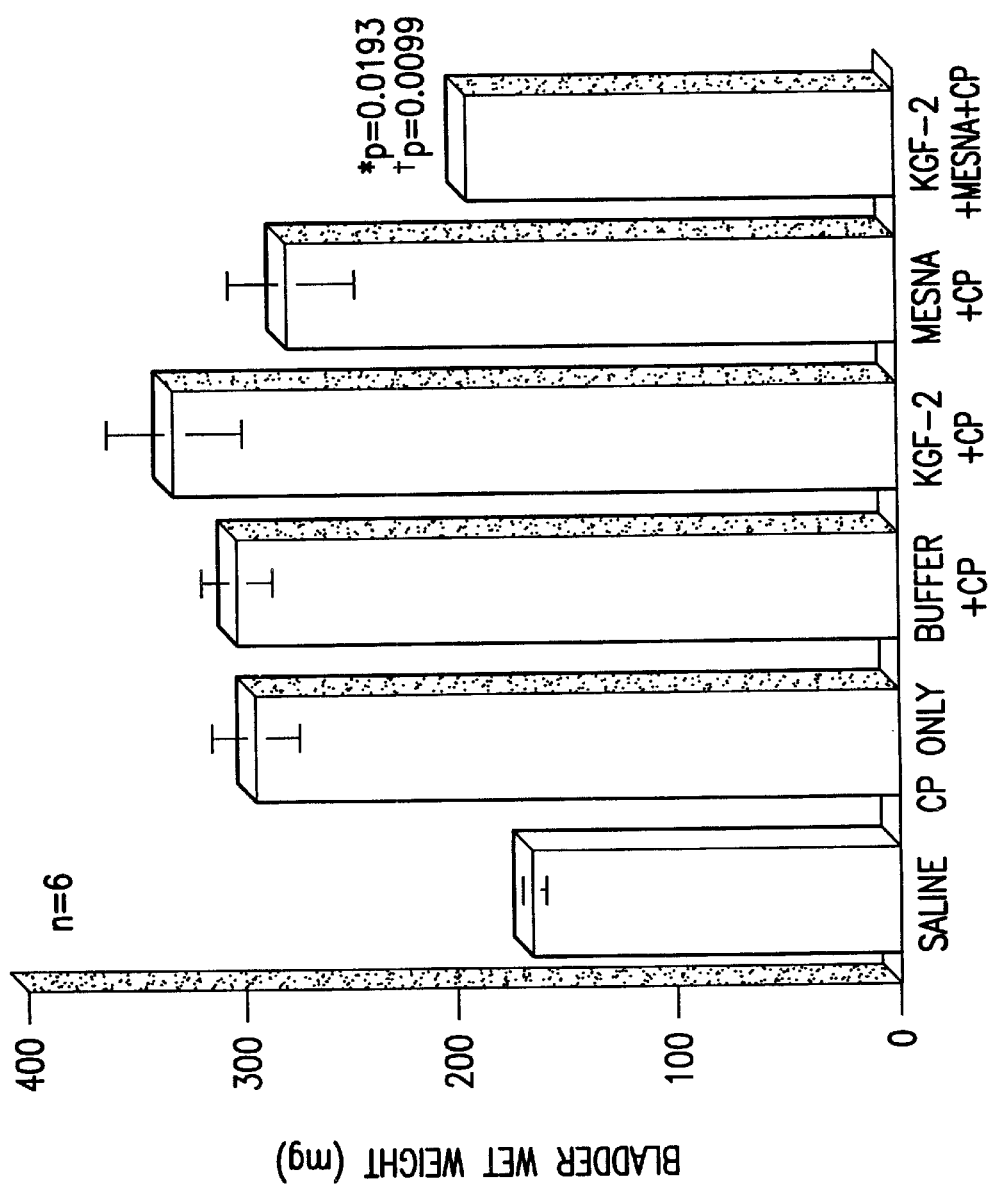

THERAPEUTIC USES OF KERATINOCYTE GROWTH FACTOR-2

This application claims the benefit of the filing dates of provisional Application No. 60/074,585 filed Feb. 13, 1998 and No. 60/114,387 filed Dec. 30, 1998, both of which are herein incorporated by reference in their entireties.

FIELD OF THE INVENTION

The present invention relates to the administration of Keratinocyte Growth Factor-2 (KGF-2) to increase levels of platelets, fibrinogen, albumin, globulin and total serum protein. Further, the present invention relates to administering KGF-2 to protect or treat the bladder and prostate. Moreover, the present invention relates to administering KGF-2 to stimulate growth of nasal, oral, and esophageal mucosa, lacrimal glands, salivary glands and Goblet cells.

BACKGROUND OF THE INVENTION

Thrombocytopenia is a condition in which there is an abnormally small number of platelets in the circulating blood (Stedman's Medical Dictionary, 26th edition, Marjory Spraycar, Editor (1995). Thrombocytopenia results from various causes, but ultimately occurs when platelets are destroyed, sequestered in the body, or not produced. The differential diagnosis of thrombocytopenia is extensive and complex, and there is a significant overlap among disorders (Doyle B, and Porter D. L. A.A.C.N. Clin. Issues 8: 469–480 (1997).

Thrombocytopenia may be caused by a variety of mechanisms including, but not limited to, drug induced hypersensitivity, idiopathic thrombocytopenia purpura (ITP), posttransfusion purpura, neonatal thrombocytopenia, bone marrow deficiencies identified with metastatic tumors to the bone, aplastic anemia, myelofibrosis, acute and monocytic leukemia, microangiopathic hemolytic anemia which includes disseminated intravascular coagulation (DIC), thrombotic thrombocytopenic purpura (TTP), hemolytic-uremic syndrome, prosthetic valve hemolytic syndrome, cancer chemotherapy, Zieve's syndrome, sepsis, HELLP preclamptic syndrome, megaloblastic anemia due to B21 and folic acid deficiency, infections such as peritonitis (without septicemia), congenital rubella syndrome, HIV-1 virus infections, Epstein-Barr infectious mononucleosis, rheumatoid-collagen diseases such as systemic lupus, hypertension of pregnancy associated with preclampsias, thyrotoxicosis and uremia (*Clinical guide to laboratory tests*. (3rd ed). Philadelphia, W.B. Saunders Company, 1995; *Clinical Laboratory Medicine. Clinical application oflaboratory data.* (6th ed.) St. Louis, Mosby, 1995).

Fibrinogen is an abundant plasma glycoprotein that is synthesized in the liver. Thrombin sequentially cleaves fibrinopeptides A and B from the α and β chains of fibrinogen to produce fibrin monomer, which then polymerizes to form a fibrin clot which is the final major step in the coagulation process. Mutations have been identified which alter the release of fibrinopeptides from the α and β chains of fibrinogen, the rate of polymerization of fibrin monomers, and the sites for fibrin cross-linking. This mutations lead to dysfibrinogenemias which are almost always inherited as autosomal dominant traits. Patients with afibrinogenemia, who have no detectable fibrinogen in plasma or platelets, may have infrequent, mild spontaneous bleeding episodes. (Harrison's Principles of Internal Medicine 11th edition Eugene Braunwald et. al., Editors (1987)).

Hypofibrinogenemia refers to a condition in which there is an abnormally low concentration of fibrinogen in the circulating blood plasma (Stedman's Medical Dictionary, 26th edition, Marjory Spraycar, Editor (1995)). Hypofibrinogenemia may be caused by a variety of conditions or afflictions including, but not limited to, abnormal hepatic synthesis such as that associated with acute hepatitis or cirrhosis, and disseminated intravascular coagulation (DIC).

Albumin, the major serum protein, is considered to be responsible for maintenance of normal serum colloid osmotic pressure, transport of certain hormones and maintaining an endogenous source of amino acids (Buehler, B. A. Ann. Clin. Lab. Sci. 8: 283–286 (1978)). Hypoalbuminemia is a condition in which there is an abnormally low concentration of albumin in the circulating blood. The serum albumin level is one of several clinical parameters of the status of general health. There is a marked correlation between low albumin levels and the incidence of morbidity and mortality in hospitalized patients. Therefore, it is not surprising to find that hypoalbuminemia is a common finding among hospitalized patients. Hypoalbuminemia is known to be associated with delayed wound healing. The hypoalbuminemic state interferes with the normal functioning of the gastrointestinal tract. Qualitative changes in the albumin molecule which occur in renal disease may damage the nephron. Low serum albumin levels may adversely affect the coagulation system (Doweiko, J. P., and Nompleggi, D. J. J.P.E.N. J. Parenter. Enteral. Nutr. 15: 476–483 (1991)).

Hypoalbuminemia can be caused by a variety of afflictions or conditions including, but not limited to, hemorrhages, burns, exudates, rheumatic diseases, granulomatous processes, most bacterial infections, viral infections accompanied by tissue destruction, tissue necrosis, vasculitis, ulcerative bowel disease, serositis, subacute bacterial endocarditis, parasitic infestations, acute and chronic liver disease, amyloidosis, malnutrition, malignancy, congestive heart failure, constrictive pericarditis, cardiac valvular disease, nephrotic syndrome, trauma and crush injuries, gastrointestinal and lymphatic fistulae, and protein-losing gastroenteropathies (*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995).

Globulin is the name for a family of proteins precipitated from plasma or serum by half-saturation with ammonium sulphate. Globulins may be fractionated by solubility, electrophoresis, ultracentrifugation, and other separation methods into many subgroups, the main subgroups being α-, β-, and γ-globulins. These differ with respect to associated lipids or carbohydrates and in their content of many physiologically important factors. Globulins include immunoglobulins in the β, and γ fractions, lipoproteins in the α and β fractions, gluco- or mucoproteins (orosomucoid, haptoglobulin), and metal binding and metal transporting proteins (such as transferrin, siderophilin, ceruloplasmin). Other substances found in globulin fractions are: macroglobulin, plasminogen, prothrombin, euglobulin, antihemophilic globulin, fibrinogen, and cryoglobulin (Stedman's Medical Dictionary, 26th edition, Marjory Spraycar, Editor (1995)).

Certain reasonably predictable changes take place in plasma protein levels in response to acute illness. Hypoglobulinemia refers to an abnormally low concentration of globulin in the circulating plasma. Hypoglobulinemia may result from a variety of conditions or afflictions including, but not limited to, alpha-1 antityrpsin deficiencies, severe liver disease, estrogen therapy, megaloblastic anemia, hypogammaglobulinemia and aggammaglobulinemia (*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995).

A decrease in total serum protein is associated with protein loss (protein-losing gastroenteropathies, acute burns, nephrotic syndrome) and decreased synthesis of protein (chronic liver disease, malabsorption syndrome, malnutrition, and agammaglobulinemia).

Hemorrhagic cystitis is a syndrome associated with certain disease states as well as exposure to drugs, viruses, and toxins. It manifests as diffuse bleeding of the endothelial lining of the bladder. Treatment includes intravesical, systemic, and nonpharmacologic therapies (West, N. J. Pharmacotherapy 17: 696–706 (1997)).

Loss of the ability to produce adequate amounts of saliva and tears is a major clinical problem affecting millions of people and there are few therapeutic options for these sufferers. Patients with xerostomia, or dry mouth, have difficulty swallowing, have painful cracks in their mouths, and experience a decrease in their ability to taste. This condition may be caused by Sjogren's syndrome, as a secondary event to radiation used with patients with head and neck tumors, and to drugs. Patients with Sjogren's syndrome sometimes have keratoconjunctivitis sicca or dry eye. This condition may be caused by damage to the lacrimal gland due to Sjogren's syndrome, sarcoidosis, aging, HIV infection, burns, etc. Patients experience irritation, blurring of vision, burning, pain, and increased risk of infections. Millions of patients suffer with Sjogren's syndrome and therapy is sub-optimal.

As is the case with xerostomia, patients with keratoconjunctivitis sicca have few therapeutic options. At this time there are approximately 10 million patients in the US which require artificial tear preparations (Lemp, M. A, *Adv. Exp. Med. Biol.* 438:791–803 (1998)). There are no treatments available at this time to stimulate replacement of the cells in the salivary and lacrimal gland cells.

Sinus infections usually occur in the setting of upper respiratory tract infections, allergies, or anatomic defects (within the sinuses or nasal septum) and may lead to symptoms of headache, facial pain, fever, and purulent rhinorrhea. (Evans K L. *Drugs* 56(1): 59–71 (1998)). The symptoms of nasal allergy and chronic ethmoid sinusitis overlap and treatment failure in allergic patients may suggest possible chronic sinusitis. Chronic ethmoidal sinusitis may be the leading cause of rhinorrhea and nasal obstruction in patients with perennial allergies. (Bertrand et al., *Acta Otorhinolaryngol Belg* 51(4):227–237 (1997)). Acute sinusitis tends to occur in patients with a history of rhinitis, which may be allergic or non-allergic in origin. Patients with anatomic variants (Evans K L. *Drugs* 56(1): 59–71 (1998)) and cystic fibrosis (Brihaye et al., *Acta Otorhinolaryngol Belg* 51(4):323–337 (1997); Ramsey et al., *J. Allergy Clin. Immunol.* 90(3Pt2):547–552 (1992); Davidson et al., *Laryngoscope* 105(4Pt1):354–358 (1995); Jones et al., *Int. J. Pediatr. Otorhinolaryngol.* 28(1):25–32 (1993)) are also at high risk for developing sinusitis. In particular, it is known that occlusion of the sinus ostia starts the cycle of events, which lead to and sustain sinusitis. (Reilly J. S. *Otolaryngology Head and Neck Surgery* 103(5):856–862(1990)). The goals of treatment for both acute and chronic sinusitis are to control the rhinitis, improve ventilation to the sinuses, and to improve the function of the sinuses for clearance of secretions. (Evans K L. *Drugs* 56(1): 59–71 (1998)).

Surgical treatment of the nasal sinuses is only considered when medical measures fail to control the sinusitis. The goals of treatment are identical: to improve ventilation and to facilitate or restore sinus drainage. An additional goal is that surgical treatment may sometimes improve the penetration of topical drugs into the sinus. Up to 250,000 procedures are performed each year in the United States. However, in the course of performing sinus surgery, the mucosal surface is stripped away or damaged. In cases where the surgery has been extensive, the underlying bone within the sinus may be exposed for periods of up to 6 months before the mucosa is fully reconstituted and recovery of ciliary density may require up to 2 years to achieve. Delayed re-epithelialization of the nasal sinuses following surgery is believed to be associated with increased risk of infection, scarring (subepithelial fibrosis) leading to recurrent disease, and cyst formation. After 2 years of follow up approximately 2–5% of patients will have recurrent disease and up to 15% may require surgical revision. (Evans K L. *Drugs* 56(1): 59–71 (1998)).

Thus, there is clearly a need in the art for therapeutic proteins capable of increasing levels of platelets, fibrinogen, albumin, globulin and total serum protein. Further, there is a need for therapies capable of treating or protecting against damage caused by cystitis. Moreover, there is a need for stimulating the proliferation of cells in the salivary and lacrimal glands; and stimulating re-epithelialization of the sinuses and the growth of nasal mucosa in the nasal sinuses after surgery.

SUMMARY OF THE INVENTION

The present invention provides isolated nucleic acid molecules comprising a polynucleotide encoding the keratinocyte growth factor (KGF-2) having the amino acid sequence is shown in FIG. 1 [SEQ ID NO:2] or the amino acid sequence encoded by the cDNA clone deposited as ATCC Deposit Number 75977 on Dec. 16, 1994. The nucleotide sequence determined by sequencing the deposited KGF-2 clone, which is shown in FIG. 1 [SEQ ID NO:1], contains an open reading frame encoding a polypeptide of 208 amino acid residues, including an initiation codon at positions 1–3, with a predicted leader sequence of about 35 or 36 amino acid residues, and a deduced molecular weight of about 23.4 kDa. The amino acid sequence of the mature KGF-2 is shown in FIG. 1, amino acid residues about 36 or 37 to 208 [SEQ ID NO:2].

The polypeptide of the present invention has been identified as a member of the FGF family, more particularly the polypeptide has been identified as KGF-2 as a result of amino acid sequence homology with other members of the FGF family.

In accordance with one aspect of the present invention, there are provided novel mature polypeptides which are KGF-2 as well as biologically active and diagnostically or therapeutically useful fragments, analogs and derivatives thereof. The polypeptides of the present invention are of human origin.

In accordance with another aspect of the present invention, there are provided isolated nucleic acid molecules encoding human KGF-2, including mRNAs, DNAs, cDNAs, genomic DNA, as well as antisense analogs thereof, and biologically active and diagnostically or therapeutically useful fragments thereof.

In accordance with another aspect of the present invention, there is provided a process for producing such polypeptides by recombinant techniques through the use of recombinant vectors, such as cloning and expression plasmids useful as reagents in the recombinant production of KGF-2 proteins, as well as recombinant prokaryotic and/or eukaryotic host cells comprising a human KGF-2 nucleic acid sequence.

In accordance with yet a further aspect of the present invention, there is provided therapeutic methods such as increasing platelet levels by administering KGF-2 for the purpose of alleviating thrombocytopenia. KGF-2 can also be used to increase the levels of plasma fibrinogen which may be found in conditions of abnormal hepatic synthesis (such as that associated with acute hepatitis or cirrhosis) and disseminated intravascular coagulation. KGF-2 can further be used to increase levels of serum albumin in patients with hypoalbuminemia. KGF-2 can also be used to increase the levels of serum globulin found in patients with hypoglobulinemia. KGF-2 can also be used to increase the levels of total serum protein in patients with protein loss and decreased protein synthesis.

KGF-2 can further be used to inhibit toxic effects on the prostate and bladder and to reduce the extent of ulceration caused by cystitis.

KGF-2 can also be used to stimulate the growth of sinus epithelia, nasal mucosa, lacrimal glands and salivary glands.

BRIEF DESCRIPTION OF THE FIGURES

FIGS. 1A–1C illustrate the cDNA and corresponding deduced amino acid sequence of the polypeptide of the present invention. The initial 35 or 36 amino acid residues represent the putative leader sequence (underlined). The standard one letter abbreviations for amino acids are used. Sequencing inaccuracies are a common problem when attempting to determine polynucleotide sequences. Sequencing was performed using a 373 Automated DNA sequencer (Applied Biosystems, Inc.). Sequencing accuracy is predicted to be greater than 97% accurate. [SEQ ID NO:1]

FIGS. 2A–2D are an illustration of a comparison of the amino acid sequence of the polypeptide of the present invention and other fibroblast growth factors. [SEQ ID NOS:13–22]

FIGS. 3A–3D show the full length mRNA and amino acid sequence for the KGF-2 gene. [SEQ ID NOS:23 and 24]

FIG. 5 shows the DNA sequence and the protein expressed from the pQE60-Cys37 construct [SEQ ID NOS:29 and 30]. The expressed KGF-2 protein contains the sequence from Cysteine at position 37 to Serine at position 208 with a 6×(His) tag attached to the N-terminus of the protein.

FIG. 9 shows the nucleotide sequence of the regulatory elements of the pHE promoter (SEQ ID NO:148). The two lac operator sequences, the Shine-Delgarno sequence (SID), and the terminal HindIII and NdeI restriction sites (italicized) are indicated.

FIG. 10 shows the DNA and protein sequence [SEQ ID NOS:38 and 39] for the *E.coli* optimized full length KGF-2.

FIGS. 11A and B show the DNA and protein sequences [SEQ ID NOS:42, 43, 54, and 55] for the E.coli optimized mature KGF-2.

FIG. 12 shows the DNA and the encoded protein sequence [SEQ ID NOS:65 and 66] for the KGF-2 deletion construct comprising amino acids 36 to 208 of KGF-2.

FIG. 13 shows the DNA and the encoded protein sequence [SEQ ID NOS:67 and 68] for the KGF-2 deletion construct comprising amino acids 63 to 208 of KGF-2.

FIG. 14 shows the DNA and the encoded protein sequence [SEQ ID NOS:69 and 70] for the KGF-2 deletion construct comprising amino acids 77 to 208 of KGF-2.

FIG. 15 shows the DNA and the encoded protein sequence [SEQ ID NOS:71 and 72] for the KGF-2 deletion construct comprising amino acids 93 to 208 of KGF-2.

FIG. 16 shows the DNA and the encoded protein sequence [SEQ ID NOS:73 and 74] for the KGF-2 deletion construct comprising amino acids 104 to 208 of KGF-2.

FIG. 17 shows the DNA and the encoded protein sequence [SEQ ID NOS:75 and 76] for the KGF-2 deletion construct comprising amino acids 123 to 208 of KGF-2.

FIG. 18 shows the DNA and the encoded protein sequence [SEQ ID NOS:77 and 78] for the KGF-2 deletion construct comprising amino acids 138 to 208 of KGF-2.

FIG. 19 shows the DNA and the encoded protein sequence [SEQ ID NOS:79 and 80] for the KGF-2 deletion construct comprising amino acids 36 to 153 of KGF-2.

FIG. 20 shows the DNA and the encoded protein sequence [SEQ ID NOS:81 and 82] for the KGF-2 deletion construct comprising amino acids 63 to 153 of KGF-2.

FIG. 21 shows the DNA sequence for the KGF-2 Cysteine-37 to Serine mutant construct [SEQ ID NO:83].

FIG. 22 shows the DNA sequence for the KGF-2 Cysteine-37/Cysteine-106 to Serine mutant construct [SEQ ID NO:84].

FIG. 39(A) shows KGF-2Δ33 treatment induces a large increase in saliva production in the treated animals.

FIG. 54 shows the synergistic effect of KGF-2Δ33 and mesna on bladder wet weight of cyclophosphamide-induced cystitis. Male SD rats (350–400 g) (n=7) received, on day 0, either buffer or 5.0 mg/kg KGF-2Δ33 intravenously and on day 1, Mesna (40 μg/g, i.v.) or both treatments on the respective administration days. Cyclophosphamide (300 mg/kg, i.p.) was administered on day 1 to all treatment groups with the exception of the saline control. One group was added as a CP control with no treatment. On day 3, animals received BrdU (100 mg/kg, i.p.) 2 hours prior to euthanasia. Bladders were fixed with 10% neutral-buffered formalin, weighed and placed in tissue cassettes for histological analysis. *Compared to CP only control; † compared to buffer control.

DETAILED DESCRIPTION

Figure 7A:
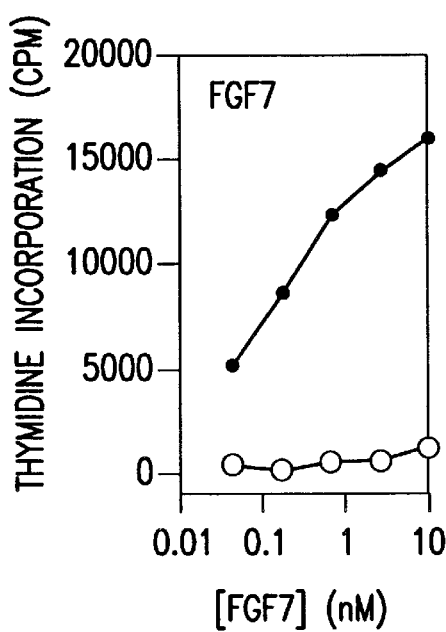
FIG. 7(A) shows the stimulation of thymidine incorporation by KGF-2 and FGF7 in Baf3 cells transfected with FGFR1b and FGFR2. The effects of KGF-2 (right panel) and FGF7 (left panel) on the proliferation of Baf3 cells transfected with FGFR1iiib (open circle) or FGFR2iiib/KGFR (solid Circle were examined. Y-axis represents the amount of [$^3$H]thymidine incorporation (cpm) into DNA of Baf3 cells. X-axis represents the final concentration of KGF-2 or FGF7 added to the tissue culture media. (B) shows the stimulation of thymidine incorporation by KGF-2Δ33 in Baf3 cells transfected with FGFR2iiib (C) shows the stimulation of thymidine incorporation by KGF-2 (white bar), KGF-2Δ33 (black bar) and KGF-2Δ28 (grey bar) in Baf3 cells transfected with FGFR2iiib.
Figures 1, 7A:
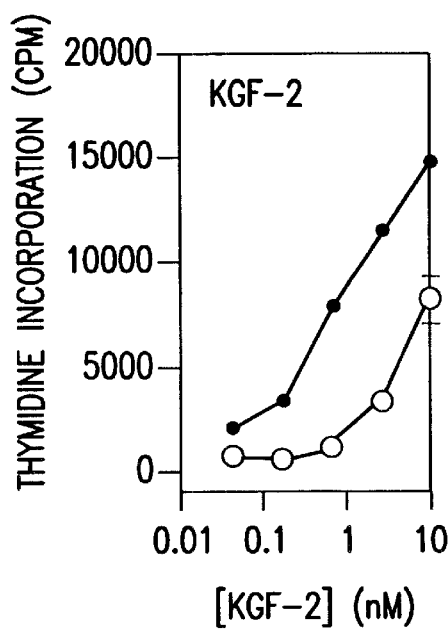

In accordance with an aspect of the present invention, there is provided an isolated nucleic acid (polynucleotide) which encodes for the polypeptide having the deduced amino acid sequence of FIG. 1 (SEQ ID NO:2) or for the polypeptide encoded by the cDNA of the clone deposited as ATCC Deposit No. 75977 on Dec. 16, 1994 at the American Type Culture Collection, Patent Depository, 10801 University Blvd, Manassas, Va. 20110-2209.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 1–3 of the nucleotide sequence shown in FIG. 1 (SEQ ID NO:1); DNA molecules comprising the coding sequence for the mature KGF-2 protein shown in FIG. 1 (last 172 or 173 amino acids) (SEQ ID NO:2); and DNA molecules which comprise a sequence substantially different from those described above but which, due to the degeneracy of the genetic code, still encode the KGF-2 protein. Of course, the genetic code is well known in the art. Thus, it would be routine for one skilled in the art to generate the degenerate variants described above.

A polynucleotide encoding a polypeptide of the present invention may be obtained from a human prostate and fetal lung. A fragment of the cDNA encoding the polypeptide was initially isolated from a library derived from a human normal prostate. The open reading frame encoding the full length protein was subsequently isolated from a randomly primed human fetal lung cDNA library. It is structurally related to the FGF family. It contains an open reading frame encoding a protein of 208 amino acid residues of which approximately the first 35 or 36 amino acid residues are the putative leader sequence such that the mature protein comprises 173 or 172 amino acids. The protein exhibits the highest degree of homology to human keratinocyte growth factor with 45% identity and 82% similarity over a 206 amino acid stretch. It is also important that sequences that are conserved through the FGF family are found to be conserved in the protein of the present invention.

In addition, results from nested PCR of KGF-2 cDNA from libraries showed that there were potential alternative spliced forms of KGF-2. Specifically, using primers flanking the N-terminus of the open reading frame of KGF-2, PCR products of 0.2 kb and 0.4 kb were obtained from various cDNA libraries. A 0.2 kb size was the expected product for KGF-2 while the 0.4 kb size may result from an alternatively spliced form of KGF-2. The 0.4 kb product was observed in libraries from stomach cancer, adult testis, duodenum and pancreas.

The polynucleotide of the present invention may be in the form of RNA or in the form of DNA, which DNA includes cDNA, genomic DNA, and synthetic DNA. The DNA may be doublestranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the predicted mature polypeptide of FIG. 1 (SEQ ID NO:2) or for the predicted mature polypeptide encoded by the deposited cDNA may include: only the coding sequence for the mature polypeptide; the coding sequence for the mature polypeptide and additional coding sequence such as a leader or secretary sequence or a proprotein sequence; the coding sequence for the mature polypeptide (and optionally additional coding sequence) and non-coding sequence, such as intron or non-coding sequence 5' and/or 3' of the coding sequence for the predicted mature polypeptide. In addition, a full length mRNA has been obtained which contains 5' and 3' untranslated regions of the gene (FIG. 3 (SEQ ID NO:23)).

As one of ordinary skill would appreciate, due to the possibilities of sequencing errors discussed above, as well as the variability of cleavage sites for leaders in different known proteins, the actual KGF-2 polypeptide encoded by the deposited cDNA comprises about 208 amino acids, but may be anywhere in the range of 200–220 amino acids; and the actual leader sequence of this protein is about 35 or 36 amino acids, but may be anywhere in the range of about 30 to about 40 amino acids.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a nonnaturally occurring variant of the polynucleotide.

Thus, the present invention includes polynucleotides encoding the same predicted mature polypeptide as shown in FIG. 1 (SEQ ID NO:2) or the same predicted mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

The present invention includes polynucleotides encoding mimetic peptides of KGF-2 which can be used as therapeutic peptides. Mimetic KGF-2 peptides are short peptides which mimic the biological activity of the KGF-2 protein by binding to and activating the cognate receptors of KGF-2. Mimetic KGF-2 peptides can also bind to and inhibit the cognate receptors of KGF-2. KGF-2 receptors include, but are not limited to, FGFR2iiib and FGFR1iiib. Such mimetic peptides are obtained from methods such as, but not limited to, phage display or combinatorial chemistry. For example the method disclosed by Wrighton et al. Science 273:458–463 (1996) to generate mimetic KGF-2 peptides.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encode polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I. et al. *Cell* 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAS which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or cDNA to determine which members of the library the probe hybridizes to.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the full-length KGF-2 polypeptide having the complete amino acid sequence in FIG. 1 (SEQ ID NO:2), including the predicted leader sequence; (b) a nucleotide sequence encoding the mature KGF-2 polypeptide (full-length polypeptide with the leader removed) having the amino acid sequence at positions about 36 or 37 to 208 in FIG. 1 (SEQ ID NO:2); (c) a nucleotide sequence encoding the full-length KGF-2 polypeptide having the complete amino acid sequence including the leader encoded by the cDNA clone contained in ATCC Deposit No. 75977; (d) a nucleotide sequence encoding the mature KGF-2 polypeptide having the amino acid sequence encoded by the cDNA clone contained in ATCC Deposit No. 75977; (e) a nucleotide sequence encoding any of the KGF-2 analogs or deletion mutants described below; or (f) a nucleotide sequence complementary to any of the nucleotide sequences in (a), (b), (c),(d), or (e).

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the KGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO: 1, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identify are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/ aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/ alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The KGF-2 variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. KGF-2 polynucleotide variants can be produced for a variety of reasons, e.g., to optimize codon expression for a particular host (change codons in the human mRNA to those preferred by a bacterial host such as E. coli).

Alternatively, whether any particular nucleic acid molecule is at least 90%, 95%, 96%, 97%, 98% or 99% identical to, for instance, the nucleotide sequence shown in FIG. 1 (SEQ ID NO:1) or to the nucleotides sequence of the deposited cDNA clone may also be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 [SEQ ID NO:1] or to the nucleic acid sequence of the deposited cDNA, irrespective of whether they encode a polypeptide having KGF-2 activity. This is because even where a particular nucleic acid molecule does not encode a polypeptide having KGF-2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having KGF-2 activity include, inter alia, (1) isolating the KGF-2 gene or allelic variants thereof in a cDNA library; (2) in situ hybridization (e.g., "FISH") to metaphase chromosomal spreads to provide precise chromosomal location of the KGF-2 gene, as described in Verma et al., Human Chromosomes: A Manual of Basic Techniques, Pergamon Press, New York (1988); and Northern Blot analysis for detecting KGF-2 mRNA expression in specific tissues.

Preferred, however, are nucleic acid molecules having sequences at least 90%, 95%, 96%, 97%, 98% or 99% identical to the nucleic acid sequence shown in FIG. 1 [SEQ ID NO:1] or to the nucleic acid sequence of the deposited cDNA which do, in fact, encode a polypeptide having KGF-2 protein activity. By "a polypeptide having KGF-2 activity" is intended polypeptides exhibiting activity similar, but not necessarily identical, to an activity of the wild-type KGF-2 protein of the invention or an activity that is enhanced over that of the wild-type KGF-2 protein (either the full-length protein or, preferably, the mature protein), as measured in a particular biological assay.

Assays of KGF-2 activity are disclosed, for example, in the Examples below. These assays can be used to measure KGF-2 activity of partially purified or purified native or recombinant protein.

KGF-2 stimulates the proliferation of epidermal keratinocytes but not mesenchymal cells such as fibroblasts. Thus, "a polypeptide having KGF-2 protein activity" includes polypeptides that exhibit the KGF-2 activity in the keratinocyte proliferation assay set forth in the Examples below and will bind to the FGF receptor isoforms 1-iiib and 2-iiib. Although the degree of activity need not be identical to that of the KGF-2 protein, preferably, "a polypeptide having KGF-2 protein activity" will exhibit substantially similar activity as compared to the KGF-2 protein (i.e., the candidate polypeptide will exhibit greater activity or not more than about tenfold less and, preferably, not more than about twofold less activity relative to the reference KGF-2 protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 [SEQ ID NO:1] will encode a polypeptide "having KGF-2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having KGF-2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

The present invention further relates to polynucleotides which hybridize to the hereinabove-described sequences if there is at least 70%, preferably at least 90%, and more preferably at least 95% and still more preferably 96%, 97%, 98%, 99% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

An example of "stringent hybridization conditions" includes overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Of course, polynucleotides hybridizing to a larger portion of the reference polynucleotide (e.g., the deposited cDNA clone), for instance, a portion 50, 75, 100, 125, 150, 175, 200, 225, 250, 275, 300, 325, 350, 375, 400, 425, 450, 475, 500, 525, 550, 575, 600, 625, 650, 675, 700, 725, or 750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 1 [SEQ ID NO:1]. By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 [SEQ ID NO:1]). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, edited by Sambrook, J., Fritsch, E. F. and Maniatis, T., (1989), Cold Spring Harbor Laboratory Press, the entire disclosure of which is hereby incorporated herein by reference.

Since a KGF-2 cDNA clone has been deposited and its determined nucleotide sequence is provided in FIG. 1 [SEQ ID NO:1], generating polynucleotides which hybridize to a portion of the KGF-2 cDNA molecule would be routine to the skilled artisan. For example, restriction endonuclease cleavage or shearing by sonication of the KGF-2 cDNA clone could easily be used to generate DNA portions of various sizes which are polynucleotides that hybridize to a portion of the KGF-2 cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the KGF-2 cDNA shown in FIG. 1 [SEQ ID NO:1]), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The invention further provides isolated nucleic acid molecules comprising a polynucleotide encoding an epitope-bearing portion of the KGF-2 protein. In particular, isolated nucleic acid molecules are provided encoding polypeptides comprising the following amino acid residues in FIG. 1 (SEQ ID NO:2), which the present inventors have determined are antigenic regions of the KGF-2 protein:

1. Gly41-Asn71: GQDMVSPEATNSSSSSFSSPSSAGRH-VRSYN [SEQ ID NO:25];
2. Lys91-Ser109: KIEKNGKVSGTKKENCPYS [SEQ ID NO:26];
3. Asn135-Tyr164: NKKGKLYGSKEFNNDCKLK-ERIEENGYNTY [SEQ ID NO 27]; and
4. Asn181-Ala199: NGKGAPRRGQKTRRKNTSA [SEQ ID NO:28].

Also, there are two additonal shorter predicted antigenic areas, Gln74-Arg78 of FIG. 1 (SEQ ID NO:2) and Gln170-Gln175 of FIG. 1 (SEQ ID NO:2). Methods for generating such epitope-bearing portions of KGF-2 are described in detail below.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

KGF-2 Polypeptides and Fragments

The present invention further relates to a polypeptide which has the deduced amino acid sequence of FIG. 1 (SEQ ID NO:2) or which has the amino acid sequence encoded by the deposited cDNA, as well as fragments, analogs and derivatives of such polypeptide.

As one of ordinary skill would appreciate, due to the possibilities of sequencing errors discussed above, as well as the variability of cleavage sites for leaders in different known proteins, the actual KGF-2 polypeptide encoded by the deposited cDNA comprises about 208 amino acids, but may be anywhere in the range of 200–220 amino acids; and the actual leader sequence of this protein is about 35 or 36 amino acids, but may be anywhere in the range of about 30 to about 40 amino acids.

The terms "fragment," "derivative" and "analog" when referring to the polypeptide, of FIG. 1 (SEQ ID NO:2) or that encoded by the deposited cDNA, means a polypeptide which retains essentially the same biological function or activity as such polypeptide. Thus, an analog includes a protein which can be activated by cleavage of the protein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretary sequence or a sequence which is employed for purification of the mature polypeptide or a protein sequence. Such fragments, derivatives and analogs are deemed to be within the scope of those skilled in the art from the teachings herein.

The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the KGF-2 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the KGF-2 polypeptide which show substantial KGF-2 polypeptide activity or which include regions of KGF-2 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Lie; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

The present invention includes mimetic peptides of KGF-2 which can be used as therapeutic peptides. Mimetic KGF-2 peptides are short peptides which mimic the biological activity of the KGF-2 protein by binding to and activating the cognate receptors of KGF-2. Mimetic KGF-2 peptides can also bind to and inhibit the cognate receptors of KGF-2. KGF-2 receptors include, but are not limited to, FGFR2iiib and FGFR1iiib. Such mimetic peptides are obtained from methods such as, but not limited to, phage display or combinatorial chemistry. For example, the method disclosed by Wrighton et al. Science 273:458–463 (1996) can be used to generate mimetic KGF-2 peptides.

The polypeptides and polynucleotides of the present invention are preferably provided in an isolated form, and preferably are purified to homogeneity.

The polypeptides of the present invention are preferably in an isolated form. By "isolated polypeptide" is intended a polypeptide removed from its native environment. Thus, a polypeptide produced and/or contained within a recombinant host cell is considered isolated for purposes of the present invention. Also intended are polypeptides that have been purified, partially or substantially, from a recombinant host cell or a native source.

The polypeptides of the present invention include the polypeptide of SEQ ID NO:2 (in particular the mature polypeptide) as well as polypeptides which have at least 90%, 95%, 96%, 97%, 98%, 99% similarity (more preferably at least 90%, 95%, 96%, 97%, 98%, 99% identity) to the polypeptide of SEQ ID NO:2 and also include portions of such polypeptides with such portion of the polypeptide (such as the deletion mutants described below) generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2: 482–489, 1981) to find the best segment of similarity between two sequences.

By a polypeptide having an amino acid sequence at least, for example, 95% "identical" to a reference amino acid sequence of a KGF-2 polypeptide is intended that the amino acid sequence of the polypeptide is identical to the reference sequence except that the polypeptide sequence may include up to five amino acid alterations per each 100 amino acids of the reference amino acid of the KGF-2 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in SEQ ID NO:2 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

Alternatively, whether any particular polypeptide is at least 90%, 95%, 96%, 97%, 98% or 99% identical to, for instance, the amino acid sequence shown in FIG. 1 [SEQ ID NO:2] or to the amino acid sequence encoded by deposited cDNA clone may also be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

As described in detail below, the polypeptides of the present invention can be used to raise polyclonal and monoclonal antibodies, which are useful in diagnostic assays for detecting KGF-2 protein expression as described below or as agonists and antagonists capable of enhancing or inhibiting KGF-2 protein function. Further, such polypeptides can be used in the yeast two-hybrid system to "capture" KGF-2 protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30, 40, 50, 60, 70, 80, 90, 100, or 150 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate KGF-2-specific antibodies include the following:

1. Gly41-Asn71: GQDMVSPEATNSSSSSFSSPSSAGRHVRSYN [SEQ ID NO:25];
2. Lys91-Ser109: KIEKNGKVSGTKKENCPYS [SEQ ID NO:26];
3. Asn135-Tyr164: NKKGKLYGSKEFNNDCKLKERIEENGYNTY [SEQ ID NO: 27]; and
4. Asn181-Ala199: NGKGAPRRGQKTRRKNTSA [SEQ ID NO:28].

Also, there are two additional shorter predicted antigenic areas, Gln74-Arg78 of FIG. 1 (SEQ ID NO:2) and Gln170-Gln175 of FIG. 1 (SEQ ID NO:2).

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 µg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, KGF-2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric KGF-2 protein or protein fragment alone (Fountoulakis et al., *J Biochem* 270:3958–3964 (1995)).

In accordance with the present invention, novel variants of KGF-2 are also described. These can be produced by deleting or substituting one or more amino acids of KGF-2. Natural mutations are called allelic variations. Allelic variations can be silent (no change in the encoded polypeptide) or may have altered amino acid sequence.

In order to attempt to improve or alter the characteristics of native KGF-2, protein engineering may be employed. Recombinant DNA technology known to those skilled in the art can be used to create novel polypeptides. Muteins and deletions can show, e.g., enhanced activity or increased stability. In addition, they could be purified in higher yield and show better solubility at least under certain purification and storage conditions. Set forth below are examples of mutations that can be constructed.

Amino Terminal and Carboxy Terminal Deletions

Various members of the FGF family have been modified using recombinant DNA technology. Positively charged molecules have been substituted or deleted in both aFGF and bFGF that are important for heparin binding. The modified molecules resulted in reduced heparin binding activity. Accordingly, it is known that the amount of modified molecule sequestered by heparin in a patient would be reduced, increasing the potency as more FGF would reach the appropriate receptor. (EP 0 298 723).

Native KGF-2 is relatively unstable in the aqueous state and it undergoes chemical and physical degradation resulting in loss of biological activity during processing and storage. Native KGF-2 is also prone to aggregation in aqueous solution, at elevated temperatures and it becomes inactivated under acidic conditions.

In order to improve or alter one or more characteristics of native KGF-2, protein engineering may be employed. Ron et al., *J. Biol. Chem.*, 268(4): 2984–2988 (1993) reported modified KGF proteins that had heparin binding activity even if the 3, 8, or 27 amino terminal amino acid residues were missing. The deletion of 3 and 8 amino acids had full activity. More deletions of KGF have been described in PCT/IB95/0097 1. The deletion of carboxyterminal amino acids can enhance the activity of proteins. One example is interferon gamma that shows up to ten times higher activity by deleting ten amino acid residues from the carboxy terminus of the protein (Dobeli et al., *J. of Biotechnology* 7:199–216 (1988)). Thus, one aspect of the invention is to provide polypeptide analogs of KGF-2 and nucleotide sequences encoding such analogs that exhibit enhanced stability (e.g., when exposed to typical pH, thermal conditions or other storage conditions) relative to the native KGF-2 polypeptide.

Particularly preferred KGF-2 polypeptides are shown below (numbering starts with the first amino acid in the protein (Met) (FIG. 1 (SEQ ID NO:2))):

---

Thr (residue 36) -- Ser (residue 208)
Cys (37) -- Ser (208)
Gln (38) - Ser (208)
Ala (39) -- Ser (208)
Leu (40) -- Ser (208)
Gly (41) -- Ser (208)
Gln (42) -- Ser (208)
Asp (43) -- Ser (208)
Met (44) -- Ser (208)
Val (45) -- Ser (208)
Ser (46) -- Ser (208)
Pro (47) -- Ser (208)
Glu (48) -- Ser (208)
Ala (49) -- Ser (208)
Thr (50) -- Ser (208)
Asn (51) -- Ser (208)
Ser (52) -- Ser (208)
Ser (53) -- Ser (208)
Ser (54) -- Ser (208)
Ser (55) -- Ser (208)
Ser (56) -- Ser (208)
Phe (57) -- Ser (208)
Ser (59) -- Ser (208)
Ser (62) -- Ser (208)
Ala (63) -- Ser (208)
Gly (64) -- Ser (208)
Arg (65) -- Ser (208)
Val (67) -- Ser (208)
Ser (69) -- Ser (208)
Val (77) -- Ser (208)
Arg (80) -- Ser (208)
Met (1), Thr (36), or Cys (37) -- His (207)
Met (1), Thr (36), or Cys (37) -- Val (206)
Met (1), Thr (36), or Cys (37) -- Val (205)
Met (1), Thr (36), or Cys (37) -- Met (204)
Met (1), Thr (36), or Cys (37) -- Pro (203)
Met (1), Thr (36), or Cys (37) -- Leu (202)
Met (1), Thr (36), or Cys (37) -- Phe (201)
Met (1), Thr (36), or Cys (37) -- His (200)
Met (1), Thr (36), or Cys (37) -- Ala (199)
Met (1), Thr (36), or Cys (37) -- Ser (198)
Met (1), Thr (36), or Cys (37) -- Thr (197)
Met (1), Thr (36), or Cys (37) -- Asn (196)
Met (1), Thr (36), or Cys (37) -- Lys (195)
Met (1), Thr (36), or Cys (37) -- Arg (194)
Met (1), Thr (36), or Cys (37) -- Arg (193)
Met (1), Thr (36), or Cys (37) -- Thr (192)
Met (1), Thr (36), or Cys (37) -- Lys (191)
Met (1), Thr (36), or Cys (37) -- Arg (188)
Met (1), Thr (36), or Cys (37) -- Arg (187)
Met (1), Thr (36), or Cys (37) -- Lys (183)

---

Preferred embodiments include the N-terminal deletions Ala (63) - Ser (208) (KGF-2Δ28) (SEQ ID NO:68) and Ser (69) - Ser (208) (KGF-2Δ33) (SEQ ID NO:96). Other preferred N-terminal and C-terminal deletion mutants are described in Examples 13 and 16(c) of the specification and include: Ala (39) - Ser (208) (SEQ ID NO:116); Pro (47) - Ser (208) of FIG. 1 (SEQ ID NO:2); Val (77) - Ser (208) (SEQ ID NO:70); Glu (93) - Ser (208) (SEQ ID NO:72); Glu (104) - Ser (208) (SEQ ID NO:74); Val (123) - Ser (208) (SEQ ID NO:76); and Gly (138) - Ser (208) (SEQ ID NO:78). Other preferred C-terminal deletion mutants include: Met (1), Thr (36), or Cys (37) - Lys (153) of FIG. 1 (SEQ ID NO:2).

Also included by the present invention are deletion mutants having amino acids deleted from both the N-terminus and the C-terminus. Such mutants include all combinations of the N-terminal deletion mutants and C-terminal deletion mutants described above, e.g., Ala (39) - His (200) of FIG. 1 (SEQ ID NO:2), Met (44) - Arg (193) of FIG. 1 (SEQ ID NO:2), Ala (63) - Lys (153) of FIG. 1 (SEQ ID NO:2), Ser (69) - Lys (153) of FIG. 1 (SEQ ID NO:2), etc. etc. etc . . . Those combinations can be made using recombinant techniques known to those skilled in the art.

Thus, in one aspect, N-terminal deletion mutants are provided by the present invention. Such mutants include those comprising the amino acid sequence shown in FIG. 1 (SEQ ID NO:2) except for a deletion of at least the first 38 N-terminal amino acid residues (i.e., a deletion of at least Met (1) - Gln (38)) but not more than the first 147 N-terminal amino acid residues of FIG. 1 (SEQ ID NO:2). Alternatively, the deletion will include at least the first 38 N-terminal amino acid residues (i.e., a deletion of at least Met (1) - Gln (38)) but not more than the first 137 N-terminal amino acid residues of FIG. 1 (SEQ ID NO:2). Alternatively, the deletion will include at least the first 46 N-terminal amino acid residues but not more than the first 137 N-terminal amino acid residues of FIG. 1 (SEQ ID NO:2). Alternatively, the deletion will include at least the first 62 N-terminal amino acid residues but not more than the first 137 N-terminal amino acid residues of FIG. 1 (SEQ ID NO:2). Alternatively, the deletion will include at least the first 68 N-terminal amino acid residues but not more than the first 137 N-terminal amino acid residues of FIG. 1 (SEQ ID NO:2). Alternatively, the deletion will include at least the first 76 N-terminal amino acid residues but not more than the first 137 N-terminal amino acid residues of FIG. 1 (SEQ ID NO:2). Alternatively, the deletion will include at least the first 92 N-terminal amino acid residues but not more than the first 137 N-terminal amino acid residues of FIG. 1 (SEQ ID NO:2). Alternatively, the deletion will include at least the first 103 N-terminal amino acid residues but not more than the first 137 N-terminal amino acid residues of FIG. 1 (SEQ ID NO:2). Alternatively, the deletion will include at least the first 122 N-terminal amino acid residues but not more than the first 137 N-terminal amino acid residues of FIG. 1 (SEQ ID NO:2).

In addition to the ranges of N-terminal deletion mutants described above, the present invention is also directed to all combinations of the above described ranges, e.g., deletions of at least the first 62 N-terminal amino acid residues but not more than the first 68 N-terminal amino acid residues of FIG. 1 (SEQ ID NO:2); deletions of at least the first 62 N-terminal amino acid residues but not more than the first 76 N-terminal amino acid residues of FIG. 1 (SEQ ID NO:2); deletions of at least the first 62 N-terminal amino acid residues but not more than the first 92 N-terminal amino acid residues of FIG. 1 (SEQ ID NO:2); deletions of at least the first 62 N-terminal amino acid residues but not more than the first 103 N-terminal amino acid residues of FIG. 1 (SEQ ID NO:2); deletions of at least the first 68 N-terminal amino acid residues but not more than the first 76 N-terminal amino acid residues of FIG. 1 (SEQ ID NO:2); deletions of at least the first 68 N-terminal amino acid residues but not more than the first 92 N-terminal amino acid residues of FIG. 1 (SEQ ID NO:2); deletions of at least the first 68 N-terminal amino acid residues but not more than the first 103 N-terminal amino acid residues of FIG. 1 (SEQ ID NO:2); deletions of at least the first 46 N-terminal amino acid residues but not more than the first 62 N-terminal amino acid residues of FIG. 1 (SEQ ID NO:2); deletions of at least the first 46 N-terminal amino acid residues but not more than the first 68 N-terminal amino acid residues of FIG. 1 (SEQ ID NO:2); deletions of at least the first 46 N-terminal amino acid residues but not more than the first 76 N-terminal amino acid residues of FIG. 1 (SEQ ID NO:2); etc. etc. etc . . .

In another aspect, C-terminal deletion mutants are provided by the present invention. Preferably, the N-terminal amino acid residue of said C-terminal deletion mutants is amino acid residue 1(Met), 36 (Thr), or 37 (Cys) of FIG. 1 (SEQ ID NO:2). Such mutants include those comprising the amino acid sequence shown in FIG. 1 (SEQ ID NO:2) except for a deletion of at least the last C-terminal amino acid residue (Ser (208)) but not more than the last 55 C-terminal amino acid residues (i.e., a deletion of amino acid residues Glu (154) - Ser (208)) of FIG. 1 (SEQ ID NO:2). Alternatively, the deletion will include at least the last C-terminal amino acid residue but not more than the last 65 C-terminal amino acid residues of FIG. 1 (SEQ ID NO:2). Alternatively, the deletion will include at least the last 10 C-terminal amino acid residues but not more than the last 55 C-terminal amino acid residues of FIG. 1 (SEQ ID NO:2). Alternatively, the deletion will include at least the last 20 C-terminal amino acid residues but not more than the last 55 C-terminal amino acid residues of FIG. 1 (SEQ ID NO:2). Alternatively, the deletion will include at least the last 30 C-terminal amino acid residues but not more than the last 55 C-terminal amino acid residues of FIG. 1 (SEQ ID NO:2). Alternatively, the deletion will include at least the last 40 C-terminal amino acid residues but not more than the last 55 C-terminal amino acid residues of FIG. 1 (SEQ ID NO:2). Alternatively, the deletion will include at least the last 50 C-terminal amino acid residues but not more than the last 55 C-terminal amino acid residues of FIG. 1 (SEQ ID NO:2).

In addition to the ranges of C-terminal deletion mutants described above, the present invention is also directed to all combinations of the above described ranges, e.g., deletions of at least the last C-terminal amino acid residue but not more than the last 10 C-terminal amino acid residues of FIG. 1 (SEQ ID NO:2); deletions of at least the last C-terminal amino acid residue but not more than the last 20 C-terminal amino acid residues of FIG. 1 (SEQ ID NO:2); deletions of at least the last C-terminal amino acid residue but not more than the last 30 C-terminal amino acid residues of FIG. 1 (SEQ ID NO:2); deletions of at least the last C-terminal amino acid residue but not more than the last 40 C-terminal amino acid residues of FIG. 1 (SEQ ID NO:2); deletions of at least the last 10 C-terminal amino acid residues but not more than the last 20 C-terminal amino acid residues of FIG. 1 (SEQ ID NO:2); deletions of at least the last 10 C-terminal amino acid residues but not more than the last 30 C-terminal amino acid residues of FIG. 1 (SEQ ID NO:2); deletions of at least the last 10 C-terminal amino acid residues but not more than the last 40 C-terminal amino acid residues of FIG. 1 (SEQ ID NO:2); deletions of at least the last 20 C-terminal amino acid residues but not more than the last 30 C-terminal amino acid residues of FIG. 1 (SEQ ID NO:2); etc. etc. etc. . .

In yet another aspect, also included by the present invention are deletion mutants having amino acids deleted from both the N-terminal and C-terminal residues. Such mutants include all combinations of the N-terminal deletion mutants and C-terminal deletion mutants described above. Such mutants include those comprising the amino acid sequence shown in FIG. 1 (SEQ ID NO:2) except for a deletion of at least the first 46 N-terminal amino acid residues but not more than the first 137 N-terminal amino acid residues of FIG. 1 (SEQ ID NO:2) and a deletion of at least the last C-terminal amino acid residue but not more than the last 55 C-terminal amino acid residues of FIG. 1 (SEQ ID NO:2). Alternatively, a deletion can include at least the first 62, 68, 76, 92, 103, or 122 N-terminal amino acids but not more than the first 137 N-terminal amino acid residues of FIG. 1 (SEQ ID NO:2) and a deletion of at least the last 10, 20, 30, 40, or 50 C-terminal amino acid residues but not more than the last 55 C-terminal amino acid residues of FIG. 1 (SEQ ID NO:2). Further included are all combinations of the above described ranges.

Substitution of Amino Acids

A further aspect of the present invention also includes the substitution of amino acids. Native mature KGF-2 contains 44 charged residues, 32 of which carry a positive charge. Depending on the location of such residues in the protein's three dimensional structure, substitution of one or more of these clustered residues with amino acids carrying a negative charge or a neutral charge may alter the electrostatic interactions of adjacent residues and may be useful to achieve increased stability and reduced aggregation of the protein. Aggregation of proteins cannot only result in a loss of activity but be problematic when preparing pharmaceutical formulations, because they can be immunogenic (Pinckard et al., *Clin. Exp. Immunol.* 2:331–340 (1967), Robbins et al., *Diabetes* 36: 838–845 (1987), Cleland et al., *Crit. Rev. Therapeutic Drug Carrier Systems* 10: 307–377 (1993)). Any modification should give consideration to minimizing charge repulsion in the tertiary structure of the protein molecule. Thus, of special interest are substitutions of charged amino acid with another charge and with neutral or negatively charged amino acids. The latter results in proteins with a reduced positive charge to improve the characteristics of KGF-2. Such improvements include increased stability and reduced aggregation of the analog as compared to the native KGF-2 protein.

The replacement of amino acids can also change the selectivity of binding to cell surface receptors. Ostade et al., *Nature* 361: 266–268 (1993), described certain TNF alpha mutations resulting in selective binding of TNF alpha to only one of the two known TNF receptors.

KGF-2 molecules may include one or more amino acid substitutions, deletions or additions, either from natural mutation or human manipulation. Examples of some preferred mutations are: Ala (49) Gln, Asn (51) Ala, Ser (54) Val, Ala (63) Pro, Gly (64) Glu, Val (67) Thr, Trp (79) Val, Arg (80) Lys, Lys (87) Arg, Tyr (88) Trp, Phe (89) Tyr, Lys (91) Arg, Ser (99) Lys, Lys (102) Gln, Lys 103(Glu), Glu (104) Met, Asn (105) Lys, Pro (107) Asn, Ser (109) Asn, Leu (111) Met, Thr (114) Arg, Glu(117) Ala, Val (120) Ile, Val (123) Ile, Ala (125) Gly, Ile (126) Val, Asn (127) Glu, Asn (127) Gln, Tyr (130) Phe, Met (134) Thr, Lys (136) Glu, Lys (137) Glu, Gly (142) Ala, Ser (143) Lys, Phe (146) Ser, Asn (148) Glu, Lys (151) Asn, Leu (152) Phe, Glu (154) Gly, Glu (154) Asp, Arg (155) Leu, Glu (157) Leu, Gly (160) His, Phe (167) Ala, Asn (168) Lys, Gln (170) Thr, Arg (174) Gly, Tyr (177) Phe, Gly (182) Gln, Ala (185) Val, Ala (185) Leu, Ala (185) Ile, Arg (187) Gln (190) Lys, Lys (195) Glu, Thr (197) Lys, Ser (198) Thr, Arg (194) Glu, Arg (194) Gln, Lys (191) Glu, Lys (191) Gln, Arg (188) Glu, Arg (188) Gln, Lys (183) Glu.

By the designation, for example, Ala (49) Gln is intended that the Ala at position 49 of FIG. 1 (SEQ ID NO:2) is replaced by Gln.

Changes are preferably of minor nature, such as conservative amino acid substitutions that do not significantly affect the folding or activity of the protein. Examples of conservative amino acid substitutions known to those skilled in the art are set forth below:

| | |
|---|---|
| Aromatic: | phenylalanine |
| | tryptophan |
| | tyrosine |
| Hydrophobic: | leucine |
| | isoleucine |
| | valine |
| Polar: | glutamine |
| | asparagine |
| Basic: | arginine |
| | lysine |
| | histidine |
| Acidic: | aspartic acid |
| | glutamic acid |
| Small: | alanine |
| | serine |
| | threonine |
| | methionine |
| | glycine |

Of course, the number of amino acid substitutions a skilled artisan would make depends on many factors, including those described above. Generally speaking, the number of substitutions for any given KGF-2 polypeptide will not be more than 50, 40, 30, 20, 10, 5, or 3, depending on the objective. For example, a number of substitutions that can be made in the C-terminus of KGF-2 to improve stability are described above and in Example 22.

Amino acids in KGF-2 that are essential for function can be identified by methods well known in the art, such as site-directed mutagenesis or alanine-scanning mutagenesis (Cunningham and Wells, *Science* 244 :1081–1085 (1989). The latter procedure introduces single alanine mutations at every residue in the molecule. The resulting mutant molecules are then tested for biological activity such as receptor binding or in vitro and in vivo proliferative activity. (See, e.g., Examples 10 and 11). Sites that are critical for ligand-receptor binding can also be determined by structural analysis such as crystallization, nuclear magnetic resonance or photoaffinity labeling. (See for example: Smith et al., *J. Mol. Biol.*, 224: 899–904(1992); and de Vos et al. *Science*, 255: 306–312(1992).)

Another aspect of the present invention substitutions of serine for cysteine at amino acid positions 37 and 106 and 150. An uneven number of cysteins means that at least one cysteine residue is available for intermolecular crosslinks or bonds that can cause the protein to adopt an undesirable tertiary structure. Novel KGF-2 proteins that have one or more cysteine replaced by serine or e.g. alanine are generally purified at a higher yield of soluble, correctly folded protein. Although not proven, it is believed that the cysteine residue at position 106 is important for function. This cysteine residue is highly conserved among all other FGF family members.

A further aspect of the present invention are fusions of KGF2 with other proteins or fragments thereof such as fusions or hybrids with other FGF proteins, e.g. KGF (FGF-7), bFGF, aFGF, FGF-5, FGF-6, etc. Such a hybrid has been reported for KGF (FGF-7). In the published PCT application no. 90/08771 a chimeric protein has been produced consisting of the first 40 amino acid residues of KGF and the C-terminal portion of aFGF. The chimera has been reported to target keratinocytes like KGF, but lacked susceptibility to heparin, a characteristic of aFGF but not KGF. Fusions with parts of the constant domain of immunoglobulins (IgG) show often an increased half-life time in vivo. This has been shown, e.g., for chimeric proteins consisting of the first two domains of the human CD4-polypeptide with various domains of the constant regions of the heavy or light chains of mammalian immunoglobulins (European Patent application, Publication No. 394 827, Traunecker et al., Nature 331, 84–86 (1988). Fusion proteins that have a disulfide-linked dimeric structure can also be more efficient in binding monomeric molecules alone (Fountoulakis et al., *J. of Biochemistry*, 270: 3958–3964, (1995)).

Antigenic/hydrophilic Parts of KGF-2

As demonstrated in FIGS. 4A–4E, there are 4 major highly hydrophilic regions in the KGF-2 protein. Amino acid residues Gly41-Asn 71, Lys91-Ser 109, Asn135-Tyr 164 and Asn 181-Ala 199 [SEQ ID NOS:25–28]. There are two additional shorter predicted antigenic areas, Gln 74-Arg 78 of FIG. 1 (SEQ ID NO:2) and Gln 170-Gln 175 of FIG. 1 (SEQ ID NO:2). Hydrophilic parts are known to be mainly at the outside (surface) of proteins and, therefore, available for antibodies recognizing these regions. Those regions are also likely to be involved in the binding of KGF-2 to its receptor(s). Synthetic peptides derived from these areas can interfere with the binding of KGF-2 to its receptor(s) and, therefore, block the function of the protein. Synthetic peptides from hydrophilic parts of the protein may also be agonistic, i.e. mimic the function of KGF-2.

Thus, the present invention is further directed to isolated polypeptides comprising a hydrophilic region of KGF-2 wherein said polypeptide is not more than 150 amino acids in length, preferably not more than 100, 75, or 50 amino acids in length, which comprise one or more of the above described KGF-2 hydrophilic regions.

Chemical Modifications

The KGF wild type and analogs may be further modified to contain additional chemical moieties not normally part of the protein. Those derivatized moieties may improve the solubility, the biological half life or absorption of the protein. The moieties may also reduce or eliminate any desirable side effects of the proteins and the like. an overview for those moieties can be found in REMINGTON'S PHARMACEUTICAL SCIENCES, 18th ed., Mack Publishing Co., Easton, Pa. (1990). Polyethylene glycol (PEG) is one such chemical moiety which has been used for the preparation of therapeutic proteins. The attachment of PEG to proteins has been shown to protect against proteolysis, Sada et al., *J. Fermentation Bioengineering* 71:137–139 (1991). Various methods are available for the attachment of certain PEG moieties. For review, see: Abuchowski et al., in Enzymes as Drugs. (Holcerberg and Roberts, eds.) pp.367–383 (1981). Many published patents describe derivatives of PEG and processes how to prepare them, e.g., Ono et al. U.S. Pat. No. 5,342,940; Nitecki et al. U.S. Pat. No. 5,089,261; Delgado et al. U.S. Pat. No. 5,349,052. Generally, PEG molecules are connected to the protein via a reactive group found on the protein. Amino groups, e.g. on lysines or the amino terminus of the protein are convenient for this attachment among others.

The entire disclosure of each document cited in this section on "Polypeptides and Peptides" is hereby incorporated herein by reference.

Vectors and Host Cells

The present invention also relates to vectors which include the isolated DNA molecules of the present invention, host cells which are genetically engineered with the recombinant vectors, and the production of KGF-2 polypeptides or fragments thereof by recombinant techniques.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the KGF-2 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequences) (promoter) to direct cDNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli,* Streptomyces, *Salmonella typhimurium;* fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

The present invention further includes novel expression vectors comprising operator and promoter elements operatively linked to nucleotide sequences encoding a protein of interest. One example of such a vector is pHE4-5 which is described in detail below.

Figure 8:
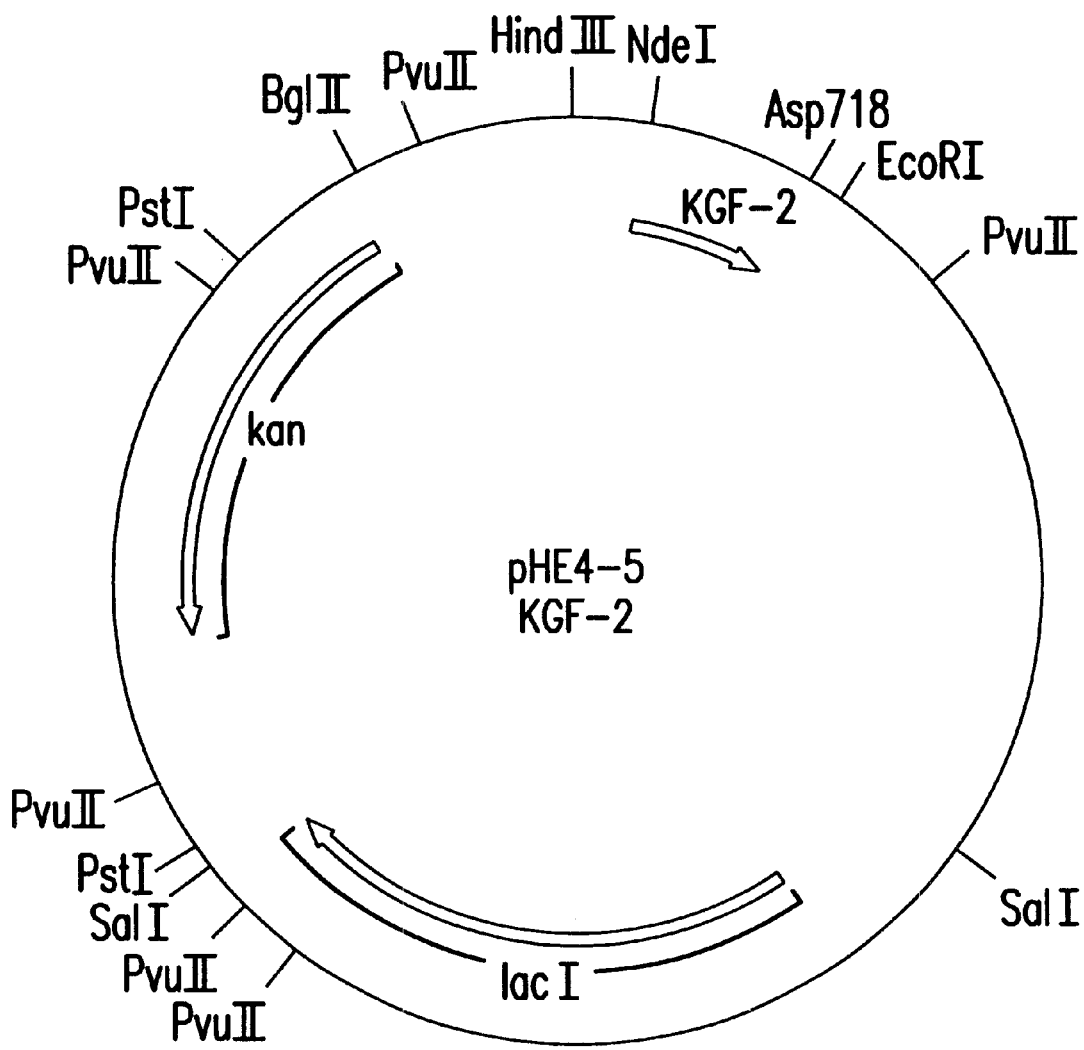
FIG. 8 shows a schematic representation of the pHE4-5 expression vector (SEQ ID NO:147) and the subcloned KGF-2 cDNA coding sequence. The locations of the kanamycin resistance marker gene, the KGF-2 coding sequence, the oriC sequence, and the lacIq coding sequence are indicated.

As shown in FIGS. 8 and 9, components of the pHE4-5 vector (SEQ ID NO:147) include: 1) a neomycinphosphotransferase gene as a selection marker, 2) an *E. coli* origin of replication, 3) a T5 phage promoter sequence, 4) two lac operator sequences, 5) a Shine-Delgamo sequence, 6) the lactose operon repressor gene (lacIq). The origin of replication (oriC) is derived from pUC19 (LTI, Gaithersburg, Md.). The promoter sequence and operator sequences were made synthetically. Synthetic production of nucleic acid sequences is well known in the art. Clontech 95/96 Catalog, pages 215–216, Clontech, 1020 East Meadow Circle, Palo Alto, Calif. 94303. A nucleotide sequence encoding a KGF-2 polypeptide is operatively linked to the promoter and operator by inserting the nucleotide sequence between the NdeI and Asp718 sites of the pHE4-5 vector.

As noted above, the pHE4-5 vector contains a lacIq gene. LacIq is an allele of the lacI gene which confers tight regulation of the lac operator. Amann, E. et al., *Gene* 69:301–315 (1988); Stark, M., *Gene* 51:255–267(1987). The lacIq gene encodes a repressor protein which binds to lac operator sequences and blocks transcription of downstream (i.e., 3') sequences. However, the lacIq gene product dissociates from the lac operator in the presence of either lactose or certain lactose analogs, e.g., isopropyl B-D-thiogalactopyranoside (IPTG). KGF-2 thus is not produced in appreciable quantities in uninduced host cells containing the pHE4-5 vector. Induction of these host cells by the addition of an agent such as IPTG, however, results in the expression of the KGF-2 coding sequence.

The promoter/operator sequences of the pHE4-5 vector (SEQ ID NO:148) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located down-stream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., Textbook of Biochemistry with Clinical Correlations, 4th Edition (1997), pages 802–807.

The pHE4 series of vectors contain all of the components of the pHE4-5 vector except for the KGF-2 coding sequence. Features of the pHE4 vectors include optimized synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4-5 vector (SEQ ID NO:147).

A cDNA encoding KGF-2 Δ33 inserted into the pHE4-5 expression vector was deposited at the ATCC on Jan. 9, 1998 as ATCC No. 209575.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L. et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual,* Second Edition, Cold Spring Harbor, N.Y. (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize receptors. For example, EP-A-O 464 533 (Canadian counterpart 2045869) discloses fusion proteins comprising various portions of constant region of immunoglobin molecules together with another human protein or part thereof. In many cases, the Fc part in fusion protein is thoroughly advantageous for use in therapy and diagnosis and thus results, for example, in improved pharmacokinetic properties (EP-A 0232 262). On the other hand, for some uses it would be desirable to be able to delete the Fc pat after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, shIL5-receptor has been fused with Fc portions for the purpose of high-throughput screening assays to identify antagonists of hIL-5. See, D. Bennett et al., *Journal of Molecular Recognition,* Vol. 8 52–58 (1995) and K. Johanson et al., *The Journal of Biological Chemistry,* Vol. 270, No. 16, pp 9459–9471 (1995).

Generally, recombinant expression vectors will include origins of replication and selectable markers permitting transformation of the host cell, e.g., the ampicillin resistance gene of *E. coli* and *S. cerevisiae* TRP1. gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA) These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The KGF-2 polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Therapeutic Applications of KGF-2

As used in the section below, "KGF-2" is intended to refer to the full-length and mature forms of KGF-2 described herein and to the KGF-2 analogs, derivatives and mutants described herein.

Increase Levels of Platelets

In one aspect, the invention is directed to increasing platelet level or number in blood for the purpose of alleviating thrombocytopenia. Determining the true cause of thrombocytopenia is a difficult and challenging clinical problem. Thrombocytopenia results from various causes, but ultimately occurs when platelets are destroyed, sequestered in the body, or not produced. The differential diagnosis of thrombocytopenia is extensive and complex, and there is a significant overlap among disorders (Doyle B. and Porter D. L., A.A.C.N. Clin. Issues Aug. 1997; 8(3): 469–480). Thrombocytopenia may be caused by a variety of mechanisms including, but not limited to, drug induced hypersensitivity, idiopathic thrombocytopenia pupura (ITP), posttransfusion purpura, neonatal thrombocytopenia, bone marrow deficiencies identified with metastatic tumors to the bone, aplastic anemia, myelofibrosis, acute and monocytic leukemia, microangiopathic hemolytic anemia which includes disseminated intravascular coagulation (DIC), thrombotic thrombocytopenic purpura (TTP), hemolytic-uremic syndrome, prosthetic valve hemolytic syndrome, cancer chemotherapy, Zieve's syndrome, sepsis, HELLP preeclamptic syndrome, megaloblastic anemia due to B21 and folic acid deficiency, infections such as peritonitis (without septicemia), congenital rubella syndrome, HIV-1 virus infections, Epstein-Barr infectious mononucleosis, rheumatoid-collagen diseases such as systemic lupus, hypertension of pregnancy associated with preeclampsia, thyrotoxicosis and uremia (*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995).

Accordingly, the present invention provides a process for administering KGF-2 polypeptides to an individual for alleviating thrombocytopenia. Suitable doses, formulations, and administration routes are described below.

Increase Levels of Fibrinogen, Albumin and Serum Proteins

Fibrinogen is a glycoprotein that is synthesized in the liver. Fibrinogen can give rise to fibrin split products (FDPs) in the following manner. Normally, thrombin catalyzes conversion of fibrinogen to fibrin by splitting two fibrinopeptide molecules, known as fibrinopeptide A and B, from the central portion of fibrinogen. This action exposes polymerization sites on the remaining portion of the fibrinogen molecule, which is now called fibrin monomer. Fibrin monomers spontaneously aggregate together in side-to-side and end-to-end configurations to form a fibrin gel. Thrombin also activates factor XIII, which helps introduce cross-linking isopeptide bonds between the fibrin monomers to form stabilized insoluble fibrin polymer. Fibrin polymer forms the scaffolding for blood clots. Fibrinolysins are naturally occurring or acquired enzymes that may attack either fibrinogen or fibrin or both, splitting off FDPs, which, in turn, are broken into smaller pieces. These split products may form a complex with fibrin monomers and interfere with polymerization. Fibrinogen degradation products can be produced by action of primary fibrinolysin on fibrinogen and also by action of plasmin on fibrinogen and fibrin monomers or fibrin clots formed in a variety of conditions, normal and abnormal. Plasmin attacks intravascular blood clots formed as part of normal hemostasis (e.g., trauma or surgery) as well as blood clots that produce disease (e.g., thrombosis or embolization).

Decreased plasma fibrinogen levels may occur from decreased liver production resulting from acute hepatitis or cirrhosis, from the action of fibrinolysins which are enzymes that destroy fibrin and may also attack fibrinogen, and from conversion of fibrinogen to fibrin that is too extensive to permit adequate replacement of the fibrinogen. Decreased levels of plasma fibrinogen may be found in conditions of abnormal hepatic synthesis such as that associated with acute hepatitis or cirrhosis. The major etiology of hypofibrinogenemia other than severe liver disease is fibrinogen depletion caused by disseminated intravascular coagulation (DIC)(*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995).

Accordingly, in a further aspect, there is provided a process for utilizing KGF-2 polypeptides to enhance or increase the fibrinogen level or number in plasma. Preferably, a KGF-2 polypeptide is administered to an individual for the purpose of alleviating hypofibrinogenemia. Suitable doses, formulations, and administration routes are described below.

Albumin is a serum protein produced by the liver which is most active in maintaining the serum oncotic pressure. Serum albumin also acts as a transport protein for some drugs and a few other substances. Hypoalbuminemia can be caused by a variety of mechanisms including, but not limited to, hemorrhages, burns, exudates, rheumatic diseases, granulomatous processes, most bacterial infections, viral infections accompanied by tissue destruction, tissue necrosis, vasculitis, ulcerative bowel disease, serositis, subacute bacterial endocarditis, parasitic infestations, acute and chronic liver disease, amyloidosis, malnutrition, malignancy, congestive heart failure, constrictive pericarditis, cardiac valvular disease, nephrotic syndrome, trauma and crush injuries, gastrointestinal and lymphatic fistulae, and protein-losing gastroenteropathies (*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995).

Accordingly, in a further aspect, there is provided a process for utilizing KGF-2 polypeptides to enhance or increase the level or number of serum albumin. Preferably, a KGF-2 polypeptide is administered to an individual for the purpose of alleviating hypoalbuminemia. Suitable doses, formulations, and administration routes are described below.

Serum globulin refers to a heterologous group of proteins such as glycoproteins, lipoproteins, and immunoglobulins. The globulins form the main transport system for various substances as well as constituting the antibody system, the clotting proteins, complement, and certain special duty substances such as the "acute reaction" proteins. Hypoglobulinemia may result from a number of conditions or afflictions including, but not limited to, alpha-1 antityrpsin deficiencies, severe liver disease, estrogen therapy, megaloblastic anemia, hypogammaglobulinemia and aggammaglobuinemia (*Clinical guide to laboratory tests.* (3rd ed). Philadelphia, W.B. Saunders Company, 1995; *Clinical Laboratory Medicine. Clinical application oflaboratory data.* (6th ed.) St. Louis, Mosby, 1995).

Accordingly, in a further aspect, there is provided a process for utilizing KGF-2 polypeptides to enhance or increase the level or number of serum globulin. Preferably, a KGF-2 polypeptide is administered to an individual for the purpose of alleviating hypoglobulinemia. Suitable doses, formulations, and administration routes are described below.

KGF-2 can also be used to increase the levels of total serum protein in individuals with protein loss and/or decreased protein synthesis. Human serum contains many proteins including albumin, globulins, prothrombin, fibrinogen, and other proteins synthesized exclusively by hepatocytes. Extensive liver injury may lead to decreased levels of these proteins (*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995). Serum albumin levels are influenced by a variety of nonhepatic factors, most notably nutritional status, hormonal factors, and plasma oncotic pressure. Nephrotic syndrome or protein-losing enteropathy may lead to depressed serum albumin levels. Low serum albumin levels are also caused by familial idiopathic dysproteinemia, a rare genetic condition in which the albumin level is greatly decreased while all the globulin fractions are elevated (*Clinical guide to laboratory tests.* (3rd ed) Philadelphia, W.B. Saunders Company, 1995; *Clinical Laboratory Medicine. Clinical application of laboratory data.* (6th ed.) St. Louis, Mosby, 1995). Serum globulins include alpha and beta globulins as well as serum immunoglobulins. Alpha-1 globulins include alpha-1 antitrypsin, alpha-1 acid glycoprotein, alpha-1-fetoprotein, and certain carrier proteins such as cortisol-binding protein (transcortin) and thyroxine-binding globulin. Alpha-1 globulin is absent or nearly so in alpha-1 antitrypsin deficiency (*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995). Alpha-2 globulins include haptoglobulin, alpha-2 macroglobulin, and ceruloplasmin. Haptoglobulin levels are decreased in severe liver disease, in patients on estrogen therapy, in megaloblastic anemia, and also in conditions in which free hemoglobin appears in the blood (RBC hemolysis) (*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995). Ceruloplasmin levels are decreased in Wilson's disease, malnutrition, nephrotic syndrome, and protein losing enteropathy. Beta globulins include transferrin, beta-lipoprotein, and several components of complement. Transferrin is frequently decreased in protein malnutrition. Gamma globulins include immunoglobulins IgG, IgA, IgM, IgD, and IgE. The gammaglobulins are decreased in hyporgammaglobulinemia and agammaglobulinemia (*Clinical guide to laboratory tests.* (3rd ed). Philadelphia, W.B. Saunders Company, 1995; *Clinical Laboratory Medicine. Clinical application of laboratory data.* (6th ed.) St. Louis, Mosby, 1995). Finally, serum contains a number of enzymes which have been used to distinguish and assess hepatocellular injury and biliary tract dysfunction or obstruction. For example, aspartate aminotransferase (AST) and alanine aminotransferase (ALT) catalyze the transfer of the γ-amino groups of aspartate and alanine, respectively, to the γ-keto groups of ketoglutarate, leading to the formation of oxaloacetic acid and pyruvic acid. Uremia may lead to spuriously low aminotransferase levels (Harrison's Principles of Internal Medicine 11th edition Eugene Braunwald et. al., Editors (1987)).

Thus, total protein loss can be caused by a variety of mechanisms including, but not limited to, protein-losing gastroenteropathies, acute burns, and nephrotic syndrome. Decreased protein synthesis can be caused by a variety of mechanisms including, but not limited to, chronic liver disease, malabsorption syndrome, malnutrition, and agammaglobulinemia. Accordingly, in a further aspect, there is provided a process for utilizing KGF-2 polypeptides to enhance or increase the level or number of total serum protein. Preferably, a KGF-2 polypeptide is administered to an individual for the purpose of alleviating diseases or conditions associated with protein loss. Suitable doses, formulations, and administration routes are described below.

Treatment of Cystitis

Hemorrhagic cystitis is a syndrome associated with certain disease states as well as exposure to drugs, viruses, and toxins. It manifests as diffuse bleeding of the endothelial lining of the bladder. Known treatments include intravesical, systemic, and nonpharmacologic therapies (West, N. J., Pharmacotherapy 17:696–706 (1997). Some cytotoxic agents used clinically have side effects resulting in the inhibition of the proliferation of the normal epithelial in the bladder, leading to potentially life-threatening ulceration and breakdown in the epithelial lining. For example, cyclophosphamide is a cytotoxic agent which is biotransformed principally in the liver to active alkylating metabolites by a mixed function microsomal oxidase system. These metabolites interfere with the growth of susceptible rapidly proliferating malignant cells. The mechanism of action is believed to involve cross-linking of tumor cell DNA (Physicians' Desk reference, 1997).

Cyclophosphamide is one example of a cytotoxic agent which causes hemorrhagic cystitis in some patients, a complication which can be severe and in some cases fatal. Fibrosis of the urinary bladder may also develop with or without cystitis. This injury is thought to be caused by cyclophosphamide metabolites excreted in the urine. Hematuria caused by cyclophosphamide usually is present for several days, but may persist. In severe cases medical or surgical treatment is required. Instances of severe hemorrhagic cystitis result in discontinued cyclophosphamide therapy. In addition, urinary bladder malignancies generally occur within two years of cyclophosphamide treatment and occurs in patients who previously had hemorrhagic cystitis (CYTOXAN (cyclophosphamide) package insert). Cyclophosphamide has toxic effects on the prostate and male reproductive systems. Cyclophosphamide treatment can result in the development of sterility, and result in some degree of testicular atrophy.

Figure 23:
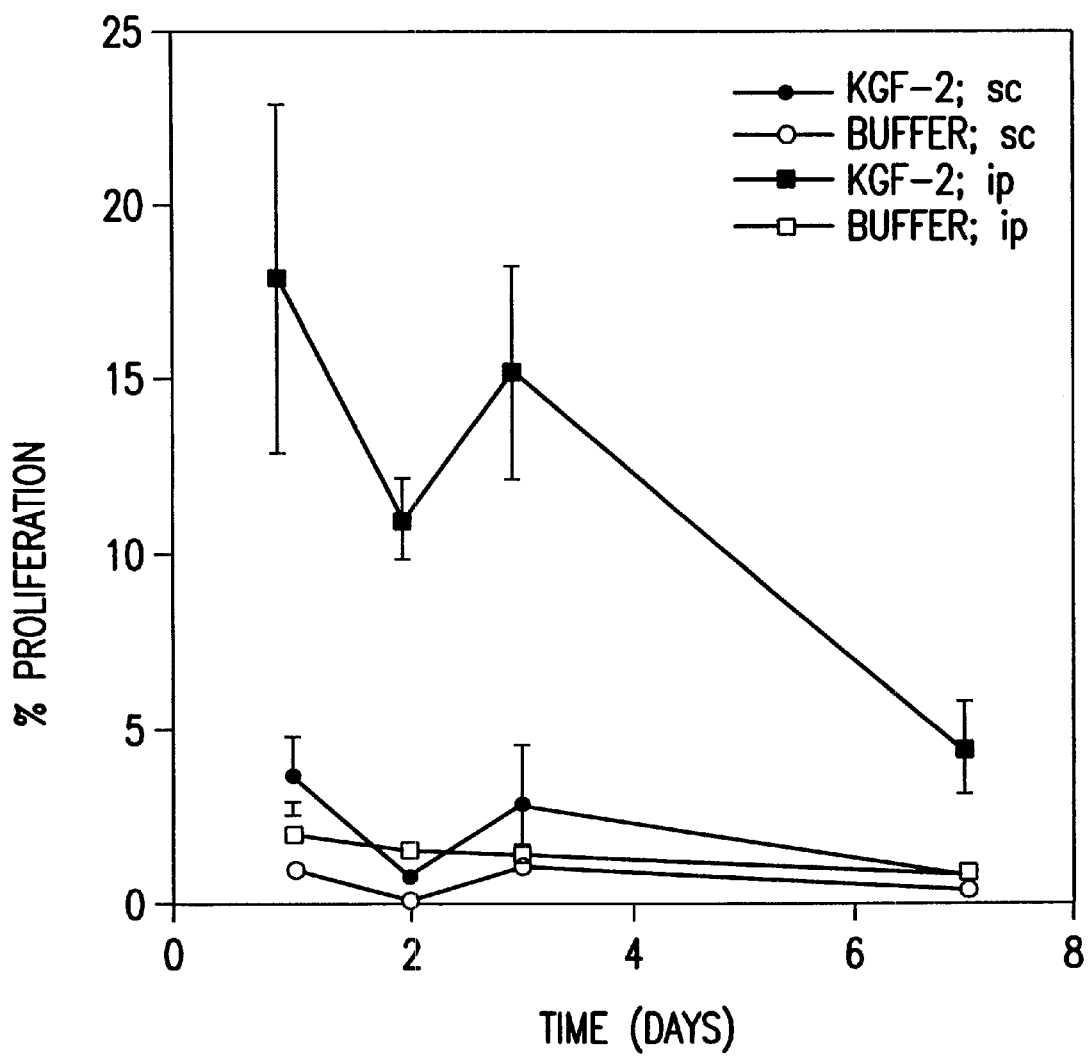
FIG. 23 shows the proliferation of bladder epithelium following ip or sc administration of KGF-2 Δ33.
Figure 24:
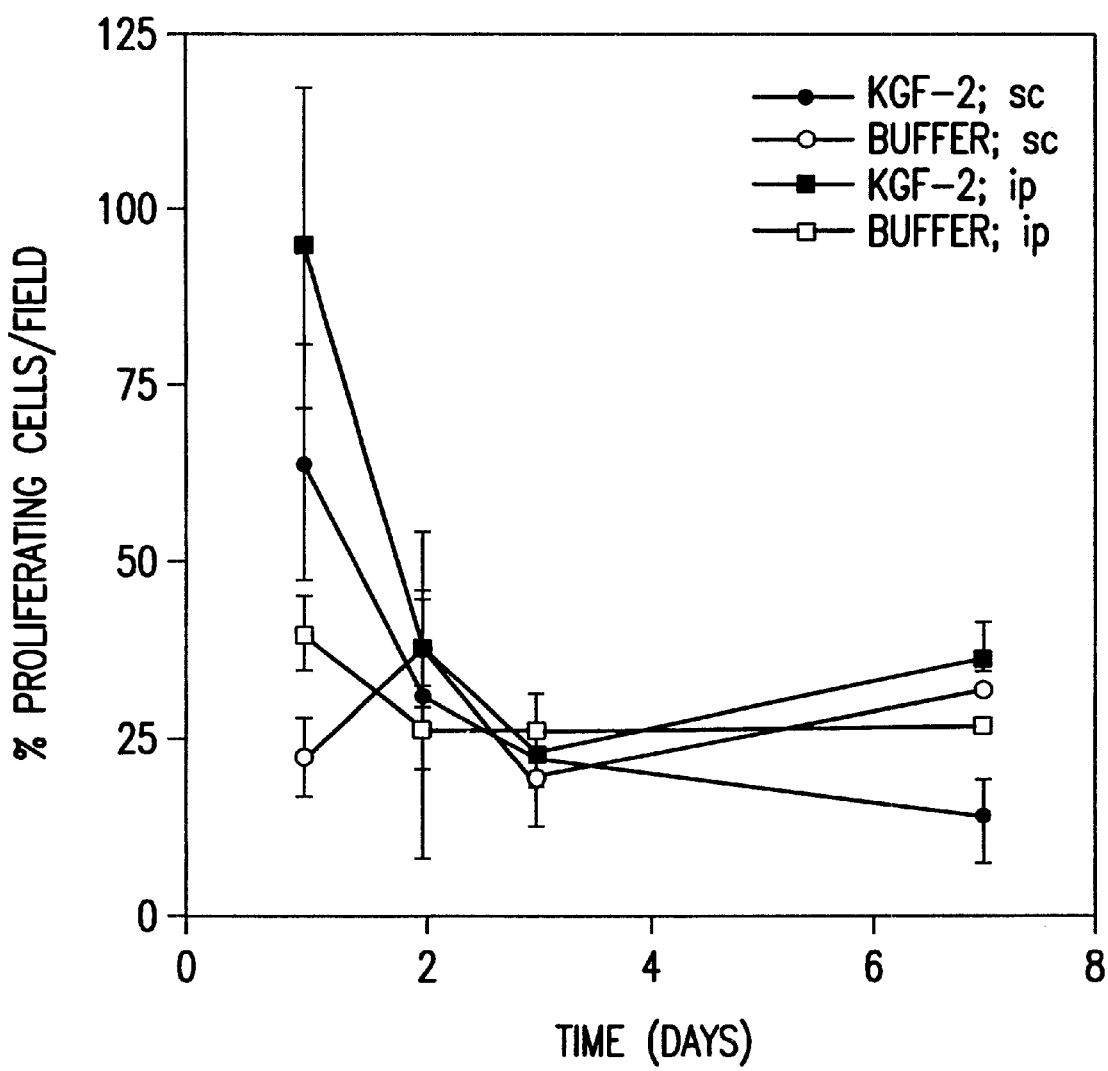
FIG. 24 shows the proliferation of prostatic epithelial cells after systemic administration of KGF-2 Δ33.

As shown in FIGS. 23 and 24, systemic administration of KGF-2 to an individual stimulates proliferation of bladder and prostatic epithelial cells. Thus, in one aspect, the present invention provides a method of stimulating proliferation of bladder epithelium and prostatic epithelial cells by administering to an individual an effective amount of a KGF-2 polypeptide. More importantly, as FIGS. 25 and 26 demonstrate, KGF-2 can be used to reduce damage caused by cytotoxic agents having side effects resulting in the inhibition of bladder and prostate epithelial cell proliferation. To reduce such damage, KGF-2 can be administered either before, after, or during treatment with or exposure to the cytotoxic agent. Accordingly, in a further aspect, there is provided a method of reducing damage caused by an inhibition of the normal proliferation of epithelial cells of the bladder or prostate by administering to an individual an effective amount of KGF-2. As indicated, inhibitors of normal proliferation of bladder or prostate epithelium include radiation therapy (causing acute or chronic radiation damage) and cytoxic agents such as chemotherapeutic or antineoplastic drugs including, but not limited to, cyclophosphamide, busulfan, and ifosfamide. In a further aspect, KGF-2 is administered to reduce or prevent fibrosis and ulceration of the urinary bladder. Preferably, KGF-2 is administered to reduce or prevent hemorrhagic cystitis. Suitable doses, formulations, and administration routes are described below.

Stimulate the Proliferation of Nasal Mucosa

Sinus infections usually occur in the setting of upper respiratory tract infections, allergies, or anatomic defects (within the sinuses or nasal septum) and may lead to symptoms of headache, facial pain, fever, and purulent rhinorrhea. (Evans K L. *Drugs* 56(1): 59–71 (1998)). The symptoms of nasal allergy and chronic ethmoid sinusitis overlap and treatment failure in allergic patients may suggest possible chronic sinusitis. Chronic ethmoidal sinusitis may be the leading cause of rhinorrhea and nasal obstruction in patients with perennial allergies. (Bertrand et al., *Acta Otorhinolaryngol Belg* 51(4):227–237 (1997)). Chronic sinusitis is identified when symptoms of nasal obstruction, rhinorrhea, post nasal drip, intermittent facial pain (Evans K L. *Drugs* 56(1): 59–71 (1998)) and anosmia (Jones et al., *Int. J. Pediatr. Otorhinolaryngol.* 28(1):25–32 (1993)) persist for 3 months or more. In addition to poor mucociliary transport and obstructed ostia, chronic sinusitis is also associated with mucosal edema, mucous hypersecretion, and persistent or recurrent infection.

Acute sinusitis tends to occur in patients with a history of rhinitis, which may be allergic or non-allergic in origin. Patients with anatomic variants (Evans K L. *Drugs* 56(1): 59–71 (1998)) and cystic fibrosis (Brihaye et al., *Acta Otorhinolaryngol Belg* 51(4):323–337 (1997); Ramsey et al., *J. Allergy Clin. Immunol.* 90(3Pt2):547–552 (1992); Davidson et al., *Laryngoscope* 105(4Pt1):354–358 (1995); Jones et al., *Int. J. Pediatr. Otorhinolaryngol.* 28(1):25–32 (1993)) are also at high risk for developing sinusitis. Acute inflammation and infection are associated with reduced mucociliary transport of secretions and obstruction of the ostia, which drain the sinuses. Initial medical treatment for acute sinusitis begins with analgesia to control pain; topical and systemic treatment of rhinitis, which may include antihistamines, mast cell stabilizers, and steroids; measures to clear secretions including steam inhalation and saline nasal douches; and when infection can be documented, antibiotics. (Evans K L. *Drugs* 56(1): 59–71 (1998)).

A general understanding of the pathophysiology of sinusitis is now available. In particular, it is known that occlusion of the sinus ostia starts the cycle of events, which lead to and sustain sinusitis. (Reilly J. S. *Otolaryngology Head and Neck Surgery* 103(5):856–862(1990)). The goals of treatment for both acute and chronic sinusitis are to control the rhinitis, improve ventilation to the sinuses, and to improve the function of the sinuses for clearance of secretions. (Evans K L. *Drugs* 56(1): 59–71 (1998)). Nasal sinus surgery is performed only after there is evidence of persistent chronic sinusitis uncontrolled by medical treatment.

Surgical treatment is only considered when medical measures fail to control the sinusitis. The goals of treatment are identical: to improve ventilation and to facilitate or restore sinus drainage. An additional goal is that surgical treatment may sometimes improve the penetration of topical drugs into the sinus. Up to 250,000 procedures are performed each year in the United States. The majority of the procedures performed use endoscopic methods (Stammberger H. *Otolaryngology Head and Neck Surgery* 94(2): 143–147 (1986); Stammberger H. *Otolaryngology Head and Neck Surgery* 94(2): 147–156 (1986)) with CT or x-ray tomographic assessment to identify specific lesions. The extent of surgery is kept to a minimum and is intended to remove only the primary anatomic cause that perpetuates the chronic sinusitis.

In the course of performing sinus surgery, the mucosal surface is stripped away or damaged. In cases where the surgery has been extensive, the underlying bone within the sinus may be exposed for periods of up to 6 months before the mucosa is fully reconstituted and recovery of ciliary density may require up to 2 years to achieve. Although not proven, delayed re-epithelialization of the nasal sinuses following surgery is believed to be associated with increased risk of infection, scarring (subepithelial fibrosis) leading to recurrent disease, and cyst formation. After 2 years of follow up approximately 2–5% of patients will have recurrent disease and up to 15% may require surgical revision. (Evans K L. *Drugs* 56(1): 59–71 (1998)) Other complications, which might be favorably impacted by accelerated re-epithelialization, include infectious complications (Evans K L. *Drugs* 56(1): 59–71 (1998)), failure to regain olfaction (Klossek et al., *Otolaryngology Head and Neck Surgery* 117(4):355–361 (1997)), recurrence of polyps (Klossek et al., *Otolaryngology Head and Neck Surgery* 117(4):355–361 (1997)) and requirement for additional post operative medical treatment (Smith et al., *Otolaryngology Head and Neck Surgery* 108(6):688–696 (1993)). Minor complications have been reported to occur in up to 8% of cases and approximately 40% of patients continued to require medical treatment for nasal congestion and discomfiture even following surgery. (Smith et al., *Otolaryngology Head and Neck Surgery* 108(6):688–696 (1993)).

Following endoscopic nasal surgery patients return at weekly intervals for repeat endoscopy and debridement. At each visit local anesthesia is applied, and the sinus cavity is cleaned, including removal of adhesions (which occur in 10–15% of cases) and mucus crusts. The duration of post op care is proportional to the extent of the surgery and the loss of the sinus epithelium. For simple cases 6 to 8 weeks of care may be needed. For complex or more extensive cases, 12 to 18 weeks may be required. Accelerated healing of the sinus epithelium would reduce the duration of postoperative discomfiture to the patient and reduce the cost of care.

Administration of KGF-2 to an individual stimulates proliferation of the sinus epithelia and nasal mucosa. KGF-2 administration also results in goblet cell hyperplasia in the respiratory epithelium of the nasal air passage way. Thus, in one aspect, the present invention provides a method of stimulating the healing of mucosa of the sinus following damage by surgery or other pathological conditions by adminstration of KGF-2. Further, the present invention, KGF-2 is administered to stimulate the healing wounds located in the nasal and sinus mucosa. The present invention also provides for KGF-2 administration to improve function of the sinuses by increasing and/or protecting ciliary density and mucosal integrity. Another aspect of the invention is to provide a method decreasing sinus infection, scarring, polyps, cyst formation and recurrance as well as increasing olfaction by KGF-2 adminstration. Suitable doses, formulations, and administration routes are described below.

Increase Proliferation of Salivary and Lacrimal Glands

Saliva is secreted from three major salivary glands: the parotid, sublingual and submandibular (or submaxillary) salivary glands. Tears are secreted from lacrimal glands. Loss of the ability to produce adequate amounts of saliva and tears is a major clinical problem affecting millions of people and there are few therapeutic options for these sufferers. Patients with xerostomia, or dry mouth, do not produce adequate amounts of saliva, have difficulty swallowing, have painful cracks in their mouths, and experience a decrease in their ability to taste. This condition may be caused by Sjogren's syndrome, as a secondary event to radiation used with patients with head and neck tumors, and to drugs. Patients with Sjogren's syndrome sometimes have keratoconjunctivitis sicca or dry eye. This condition may be caused by damage to the lacrimal gland due to Sjogren's syndrome, sarcoidosis, aging, HIV infection, burns, etc. (Lemp, M. A, *Adv. Exp. Med. Biol.* 438:791–803 (1998)). Patients experience irritation, blurring of vision, burning, pain, and increased risk of infections. Millions of patients suffer with Sjogren's syndrome and therapy is sub-optimal. Stress is placed on reducing the risk of dental caries and the use of moistening agents. If there is remaining salivary tissue patients are treated with pilocarpine, which induces saliva production (Guchelaar, H. J. and Meerwaldt, V. A., *Support Care Cancer* 5:281–288 (1997); Garg, A. C. and Malo, M., *J. Am. Dent. Assoc.* 128:1128–1133 (1997); Wiseman, L. R. and Faulds, D., *Drugs* 49:143–155 (1995); and LeVeque, F. G., et al., *J. Clin. Oncol.* 11:1124–1131 (1993)). A recent study has shown that treatment with IFN-α can reduce lymphocytic infiltration in the salivary glands of patients with Sjogren's syndrome and improve function (Shiozawa, S., et al., *J. Interferon Cytokine Res.* 18:255–262 (1998)). However, such therapy, if approved, would impact only those patients whose salivary gland dysfunction is due to this autoimmune disease.

As is the case with xerostomia, patients with keratoconjunctivitis sicca have few therapeutic options. At this time there are approximately 10 million patients in the US which require artificial tear preparations (Lemp, M. A, *Adv. Exp. Med. Biol.* 438:791–803 (1998)). There are no treatments available at this time to stimulate replacement of the cells in the salivary and lacrimal gland cells.

Two classifications of patients with "dry eye" are commonly used (Pflugfelder, S. C, *Adv. Dent. Res.* 10(1): 9–12 (1996)). One class being aqueous adequate dry eye. This clinical disorder is associated with meibomian gland dysfunction resulting in a deficiency in the superficial lipid layer of the tear film. Drop out of meibomian glands can be visualized by transillumination biomicroscopy of the eyelids. The second class being aqueous deficient dry eye. This clinical disorder may be immunologic (Sjogren's syndrome) or non-immunologic (non-Sjogren's syndrome). Aqueous tear deficiencies lead to ocular surface disease, termed keratoconjunctivitis sicca, which results from either pathology in the lacrimal gland or in mucin-producing epithelial cells. Lower goblet cell densities have been reported in the conjunctival epithelium in patients with dry eye syndrome (Ralph, R. A., *Investigative Ophthalmology* 14 (4): 299–302, (1975)).

Although dry eye syndromes have not been associated with deficiencies in specific growth factors, the lacrimal gland produces epidermal growth factor, which may play a role in ocular surface wound healing (Wilson, S. E., *American Journal of Ophthalmology* 111 (6): 763–765 (1991)). The presence of endogenous growth factors in lacrimal secretions provides the rationale for the use of topically applied keratinocyte growth factor to support the growth and differentiation of the conjunctival epithelium. In addition, atrophy or losses of secretory acini in the lacrimal gland contribute to defective tear production.

KGF-2 effects on the proliferative rate of cells in the salivary and lacrimal glands in normal rats were investigated in Example 24. Three major salivary glands exist in mammals: the parotid, sublingual and submandibular or submaxillary salivary glands. One intravenous administration of KGF-2 induced an almost forty-fold increase in the proliferation of serous cells in the parotid gland, an eighteen-fold elevation in the proliferation of serous and mucous cells in the submandibular gland, and a ten-fold increase in the proliferation of serous cells in the lacrimal gland. The enhanced proliferation in the salivary and lacrimal gland cells induced by KGF-2 was reversible.

KGF-2 produces a dramatic increase in the proliferation of normal serous and mucous secretory cells in salivary and lacrimal glands of normal rats but does not appear to elicit a proliferative response of ductal cells. (See, Example 24). This effect on the salivary and lacrimal glands reverses upon removal of treatment suggesting KGF-2 would prove safe and effective in promoting regeneration of the cells of these glands.

In addition to stimulating proliferation of the salivary glands, daily i.v. injections of KGF-2Δ33 resulted in grossly visible thickening of the oral and esophageal mucosa in cynomolgus monkeys. (See, Example 36). The grossly visible thickening of the oral and esophageal mucosa correlated with oral and esophageal mucosal hyperkeratosis.

Since KGF-2Δ33 has shown proliferative effects on secretory tissues such as salivary glands and the pancreas, the effect of systemic administration of KGF-2Δ33 on the lacrimal glands was also investigated in Example 25. The results demonstrates that the lacrimal gland proliferates after 1, 2, and 3 daily i.v. treatments with KGF-2Δ33. However, the gland fails to demonstrate elevated proliferation after 7 daily administrations of this growth factor, a situation that has been observed in many organs and tissues. (See, Example 25). These results indicate that topical or systemic administration of KGF-2Δ33 would be expected stimulate a therapeutic increase in the secretory capacity of the glands by its proliferative effect on lacrimal epithelial cells.

Accordingly, the invention provides for a method of stimulating the growth of the parotid, sublingual and submandibular (or submaxillary) salivary gland cells by administration of KGF-2 to a patient in need thereof. The invention also provides a method of stimulating the growth of lacrimal gland cells by administration of KGF-2 to a patient in need thereof. In particular, KGF-2 can be administered to treat or prevent keratoconjunctivitis sicca, xerostomia or other pathologies and injuries to the lacrimal gland, salivary gland or mucosa caused by radiation therapy, autoimmune disease, sarcoidosis, aging, HIV infection, burns, etc. Suitable doses, formulations, and administration routes are described below.

Stimulating Proliferation of Goblet Cells

As indicated above, administration of KGF-2 to an individual also stimulates proliferation of Goblet cells in the respiratory epithelium of the nasal air passage way (Example 37). As demonstrated in Example 29, KGF-2 administration also results in proliferation of Goblet cells in the conjunctiva. The present inventors have further demonstrated that KGF-2 administration stimulates proliferation of Goblet cells in the large and small intestines. Thus, the present invention further provides a method for stimulating proliferation of Goblet cells by administration of KGF-2 to an individual in need thereof. Stimulating Goblet cell proliferation can be used for a number of purposes, including treating or preventing dry eye and radiation induced damage (such as during cancer therapies). Suitable doses, formulations, and administration routes are described below.

Lung Epithelial Cell Proliferation

KGF-2 stimulates proliferation of lung epithelial cells. Thus, KGF-2 can be administered prophylactically to reduce or prevent damage to the lungs caused by various pathological states. KGF-2 can also be administered during or after a damaging event occurs to promote healing. For example, KGF-2 can stimulate proliferation and differentiation and promote the repair of alveoli and bronchiolar epithelium to prevent, attenuate, or treat acute or chronic lung damage. Emphysema, which results in the progressive loss of alveoli, and inhalation injuries, i.e., resulting from smoke inhalation and burns, that cause necrosis of the bronchiolar epithelium and alveoli could be effectively treated using KGF-2 as could damage attributable to chemotherapy, radiation treatment, lung cancer, asthma, black lung and other lung damaging conditions. Also, KGF-2 could be used to stimulate the proliferation of and differentiation of type II pneumocytes, which may help treat or prevent disease such as hyaline membrane diseases, such as infant respiratory distress syndrome and bronchopulmonary dysplasia, in premature infants.

KGF-2 stimulates proliferation of lung epithelial cells by direct intratracheal administration. Further, administration of nebulized KGF-2 also stimulates cell proliferation as does KGF-2 administered intraveneously. Moreover, as demonstrated in Example 32, KGF-2 is useful prophylactically for lung fibrosis.

As used herein, by "individual" is intended an animal, preferably a mammal (such as apes, cows, horses, pigs, boars, sheep, rodents, goats, dogs, cats, chickens, monkeys, rabbits, ferrets, whales, and dolphins), and more preferably a human.

Pharmaceutical Compositions

The KGF-2 polypeptides of the present invention may be employed in combination with a suitable pharmaceutical carrier to comprise a pharmaceutical composition. Such compositions comprise a therapeutically effective amount of the polypeptide, agonist or antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The polypeptide having KGF-2 activity may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in *Remington's Pharmaceutical Sciences* (latest edition), Mack Publishing Company, Easton, Pa.

The KGF-2 composition to be used in the therapy will be formulated and dosed in a fashion consistent with good medical practice, taking into account the clinical condition of the individual patient (especially the side effects of treatment with KGF-2 alone), the site of delivery of the KGF-2 composition, the method of administration, the scheduling of administration, and other factors known to practitioners. The "effective amount" of KGF-2 for purposes herein is thus determined by such considerations.

The pharmaceutical compositions may be administered in a convenient manner such as by the oral, topical, intravenous, intraperitoneal, intramuscular, intraarticular, subcutaneous, intranasal, intratracheal, intraocular, inhalation, or intradermal routes. The pharmaceutical compositions are administered in an amount which is effective for treating and/or prophylaxis of the specific indication. In most cases, the KGF-2 dosage is from about 1 µg/kg to about 30 mg/kg body weight daily, taking into account the routes of administration, symptoms, etc. However, the dosage can be as low as 0.001 µg/kg. For example, in the specific case of topical administration dosages are preferably administered from about 0.01 µg to 9 mg per cm$^2$. In the case of intranasal and intraocular administration, dosages are preferably administered from about 0.001 µg/ml to about 10 mg/ml, and more preferably from about 0.05 mg/ml to about 4 mg/ml.

As a general proposition, the total pharmaceutically effective amount of the KGF-2 administered parenterally per more preferably dose will be in the range of about 1 µg/kg/day to 100 mg/kg/day of patient body weight, although, as noted above, this will be subject to therapeutic discretion. If given continuously, the KGF-2 is typically administered at a dose rate of about 1 µg/kg/hour to about 50 µg/kg/hour, either by 1–4 injections per day or by continuous subcutaneous infusions, for example, using a mini-pump. An intravenous bag solution or bottle solution may also be employed.

More preferably, KGF-2 is administered intravenously at dose range of about 0.5 mg/kg to about 30 mg/kg to treat cystitis, hypoalbuminemia, hypofibrinogenimia, hypogammaglobulinemia, hemorrhagic cystitis, stimulating salivary gland epithelia, lung damage or injuries, stimulating sinus and nasal mucosa. KGF-2 is preferably nebulized and administered by inhalation at a dose range of about 6 mg to about 20 mg to treat pulmonary diseases and conditions as well as for nasal and sinus epithelium stimulation.

A course of KGF-2 treatment to affect the fibrinolytic system appears to be optimal if continued longer than a certain minimum number of days, 7 days in the case of the mice. The length of treatment needed to observe changes and the interval following treatment for responses to occur appears to vary depending on the desired effect. Such treatment lengths are indicated in the Examples below. The KGF-2 polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(–)-3-hydroxybutyric acid (EP 133,988). Sustained-release KGF-2 compositions also include liposomally entrapped KGF-2. Liposomes containing KGF-2 are prepared by methods known per se: DE 3,218,121; Epstein, et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal KGF-2 therapy.

For parenteral administration, in one embodiment, the KGF-2 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

KGF-2 may also be administered to the eye to treat lacrimal gland injuries, disorders and pathologies in animals and humans as a drop, or within ointments, gels, liposomes, or biocompatible polymer discs, pellets or carried within contact lenses. The intraocular composition may also contain a physiologically compatible ophthalmic vehicle as those skilled in the art can select using conventional criteria. The vehicles may be selected from the known ophthalmic vehicles which include but are not limited to water, polyethers such s polyethylene glycol 400, polyvinyls such as polyvinyl alcohol, povidone, cellulose derivatives such as carboxymethylcellulose, methylcellulose and hydroxypropyl methylcellulose, petroleumn derivatives such as mineral oil and white petrolatum, animal fats such as lanolin, vegetable fats such as peanut oil, polymers of acrylic acid such as carboxylpolymethylene gel, polysaccharides such as dextrans and glycosaminoglycans such as sodium chloride and potassium, chloride, zinc chloride and buffer such as sodium bicarbonate or sodium lactate. High molecular weight molecules can also be used. Physiologically compatible preservatives which do not inactivate the KGF-2 present in the composition include alcohols such as chlorobutanol, benzalknonium chloride and EDTA, or any other appropriate preservative known to those skilled in the art.

KGF-2 can also be intranasally administered to the nasal mucosa to treat disorders, injuries and pathologies of the nasal mucosa and sinus epithelia in animals and humans as drops or in a spray form. Various types of nasal delivery devices are well known in the art. In general, peptides are administered in an aqueous solution are often administered by means of metered-dose spray pumps. For intranasal administration, suspensions will generally be aqueous solutions which contain a physiologically compatible vehicle as those skilled in the art can select using conventional criteria. For example, the suspension may be prepared from water alone (e.g., sterile or pyrogen-free water), water and a physiologcially acceptable non aqueous vehicle (e.g., ethanol, propylene glycol, polyethylene glycols such as PEG 400, etc.). Such suspensions may additionally contain other excipients, for example, preservatives (e.g., benzalkonium chloride, phenylethylalchohol, and other known quaternary amines, etc.), wetting agents/surfactants (e.g., polysorbates such as Tween 80; sorbitan esters such as Span 80), buffering agents (e.g., acetic acid/sodium acetate, citric acid/disodium hydrogen phosphate, sodium dihydrogen phosphate/disodium hydrogen phosphate, and citric acid/sodium citrate, etc.), osmotic pressure controlling agents (e.g., sodium chloride), muscosal absorption enhancers (e.g., bile salts, monolauryl esters of macrogols, phospholipids and fusidate derivatives), and viscosity enhancers (e.g., acacia, bentonite, carboxymethylcellulose, gelatin, hydroxymethylcellulose, methylcellulose and the like).

KGF-2 intranasal administration may also be achieved by means of an aerosol formulation in which the peptide composition is provided in a pressurized pack with a suitable propellant such as a chlorofluorocarbon (CFC), a hydrofluorocarbon (HFC), carbon dioxide or other suitable gas. The aerosol may also contain a surfactant such as lecithin. The dose of the drug may be controlled by a metered valve device well known to those in the art.

Generally, the formulations are prepared by contacting the KGF-2 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mack Publishing Company, Easton, Pa.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

KGF-2 is typically formulated in such vehicles at a concentration of about 0.01 $\mu$g/ml to 100 mg/ml, preferably 0.01 $\mu$g/ml to 10 mg/ml, at a pH of about 3 to 8. It will be understood that the use of certain of the foregoing excipients, carriers, or stabilizers will result in the formation of KGF-2 salts.

KGF-2 to be used for therapeutic administration must be sterile. Sterility is readily accomplished by filtration through sterile filtration membranes (e.g., 0.2 micron membranes). Therapeutic KGF-2 compositions generally are placed into a container having a sterile access port, for example, an intravenous solution bag or vial having a stopper pierceable by a hypodermic injection needle.

KGF-2 ordinarily will be stored in unit or multi-dose containers, for example, sealed ampules or vials, as an aqueous solution or as a lyophilized formulation for reconstitution. As an example of a lyophilized formulation, 10 ml vials are filled with 5 ml of sterile-filtered 1% (w/v) aqueous KGF-2 solution, and the resulting mixture is lyophilized. The infusion solution is prepared by reconstituting the lyophilized KGF-2 using bacteriostatic Water-for-Injection.

Dosaging may also be arranged in a patient specific manner to provide a predetermined concentration of an KGF-2 activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

Pharmaceutical compositions of the invention may be administered orally, rectally, parenterally, intracisternally, intradermally, intravaginally, intraperitoneally, topically (as by powders, ointments, gels, creams, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Preferred KGF-2 formulations are described in U.S. Provisional Application No. 60/068,493, filed Dec. 22, 1997, and the U.S. Non Provisional Application, filed on Dec. 22, 1998, both of which are herein incorporated by reference.

Gene Therapy

The KGF-2 polypeptide of the present invention may be employed by expression of the polypeptide in vivo, which is often referred to as "gene therapy". The gene therapy method relates to the introduction of nucleic acid (DNA, RNA and antisense DNA or RNA) sequences encoding KGF-2 polypeptides into an animal to achieve expression of a KGF-2 polypeptide. Such gene therapy and delivery techniques are known in the art. See, for example, WO 90/11092, which is herein incorporated by reference.

As discussed more fully below, the KGF-2 polynucleotide sequences preferably have a therapeutic effect after being taken up by a cell. Examples of polynucleotides that are themselves therapeutic are anti-sense DNA and RNA; DNA coding for an anti-sense RNA; or DNA coding for tRNA or rRNA to replace defective or deficient endogenous molecules. For example, a promoter may be operably linked to a DNA sequence encoding for an antisense RNA. The antisense RNA oligonucleotide hybridizes to the mRNA in vivo and blocks translation of an mRNA molecule into a polypeptide (Okano, *J. Neurochem* 56:560 (1991)). The antisense RNA must be of sufficient length and complementarity to prevent translation of its target mRNA.

The heterologous polynucleotides can also code for therapeutic polypeptides. Therapeutic polypeptides include those that can compensate for defective or deficient polypeptide in an animal, or those that act through toxic effects to limit or remove harmful cells from the body. In the present invention, the therapeutic polypeptide comprise KGF-2 polypeptides.

Thus, for example, cells from a patient may be engineered with a polynucleotide (DNA or RNA) comprising KGF-2 polynucleotide operably linked to a promoter ex vivo, with the engineered cells then being provided to a patient to be treated with the KGF-2 polypeptide. Such methods are well-known in the art. For example, see Belldegrun, A., et al., *J. Natl. Cancer Inst.* 85: 207–216 (1993); Ferrantini, M. et al., *Cancer Research* 53: 1107–1112 (1993); Ferrantini, M. et al., *J. Immunology* 153: 4604–4615 (1994); Kaido, T., et al., *Int. J. Cancer* 60: 221–229 (1995); Ogura, H., et al., *Cancer Research* 50: 5102–5106 (1990); Santodonato, L., et al., *Human Gene Therapy* 7:1–10 (1996); Santodonato, L., et al., *Gene Therapy* 4:1246–1255 (1997); and Zhang, J.-F. et al., *Cancer Gene Therapy* 3: 31–38 (1996)). The cells to be engineered may be any cell type where KGF-2 may have a therapeutic effect. Such cells include, but are not limited to, muscle cells, epithelial cells, bladder, prostate, testes, lacrimal gland, salivary gland, sinus epithelia, conjunctiva, bone marrow stem and progenitor cells, lung, liver, pancreas, esophagus, etc . . . These engineered cells may be reintroduced into the patient through direct injection to the tissue of origin, the tissues surrounding the tissue of origin, veins or arteries; or through catheter injection.

Similarly, cells may be engineered in vivo for expression of a therapeutic polypeptide in vivo by, for example, procedures known in the art. The constructs can be delivered by any method that delivers materials to the cells of an animal, such as injection into the interstitial space of tissues. The constructs may be delivered in a pharmaceutically acceptable liquid or aqueous carrier well known to those skilled in the art.

In certain embodiments, the KGF-2 polynucleotide constructs may be delivered as naked polynucleotides. By "naked" polynucleotides is meant that the polynucleotides are free from any delivery vehicle that acts to assist, promote, or facilitate entry into the cell, including viral sequences, viral particles, liposome formulation, lipofectin, precipitating agents and the like. Such methods are well known in the art and described, for example, in U.S. Pat. Nos. 5,593,972, 5,589,466, and 5,580,859.

The naked polynucleotides used in the invention can be those which do not integrate into the genome of the host cell. These may be non-replicating sequences, or specific replicating sequences genetically engineered to lack the genome-integration ability. Alternatively, the naked polynucleotides used in the invention may integrate into the genome of the host cell by, for example, homologous recombination, as discussed below. Preferably, the naked KGF-2 polynucleotide construct is contained in a plasmid. Suitable expression vectors for include, but are not limited to, vectors such as pRSVcat (ATCC 37152), pSVL and MSG (Pharmacia, Uppsala, Sweden), pSV2dhfr (ATCC 37146) and pBC12MI (ATCC 67109). Additional suitable plasmids are discussed in more detail above.

The naked polynucleotides can be administered to any tissue (such as muscle tissue) or organ, as described above. In another embodiment, the naked polynucleotides are administered to the tissue surrounding the tissue of origin. In another embodiment, the naked polynucleotides are administered systemically, through intravenous injection.

The naked polynucleotides are delivered by any method known in the art, including, but not limited to, direct needle injection at the delivery site, intravenous injection (especially portal vein injection), topical administration, catheter infusion, and so-called "gene guns". These delivery methods are known in the art and discussed in more detail below.

For naked polynucleotide injection, an effective dosage amount of polynucleotide will be in the range of from about 0.05 µg/kg body weight to about 50 mg/kg body weight. Preferably, the dosage will be from about 0.005 mg/kg to about 20 mg/kg and more preferably from about 0.05 mg/kg to about 5 mg/kg. The appropriate and effective dosage of the polynucleotide construct can readily be determined by those of ordinary skill in the art and may depend on the condition being treated and the route of administration.

The constructs may also be delivered with delivery vehicles such as viral sequences, viral particles, liposome formulations, lipofectin, precipitating agents, etc. Such methods of delivery are known in the art. For example, the polynucleotide construct can be delivered specifically to hepatocytes through the method of Wu et al., *J. Biol. Chem.* 264:6985–16987 (1989).

In certain embodiments, the KGF-2 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci. USA* (1987) 84:7413–7416); mRNA (Malone et al., *Proc. Natl. Acad. Sci. USA* (1 989) 86:6077–6081); and purified transcription factors (Debs et al., *J. Biol. Chem.* (1990) 265:10189–10192), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Feigner et al., *Proc. Natl Acad. Sci. USA* (1987) 84:7413–7416). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 for a description of the synthesis of DOTAP (1,2-bis(oleoyloxy)-3-(trimethylammonio)propane) liposomes. Preparation of DOTMA liposomes is explained in the literature, see, e.g., P. Felgner et al., *Proc. Natl. Acad. Sci. USA* 84:7413–7417. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15° C. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., *Methods of Immunology* (1983), 101:512–527. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys. Acta* (1975) 394:483; Wilson et al., *Cell* (1979) 17:77); ether injection (Deamer, D. and Bangham, A., *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); detergent dialysis (Enoch, H. and Strittmatter, P., *Proc. Natl. Acad. Sci. USA* (1979) 76:145); and reverse-phase evaporation (REV) (Fraley et al., *J. Biol. Chem.* (1980) 255:10431; Szoka, F. and Papahadjopoulos, D., *Proc. Natl. Acad. Sci. USA* (1978) 75:145; Schaefer-Ridder et al., *Science* (1982) 215:166).

Additional examples of useful cationic lipids include dipalmitoyl-phophatidylethanolamine 5-carboxyspennylamide (DPPES); 5-carboxyspermylglycine dioctadecylamide (DOGS); dimethyldioctdecyl-ammonium bromide (DDAB); and (±)-N,N-dimethyl-N-[2-(sperminecarboxamido)ethyl]-2,3-bis(dioleyloxy)-1-propaniminium pentahydrochloride (DOSPA). Non-diether cationic lipids, such as DL-1,2-dioleoyl-3-dimethylaminopropyl-β-hydroxyethylammonium (DORI diester), 1,2-O-dioleyl-3-dimethylaminopropyl-β-hydroxyethylammonium (DORIE diether), 1-O-oleyl-2-oleoyl-3-dimethylaminopropyl-β-hydroxyethylammonium (DORI ester/ether), and their salts promote in vivo gene delivery. Cationic cholesterol derivatives such as, {3β[N-N',N'-dimethylamino)ethane]-carbomoyl}-cholesterol (DC-Chol), are also useful.

Preferred cationic lipids include: (±)-N-(2-hydroxyethyl)-N,N-dimethyl-2,3-bis(tetradecyloxy)-1-propaniminium bromide; 3,5-(N,N-di-lysyl)diaminobenzoylglycyl-3-(DL-1,2-dioleoyl-dimethylaminopropyl-β-hydroxyethylamine) (DLYS-DABA-GLY-DORI diester); 3,5-(NN-dilysyl)-diaminobenzoyl-3-(DL-1,2-dioleoyl-dimethylaminopropyl-β-hydroxyethylamine) (DLYS-DABA-DORI diester); and 1,2-dioleoyl-sn-glycero-3-phosphoethanolamine. Also preferred is the combinations of the following lipids: (±)-N-(2-hydroxyethyl)-N,N-dimethyl-2,3-bis(tetradecyloxy)-1-propaniminium bromide and 1,2-dioleoyl-sn-glycero-3-phosphoethanolamine; and (±)-N-(2-hydroxyethyl)-N,N-dimethyl-2,3-bis(tetradecyloxy)-1-propaniminium bromide, and 1,2-dioleoyl-sn-glycero-3-phosphoethanolamine in a 1:1 ratio.

The lipid formulations may have a cationic lipid alone, or also include a neutral lipid such as cardiolipin, phosphatidylcholine, phosphatidylethanolamine, dioleoylphosphatylcholine, dioleoylphosphatidylethanolamine, 1,2-dioleoyl-sn-glycero-3-phosphatidylethanolamine (DOPE), sphingomyelin, and mono-, di- or tri-acylglycerol).

Lipid formulations may also have cationic lipid together with a lysophosphatide. The lysophosphatide may have a neutral or a negative head group. Useful lysophosphatides include lysophosphatidylcholine, lysophosphatidylethanolamine, and 1-oleoyl lysophosphatidylcholine. Lyso-phosphatide lipids are present Other additives, such as cholesterol, fatty acid, ganglioside, glycolipid, neobee, niosome, prostaglandin, sphingolipid, and any other natural or synthetic amphiphiles, can be used. A preferred molar ratio of cationic lipid to neutral lipid in these lipid formulations is from about 9:1 to about 1:9; an equimolar ratio is more preferred in the lipid-containing formulation in a 1:2 ratio of lysolipid to cationic lipid.

Generally, the ratio of DNA to liposomes will be from about 10:1 to about 1:10. Preferably, the ratio will be from about 5:1 to about 1:5. More preferably, the ratio will be about 3:1 to about 1:3. Still more preferably, the ratio will be about 1:1.

U.S. Pat. No. 5,676,954 reports on the injection of genetic material, complexed with cationic liposomes carriers, into mice. U.S. Patent Nos. 4,897,355, 4,946,787, 5,049,386, 5,459,127, 5,589,466, 5,693,622, 5,580,859, 5,703,055, and international publication no. WO 94/9469 provide cationic lipids for use in transfecting DNA into cells and mammals. U.S. Pat. Nos. 5,589,466, 5,693,622, 5,580,859, 5,703,055, and international publication no. WO 94/9469 provide methods for delivering DNA-cationic lipid complexes to mammals.

In certain embodiments, cells are be engineered, ex vivo or in vivo, using a retroviral particle containing RNA which comprises a polynucleotide encoding KGF-2 operably linked to a promoter. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include a KGF-2 polynucleotide operably linked to a promoter. Such retroviral vector particles then may be employed, to transduce eukaryotic cells, either in vitro or in vivo. The transduced eukaryotic cells will express the desired polypeptide.

In certain other embodiments, cells are engineered, ex vivo or in vivo, with the KGF-2 polynucleotide operably linked to a promoter contained in an adenovirus vector. Adenovirus can be manipulated such that it encodes and expresses the desired gene product, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) *Am. Rev. Respir. Dis.* 109:233–238). Finally, adenovirus mediated gene transfer has been demonstrated in a number of instances including transfer of alpha-1-antitrypsin and CFTR to the lungs of cotton rats (Rosenfeld, M. A. et al. (1991) *Science* 252:431–434; Rosenfeld et al., (1992) *Cell* 68:143–155). Furthermore, extensive studies to attempt to establish adenovirus as a causative agent in human cancer were uniformly negative (Green, M. et al. (1979) *Proc. Natl. Acad. Sci. USA* 76:6606).

Suitable adenoviral vectors useful in the present invention are described, for example, in Kozarsky and Wilson, *Curr. Opin. Genet. Devel.* 3:499–503 (1993); Rosenfeld et al., *Cell* 68:143–155 (1992); Engelhardt et al., *Human Genet. Ther.* 4:759–769 (1993); Yang et al., *Nature Genet.* 7:362–369 (1994); Wilson et al., *Nature* 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the KGF-2 polynucleotide of the present invention, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., *Curr. Topics in Microbiol. Immunol.* 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The KGF-2 polynucleotide construct is inserted into the AAV vector using standard cloning methods, such as those found in Sambrook et al., *Molecular Cloning: A Laboratory Manual,* Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the KGF-2 polynucleotide construct. These viral particles are then used to transduce eukaryotic cells, either ex vivo or in vivo. The transduced cells will contain the KGF-2 polynucleotide construct integrated into its genome, and will express the molecule of interest.

Another method of gene therapy involves operably associating heterologous control regions (e.g., a promoter of interest) and endogenous polynucleotide sequences (e.g., KGF-2) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932–8935 (1989); and Zijlstra et al., *Nature* 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter of interest with targeting sequences flanking the promoter of interest. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence (e.g., KGF-2) is placed under the control of the promoter. The promoter then drives the expression of the endogenous sequence (e.g., KGF-2).

KGF-2 polynucleotides of the present invention may be used in gene therapy to treat metabolic, infectious and other diseases described herein. Preferably, a KGF-2 polynucleotide of the present invention is operably linked a promoter so as to alleviate the symptoms of, or cures the disease to be treated as described in detail herein.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., *Science* 243:375 (1989)).

A preferred method of local administration is by direct injection. Preferably, a recombinant molecule of the present invention complexed with a delivery vehicle is administered by direct injection into or locally within the area of the liver. Administration of a composition locally within the area of the liver refers to injecting the composition centimeters and preferably, millimeters within the liver.

Another method of local administration is to contact a KGF-2 polynucleotide-promoter construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site, for example, ligands for targeting the vehicle to a tissue of interest. Targeting vehicles for other tissues and organs are well known to skilled artisans.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189:11277–11281,1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

EXAMPLE 1

Bacterial Expression and Purification of KGF-2

The DNA sequence encoding KGF-2 ATCC # 75977, is initially amplified using PCR oligonucleotide primers corresponding to the 5' and 3' end sequences of the processed KGF-2 cDNA (including the signal peptide sequence). The 5' oligonucleotide primer has the sequence 5' CCCCACATGTGGAAATGGATACTGACACATTGTGCC 3' (SEQ IN NO:3) contains an Afl III restriction enzyme site including and followed by 30 nucleotides of KGF-2 coding sequence starting from the presumed initiation codon. The 3' sequence 5' CCCAAGCTTCCACAAACGTTGCCTTC-CTCTATGAG 3' (SEQ ID NO:4) contains complementary sequences to Hind III site and is followed by 26 nucleotides of KGF-2. The restriction enzyme sites are compatible with the restriction enzyme sites on the bacterial expression vector pQE-60 (Qiagen, Inc. Chatsworth, Calif.). pQE-60 encodes antibiotic resistance (Amp$^r$), a bacterial origin of replication (ori), an IPTG-regulatable promoter operator (P/0), a ribosome binding site (RBS), a 6-His tag and restriction enzyme sites. pQE-60 is then digested with NcoI and HindIII. The amplified sequences are ligated into pQE-60 and are inserted in frame. The ligation mixture is then used to transform *E. coli* strain M15/rep 4 (Qiagen, Inc.) by the procedure described in Sambrook, J., et al., *Molecular Cloning: A Laboratory Manual*, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analyses. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG interacts with the lacI repressor to cause it to dissociate from the operator, forcing the promoter to direct transcription. Cells are grown an extra 3 to 4 hours. Cells are then harvested by centrifugation. The cell pellet is solubilized in the chaotropic agent 6 Molar Guanidnine HCl. After clarification, sloubilized KGF-2 is purified from this solution by chromatography on a Heparin affinity column under conditions that allow for tight binding of the proteins (Hochuli, E., et al., *J. Chromatography* 411:177–184 (1984)). KGF-2 (75% pure) is eluted from the column by high salt buffer.

EXAMPLE 2

Bacterial Expression and Purification of a Truncated Version of KGF-2

The DNA sequence encoding KGF-2, ATCC # 75977, is initially amplified using PCR oligonucleotide primers corresponding to the 5' and 3' sequences of the truncated version of the KGF-2 polypeptide. The truncated version comprises the polypeptide minus the 36 amino acid signal sequence, with a methionine and alanine residue being added just before the cysteine residue which comprises amino acid 37 of the full-length protein. The 5' oligonucleotide primer has the sequence 5' CATGCCATGGCGTGC-CAAGCCCTTGGTCAGGTCAGGACATG 3' (SEQ ID NO:5) contains an NcoI restriction enzyme site including and followed by 24 nucleotides of KGF-2 coding sequence. The 3' primer 5' CCCAAGCTTCCACAAACGTTGCCT-TCCTCTATGAG 3' (SEQ ID NO:6) contains complementary sequences to Hind III site and is followed by 26 nucleotides of the KGF-2 gene. The restriction enzyme sites are compatible with the restriction enzyme sites on the bacterial expression vector pQE-60 (Qiagen, Inc. Chatsworth, Calif. pQE-60 encodes antibiotic resistance (Amp$^r$), a bacterial origin of replication (ori), an IPTG-regulatable promoter operator (P/0), a ribosome binding site (RBS), a 6-His tag and restriction enzyme sites. pQE-60 is then digested with NcoI and HindIII. The amplified sequences are ligated into pQE-60 and are inserted in frame. The ligation mixture is then used to transform *E. coli* strain M15/rep4 (Qiagen, Inc.) by the procedure described in Sambrook, J., et al., *Molecular Cloning: A Laboratory Manual*, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6 IPTG ("Isopropyl-B-D-thiogalacto pyranoside") is then added to a final concentration of 1 mM. IPTG induces by inactivating th laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized KGF-2 is purified from this solution by chromatography on a Heparin affinity column under conditions that allow for tight binding the proteins (Hochuli, E. et al., *J. Chromatography* 411:177–184 (1984)). KGF-2 protein is eluted from the column by high salt buffer.

EXAMPLE 3

Cloning and Expression of KGF-2 Using the Baculovirus Expression System

The DNA sequence encoding the full length KGF-2 protein, ATCC # 75977, is amplified using PCR oligonucleotide primers corresponding to the 5' and 3' sequences of the gene:

The 5' primer has the sequence 5' GCGGGATCCGCATCATGTGGAAATGGATACTCAC3' (SEQ ID NO:7) and contains a BamHI restriction enzyme site (in bold) followed by 6 nucleotides resembling an efficient signal for the initiation of translation in eukaryotic cells (Kozak, M., *J. Mol. Biol.*, 196:947–950 (1987)) and just behind the first 17 nucleotides of the KGF-2 gene (the initiation codon for translation "ATG" is underlined).

The 3' primer has the sequence 5' GCGCGGTACCACAAACGTTGCCTTCCT 3' (SEQ ID NO:8) and contains the cleavage site for the restriction endonuclease Asp718 and 19 nucleotides complementary to the 3' non-translated sequence of the KGF-2 gene. The amplified sequences are isolated from a 1% agarose gel using a commercially available kit from Qiagen, Inc., Chatsworth, Calif. The fragment is then digested with the endonucleases BamHI and Asp718 and then purified again on a 1% agarose gel. This fragment is designated F2.

The vector pA2 (modification of pVL941 vector, discussed below) is used for the expression of the KGF-2 protein using the baculovirus expression system (for review see: Summers, M. D. & Smith, G. E., *A manual of methods for baculovirus vectors and insect cell culture procedures,* Texas Agricultural Experimental Station Bulletin No. 1555 (1987)). This expression vector contains the strong polyhedrin promoter of the Autographa californica nuclear polyhidrosis virus (AcMNPV) followed by the recognition sites for the restriction endonucleases BamHI and Asp718. The polyadenylation site of the simian virus (SV) 40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used such as pAc373, pVL941 and pAcIM1 (Luckow, V. A. & Summers, M. D., *Virology*, 170:31–39).

The plasmid is digested with the restriction enzymes BamHI and Asp718. The DNA is then isolated from a 1% agarose gel using the commercially available kit (Qiagen, Inc., Chatsworth, Calif.). This vector DNA is designated V2.

Fragment F2 and the plasmid V2 are ligated with T4 DNA ligase. *E. coli* HB101 cells are then transformed and bacteria identified that contained the plasmid (pBacKGF-2) with the KGF-2 gene using PCR with both cloning oligonucleotides. The sequence of the cloned fragment is confirmed by DNA sequencing.

5 μg of the plasmid pBacKGF-2 is co-transfected with 1.0 μg of a commercially available linearized baculovirus ("BaculoGold™ baculovirus DNA", Pharmingen, San Diego, Calif.) using the lipofection method (Felgner, et al., *Proc. Natl. Acad. Sci. USA,* 84:7413–7417(1987)).

1 μg of BaculoGold™ virus DNA and 5 μg of the plasmid pBacKGF-2 are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf 9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-KGF-2 at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 4

Most of the vectors used for the transient expression of the KGF-2 protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the immediate early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkart cells, mouse NIH3T3 and C127 cells, Cos 1, Cos 7 and CV1, African green monkey cells, quail QC1–3 cells, 293T cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

A. Expression of Recombinant KGF-2 in COS Cells

The expression of plasmid, KGF-2 HA was derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. The HA tag correspond to an epitope derived from the influenza hemagglutinin protein as previously described (Wilson, I., et al., *Cell* 37:767, (1984)). The infusion of HA tag to the target protein allows easy detection of the recombinant protein with an antibody that recognizes the HA epitope. A DNA fragment encoding the entire KGF-2 precursor HA tag fused in frame with the HA tag, therefore, the recombinant protein expression is directed under the CMV promoter.

The plasmid construction strategy is described as follows:

The DNA sequence encoding KGF-2, ATCC # 75977, is constructed by PCR using two primers: the 5' primer 5' TAACGAGGATCCGCCATCATGTG-GAAATGGATACTGACAC 3' (SEQ ID NO:9) contains a BamHI site followed by 22 nucleotides of KGF-2 coding sequence starting from the initiation codon; the 3' primer 5' TAAGCACTCGAGTGAGTGTACCACCAT-TGGAAGAAATG 3' (SEQ ID NO:10) contains complementary sequences to an XhoI site, HA tag and the last 26 nucleotides of the KGF-2 coding sequence (not including the stop codon). Therefore, the PCR product contains a BamHI site, KGF-2 coding sequence followed by an XhoI site, an HA tag fused in frame, and a translation termination stop codon next to the HA tag. The PCR amplified DNA fragment and the vector, pcDNA-3'HA-KGF-2. The ligation mixture is transformed into *E. coli* strain XL1 Blue (Stratagene Cloning Systems, La Jolla, Calif.) the transformed culture is plated on ampicillin media plates and resistant colonies are selected. Plasmid DNA was isolated from transformants and examined by PCR and restriction analysis for the presence of the correct fragment. For expression of the recombinant KGF-2, COS cells were transfected with the expression vector by DEAE-DEXTRAN method (Sambrook, J., et al., *Molecular Cloning: A Laboratory Manual*, Cold Spring Laboratory Press, (1989)). The expression of the KGF-2 HA protein was detected by radiolabelling and immunoprecipitation method (Harlow, E. & Lane, D., *Antibodies: A Laboratory Manual*, Cold Spring Harbor Laboratory Press, (1988)). Cells were labeled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson I., et al., *Id.* 37:767 (1984)). Both cell lysate and culture media were precipitated with a HA specific monoclonal antibody. Proteins precipitated were analyzed on 15% SDS-PAGE gels.

B. Expression and Purification of Human KGF-2Protein Using the CHO Expression System The vector pC 1 is used for the expression of KFG-2 protein. Plasmid pC1 is a derivative of the plasmid pSV2-dhfr [ATCC Accession No. 37146]. Both plasmids contain the mouse DHFR gene under control of the SV40 early promoter. Chinese hamster ovary—or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, PvuII, and NruI. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTL VI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding KFG-2, ATCC No. 75977, is amplified using PCR oligonucleotide primers corresponding to the 5' and 3' sequences of the gene:

The 5' primer has the sequence 5'TAACGA GGATCCGCCATCATGTGGAAATGGATACTGACAC 3' (SEQ ID NO:9) containing the underlined BamH1 restriction enzyme site followed by 21 bases of the sequence of KGF-2 of FIG. 1 (SEQ ID NO:1). Inserted into an expression vector, as described below, the 5' end of the amplified fragment encoding human KGF-2 provides an efficient signal peptide. An efficient signal for initiation of translation in eukaryotic cells, as described by Kozak, M., *J. Mol. Biol.* 196:947–950 (1989) is appropriately located in the vector portion of the construct.

The 3' primer has the sequence 5' TAAGCA GGATCCTGAGTGTACCACCATTGGAAGAAATG 3' (SEQ ID NO:10) containing th BamH1 restriction followed by nucleotides complementary to the last 26 nucleotides of the KGF-2 coding wequence set out in FIG. 1 (SEQ ID NO:1), not including the stop codon.

The amplified fragments are isolated from a 1% agarose gel as described above and then digested with the endonuclease BamHI and then purified again on a 1% agarose gel.

The isolated fragment and the dephosphorylated vector are then ligated with /T4 DNA ligase. *E. coli* HB101 cells are then transformed and bacteria identified that contained the plasmid pC1. The sequence and orientation of the inserted gene is confirmed by DNA sequencing.

Transfection of CHO-DHFR-cells

Chinese hamster ovary cells lacking an active DHFR enzyme are used for transfection. 5 µg of the expression plasmid C1 are cotransfected with 0.5 µg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated for 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE.

EXAMPLE 5

Transcription and Translation of Recombinant KGF-2 in vitro

A PCR product is derived from the cloned cDNA in the pA2 vector used for insect cell expression of KGF-2. The primer used for this PCR were: 5'ATTAACCCTCAC-TAAAGGGAGGCCATGTGGAAATG-GATACTGACACATTGTGCC3' (SEQ ID NO:11) and 5' CCCAAGCTTCCACAAACGTTGCCTTCCTCTATGAG 3' (SEQ ID NO:12).

The first primer contains the sequence of a T3 promoter 5' to the ATG initiation codon. The second primer is complimentary to the 3' end of the KGF-2 open reading frame, and encodes the reverse complement of a stop codon.

The resulting PCR product is purified using a commercially available kit from Qiagen. 0.5 µg of this DNA is used as a template for an in vitro transcription-translation reaction. The reaction is performed with a kit commercially available from Promega under the name of TNT. The assay is performed as described in the instructions for the kit, using radioactively labeled methionine as a substrate, with the exception that only ½ of the indicated volumes of reagents are used and that the reaction is allowed to proceed at 33° C. for 1.5 hours.

Five µl of the reaction is electrophoretically separated on a denaturing 10 to 15% polyacrylamide gel. The gel is fixed for 30 minutes in a mixture of water:Methanol:Acetic acid at 6:3:1 volumes respectively. The gel is then dried under heat and vacuum and subsequently exposed to an X-ray film for 16 hours. The film is developed showing the presence of a radioactive protein band corresponding in size to the conceptually translated KGF-2, strongly suggesting that the cloned cDNA for KGF-2 contains an open reading frame that codes for a protein of the expected size.

EXAMPLE 6

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added.) This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, *DNA*, 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase.

The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 7
Tissue Distribution of KGF-2 mRNA Expression

Northern blot analysis is carried out to examine the levels of expression of the gene encoding the KGF-2 protein in human tissues, using methods described by, among others, Sambrook et al., cited above. A probe corresponding to the entire open reading frame of KGF-2 of the present invention (SEQ ID NO:1) was obtained by PCR and was labeled with $^{32}P$ using the rediprime™ DNA labeling system (Amersham Life Science), according to manufacturer's instructions. After labelling, the probe was purified using a CHROMA SPIN-100™ column (Clontech Laboratories, Inc.), according to manufacturer's protocol number PT1200-1. The purified labelled probe was then used to examine various human tissues for the expression of the gene encoding KGF-2.

Multiple Tissue Northern (MTN) blots containing poly A RNA from various human tissues (H) or human immune system tissues (IM) were obtained from Clontech and were examined with labelled probe using ExpressHyb™ Hybridization Solution (Clontech) according to manufacturer's protocol number PT1190-1. Following hybridization and washing, the blots are mounted and exposed to film at −70° C. overnight, and films developed according to standard procedures.

A major mRNA species of apporximately 4.2 kb was observed in most human tissues. The KGF-2 mRNA was relatively abundant in heart, pancreas, placenta and ovary. A minor mRNA species of about 5.2 kb was also observed ubiquitously. The identity of this 5.2 kb mRNA species was not clear. It is possible that the 5.2 kb transcript encodes an alternatively spliced form of KGF-2 or a third member of the KGF family. The KGF-2 cDNA was 4.1 kb, consistent with the size of the mRNA of 4.2 kb.

EXAMPLE 8
Keratinocyte Proliferation Assays

Dermal keratinocytes are cells in the epidermis of the skin. The growth and spreading of keratinocytes in the skin is an important process in wound healing. A proliferation assay of keratinocyte is therefore a valuable indicator of protein activities in stimulating keratinocyte growth and consequently, wound healing.

Keratinocytes are, however, difficult to grow in vitro. Few keratinocyte cell lines exist. These cell lines have different cellular and genetic defects. In order to avoid complications of this assay by cellular defects such as loss of key growth factor receptors or dependence of key growth factors for growth, primary dermal keratinocytes are chosen for this assay. These primary keratinocytes are obtained from Clonetics, Inc. (San Diego, CAalif.).

Keratinocyte Proliferation Assay with AlamarBlue alamarBlue is a viable blue dye that is metabolized by the mitochondria when added to the culture media. The dye then turns red in tissue culture supernatants. The amounts of the red dye may be directly quantitated by reading difference in optical densities between 570 nm and 600 nm. This reading reflects cellular activities and cell number.

Normal primary dermal keratinocytes (CC-0255, NHEK-Neo pooled) are purchased from Clonetics, Inc. These cells are passage 2. Keratinocytes are grown in complete keratinocyte growth media (CC-3001, KGM; Clonetics, Inc.) until they reach 80% confluency. The cells are trypsinized according to the manufacturer's specification. Briefly, cells were washed twice with Hank's balanced salt solution. 2–3 ml of trypsin was added to cells for about 3–5 min at room temperature. Trypsin neutralization solution was added and cells were collected. Cells are spun at 600×g for 5 min at room temperature and plated into new flasks at 3,000 cells per square centimeter using pre-warmed media.

For the proliferation assay, plate 1,000–2,000 keratinocytes per well of the Corning flat bottom 96-well plates in complete media except for the outermost rows. Fill the outer wells with 200 μl of sterile water. This helps to keep temperature and moisture fluctuations of the wells to the minimum. Grow cells overnight at 37 ° C. with 5% $CO_2$. Wash cells twice with keratinocyte basal media (CC-3101, KBM, Clonetics, Inc.) and add 100 μl of KBM into each well. Incubate for 24 hours. Dilute growth factors in KBM in serial dilution and add 100 μl to each well. Use KGM as a positive control and KBM as a negative control. Six wells are used for each concentration point. Incubate for two to three days. At the end of incubation, wash cells once with KBM and add 100 μl of KBM with 10% v/v alamarBlue pre-mixed in the media. Incubate for 6 to 16 hours until media color starts to turn red in the KGM positive control. Measure O.D. 570 nm minus O.D. 600 nm by directly placing plates in the plate reader.

Results

Stimulation of Keratinocyte Proliferation by KGF-2

Figure 4A:
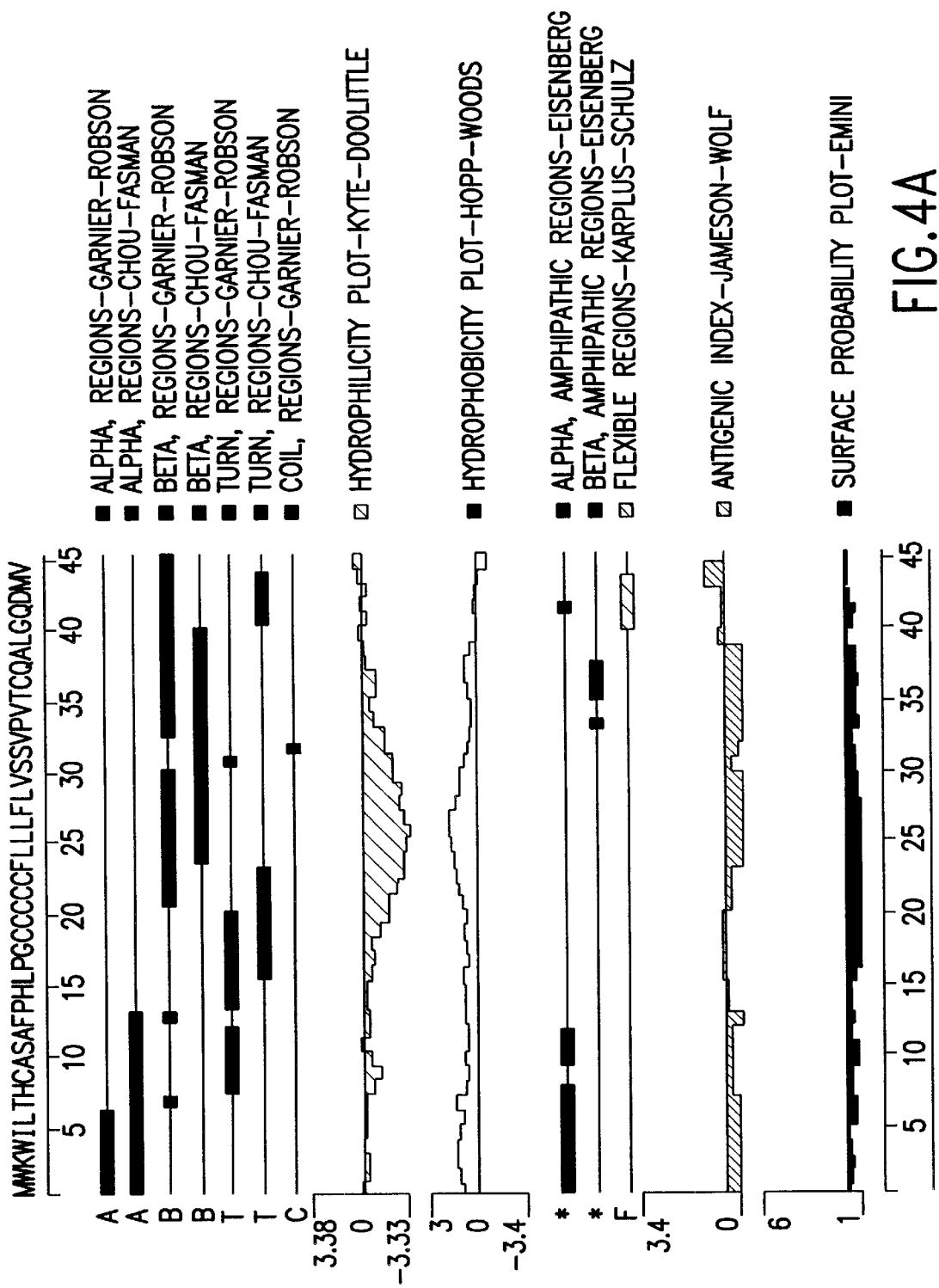
FIGS. 4A–4E show an analysis of the KGF-2 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues amino acid residues 41–109 in FIG. 1 [SEQ ID NO:2] correspond to the shown highly antigenic regions of the KGF-2 protein. Hydrophobic regions (Hopp-Woods Plot) fall below the median line (negative values) while hydrophilic regions (Kyte-Doolittle Plot) are found above the median line (positive values, e.g. amino acid residues 41–109). The plot is over the entire 208 amino acid ORF.
Figure 4B:
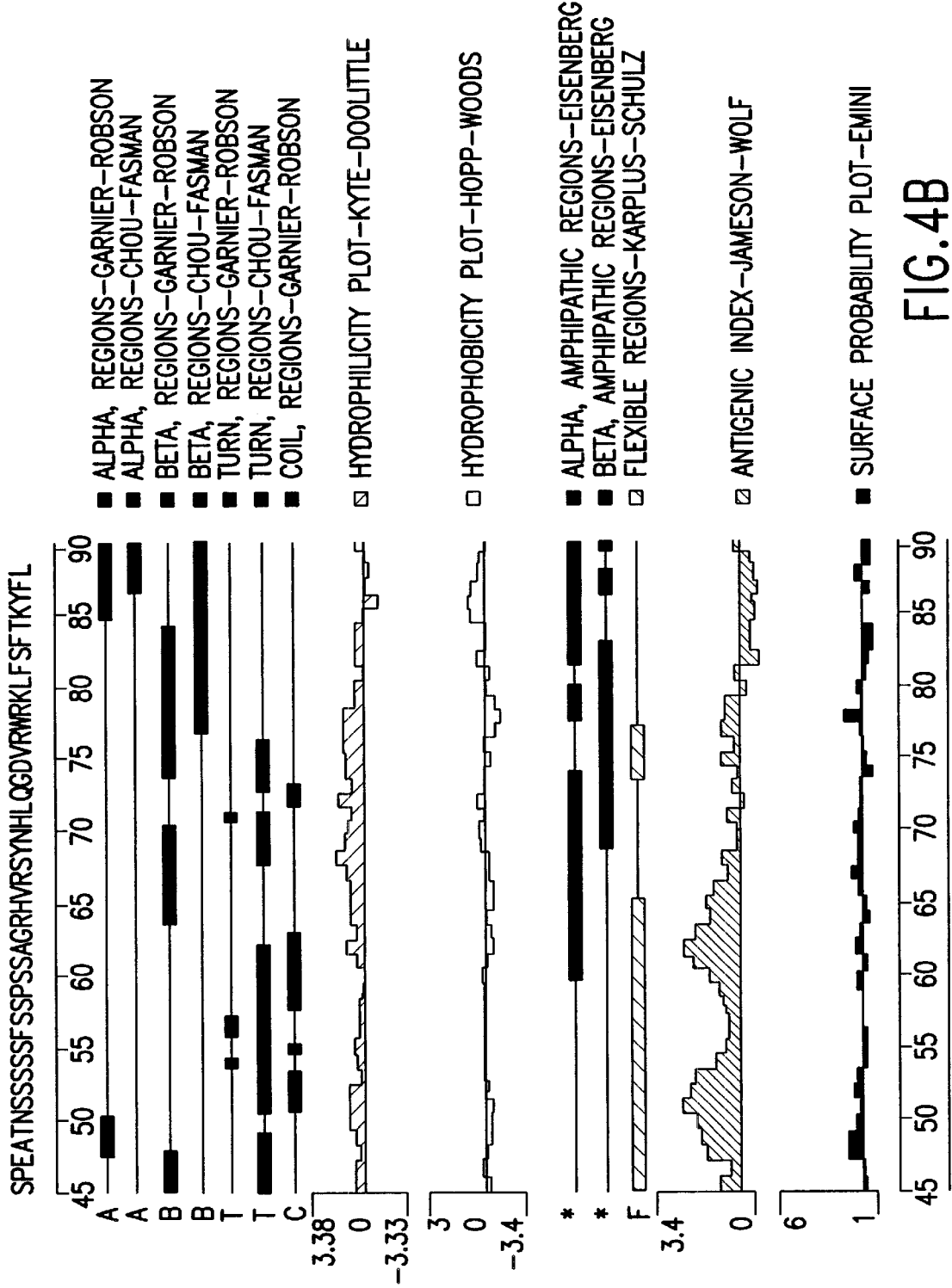
Figure 4C:
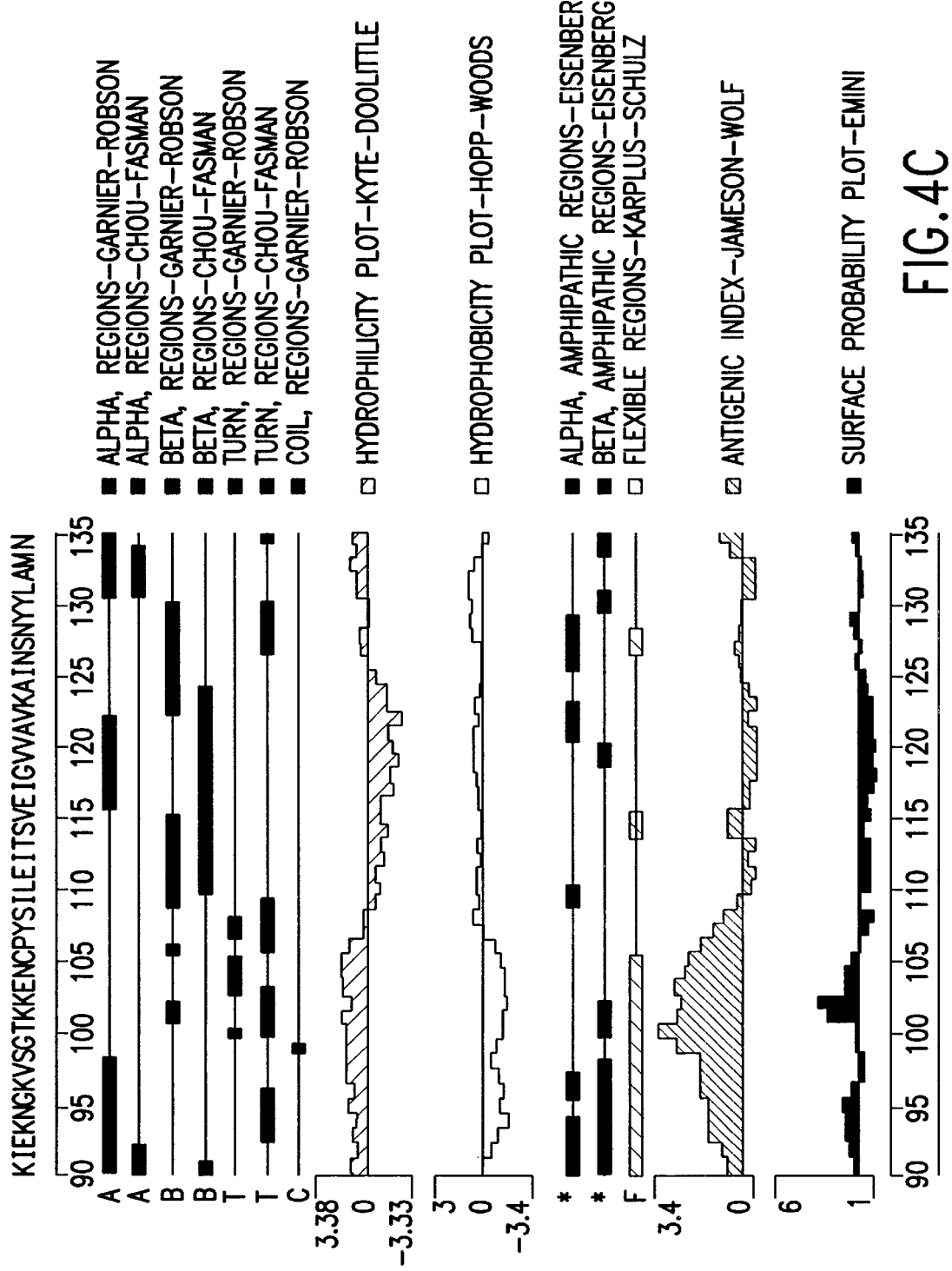
Figure 4D:
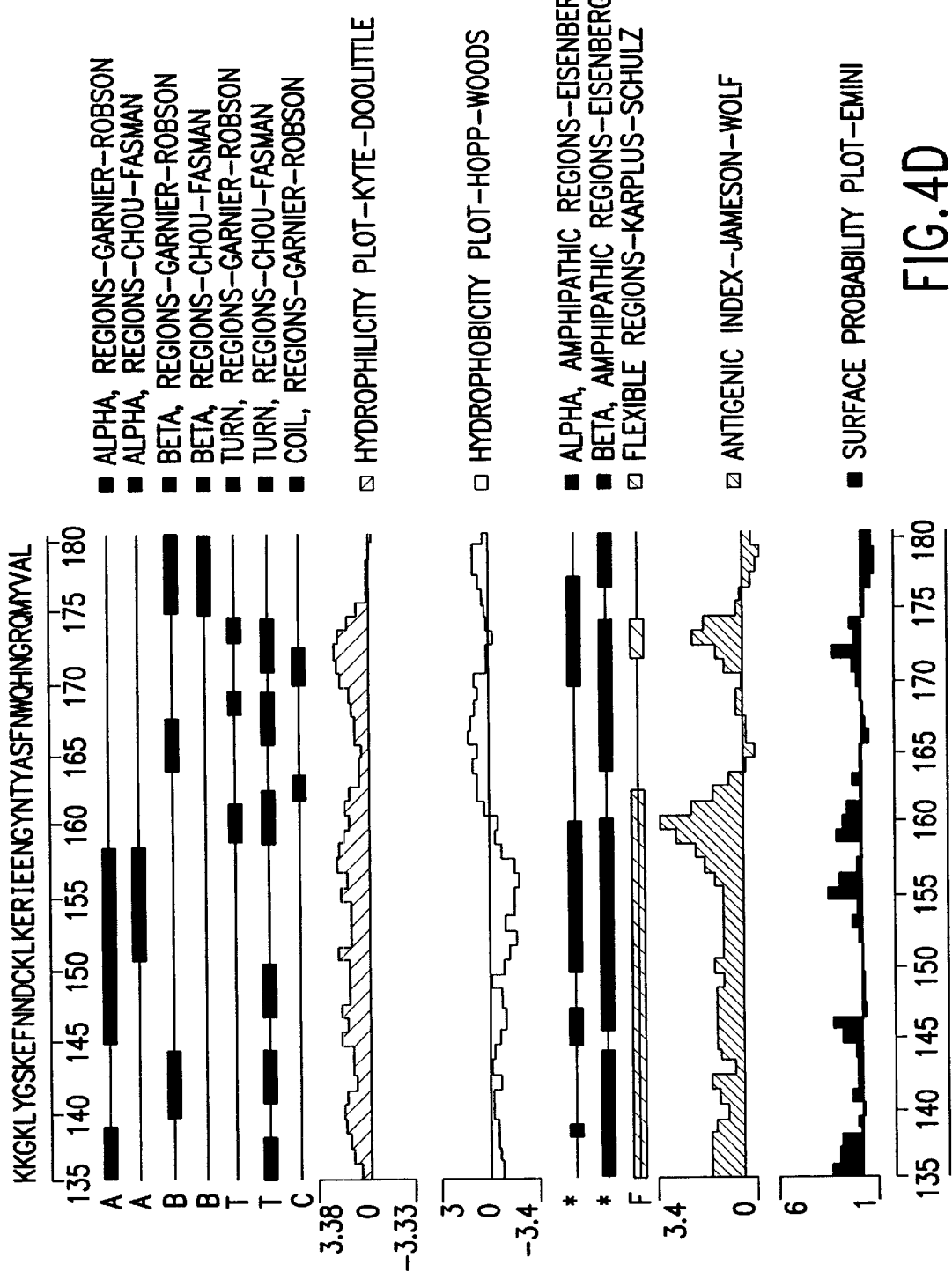
Figure 4E:
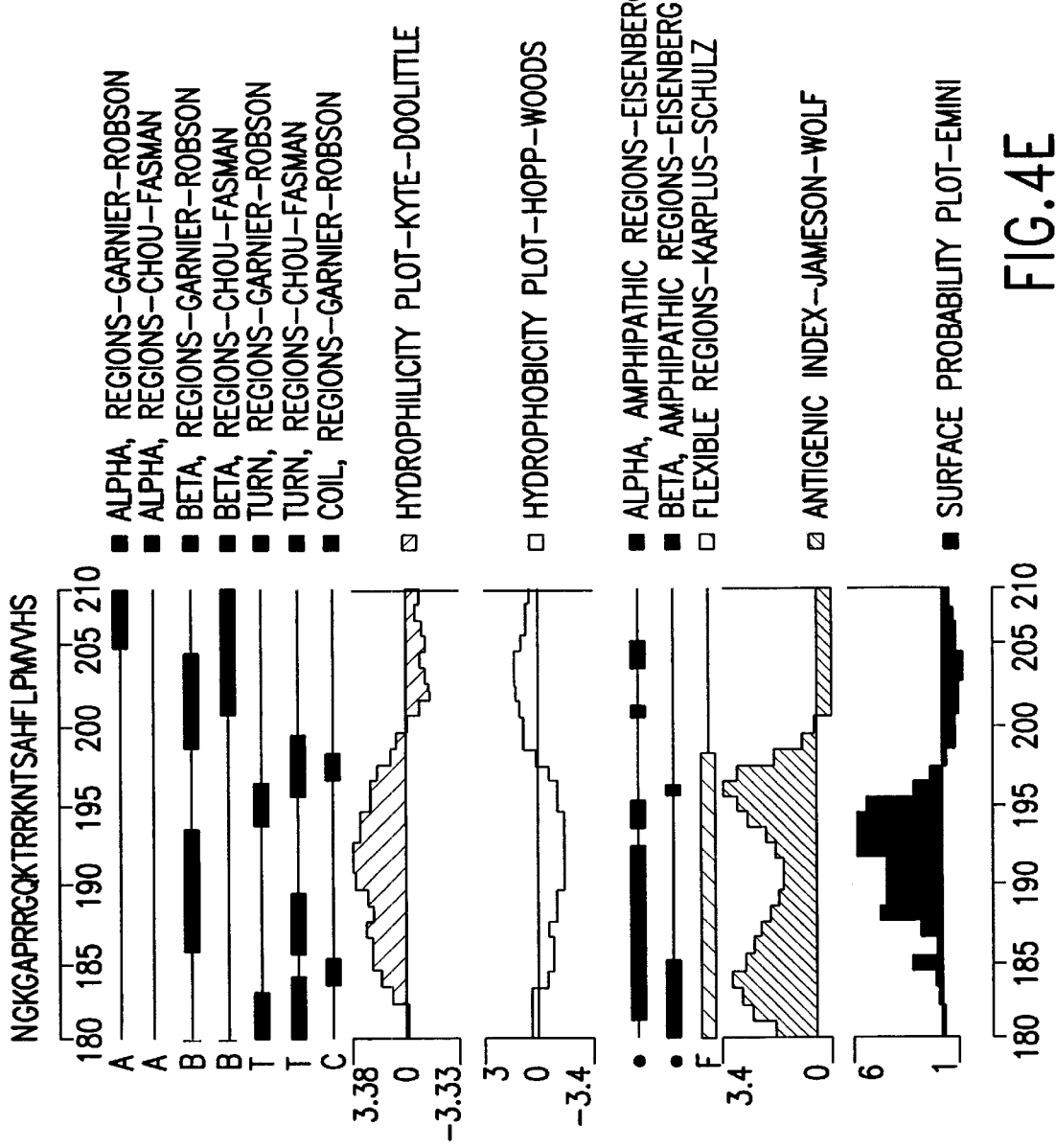
Figure 6A:
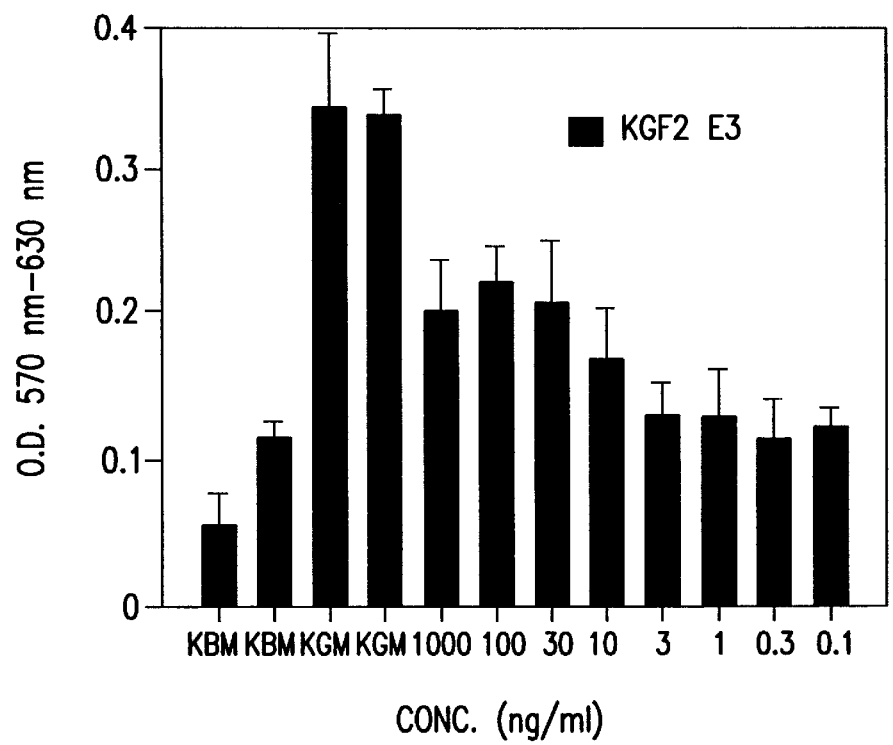
FIG. 6(A) shows the stimulation of normal primary epidermal keratinocyte proliferation by KGF-2. (B) shows the stimulation of normal primary epidermal keratinocyte proliferation by KGF-2 Δ33. (C) shows the stimulation of normal primary epidermal keratinocyte proliferation by KGF-2 Δ28. Human normal primary epidermal keratinocytes were incubated with various concentrations of KGF-2, KGF-2 Δ33 or KGF-2 Δ28 for three days. For all three experiments alamarBlue was then added for 16 hr and the intensity of the red color converted from alamarBlue by the cells was measured by the difference between O.D. 570 nm and O.D. 600 nm. For each of the KGF-2 proteins a positive control with complete keratinocyte growth media (KGM), and a negative control with keratinocyte basal media (KBM) were included in the same assay plate.
Figure 6B:
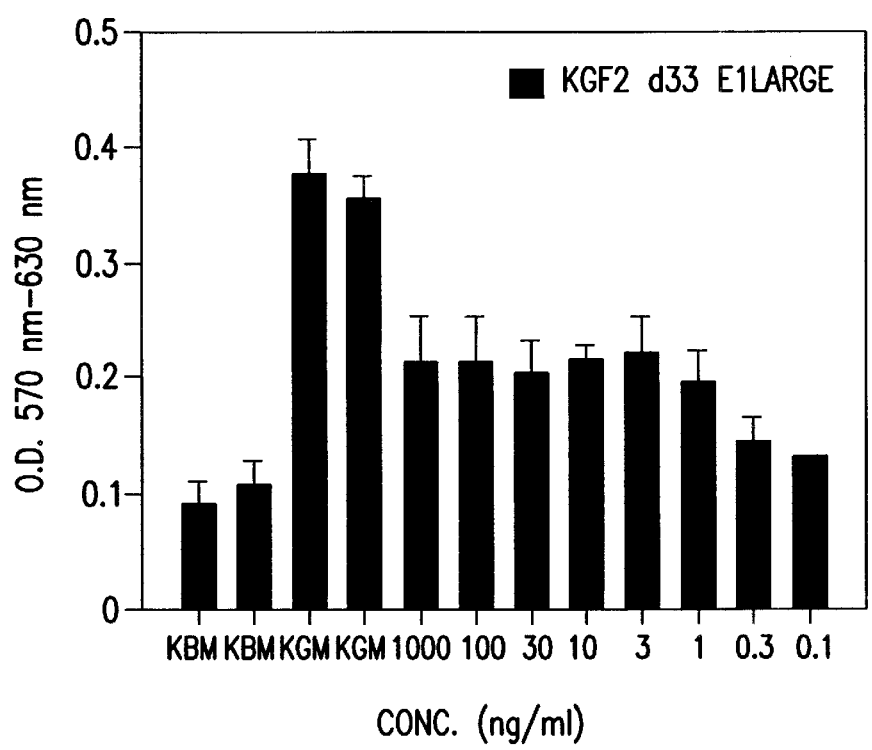
Figure 6C:
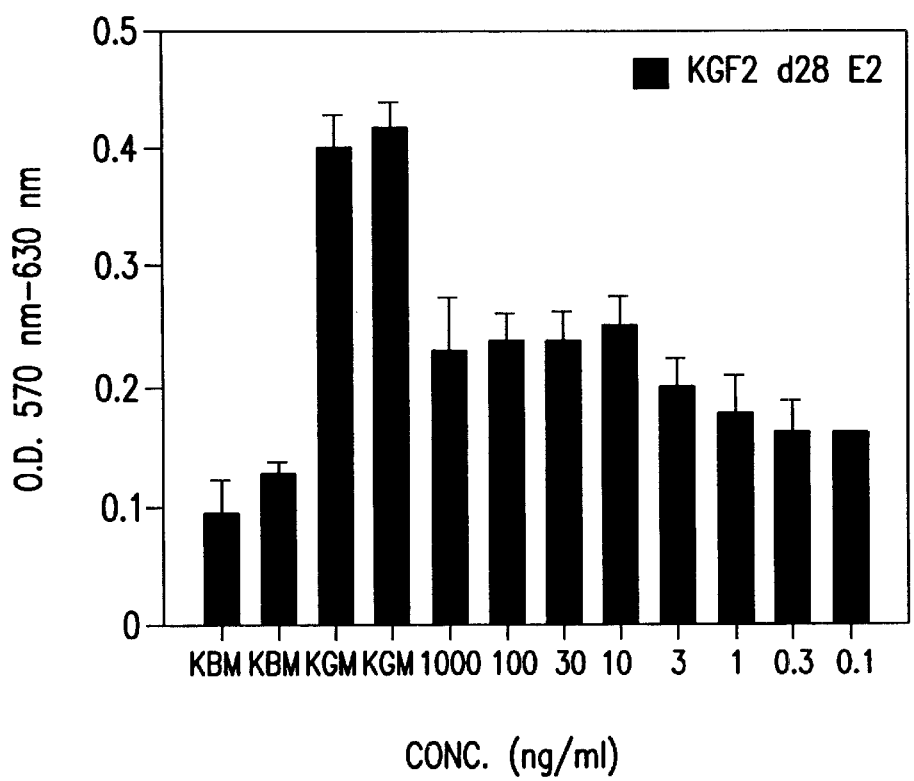

To demonstrate that KGF-2 (Cys37-Ser208 with a 6× (His) tag (SEQ ID NOs: 29–30; FIG. 5) and N-terminal deletion mutants KGF-2Δ33 and KGF-2Δ28 were active in stimulating epidermal keratinocyte growth, normal primary human epidermal keratinocytes were incubated with the *E. coli*-expressed and purified KGF-2 protein (batch number E3), KGF-2Δ33 (batch number E1) and KGF-2Δ28 (batch number E2). The KGF-2 protein stimulated the growth of epidermal keratinocytes with an EC50 of approximately 5 ng/ml, equivalent to that of FGF7/KGF-1 (FIG. 6A). In contrast, other FGF's such as FGF-1 and FGF-2 did not stimulate the growth of primary keratinocytes. The EC50 for KGF-2Δ33 was 0.2 ng/ml and that for KGF-2Δ28 2ng/ml (See FIGS. 6B and C). Thus, KGF-2 appeared to be as potent as FGF7/KGF in stimulating the proliferation of primary epidermal keratinocytes. However, KGF-2Δ33 is more potent in stimulating keratinocyte proliferation than the "Cys (37)" KGF-2 described above and the KGF-2Δ28.

Scarring of wound tissues involves hyperproliferation of dermal fibroblasts. To determine whether the stimulatory effects of KGF-2 was specific for keratinocytes but not for fibroblasts, mouse Balb.c.3T3 fibroblasts and human lung fibroblasts were tested. Neither types of fibroblasts responded to KGF-2 in proliferation assays. Therefore, KGF-2 appeared to be a mitogen specific for epidermal keratinocytes but not mesenchymal cells such as fibroblasts. This suggested that the likelihood of KGF-2 causing scarring of the wound tissues was low.

EXAMPLE 9

A. Mitogenic Effects of KGF-2 on Cells Transfected with Specific FGF Receptors

To determine which FGF receptor isoform(s) mediate the proliferative effects of KGF-2, the effects of KGF-2 on cells expressing specific FGF receptor isoforms were tested according to the method described by Santos-Ocampo et al. *J. Biol. Chem.* 271:1726–1731 (1996). FGF7/KGF was known to induce mitogenesis of epithelial cells by binding to and specifically activating the FGFR2iiib form (Miki et al. *Science* 251:72–75 (1991)). Therefore, the proliferative effects of KGF-2 in mitogenesis assays were tested using cells expressing one of the following FGF receptor isoforms: FGFR1iiib, FGFR2iiib, FGFR3iiib, and FGFR4.

Mitogenesis Assay of Cells Expressing FGF Receptors

Thymidine incorporation of BaF3 cells expressing specific FGF receptors were performed as described by Santos-Ocampo et al. *J. Biol. Chem.* 2 71:1726–1731(1996). Briefly, BaF3 cells expressing specific FGF receptors were washed and resuspended in Dubeco's modified Eagle's medium, 10% neonatal bovine serum, L-glutanime. Approximately 22,500 cells were plated per well in a 96-well assay plate in media containing 2 μg/ml Heparin. Test reagents were added to each well for a total volume of 200 μl per well. The cells were incubated for 2 days at 37° C. To each wll, 1 μCi of $^3$H-thymidine was then added in a volume of 50 μl. Cells were harvested after 4–5 hours by filtration through glass fiber paper. Incorporated $^3$H-thymidine was counted on a Wallac beta plate scintillation counter.

Results

The results revealed that KGF-2 protein (Thr (36)-Ser (208) of FIG. 1 (SEQ ID NO:2) with a N-terminal Met added thereto) strongly stimulated the proliferation of Baf3 cells expressing the KGF receptor, FGFR2iiib isoform, as indicated by $^3$H-thymidine incorporation (FIG. 7A). Interestingly, a slight stimulatory effect of KGF-2 on the proliferation of Baf3 cells expressing the FGFR1iiib isoform was observed. KGF-2 did not have any effects on cells expressing the FGFR3iiib or the FGFR4 forms of the receptor.

FGF7/KGF stimulated the proliferation of cells expressing the KGF receptor, FGFR2iiib but not FGFR1iiib isoform. The difference between KGF-2 and FGF7/KGF was intriguing. In the control experiments, aFGF stimulated its receptors, FGFR1iiib and iiic and bFGF stimulated its receptor FGFR2iiic. Thus, these results suggested that KGF-2 binds to FGFR2iiib isoform and stimulates mitogenesis. In contrast to FGF7/KGF, KGF-2 also binds FGFR 1iiib isoform and stimulates mitogenesis.

B. Mitogenic Effects of KGF-2Δ33 on Cells Transfected with Specific FGF Receptors As demonstrated above FGFs or KGF-1 and -2 both bind to and activate the FGF 2iiib receptor (FGFR 2iiib). The proliferative effects of KGF-2Δ33 in mitogenesis assays were tested using cells expressing one of the following FGF receptor isoforms: FGFR2iiib or FGFR2iiic (the 2iiic receptor-transfected cells are included as a negative control).

The experiments were performed as above in part A of this example. Briefly, BaF3 cells were grown in RPMI containing 10% bovine calf serum (BCS—not fetal serum), 10% conditioned medium from cultures of WEHI3 cells (grown in RPMI containing 5%BCS), 50 nM β-mercaptoethanol, L-Glu (2% of a 100× stock) and pen/strep (1% of a 100× stock).

For the assay, BaF3 cells were rinsed twice in RPMI medium containing 10% BCS and 1 μg/ml heparin. BaF3 cells (22,000/well) were plated in a 96-well plate in 150 μl of RPMI medium containing 10% BCS and 1 μg/ml heparin. Acidic FGF, basic FGF, KGF-1 (HG15400) or KGF-2 proteins (HG03400, 03401, 03410 or 03411) were added at concentrations from approximately 0 to 10 nM. The cells were incubated in a final volume of 200 μl for 48 hours at 37° C. All assays were done in triplicate. Tritiated thymidine (0.5 μCi) was added to each well for 4 hours at 37° C. and the cells were then harvested by filtration through a glass fiber filter. The total amount of radioactivity incorporated was then determined by liquid scintillation counting. The following positive controls were used: basic FGF and acidic FGF for FGFR2iiic cells; acidic FGF and KGF-1 for FGFR2iiib cells. The following negative controls were used: Basal medium (RPMI medium containing 10% BCS and 1 μg/ml heparin).

Results

Figure 7B:
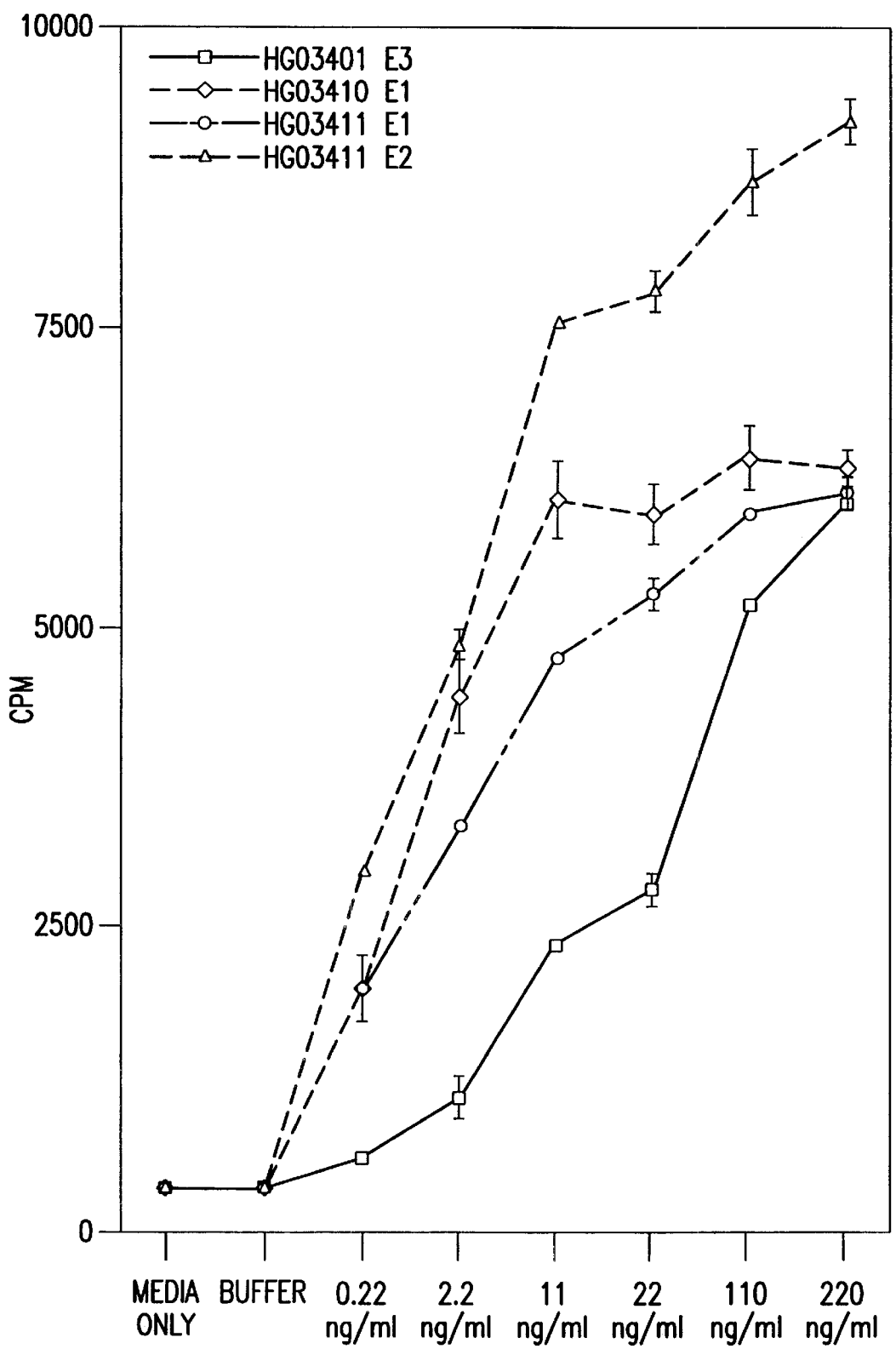
Figure 7C:
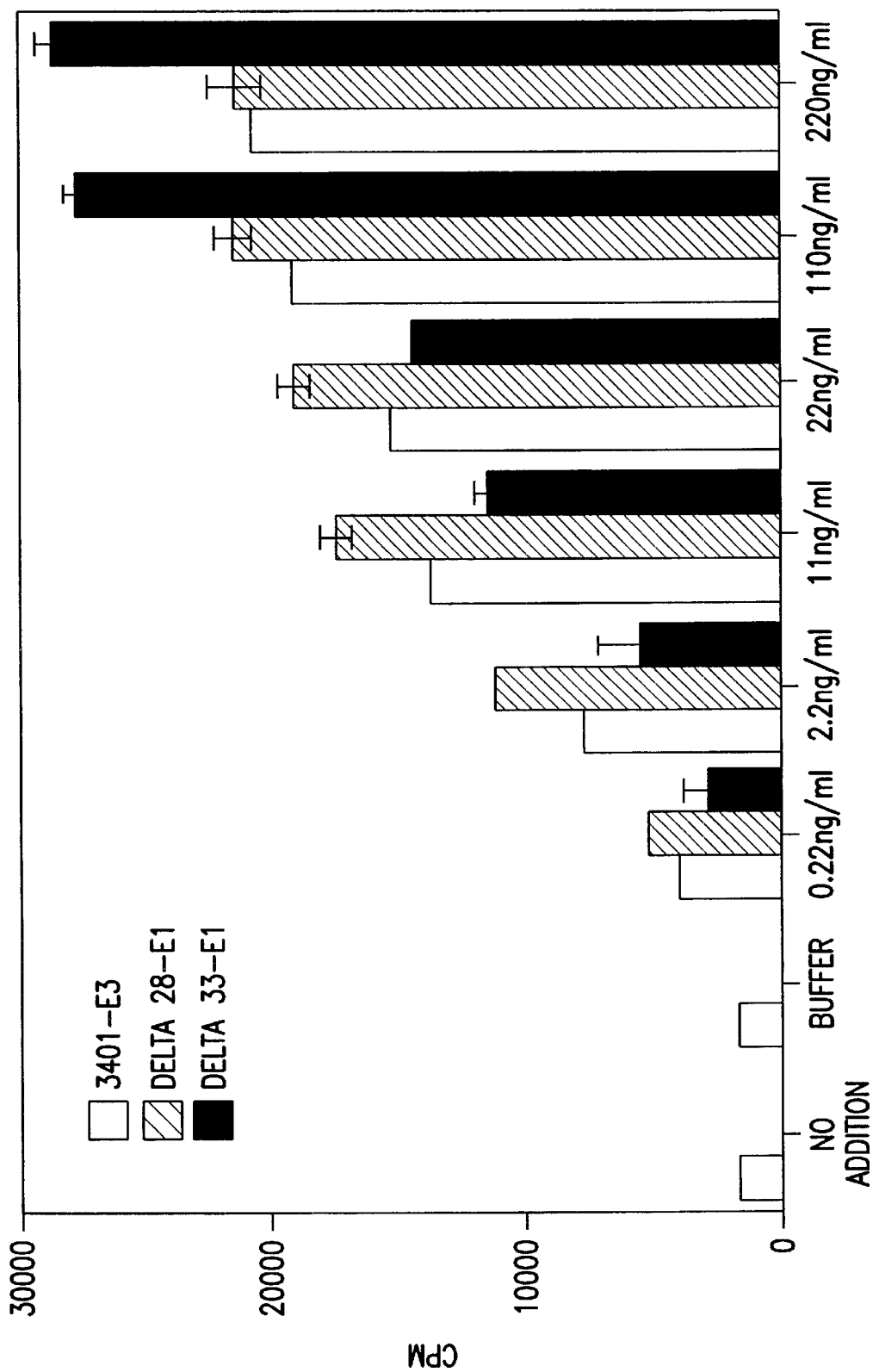

The results revealed that KGF-2 (Thr (36)-Ser (208) with N-terminal Met added), KGF-2Δ33 and KGF-2Δ28 proteins strongly stimulated the proliferation of BaF3 cells expressing the KGF receptor, FGFR2iiib isoform, as indicated by $^3$H-thymidine incorporation (FIGS. 7A–C). The KGF-2 proteins did not have any effects on cells expressing the FGFR2iiic forms of the receptor. These results suggested that KGF-2 proteins bind to FGFR2iiib isoform and stimulates mitogenesis. In addition, it appears that KGF-2Δ33 was able to stimulate the proliferation of the BaF3 cells better than the KGF-2 (Thr (36)-Ser (208)).

EXAMPLE 10

A. Construction of *E. coli* Optimized Full Length KGF-2

In order to increase expression levels of full length KGF-2 in an *E. coli* expression system, the codons of the amino terminal portion of the gene were optimized to highly used *E. coli* codons. For the synthesis of the optimized region of KGF-2, a series of six oligonucleotides were synthesized: numbers 1–6 (sequences set forth below). These overlapping oligos were used in a PCR reaction for seven rounds at the following conditions:

| Denaturation | 95 degrees | 20 seconds |
| Annealing | 58 degrees | 20 seconds |
| Extension | 72 degrees | 60 seconds |

A second PCR reaction was set up using 1 μl of the first PCR reaction with KFG-2 sythetic primer 6 as the 3' primer and KGF-2 synthetic 5' BamHI as the 5' primer using the same conditions as described above for 25 cycles. The product produced by this final reaction was restricted with AvaII and BamHI. The KGF-2 construct of Example 1 was restricted with AvaII and HindIII and the fragment was isolated. These two fragments were cloned into pQE-9 restricted with BamHI and HindIII in a three fragment ligation.

Primers used for constructing the optimized synthetic KGF-2 1/208:
KGF-2 Synthetic Primer 1:
ATGTGGAAATGGATACTGACCCACT-GCGCTTCTGCTTTCCGCACCTGC-CGGGTTGCTGCTGCTGCTGCTTCCTGCT-GCTGTTC (SEQ ID NO: 31)
KGF-2 Synthetic Primer 2:
CCGGAGAAACCATGTCCTGACCCAGAGC-CTGGCAGGTAACCGGAACAGAAGAAAC-CAGGAACAGCAGCAGGAAGCAGCAGCA (SEQ ID NO: 32)
KGF-2 Synthetic Primer 3:
GGGTCAGGACATGGTTTCTCCGGAAGC-TACCAACTCTTCTTCTTCTTCTTTCTCT-TCTCCGTCTTCTGCTGGTCGTCACG (SEQ ID NO: 33)
KGF-2 Synthetic Primer 4:
GGTGAAAGAGAACAGTTTACGCCAAC-GAACGTCACCCTGCAGGTGGTTGTAA-GAACGAACGTGACGACCAGCAGAAGACGG (SEQ ID NO:34)
KGF-2 Synthetic Primer 5:
CGTTGGCGTAAACTGTTCTCTTTCAC-CAAATACTTCCTGAAAATC-GAAAAAAACGGTAAAGTTTCTGGGACCAAA (SEQ ID NO:35)
KGF-2 Synthetic Primer 6:
TTTGGTCCCAGAAACTTTAC-CGTTTTTTTCGATTTTCAG (SEQ ID NO:36)
KGF-2 Synthetic 5' BamHI
AAAGGATCCATGTGGAAATGGATACT-GACCCACTGC (SEQ ID NO:37)

The resulting clone is shown in FIG. 10 (SEQ ID NOS: 38 and 39).

B. Construction of E. coli Optimized Mature KGF-2

In order to further increase expression levels of the mature form of KGF-2 in an E. coli expression system, the codons of the amino terminal portion of the gene were optimized to highly used E. coli codons. To correspond with the mature form of KGF-1, a truncated form of KGF-2 was constructed starting at threonine 36. E. coli synthetic KGF-2 from Example 10A was used as a template in a PCR reaction using BspHI 5' KGF-2 as the 5' primer (sequence given below) and HindIII 3' KGF-2 as the 3' primer (sequence given below). Amplification was performed using standard conditions as given above in Example 10A for 25 cycles. The resulting product was restricted with BspHI and HindII and cloned into the E. coli expression vector pQE60 digested with NcoI and HindIII.

BspHI 5' KGF-2 Primer:
TTTCATGACTTGTCAAGCTCTGGGTCAA-GATATGGTTC (SEQ ID NO:40)
HindIII 3' KGF-2 Primer:
GCCCAAGCTTCCACAAACGTTGCCTTCC (SEQ ID NO:41)

The resulting clone is shown in FIG. 11A (SEQ ID NO:42 and 43).

C. Construction of an Alternate E. coli Optimized Mature KGF-2

In order to further increase expression levels of the mature form of KGF-2 in an E. coli expression system, the codons of 53 amino acids at the amino terminal portion of the E. coli optimized gene were changed to alternate highly used E. coli codons. For the synthesis of the optimized region of KGF-2, a series of six oligonucleotides were synthesized: numbers 18062, 18061, 18058, 18064, 18059, and 18063 (sequences set forth below). These overlapping oligos were used in a PCR reaction for seven rounds at the following conditions:

| Denaturation | 95 degrees | 20 seconds |
| Annealing | 58 degrees | 20 seconds |
| Extension | 72 degrees | 60 seconds |

Following the seven rounds of synthesis, a 5' primer to this region, 18169 and a 3' primer to this entire region, 18060, were added to a PCR reaction, containing 1 microliter from the initial reaction of the six oligonucleotides. This product was amplified for 30 rounds using the following conditions:

| Denaturation | 95 degrees | 20 seconds |
| Annealing | 55 degrees | 20 seconds |
| Extension | 72 degrees | 60 seconds |

A second PCR reaction was set up to amplify the 3' region of the gene using primers 18066 and 18065 under the same conditions as described above for 25 rounds. The resulting products were separated on an agarose gel. Gel slices containing the product were diluted in 10 mM Tris, 1 mM EDTA, pH 7.5 One microliter each from each of diluted gel slices were used in an additional PCR reaction using primer 18169 as the 5' primer, and primer 18065 as the 3' primer. The product was amplified for 25 cycles using the same conditions as above. The product produced by this final reaction was and restricted with Eco R1 and HindIII, and cloned into pQE60, which was also cut with Eco R1 and HindIII (pQE6 now).

Sequences of the 5' Synthetic Primers:
18169 KGF2 5' EcoRI/RBS:
TCAGTGAATTCATTAAAGAGGAGAAAT-TAATCATGACTTGCCAGG [SEQ ID NO:44]
18062 KGF2 synth new R1 sense:
TCATGACTTGCCAGGCACTGGGTCAAGA-CATGGTTTCCCCGGAAGCTA [SEQ ID NO:45]
18061 KGF2 synth R2 sense:
GCTTCAGCAGCCCATCTAGCGCAG-GTCGTCACGTTCGCTCTTACAACC [SEQ ID NO:46]
18058 KGF2 Synth R3 sense:
GTTCGTTGGCGCAAACTGTTCAGCTT-TACCAAGTACTTCCTGAAAATC [SEQ ID NO:47]
18066 KGF 2 20 bp Ava II sense:
TCGAAAAAAACGGTAAAGTTTCTGGGAC [SEQ ID NO:48]
18064 KGF2 synth F1 antisense:
GATGGGCTGCTGAAGCTAGAGCTG-GAGCTGTTGGTAGCTTCCGGGGAA [SEQ ID NO:49]
18059 KGF2 Synth F2 antisense:
AACAGTTTGCGCCAACGAACATCACCCT-GTAAGTGGTTGTAAGAG [SEQ ID NO:50]
18063 KGF2 Synth F3 antisense:
TTCTTGGTCCCAGAAACTTTAC-CGTTTTTTTCGATTTTCAGGAAGTA [SEQ ID NO:51]
18060 KGF 2 Ava II antisense:
TTCTTGGTCCCAGAAACTTTACCG [SEQ ID NO:52]
18065 KGF2 HindIII 3' Stop:
AGATCAGGCTTCTATTATTATGAGTG-TACCACCATTGGAAGAAAG [SEQ ID NO:53]

The sequence of the synthetic KGF-2 gene and it corresponding amino acid is shown in FIG. 11B (SEQ ID NO: 54 and 55)

EXAMPLE 11
Construction of KGF-2 Deletion Mutants

Deletion mutants were constructed from the 5' terminus and 3' terminus of KGF-2 gene using the optimized KGF-2 construct from Example 10 as a template. The deletions were selected based on regions of the gene that might negatively affect expression in E. coli. For the 5' deletion the primers listed below were used as the 5' primer. These primers contain the indicated restriction site and an ATG to code for the initiator methionine. The KGF-2 208 amino acid 3' HindIII primer was used for the 3' primer. PCR amplification for 25 rounds was performed using standard conditions as set forth in Example 10. The products for the KGF-2 36aa/208aa deletion mutant were restricted BspHI for the 5' site and HindIII for the 3' site and cloned into the pQE60 which has been digested with BspHI and HindIII. All other products were restricted with NcoI for the 5' restriction enzyme and HindIII for the 3' site, and cloned into the pQE60 which had been digested with NcoI and HindIII. For KGF-2, 36aa/153aa and 128aa 3' HindIII was used as the 3' primer with KGF-2 36aa/208aa as the 5' primer. For KGF-2 62aa/153aa, 128aa 3' HindIII was used as the 3' primer with KGF-2 62aa/208aa as the 5' primer. The nomenclature of the resulting clones indicates the first and last amino acid of the polypeptide that results from the deletion. For example, KGF-2 36aa/153aa indicates that the first amino acid of the deletion mutant is amino acid 36 and the last amino acid is amino acid 153 of KGF-2. Further, as indicated in FIGS. 12–20, each mutant has N-terminal Met added thereto.

Sequences of the Deletion Primers
KGF-2 36aa/208aa:
5' BspHI GGACCCTCATGACCTGCCAG-GCTCTGGGTCAGGAC (SEQ ID NO:56)
KGF-2 63aa/208aa:
5' NcoI GGACAGCCATGGCTGGTCGTCACGTTCG (SEQ ID NO:57)
KGF-2 77aa/208aa:
5' NcoI GGACAGCCATGGTTCGTTGGCGTAACTG (SEQ ID NO:58)
KGF-2 93aa/208aa:
5' NcoI GGACAGCCATGGAAAAAAACGG-TAAAGTTTC (SEQ ID NO:59)
KGF-2 104aa/208aa:
5' NcoI GGACCCCCATGGAGAACTGCCCGTAGAGC (SEQ ID NO:60)
KGF-2 123aa/208aa:
5' NcoI GGACCCCCATGGTCAAAGCCATTAACAG-CAAC (SEQ ID NO:61)
KGF-2 138aa/208aa:
5' NcoI GGACCCCCATGGGGAAACTCTATGGCT-CAAAAG (SEQ ID NO:62)
KGF-2 3' HindIII: (Used for all Above Deletion Clones)
CTGCCCAAGCTTATTATGAGTGTACCAC-CATTGGAAG (SEQ ID NO:63)
KGF-2 36aa/153aa:
5'BsphI (as above)
3'HindIII CTGCCCAAGCTTATTACTTCAGCTTA-CAGTCATTGT (SEQ ID NO:64)
KGF-2 63aa/153aa:
5'NocI and 3'HindIII, as above The sequences for the resulting deletion mutations are set forth in FIGS. 12–20. [SEQ ID NOS:65–82]

EXAMPLE 12
Construction of Cysteine Mutants of KGF-2

Construction of C-37 mutation primers 5457 5' BsphI and 5258 173aa 3' HindIII were used to amplify the KGF-2 templated from Example 10A. Primer 5457 5' BsphI changes cysteine 37 to a serine. Amplification was done using the standard conditions outlined above in Example 10A for 25 cycles. The resulting product was restricted with BspHI and HindIII and cloned into E. coli expression vector pQE60, digested with BspHI and HindIII. (FIG. 21) (SEQ ID NO:83).

For mutation of Cysteine 106 to serine, two PCR reactions were set up for oligonucleotide site directed mutagenesis of this cysteine. In one reaction, 5453 BsphI was used as the 5' primer, and 5455 was used as the 3' primer in the reaction. In a second reaction, 5456 was used as the 5' primer, and 5258 HindIII was used as the 3' primer. The reactions were amplified for 25 rounds under standard conditions as set forth in Example 10. One microliter from each of these PCR reactions was used as template in a subsequent reaction using, as a 5' primer, 5453 BsphI, and as a 3' primer, 5258 HindIII. Amplification for 25 rounds was performed using standard conditions as set forth in Example 10. The resulting product was restricted with BspHI and HindIII and cloned into the E. coli expression vector pQE60, which was restricted with NcoI and HindIII.

Two PCR reactions were required to make the C-37/C-106 mutant. Primers 5457 BsphI and 5455 were used to create the 5' region of the mutant containing cysteine 37 to serine substitution, and primer 5456 and 5258 HindIII were used to create the 3' region of the mutant containing cysteine 106 to serine substitution. In the second reaction, the 5457 BsphI primer was used as the 5' primer and the 5258 HindIII primer was used as the 3' primer to create the C-37/C-106 mutant using 1 µl from each of the initial reactions together as the template. This PCR product was restricted with BsphI and HindIII, and cloned into pQE60 that had been restricted with NcoI and HindIII. The resulting clone is shown in FIG. 22 (SEQ ID NO:84)

Sequences of the Cysteine Mutant Primers
5457 BspHI: GGACCCTCATGACCTCTCAG-GCTCTGGGT (SEQ ID NO:85)
5456: AAGGAGAACTCTCCGTACAGC (SEQ ID NO: 86)
5455: GCTGTACGGTCTGTTCTCCTT (SEQ ID NO: 87)
5453 BspHI: GGACCCTCATGACCTGCCAG-GCTCTGGGTCAGGAC (SEQ ID NO: 88)
5258 HindIII: CTGCCCAAGCTTATTATGAGTGTAC-CACCATTGGAAG (SEQ ID NO: 89)

EXAMPLE 13
Production and Purification of KGF-2

The DNA sequence encoding the optimized mature protein described in Example 10B (i.e., amino acids T36 through S208 of KGF-2) was cloned into plasmid pQE-9 (Qiagen). E coli (M15/rep4;Qiagen) were grown to stationary phase overnight at 37° C. in 1B containing 100 µg/ml Ampicillin and 25 µg/ml Kanamycin. This culture was used to innoculate fresh LB media containing containing 100 µg/ml Ampicillin and 25 µg/ml Kanamycin at a dilution of 1:50. The cells were grown at 37° C. to an $O.D._{595}$ of 0.7, induced by the addition of isopropyl 1-thio-b-D-galactopyranoside (IPTG) to a final concentration of 1 mM. After 3–4 hours, the cells were harvested by centrifugation, and resuspended in a buffer containing 60 mM $NaPO_4$ and 360 mM NaCl at a ratio of 5 volumes of buffer: 1 volume of cell paste. After disruption in a Mautin Gaulin, the extract was adjusted to pH to 8.0 by the addition of NaOH and clarified by centrifugation.

The clarified soluble extract was applied to a Poros HS-50 column (2.0×10.0 cm; PerSeptive Biosystems, Inc.) and bound proteins step-eluted with 50 mM $NaPO_4$ pH 8.0 containing 0.5M, 1.0M and 1.5M NaCl. The KGF-2 in the 1.5M salt fraction which was the diluted five-fold with 50 mM NaPO$_4$ pH 6.5 to a final salt concentration of 300 mM. This KGF-2 containing fraction was then passed sequentially over a Poros HQ-20 column (2.0×7.0 cm; PerSeptive Biosystems, Inc.) and then bound to a Poros HQ-20 column (2.0×9.0 cm; PerSeptive Biosystems, Inc.). KGF-2 containing fractions that eluted at about 500 mM to about 750 mM NaCl were pooled, diluted and re-applied to an CM-20 column to concentrate. Finally, the protein was separated on a gel filtration column (S-75; Pharmacia) in 40 mM NaOAC pH6.5; 150 mM NaCl (Batch E-5) Alternatively, the gel filtration column was run in Phosphate Buffered Saline (PBS, Batch E-4). KGF-2 containing fractions were pooled and protein concentration determined by Bio-Rad Protein Assay. Proteins were judged to be <90% pure by SDS-PAGE. Finally, endotoxin levels determined by Limulus Amebocyte Lysate Assay (Cape Cod Associates) were found to be ≦1 Eu/mg. Proteins prepared in this way were able to bind haparin which is a hallmark of FGF family members.

EXAMPLE 14

A. Construction of N-terminal Deletion Mutant KGF-2Δ33

To increase the level of expression of KGF2 in *E.coli*, and to enhance the solubilty and stability properties of *E.coli* expressed KGF2, a deletion variant KGF-2Δ33 (KGF-2 aa 69–208) (SEQ ID NO:96) which removes the first 68 amino acids of the pre-processed KGF2 was generated. The rationale for creating this deletion variant was based on the following observations. Firstly, mature KGF2(KGF-2 aa 36–208) contains an uneven number (three) of cysteine residues which can lead to aggregation due to intra-molecular disulphide bridge formation. The KGF Δ33 deletion variant contains only two cysteine residues, which reduces the potential for intra-molecular disulphide bridge formation and subsequent aggregation. A decrease in aggregation should lead to an increase in the yield of active KGF2 protein. Secondly, the KGF Δ33 deletion variant removes a poly-serine stretch which is not present in KGF-1 and does not appear to be important for activity, but may hinder expression of the protein in *E. coli*. Thus, removal of the poly-serine stretch may increase expression levels of active KGF-2 protein. Thirdly, expression of KGF Δ33 in *E.coli*, results in natural cleavage of KGF-2 between residues 68 and 69. Thus, it is anticipated that KGF2 Δ33 will be processed efficiently and will be stable in *E.coli*.

Construction of KGF-2Δ33 in pQE6

To permit Polymerase Chain Reaction directed amplification and sub-cloning of KGF2 Δ33 into the *E.coli* protein expression vector, pQE6, two oligonucleotide primers (5952 and 19138) complementary to the desired region of KGF2 were synthesized with the following base sequence.

Primer 5952: 5' GCGGCACATGTCTTACAACCACCTG-CAGGGTG 3' (SEQ ID NO:91)

Primer 19138: 5' GGGCCCAAGCTTATGAGTGTACCAC-CAT 3' (SEQ ID NO:92)

In the case of the N-terminal primer (5952), an AflIII restriction site was incorporated, while in the case of the C-terminal primer (19138) a HindIII restriction site was incorporated. Primer 5952 also contains an ATG sequence adjacent and in frame with the KGF2 coding region to allow translation of the cloned fragment in *E.coli*, while primer 19138 contains two stop codons (preferentially utilized in *E.coli*) adjacent and in frame with the KGF2 coding region which ensures correct translational termination in *E.coli*.

The Polymerase Chain Reaction was performed using standard conditions well known to those skilled in the art and the nucleotide sequence for the mature KGF-2 (aa 36–208) (constructed in Example 10C) as template. The resulting amplicon was restriction digested with AflIII and HindIII and subcloned into NcoI/HindIII digested pQE6 protein expression vector.

Construction of KGF-2Δ33 in pHE1

To permit Polymerase Chain Reaction directed amplification and subcloning of KGF2 Δ33 into the *E.coli* expression vector, pHE1, two oligonucleotide primers (6153 and 6150) corresponding to the desired region of KGF2 were synthesized with the following base sequence.

Primer 6153: 5' CCGGCGGATCCCATATGTCTTACAAC-CACCTGCAGG 3' (SEQ ID NO:93)

Primer 6150: 5' CCGGCGGTACCTTATTATGAGTGTAC-CACCATTGG 3' (SEQ ID NO:94)

In the case of the N-terminal primer (6153), an NdeI restriction site was incorporated, while in the case of the C-terminal primer (6150) an Asp718 restriction site was incorporated. Primer 6153 also contains an ATG sequence adjacent and in frame with the KGF2 coding region to allow translation of the cloned fragment in *E.coli*, while primer 6150 contains two stop codons (preferentially utilized in *E.coli*) adjacent and in frame with the KGF2 coding region which ensures correct translational termination in *E.coli*.

The Polymerase Chain Reaction was performed using standard conditions well known to those skilled in the art and the nucleotide sequence for the mature KGF-2 (aa 36–208) (constructed in Example 10C) as template. The resulting amplicon was restriction digested with NdeI and Asp718 and subcloned into NdeI/Asp718 digested pHE1 protein expression vector.

Nucleotide Sequence of KGF-2 Δ33
ATGTCTTACAACCACCTGCAGGGT-GACGTTCGTTGGCGTAAACTGT-TCTCTTTCACCAAATACTTCCT-GAAAATCGAAAAAAACGGTAAAGTTTCTGGGA CCAAGAAGGAGAACTGCCCGTACAG-CATCCTGGAGATAACATCAGTA-GAAATCGGAGTTGTTGCCGTCAAAGC-CATTAACAGCAACTATTACTTAGCCATGAACAA GAAGGGGAAACTCTATGGCTCAAAA-GAATTTAACAATGACTGTAAGCTGAAG-GAGAGGATAGAGGAAAATGGATA-CAATACCTATGCATCATTTAACTGGCAGCATAAT GGGAGGCAAATGTATGTGGCATTGAATG-GAAAAGGAGCTCCAAGGAGAGGACA-GAAAACACGAAGGAAAAACACCTCTGCT-CACTTTCTTCCAATGGTGGTACACTCATAA (SEQ ID NO:95)

Amino Acid Sequence of KGF-2 Δ33
MSYNHLQGDVRWRKLFSFTKYFLK-IEKNGKVSGTKKENCPYSILEITS-VEIGVVAVKAINSNYYLAMNKKGKLYG-SKEFNNDCKLKERIEENGYNTYASFNWQHNGRQ MYVALNGKGAPRRGQKTRRKNTSAHFLPMVVHS (SEQ ID NO:96)

B. Construction of an Optimized KGF-2Δ33

In order to increase the expression levels of KGF2 Δ33 in *E.coli*, the codons of the complete gene were optimized to match those most highly used in *E.coli*. As the template utilised to generate the KGF2 Δ33 was codon optimized within the N-terminal region, the C-terminal amino acids (84–208) required optimization.

Firstly, amino acids 172–208 were codon optimized to generate KGF2Δ33(s172–208). This was achieved by an overlapping PCR strategy. Oligonucleotides PM07 and PM08 (corresponding to amino acids 172–208) were combined and annealed together by heating them to 70° C. and allowing them to cool to 37° C. The annealed oligonucleotides were then utilized as template for a standard PCR reaction which was directed by primers PM09 and PM10. In a separate PCR reaction following standard conditions well known to those skilled in the art and using KGF2Δ33 as template, oligonucleotides PM05 (which overlaps with the Pst1 site within coding region of KGF2) and PM11 were used to amplify the region of KGF2 corresponding to amino acids 84–172. In a third PCR reaction, the product of the first PCR reaction (corresponding to codon optimized amino acids 172–208) and the product of the second PCR reaction (corresponding to codon non-optimized amino acids 84–172) were combined and used as template for a standard PCR reaction directed by oligonucleotides PM05 and PM10. The resulting amplicon was digested with Pst1/HindIII and sub-cloned into Pst1/HindIII digested pQE6KGF2Δ33, effectively substituting the corresponding non codon optimized region, and creating pQE6KGF2Δ33(s172–208).

To complete the codon optimization of KGF2, a synthetic gene codon optimized for the region of KGF2 corresponding to amino acids 84–172 was generated utilising overlapping oligonucleotides. Firstly, four oligonucleotides (PM31, PM32, PM33 and PM 34) were combined and seven cycles of the following PCR was performed: 94° C., 30 secs; 46.5° C., 30 secs; and 72° C., 30 secs.

A second PCR reaction directed by primers PM35 and PM36 was then performed following standard procedures, utilizing 1 μl of the first PCR reaction as template. The resulting codon optimized gene fragment was then digested with Pst1/Sal1 and subcloned into Pst1/Sal1 digested pQE6KGF2Δ33(s172–208) to create a fully optimized KGF2 encoding gene, pQE6KGF2Δ33s.

To create an alternative E.coli protein expression vector, KGF2Δ33s was PCR amplified utilising primers PM102 and PM130 on pQE6KGF2Δ33s. The resulting amplicon was digested with NdeI and EcoRV and subcloned into the pHE11 expression vector which had been digested with NdeI and Asp718 (blunt ended) to create pHE1Δ33s.

Oligonucleotide Sequences used in construction of codon optimized KGF2 Δ33s:
PM05: CAACCACCTGCAGGGTGACG (SEQ ID NO:97)
PM07: AACGGTCGACAAATGTATGTGGCACT-GAACGGTAAAGGTGCTCCACGTCGTGGT-CAGAAAACCCGTCGTAAAAACACC (SEQ ID NO:98)
PM08: GGGCCCAAGCTTAAGAGTGTACCACCAT-TGGCAGAAAGTGAGCAGAGGTGTTTT-TACGACGGGTTTTCTGACCACG (SEQ ID NO:99)
PM09: GCCACATACATTTGTCGACCGTT (SEQ ID NO:100)
PM10: GGGCCCAAGCTTAAGAGTG (SEQ ID NO:101)
PM11: GCCACATACATTTGTCGACCGTT (SEQ ID NO:102)
PM31: CTGCAGGGTGACGTTCGTTGGCG-TAAACTGTTCTCCTTCACCAAATACTTC-CTGAAAATCGAAAAAACGG-TAAAGTTTCTGGTACCAAG (SEQ ID NO:103)
PM32: AGCTTTAACAGCAACAACAC-CGATTTCAACGGAGGTGATTCCAG-GATGGAGTACGGGCAGTTTTCTTTCTTG-GTACCAGAAACTTTACC (SEQ ID NO:104)
PM33: GGTGTTGTTGCTGTTAAAGCTAT-CAACTCCAACTACTACCTGGCTATGAA-CAAGAAAGGTAAACTGTACGGTTCCAAA-GAATTAACAAC (SEQ ID NO: 105)
PM34: GTCGACCGTTGTGCTGCCAGTTGAAG-GAAGCGTAGGTGTTGTAACCGTTTTCT-TCGATACGTTCTTTCAGTTTACAGTCGT-TGTTAAATTCTTTGGAACC (SEQ ID NO:106)

PM35: GCGGCGTCGACCGTTGTGCTGCCAG (SEQ ID NO:107)
PM36: GCGGCCTGCAGGGTGACGTTCGTTGG (SEQ ID NO:108)
PM 102: CCGGCGGATCCCATATGTCTTACAAC-CACCTGCAGG (SEQ ID NO:109)
PM130: CGCGCGATATCTTATTAAGAGTGTAC-CACCATTG (SEQ ID NO:110)
Nucleotide Sequence of KGF-2 Δ33(s172–208)
ATGTCTTACAACCACCTGCAGGGT-GACGTTCGTTGGCGTAAACTGTTCTCCT-TCACCAAATACTTCCTGAAAATC-GAAAAAAACGGTAAAGTTTCTGGTACCAAGAA AGAAAACTGCCCGTACTCCATCCTG-GAAATCACCTCCGTTGAAATCGGTGT-TGTTGCTGTTAAAGCTATCAACTCCAAC-TACTACCTGGCTATGAACAAGAAAGGTAAACT GTACGGTTCCAAAGAATTTAACAAC-GACTGTAAACTGAAAGAACGTATCGAA-GAAAACGGTTACAACACCTACGCTTCCT-TCAACTGGCAGCACAACGGTCGACAAATGTATG TGGCACTGAACGGTAAAGGTGCTC-CACGTCGTGGTCAGAAAACCCGTCG-TAAAAACACCTCTGCTCACTTTCTGC-CAATGGTGGTACACTCTTAA (SEQ ID NO:111)
Amino Acid Sequence of KGF-2 Δ33(s172–208)
MSYNHLQGDVRWRKLFSFTKYFLK-IEKNGKVSGTKKENCPYSILEITS-VEIGVVAVKAINSNYYLAMNKKGKLYG-SKEFNNDCKLKERIEENGYNTYASFNWQHNGRQ MYVALNGKGAPRRGQKTRRKNTSAHFLPMVVHS (SEQ ID NO:112)
C. Construction of N-terminal Deletion Mutant KGF-2Δ4

To increase the level of expression of KGF2 in E.coli and to enhance the stability and solubility properties of E.coli expressed KGF2, a deletion variant KGF2Δ4 (amino acids 39–208) which removes the first 38 amino acids of pre-processed KGF2 was constructed, including the cysteine at position 37. As the resulting KGF2 deletion molecule contains an even number of cysteines, problems due to aggregation caused by intra-molecular disulphide bridge formation should be reduced, resulting in an enhanced level of expresssion of active protein.

To permit Polymerase Chain Reaction directed amplification and sub-cloning of KGF2 Δ4 into the E.coli protein expression vector, pQE6, two oligonucleotide primers (PM61 and 19138) were synthesized with the following base sequence.
PM61: CGCGGCCATGGCTCTGGGTCAGGACATG (SEQ ID NO:113)
19138: GGGCCCAAGCTTATGAGTGTACCACCAT (SEQ ID NO:114)

In the case of the N-terminal primer (PM61), an NcoI restriction site was incorporated, while in the case of the C-terminal primer (19138) a HindIII restriction site was incorporated. PM61 also contains an ATG sequence adjacent and in frame with the KGF2 coding region to allow translation of the cloned fragment in E.coli, while 19138 contains a stop codon (preferentially utilized in E.coli) adjacent to and in frame with the KGF2 coding region which ensures correct translational termination in E.coli.

The Polymerase Chain Reaction was performed using standard conditions well known to those skilled in the art and the full length KGF2 (aa 36–208) as template (constructed in Example 10C). The resulting amplicon was restriction digested with NcoI and HindIII and subcloned into NcoI/HindIII digested pQE6 protein expression vector.

Nucleotide Sequence of KGF-2 Δ4
ATGGCTCTGGGTCAAGATATGGTTTCTC-
CGGAAGCTACCAACTCTTCCTCTTC-
CTCTTCTCTTCCCCGTCTTCCGCTG-
GTCGTCACGTTCGTTCTTACAACCACCTGCAGG
GTGACGTTCGTTGGCGTAAACTGT-
TCTCTTTCACCAAATACTTCCT-
GAAAATCGAAAAAAACGG-
TAAAGTTTCTGGGACCAAGAAGGAGAACTGCC
CGTACAGCATCCTGGAGATAACATCAG-
TAGAAATCGGAGTTGTTGCCGTCAAAGC-
CATTAACAGCAACTATTACTTAGCCAT-
GAACAAGAAGGGGAAACTCTATGGCTCAAAAG
AATTTAACAATGACTGTAAGCTGAAG-
GAGAGGATAGAGGAAAATGGATA-
CAATACCTATGCATCATTTAACTGGCAG-
CATAATGGGAGGCAAATGTATGTGGCATTGAAT
GAAAAGGAGCTCCAAGGAGAGGACA-
GAAAACACGAAGGAAAAACACCTCTGCT-
CACTTTCTTCCAATGGTGGTACACTCATAA (SEQ ID NO: 115)

Amino Acid Sequence of KGF-2Δ4
MALGQDMVSPEATNSSSSSF-
SSPSSAGRHVRSYNHLQGDVRWRKLFS-
FTKYFLKIEKNGKVSGTKKENCPYSILE-
ITSVEIGVVAVKAINSNYYLAMNKKGKLYGSKEF
NNDCKLKERIEENGYNTYASFNWQH-
NGRQMYVALNGKGAPRRGQKTRRKNT-
SAHFLPMVVHS (SEQ ID NO:116)

EXAMPLE 15
Construction of Carboxy Terminal Mutations in KGF-2

The carboxyl terminus of KGF-2 is highly charged. The density of these charged residues may affect the stability and consequently the solubility of the protein. To produce muteins that might stabilize the protein in solution a series of mutations were created in this region of the gene.

To create point mutants 194R/E, 194R/Q, 191 K/E, 191 K/Q, 188R/E, 188R/Q, the 5952 KGFΔ33 5' Afl III 5' primer was used with the indicated 3' primers, which contain the appropriate point mutations for KGF-2, in PCR reactions using standard conditions well known to those skilled in the art with KGF-2Δ33 as template. The resulting products were restricted with AflIII and Hind III and cloned into the E. coli expression vector, pQE60 restricted with NcoI and Hind III.

KGF-2Δ33,194 R/E Construction
The following primers were used:
5952 KGF Δ 33 5' Afl III:
5' GCGGCACATGTCTTACAACCACCTGCAGGGTG 3' (SEQ ID NO:117)
KGF2 3'HindIII 194aa R to E:
5'CTGCCC
AAGCTTTTATGAGTGTACCACCATTGGAAGAAA
GTGAGCAGAGGTGTTTTT
TTCTCGTGTTTTCTGTCC 3' (SEQ ID NO:118)
KGF-2Δ33,194 R/E Nucleotide Sequence
ATGTCTTACAACCACCTGCAGGGT-
GACGTTCGTTGGCGTAAACTGT-
TCTCTTTCACCAAATACTTCCT-
GAAAATCGAAAAAAACGGTAAAGTTTCTGGGA
CCAAGAAGGAGAACTGCCCGTACAG-
CATCCTGGAGATAACATCAGTA-
GAAATCGGAGTTGTTGCCGTCAAAGC-
CATTAACAGCAACTATTACTTAGCCATGAACAA
GAAGGGGAAACTCTATGGCTCAAAA-
GAATTTAACAATGACTGTAAGCTGAAG-
GAGAGGATAGAGGAAAATGGATA-
CAATACCTATGCATCATTTAACTGGCAGCATAAT
GGGAGGCAAATGTATGTGGCATTGAATG-
GAAAAGGAGCTCCAAGGAGAGGACA-
GAAAACACGA
GAAAAAAACACCTCTGCTCACTTTCTTCCAATG
GTGGTACACTCATAG (SEQ ID NO:119)
KGF-2Δ33,194 R/E Amino Acid Sequence
MSYNHLQGDVRWRKLFSFTKYFLK-
IEKNGKVSGTKKENCPYSILEITS-
VEIGVVAVKAINSNYYLAMNKKGKLYG-
SKEFNNDCKLKERIEENGYNTYASFNWQHNGRQ
MYVALNGKGAPRRGQKTREKNTSAHFLPMVVHS (SEQ ID NO:120)
KGF-2 Δ33,194 R/Q Construction
The following primers were used:
5952 KGF Δ33 5' Afl III:
5' GCGGCACATGTCTTACAACCACCTGCAGGGTG 3' (SEQ ID NO:121)
KGF2 3' HindIII 194 aa R to Q:
5'CTGCCC
AAGCTTTTATGAGTGTACCACCATTGGAAGAAA
GTGAGCAGAGGTGTTTTT
CTGTCGTGTTTTCTGTCC 3' (SEQ ID NO:122)
KGF-2 Δ33,194 R/Q Nucleotide Sequence
ATGTCTTACAACCACCTGCAGGGT-
GACGTTCGTTGGCGTAAACTGT-
TCTCTTTCACCAAATACTTCCT-
GAAAATCGAAAAAAACGGTAAAGTTTCTGGGA
CCAAGAAGGAGAACTGCCCGTACAG-
CATCCTGGAGATAACATCAGTA-
GAAATCGGAGTTGTTGCCGTCAAAGC-
CATTAACAGCAACTATTACTTAGCCATGAACAA
GAAGGGGAAACTCTATGGCTCAAAA-
GAATTTAACAATGACTGTAAGCTGAAG-
GAGAGGATAGAGGAAAATGGATA-
CAATACCTATGCATCATTTAACTGGCAGCATAAT
GGGAGGCAAATGTATGTGGCATTGAATG-
GAAAAGGAGCTCCAAGGAGAGGACA-
GAAAACACGA
CAGAAAAACACCTCTGCTCACTTTCTTCCAAT
GGTGGTACACTCATAG (SEQ ID NO:123)
KGF-2 Δ33,194 R/Q Amino Acid Sequence
MSYNHLQGDVRWRKLFSFTKYFLK-
IEKNGKVSGTKKENCPYSILEITS-
VEIGVVAVKAINSNYYLAMNKKGKLYG-
SKEFNNDCKLKERIEENGYNTYASFNWQHNGRQ
MYVALNGKGAPRRGQKTRQKNTSAHFLPMVVHS (SEQ ID NO:124)
KGF-2Δ33,191 K/E Construction
The following primers were used:
5952 KGF Δ 33 5' Afl III:
5' GCGGCACATGTCTTACAACCACCTGCAGGGTG 3' (SEQ ID NO:125)
KGF2 3' HindIII 191aa K to E
5'CTGCCC
AAGCTTTTATGAGTGTACCACCATTGGAAGAAA
GTGAGCAGAGGTGTTTTTCCTTCGTGT
TTCCTGTCCTCTCCTTGG 3' (SEQ ID NO:126)
KGF-2Δ33,191 K/E Nucleotide Sequence
ATGTCTTACAACCACCTGCAGGGT-
GACGTTCGTTGGCGTAAACTGT-
TCTCTTTCACCAAATACTTCCT-
GAAAATCGAAAAAAACGGTAAAGTTTCTGGGA
CCAAGAAGGAGAACTGCCCGTACAG-
CATCCTGGAGATAACATCAGTA-
GAAATCGGAGTTGTTGCCGTCAAAGC-
CATTAACAGCAACTATTACTTAGCCATGAACAA
GAAGGGGAAACTCTATGGCTCAAAA- GAATTTAACAATGACTGTAAGCTGAAG-
GAGAGGATAGAGGAAAATGGATA-
CAATACCTATGCATCATTTAACTGGCAGCATAAT
GGGAGGCAAATGTATGTGGCATTGAATG-
GAAAAGGAGCTCCAAGGAGAGGACAG
GAAACACGAAGGAAAAACACCTCTGCTCACTT
TCTTCCAATGGTGGTACACTCATAG (SEQ ID
NO:127)
KGF-2Δ33,191 K/E Amino Acid Sequence
MSYNHLQGDVRWRKLFSFTKYFLK-
IEKNGKVSGTKKENCPYSILEITS-
VEIGVVAVKAINSNYYLAMNKKGKLYG-
SKEFNNDCKLKERIEENGYNTYASFNWQHNGRQ
MYVALNGKGAPRRGQETRRKNTSAHFLPMVVHS
(SEQ ID NO: 128)
KGF-2 Δ33,191 K/Q Construction
The following primers were used:
5952 KGFΔ33 5' Afl III:
5' GCGGCACATGTCTTACAACCACCTGCAGGGTG 3'
(SEQ ID NO:129)
KGF2 3' HindIII 191aa K to Q
5'                                                                                  CTGCCC
AAGCTTTTATGAGTGTACCACCATTGGAAGAAA
GTGAGCAGAGGTGTTTTTCCTTCGTGT
CTGCTGTCCTCTCCTTGG 3' (SEQ ID NO: 130)
KGF-2 Δ33, 191 K/Q Nucleotide Sequence
ATGTCTTACAACCACCTGCAGGGT-
GACGTTCGTTGGCGTAAACTGT-
TCTCTTTCACCAAATACTTCCT-
GAAAATCGAAAAAAACGGTAAAGTTTCTGGGA
CCAAGAAGGAGAACTGCCCGTACAG-
CATCCTGGAGATAACATCAGTA-
GAAATCGGAGTTGTTGCCGTCAAAGC-
CATTAACAGCAACTATTACTTAGCCATGAACAA
GAAGGGGAAACTCTATGGCTCAAAA-
GAATTTAACAATGACTGTAAGCTGAAG-
GAGAGGATAGAGGAAAATGGATA-
CAATACCTATGCATCATTTAACTGGCAGCATAAT
GGGAGGCAAATGTATGTGGCATTGAATG-
GAAAAGGAGCTCCAAGGAGAGGACAG
CAGACACGAAGGAAAAACACCTCTGCTCACTT
TCTTCCAATGGTGGTACACTCATAG (SEQ ID NO: 131)
KGF-2 Δ33, 191 K/Q Amino Acid Sequence
MSYNHLQGDVRWRKLFSFTKYFLK-
IEKNGKVSGTKKENCPYSILEITS-
VEIGVVAVKAINSNYYLAMNKKGKLYG-
SKEFNNDCKLKERIEENGYNTYASFNWQHNGRQ
MYVALNGKGAPRRGQQTRRKNTSAHFLPMVVHS
(SEQ ID NO: 132)
KGF-2Δ33, 188R/E Construction
The following primers were used:
5952 KGFΔ33 5' Afl III:
5' GCGGCACATGTCTTACAACCACCTGCAGGGTG 3'
(SEQ ID NO: 133)
KGF2 3' HindIII 188aa R to E:
5'CTGCCC
AAGCTTTTATGAGTGTACCACCATTGGAAGAAA
GTGAGCAGAGGTGTTTTTCCTTCGT-
GTTTTCTGTCCTTCCCTTGGAGCTCCTTT 3' (SEQ ID NO:134)
KGF-2Δ33, 188R/E Nucleotide Sequence
ATGTCTTACAACCACCTGCAGGGT-
GACGTTCGTTGGCGTAAACTGT-
TCTCTTTCACCAAATACTTCCT-
GAAAATCGAAAAAAACGGTAAAGTTTCTGGGA
CCAAGAAGGAGAACTGCCCGTACAG-
CATCCTGGAGATAACATCAGTA-
GAAATCGGAGTTGTTGCCGTCAAAGC-
CATTAACAGCAACTATTACTTAGCCATGAACAA
GAAGGGGAAACTCTATGGCTCAAAA-
GAATTTAACAATGACTGTAAGCTGAAG-
GAGAGGATAGAGGAAAATGGATA-
CAATACCTATGCATCATTTAACTGGCAGCATAAT
GGGAGGCAAATGTATGTGGCATTGAATG-
GAAAAGGAGCTCCAAGG
GAAGGACAGAAAACACGAAGGAAAAACACC
TCTGCTCACTTTCTTCCAATGGTGGTA-
CACTCATAG (SEQ ID NO:135)
KGF-2Δ33, 188R/E Amino Acid Sequence
MYNHLQGDVRWRKLFSFTKYFLK-
IEKNGKVSGTKKENCPYSILEITS-
VEIGVVAVKAINSNYYLAMNKKGKLYG-
SKEFNNDCKLKERIEENGYNTYASFNWQHNGRQ
MYVALNGKGAPREGQKTRRKNTSAHFLPMVVHS
(SEQ ID NO: 136)
KGF-2Δ33, 188 R/Q Construction
The following primers were used:
5952 KGF Δ33 5' Afl III:
5' GCGGCACATGTCTTACAACCACCTGCAGGGTG 3'
(SEQ ID NO:137)
KGF2 3' HindIII 188aa R to Q:
5'CTGCCC
AAGCTTTTATGAGTGTACCACCATTGGAAGAAA
GTGAGCAGAGGTGTTTTTCCTTCGT-
GTTTTCTGTCCCTGCCTTGGAGCTCCTTT 3' (SEQ ID NO:138)
KGF-2Δ33, 188 R/Q Nucleotide Sequence
ATGTCTTACAACCACCTGCAGGGT-
GACGTTCGTTGGCGTAAACTGT-
TCTCTTTCACCAAATACTTCCT-
GAAAATCGAAAAAAACGGTAAAGTTTCTGGGA
CCAAGAAGGAGAACTGCCCGTACAG-
CATCCTGGAGATAACATCAGTA-
GAAATCGGAGTTGTTGCCGTCAAAGC-
CATTAACAGCAACTATTACTTAGCCATGAACAAG
AAGGGGAAACTCTATGGCTCAAAA-
GAATTTAACAATGACTGTAAGCTGAAG-
GAGAGGATAGAGGAAAATGGATA-
CAATACCTATGCATCATTTAACTGGCAGCATAAT
GGGAGGCAAATGTATGTGGCATTGAATG-
GAAAAGGAGCTCCAAGG
CAGGGACAGAAAACACGAAGGAAAAACACCT
CTGCTCACTTTCTTCCAATGGTGGTA-
CACTCATAG (SEQ ID NO:139)
KGF-2Δ33, 188 R/Q Amino Acid Sequence
MSYNHLQGDVRWRKLFSFTKYFLK-
IEKNGKVSGTKKENCPYSILEITS-
VEIGVVAVKAINSNYYLAMNKKGKLYG-
SKEFNNDCKLKERIEENGYNTYASFNWQHNGRQ
MYVALNGKGAPRQGQKTRRKNTSAHFLPMVVHS
(SEQ ID NO:140)
KGF-2 Δ33, 183K/E Construction
For mutation 183K/E, two PCR reactions were set up for oligonucleotide site directed mutagenesis of this lysine. In one reaction, 5952 KGFΔ 33 5' AflIII was used as the 5' primer, and KGF2 183aa K to E antisense was used as the 3' primer in the reaction. In a second reaction, KGF2 5' 183aa K to E sense was used as the 5' primer, and KGF2 3' HindIII TAA stop was used as the 3' primer. KGF-2 Δ33 was used as template for these reactions. The reactions were amplified under standard conditions well known to those skilled in the art. One microliter from each of these PCR reactions was used as template in a subsequent reaction using, as a 5' primer, 5453 BsphI, and as a 3' primer, 5258 HindIII. Amplification was performed using standard conditions well known to those skilled in the art. The resulting product was restricted with Afl III and HindIII and cloned into the *E. coli* expression vector pQE60, which was restricted with NcoI and HindIII.

The following primers were used:
5952 KGF Δ33 5' Afl III:
5' GCGGCACATGTCTTACAACCACCTGCAGGGTG 3' (SEQ ID NO:141)
KGF2 5' 183aa K to E sense:
5' TTGAATGGAGAAGGAGCTCCA 3' (SEQ ID NO:142)
KGF2 183aa K to E antisense:
5' TGGAGCTCCTTCTCCATTCAA 3' (SEQ ID NO:143)
KGF2 3' HindIII TAA stop:
5' CTGCCCAAGCTTTTATGAGTGTACCACCATTGG 3' (SEQ ID NO:144)
KGF-2 Δ33, 183K/E Nucleotide Sequence
ATGTCTTACAACCACCTGCAGGGT-
GACGTTCGTTGGCGTAAACTGT-
TCTCTTTCACCAAATACTTCCT-
GAAAATCGAAAAAAACGGTAAAGTTTCTGGGA
CCAAGAAGGAGAACTGCCCGTACAG-
CATCCTGGAGATAACATCAGTA-
GAAATCGGAGTTGTTGCCGTCAAAGC-
CATTAACAGCAACTATTACTTAGCCATGAACAA
GAAGGGGAAACTCTATGGCTCAAAA-
GAATTTAACAATGACTGTAAGCTGAAG-
GAGAGGATAGAGGAAAATGGATA-
CAATACCTATGCATCATTTAACTGGCAGCATAAT
GGGAGGCAAATGTATGTGGCATTGAATGGA
GAAGGAGCTCCAAGGAGAGGACAGAAAACAC
GAAGGAAAAACACCTCTGCTCACTTTCT-
TCCAATGGTGGTACACTCATAG (SEQ ID NO:145)
KGF-2 Δ33, 183K/E Amino Acid Sequence
MSYNHLQGDVRWRKLFSFTKYFLK-
IEKNGKVSGTKKENCPYSILEITS-
VEIGVVAVKAINSNYYLAMNKKGKLYG-
SKEFNNDCKLKERIEENGYNTYASFNWQHNGRQ
MYVALNGEGAPRRGQKTRRKNTSAHFLPMVVHS (SEQ ID NO:146)

EXAMPLE 16
Effects of KGF-2 Δ33 on Normal Urinary Bladder and Prostate and in Cyclophosphamide-Induced Hemorrhagic Cystitis in Rats This example demonstrates that KGF-2 Δ33 is capable of stimulating urinary bladder proliferation in normal rats and that there is a therapeutic effect of KGF-2 Δ33 in a rat model of cyclophosphamide-induced hemorrhagic cystitis.

Some cytotoxic agents used clinically have side effects resulting in the inhibition of the proliferation of the normal epithelium in the bladder, leading to potentially life-threatening ulceration and breakdown in the epithelial lining of the bladder. For example, cyclophosphamide causes hemorrhagic cystitis in some patients, a complication which can be severe and in some cases fatal. Fibrosis of the urinary bladder may also develop with or without cystitis. This injury is thought to be caused by cyclophosphamide metabolites excreted in the urine. Hematuria caused by cyclophosphamide usually is present for several days, but may persist. In severe cases medical or surgical treatment is required. Instances of severe hemorrhagic cystitis result in discontinued cyclophosphamide therapy. In addition, urinary bladder malignancies. generally occur within two years of cyclophosphamide treatment and occurs in patients who previously had hemorrhagic cystitis (CYTOXAN (cyclophosphamide) package insert). Cyclophosphamide has toxic effects on the prostate and male reproductive systems. Cyclophosphamide treatment can result in the development of sterility, and result in some degree of testicular atrophy.

Effects of KGF-2 Δ33 on Normal Bladder, Testes and Prostate Experimental Design

Male Sprague-Dawley rats (160–220 g), (n=4 to 6/treatment group) were used in these studies. KGF-2 Δ33 was administered at a dose of 5 mg/kg/day.

Daily ip or sc injections of recombinant KGF-2 Δ33 or buffer (40 mM sodium acetate+150 mM NaCl at pH 6.5) were administered for a period of 1–7 days and the rats were sacrificed the following day. To examine the reversibility of effects induced with KGF-2 Δ33, additional animals were injected ip daily for 7 days with KGF-2 Δ33 or buffer and sacrificed after a 7 day treatment-free period.

On the day of sacrifice, rats were injected ip with 100 mg/kg of BrdU. Two hours later the rats were overdosed with ether and selected organs removed. Samples of tissues were fixed in 10% neutral buffered formalin for 24 hours and paraffin embedded. To detect BrdU incorporation into replicating cells, five micron sections were subjected to immunohistochemical procedures using a mouse anti-BrdU monoclonal antibody and the ABC Elite detection system. The sections were lightly counterstained with hematoxylin.

Sections were read by blinded observers. The number of proliferating cells was counted in 10 random fields per animal at a 10× magnification for the prostate. To assess the effects of KGF-2 Δ33 in the bladder, cross-sections of these tissues were prepared and the number of proliferating and non-proliferating cells were counted in ten random fields at 20× magnification. The results are expressed as the percentage of labeled to unlabeled cells. Data are presented as mean+SEM. Statistical analyses (two-tailed unpaired t-test) were performed with the StatView Software Package and statistical significance is defined as $p<0.05$.

Results

Bladder

Intraperitoneal injection of KGF-2 Δ33 induced proliferation of bladder epithelial cells over the 7 day study period (solid squares, FIG. 23) but this did not influence the weight of the organ. Subcutaneous administration elicited a small increase in proliferation but this failed to achieve statistical significance (solid circles, FIG. 23).

Prostate and Testes

Both sc and ip administration of KGF-2 Δ33 induced significant proliferation of the prostate (FIG. 24) but this normalized after two injections. Prolonged ip treatment with KGF-2 Δ33 did not increase the weight of the prostate or testes.

Effects of KGF-2 Δ33 on Cyclophosphamide-Induced Hemorrhagic Cystitis Experimental Design Male Sprague Dawley rats (300–400 g) (n=5/ group) were injected i.v. via the tail vein with buffer placebo or KGF-2 Δ33 at concentrations of 1 or 5 mg/kg 24 hours prior to a 200 mg/kg i.p. injection of cyclophosphamide. On the final day, 48 hours after cyclophosphamide injection, rats were injected ip with 100 mg/kg of BrdU. Two hours later the rats were killed by $CO_2$ administration. Fixation of the bladder was done by direct injection of 10% formalin into the lumen of the bladder and rinsing of the exterior of the bladder with formalin. After 5 minutes, the bladder and prostate were removed. The urinary bladder and prostate gland were paraffin embedded, cross-sectioned and stained with H&E and a mouse anti-BrdU monoclonal antibody. The extent of urothelial damage was assessed using the following scoring system: Bladders were graded by two independent observers to describe the extent of the loss of urothelium. (Urothelial damage was scored as 0, 25%, 50%, 75% and 100% loss of the urothelium). In addition, the thickness of the bladder wall was measured at 10 random sites per section and expressed in µm Results Macroscopic Observations In rats treated with placebo and cyclophosphamide, bladders were thick and rigid. Upon injection of 10% formalin, very little expansion of the bladders was noted. However, in the groups pretreated with KGF-2 Δ33, a greater elasticity of the bladder was noted upon direct injection with formalin suggesting a lesser degree of fibrosis.

Microscopic Observations

Bladder

Figure 25:
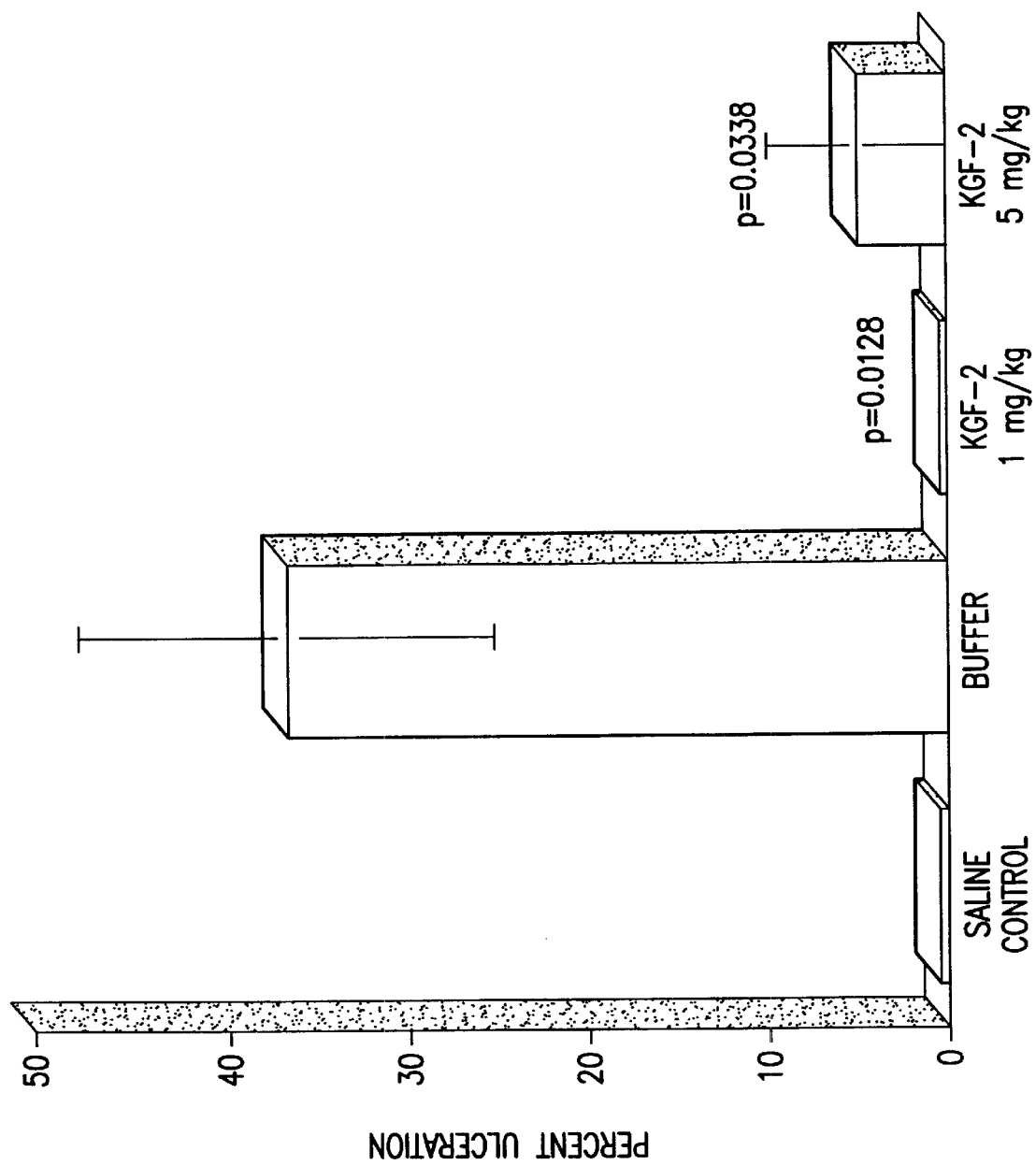
FIG. 25 shows the effect of KGF-2 Δ33 on bladder wall ulceration in a cyclophosphamide-induced hemorrhagic cystitis model in the rat.

FIG. 25 shows the results of KGF-2 Δ33 pretreatment on the extent of ulceration in the bladder. In normal rats treated with i.p. saline (saline control), the bladders appeared normal histologically and no ulceration of the urothelium was observed. Administration of 200 mg/kg i.p. of cyclophosphamide resulted in ulceration of the bladder epithelium that was between 25 and 50% of the total epithelial area (with a mean of 37%). Administration of KGF-2 Δ33 24 hours prior to cyclophosphamide resulted in a significant reduction in the extent of ulceration (1 mg/kg 0.4% p=0.0128, and 5 mg/kg 5%, p=0.0338%) when compared to placebo treated animals receiving cyclophosphamide.

Figure 26:
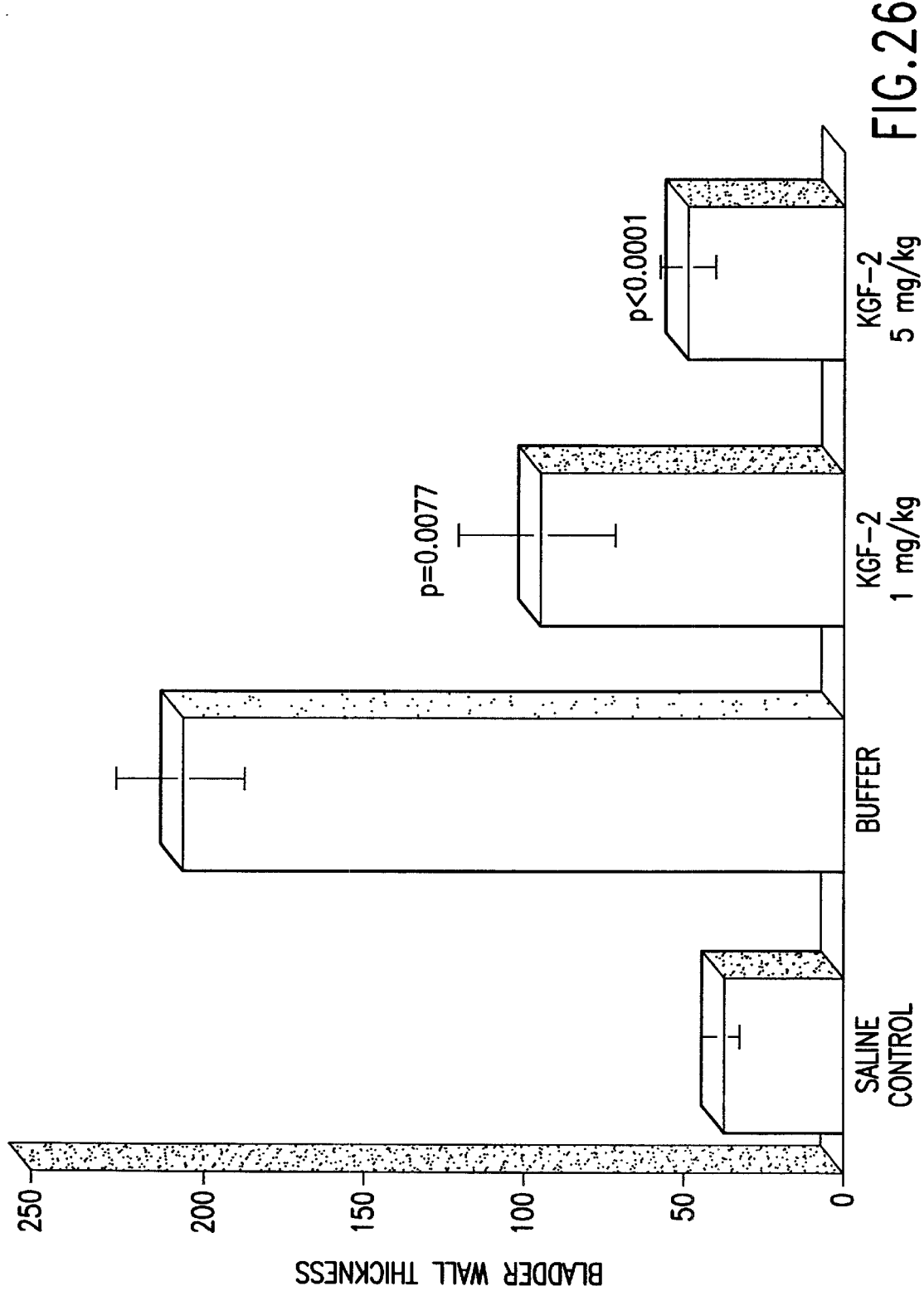
FIG. 26 shows the effect of KGF-2 Δ33 on bladder wall thickness in a cyclophosphamide-induced cystitis rat model.

FIG. 26 shows the effects of KGF-2 Δ33 on the thickness of the urinary bladder wall which includes epithelium, smooth muscle layers and the serosal surface. In groups treated with buffer alone, the thickness of the bladder wall is approximately 40 µm. Treatment with cyclophosphamide results in a 5 fold increase in bladder wall thickness to 210 µm. KGF-2 Δ33 pretreatment of cyclophosphamide treated animals resulted in a significant inhibition of cyclophosphamide enlargement of the bladder wall (1 mg/kg 98.6 µm (p=0.007) and at 5 mg/kg 52.3 µm (p<0.0001)) when compared to the cyclophosphamide treatment alone.

Prostate Gland

In rats receiving buffer and cyclophosphamide, marked atrophy of the prostatic glands (acini) was observed accompanied by enlargement of interstitial spaces with remarkable edema when compared to normals. In addition, epithelial cells lining the prostatic glands were observed to be much shorter and less dense than in corresponding normal prostatic tissue. KGF-2 Δ33 pretreatment at both 1 mg/kg and 5 mg/kg displayed a normal histological appearance of the prostatic gland. No increase in the interstitial spaces or edema was observed, and the epithelial cells lining the prostatic glands were similar in size and density to normal prostatic tissue.

Conclusion

The results demonstrate that KGF-2 specifically induces proliferation of bladder epithelial cells and the epithelial cells lining the prostatic glands. The results also demostrate that KGF-2 specifically results in a significant reduction in the extent of ulceration in cyclophosphamide-induced hemorrhagic cystitis.

EXAMPLE 17

Effects of KGF-2 Δ33 on Platelet Levels in Rats

This experiment demonstrates that KGF-2Δ33 increases platelet levels.

Experimental Design

Adult Sprague-Dawley rats were treated daily with a sc injection of buffer or doses of KGF-2Δ33 (as shown in the Table below) for a period of 4 weeks. One set of animals was sacrificed at this time. Another set was sacrificed after a 4 week recovery period. Blood samples were taken by orbital sinus puncture after an overnight fast and collected in tubes containing EDTA anticoagulant or 3.13% w/v aqueous trisodium citrate anticoagulant for hematology and coagulation assays, respectively. Blood chemistry was performed on samples taken into lithium heparin anticoagulant.

Results

As shown in the Table below, significant increases in platelet levels were demonstrated in both male and female rats at 0.3 mg/kg ($p<0.05$), 1 mg/kg ($p<0.01$), 3 mg/kg ($p<0.01$), and 10 mg/kg ($p<0.001$) KGF-2Δ33 treatment relative to buffer controls. In most instances these effects were reversible after a 4-week recovery period.

Effect of KGF-2Δ33 on platelet levels in rats

| Treatment | Sex | After 4 weeks of treatment Platelet ($10^{-3}/\mu l$) | After 4 weeks of recovery Platelet ($10^{-3}/\mu l$) |
|---|---|---|---|
| Buffer | Male | 1166 ± 116 | 1083 ± 69 |
| 0.3 mg/kg | Male | 1277 ± 96* | 1048 ± 116 |
| 1 mg/kg | Male | 1364 ± 166** | 1124 ± 101 |
| 3 mg/kg | Male | 1327 ± 74** | 1129 ± 57 |
| 10 mg/kg | Male | 1465 ± 152*** | 1248 ± 62* |
| Buffer | Female | 1125 ± 182 | 1078 ± 123 |
| 0.3 mg/kg | Female | 1243 ± 145* | 1091 ± 106 |
| 1 mg/kg | Female | 1328 ± 135** | 1084 ± 98 |
| 3 mg/kg | Female | 1339 ± 116** | 1151 ± 177 |
| 10 mg/kg | Female | 1533 ± 157*** | 1233 ± 146 |

*$p < 0.05$, $p < 0.01$, *$p < 0.001$

EXAMPLE 18

Effects of KGF-2 Δ33 on Plasma Fibrinogen in Rats

This experiment demonstrates that KGF-2Δ33 increases plasma fibrinogen levels.

Experimental Design

Adult Sprague-Dawley rats were treated daily with a sc injection of buffer or doses of KGF-2Δ33 (as shown in the Table below) for a period of 4 weeks. One set of animals was sacrificed at this time. Another set was sacrificed after a 4 week recovery period. Blood samples were taken by orbital sinus puncture after an overnight fast and collected in tubes containing EDTA anticoagulant or 3.13% w/v aqueous trisodium citrate anticoagulant for hematology and coagulation assays, respectively. Blood chemistry was performed on samples taken into lithium heparin anticoagulant.

Results

As shown in the Table below, significant increases in plasma fibrinogen levels were demonstrated in male rats at 3 mg/kg ($p<0.001$) and 10 mg/kg ($p<0.001$) KGF-2Δ33 treatment relative to buffer controls, and in female rats at 1 mg/kg ($p<0.001$), 3 mg/kg ($p<0.001$), and 10 mg/kg ($p<0.001$) KGF-2Δ33 treatment relative to buffer controls. In most instances these effects were reversible after a 4-week recovery period.

Effect of KGF-2Δ33 on Plasma Fibrinogen Levels in Rats

| Treatment | Sex | After 4 weeks of treatment Fibrinogen (mg/dl) | After 4 weeks of recovery Fibrinogen (m/dl) |
|---|---|---|---|
| Buffer | Male | 248 ± 24 | 214 ± 14 |
| 0.3 mg/kg | Male | 252 ± 23 | 202 ± 14 |
| 1 mg/kg | Male | 287 ± 49* | 219 ± 10 |

-continued

Effect of KGF-2Δ33 on Plasma Fibrinogen Levels in Rats

| Treatment | Sex | After 4 weeks of treatment Fibrinogen (mg/dl) | After 4 weeks of recovery Fibrinogen (m/dl) |
|---|---|---|---|
| 3 mg/kg | Male | 315 ± 24*** | 220 ± 10 |
| 10 mg/kg | Male | 378 ± 46*** | 222 ± 21 |
| Buffer | Female | 194 ± 24 | 171 ± 25 |
| 0.3 mg/kg | Female | 215 ± 29 | 195 ± 24 |
| 1 mg/kg | Female | 248 ± 19*** | 191 ± 14 |
| 3 mg/kg | Female | 248 ± 23*** | 175 ± 15 |
| 10 mg/kg | Female | 303 ± 44*** | 182 ± 19 |

*$p < 0.05$, $p < 0.01$, *$p < 0.001$

EXAMPLE 19
Effects of KGF-2 Δ33 on Total Serum Protein Levels in Rats

This experiment demonstrates that KGF-2Δ33 increases total serum protein levels

Experimental Design

Adult Sprague-Dawley rats were treated daily with a sc injection of buffer or doses of KGF-2Δ33 (as shown in the Table below) for a period of 4 weeks. One set of animals was sacrificed at this time. Another set was sacrificed after a 4 week recovery period. Blood samples were taken by orbital sinus puncture after an overnight fast and collected in tubes containing EDTA anticoagulant or 3.13% w/v aqueous trisodium citrate anticoagulant for hematology and coagulation assays, respectively. Blood chemistry was performed on samples taken into lithium heparin anticoagulant.

Results

As shown in the Table below, significant increases in total serum protein levels were demonstrated in male and female rats at 1 mg/kg ($p<0.001$), 3 mg/kg ($p<0.001$), and 10 mg/kg ($p<0.001$) KGF-2Δ33 treatment relative to buffer controls. In some instances these effects were reversible after a 4-week recovery period.

Effect of KGF-2Δ33 on Total Serum Protein Levels in Rats

| Treatment | Sex | After 4 weeks of treatment Total Protein (g/dl) | After 4 weeks of recovery Total Protein (g/dl) |
|---|---|---|---|
| Buffer | Male | 5.9 ± 0.3 | 6.4 ± 0.5 |
| 0.3 mg/kg | Male | 6.1 ± 0.3 | 6.2 ± 0.3 |
| 1 mg/kg | Male | 6.6 ± 0.2*** | 6.5 ± 0.2 |
| 3 mg/kg | Male | 6.7 ± 0.4*** | 6.3 ± 0.2 |
| 10 mg/kg | Male | 6.9 ± 0.4*** | 6.1 ± 0.0 |
| Buffer | Female | 5.9 ± 0.3 | 6.7 ± 0.2 |
| 0.3 mg/kg | Female | 6.1 ± 0.2 | 6.6 ± 0.1 |
| 1 mg/kg | Female | 6.6 ± 0.2*** | 6.5 ± 0.3 |
| 3 mg/kg | Female | 6.9 ± 0.3*** | 6.5 ± 0.2 |
| 10 mg/kg | Female | 7.0 ± 0.4*** | 6.3 ± 0.3* |

*$p < 0.05$, $p < 0.01$, *$p < 0.001$

EXAMPLE 20
Effects of KGF-2 Δ33 on Serum Albumin Levels in Rats

This experiment demonstrates that KGF-2Δ33 increases serum albumin levels.

Experimental Design

Adult Sprague-Dawley rats were treated daily with a sc injection of buffer or doses of KGF-2Δ33 (as shown in the Table below) for a period of 4 weeks. One set of animals was sacrificed at this time. Another set was sacrificed after a 4 week recovery period. Blood samples were taken by orbital sinus puncture after an overnight fast and collected in tubes containing EDTA anticoagulant or 3.13% w/v aqueous trisodium citrate anticoagulant for hematology and coagulation assays, respectively. Blood chemistry was performed on samples taken into lithium heparin anticoagulant.

Results

As shown in the Table below, significant increases in serum albumin levels were demonstrated in male rats at 1 mg/kg ($p<0.01$), 3 mg/kg ($p<0.001$), and 10 mg/kg ($p<0.001$) KGF-2Δ33 treatment relative to buffer controls, and in female rats at 1 mg/kg ($p<0.001$), 3 mg/kg ($p<0.001$), and 10 mg/kg ($p<0.001$) KGF-2Δ33 treatment relative to buffer controls. In most instances these effects were reversible after a 4-week recovery period.

Effect of KGF-2Δ33 on Serum Albumin Levels in Rats

| Treatment | Sex | After 4 weeks of treatment Albumin (g/dl) | After 4 weeks of recovery Albumin (g/dl) |
|---|---|---|---|
| Buffer | Male | 3.4 ± 0.2 | 3.4 ± 0.2 |
| 0.3 mg/kg | Male | 3.5 ± 0.1 | 3.4 ± 0.1 |
| 1 mg/kg | Male | 3.6 ± 0.1** | 3.5 ± 0.0 |
| 3 mg/kg | Male | 3.7 ± 0.2*** | 3.4 ± 0.2 |
| 10 mg/kg | Male | 3.7 ± 0.2*** | 3.3 ± 0.1 |
| Buffer | Female | 3.4 ± 0.2 | 3.8 ± 0.1 |
| 0.3 mg/kg | Female | 3.4 ± 0.2 | 3.7 ± 0.1 |
| 1 mg/kg | Female | 3.7 ± 0.1*** | 3.6 ± 0.1* |
| 3 mg/kg | Female | 3.9 ± 0.2*** | 3.5 ± 0.1** |
| 10 mg/kg | Female | 3.9 ± 0.2*** | 3.5 ± 0.2** |

*$p < 0.05$, $p < 0.01$, *$p < 0.001$

EXAMPLE 21
Effects of KGF-2 Δ33 on Serum Globulin Levels in Rats

This experiment demonstrates that KGF-2Δ33 increases serum globulin levels.

Experimental Design

Adult Sprague-Dawley rats were treated daily with a sc injection of buffer or doses of KGF-2Δ33 (as shown in the Table below) for a period of 4 weeks. One set of animals was sacrificed at this time. Another set was sacrificed after a 4 week recovery period. Blood samples were taken by orbital sinus puncture after an overnight fast and collected in tubes containing EDTA anticoagulant or 3.13% w/v aqueous trisodium citrate anticoagulant for hematology and coagulation assays, respectively. Blood chemistry was performed on samples taken into lithium heparin anticoagulant.

Results

As shown in the Table below, significant increases in serum globulin levels were demonstrated in male and female rats at 1 mg/kg ($p<0.001$), 3 mg/kg ($p<0.001$), and 10 mg/kg ($p<0.001$) KGF-2Δ33 treatment relative to buffer controls. In some instances these effects were reversible after a 4-week recovery period.

Effect of KGF-2Δ33 on Serum Globulin Levels in Rats

| Treatment | Sex | After 4 weeks of treatment Globulin (g/dl) | After 4 weeks of recovery Globulin (g/dl) |
|---|---|---|---|
| Buffer | Male | 2.5 ± 0.2 | 3.0 ± 0.3 |
| 0.3 mg/kg | Male | 2.6 ± 0.2 | 2.8 ± 0.2 |
| 1 mg/kg | Male | 2.9 ± 0.1*** | 3.1 ± 0.2 |
| 3 mg/kg | Male | 3.0 ± 0.2*** | 2.9 ± 0.1 |

-continued

Effect of KGF-2Δ33 on Serum Globulin Levels in Rats

| Treatment | Sex | After 4 weeks of treatment Globulin (g/dl) | After 4 weeks of recovery Globulin (g/dl) |
|---|---|---|---|
| 10 mg/kg | Male | 3.2 ± 0.2*** | 2.8 ± 0.1 |
| Buffer | Female | 2.5 ± 0.1 | 2.9 ± 0.1 |
| 0.3 mg/kg | Female | 2.7 ± 0.1 | 2.9 ± 0.1 |
| 1 mg/kg | Female | 2.9 ± 0.1*** | 2.9 ± 0.2 |
| 3 mg/kg | Female | 3.0 ± 0.2*** | 3.0 ± 0.2 |
| 10 mg/kg | Female | 3.1 ± 0.3*** | 2.8 ± 0.2 |

*p < 0.05, p < 0.01, *p < 0.001

EXAMPLE 22

Effect of KGF-2 on the Proliferation of Cells in Normal Rats

Introduction

KGF-2, a member of the FGF family, induces proliferation of normal human and rat keratinocytes. It has approximately 57% homology to KGF-1 (a member of the FGF family). KGF-1 has been reported to induce proliferation of epithelia of many organs (Housley et al., Keratinocyte growth factor induces proliferation of hepatocytes and epithelial cells throughout the rat gastrointestinal tract. *J Clin Invest* 94: 1764–1777 (1994); Ulich et al., Keratinocyte growth factor is a growth factor for type II pneumocytes in vivo. *J Clin Invest* 93: 1298–1306 (1994); Ulich et al., Keratinocyte growth factor is a growth factor for mammary epithelium in vivo. The mammary epithelium of lactating rats is resistant to the proliferative action of keratinocyte growth factor. *Am J Pathol* 144:862–868 (1994); Nguyen et al., Expression of keratinocyte growth factor in embryonic liver of transgenic mice causes changes in epithelial growth and differentiation resulting in polycystic kidneys and other organ malformations. *Oncogene* 12:2109–2119 (1996); Yi et al., Keratinocyte growth factor induces pancreatic ductal epithelial proliferation. *Am J Pathol* 145:80–85 (1994); and Yi et al., Keratinocyte growth factor causes proliferation of urothelium in vivo. *J Urology* 154:1566–1570 (1995)). We performed similar experiments with KGF-2 to determine if it induces proliferation of normal epithelia in rats when administered systemically using sc and ip routes.

Methods

Male Sprague-Dawley rats, weighing 160–220 g, were obtained from Harlan Sprague Dawley for these studies. KGF-2 Δ33 (HG0341 1-E2) was administered at a dose of 5 mg/kg/day. Daily ip or sc injections of KGF-2 Δ33 or recombinant buffer (40 mM sodium acetate+150 mM NaCl at pH 6.5) were administered for a period of 1–7 days and the rats were sacrificed the following day (see below). To examine the reversibility of effects induced with KGF-2 Δ33, additional animals were injected ip daily for 7 days with KGF-2 Δ33 or buffer and sacrificed after a 7 day treatment-free period.

On the day of sacrifice, rats were injected ip with 100 mg/kg of BrdU. Two hours later the rats were overdosed with ether and selected organs removed. In some studies organ weights were recorded. Samples of tissues were fixed in 10% neutral buffered formalin for 24 hours and paraffin embedded. To detect BrdU incorporation into replicating cells, five micron sections were subjected to immunohistochemical procedures using a mouse anti-BrdU monoclonal antibody (Boehringer Mannheim) and the ABC Elite detection system (Vector Laboratories). The sections were lightly counterstained with hematoxylin.

Sections were read by blinded observers. The number of proliferating cells was counted in 10 random fields per animal at a 10× magnification for the following tissues: liver, pancreas, prostate, and heart. Ten random fields were used also for the lung analysis except the proliferation was quantitated at 20× magnification. Since the kidney has many functionally discrete areas, the proliferation was assessed in a coronal cross-section taken through the center of one kidney per animal. To assess the effects of KGF-2 Δ33 in the esophagus and bladder, cross-sections of these tissues were prepared and the number of proliferating and non-proliferating cells were counted in ten random fields at a 10× and 20× magnification, respectively. The results are expressed as the percentage of labeled to unlabeled cells.

Data are presented as mean±SEM. Statistical analyses (two-tailed unpaired t-test) were performed with the StatView Software Package (Abacus Concepts, Inc., Berkeley, Calif.) and statistical significance is defined as p<0.05.

Results

Figure 27:
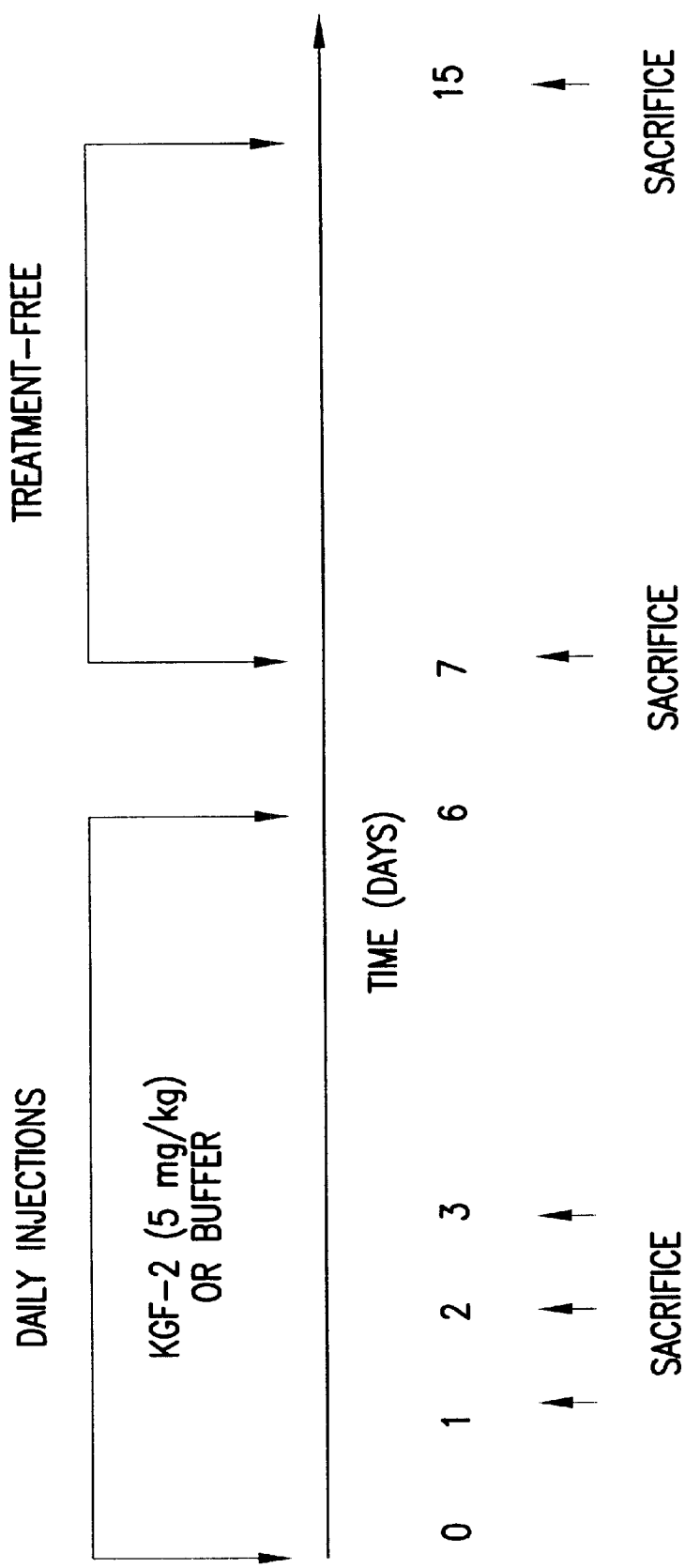
FIG. 27 provides an overview of the study design to determine whether KGF-2 Δ33 induces proliferation of normal epithelia in rats when administered systemically using SC and IP routes.

FIG. 27 shows an overview of the experimental protocol. Six animals were used per group. However, during the analysis by the blinded observers it became clear that occasionally the BrdU injection was unsuccessful. Before the results were uncoded, the data from 8 rats out of 116 rats (or 7% of the animals) were excluded from the study and the resultant group sizes are shown in the Table below.

Group Sizes Used in These Studies

| Treatment | Time | n = ip | n = sc |
|---|---|---|---|
| KGF-2 Δ33 | 1 day | 6 | 5 |
| buffer | 1 day | 6 | 6 |
| KGF-2 Δ33 | 2 days | 6 | 4 |
| buffer | 2 days | 6 | 6 |
| KGF-2 Δ33 | 3 days | 5 | 5 |
| buffer | 3 days | 5 | 5 |
| KGF-2 Δ33 | 7 days | 6 | 6 |
| buffer | 7 days | 6 | 5 |
| KGF-2 Δ33 | 7 days + 7 days treatment-free | 6 | ND |
| buffer | 7 days + 7 days treatment-free | 6 | ND |

Liver

Figure 28:
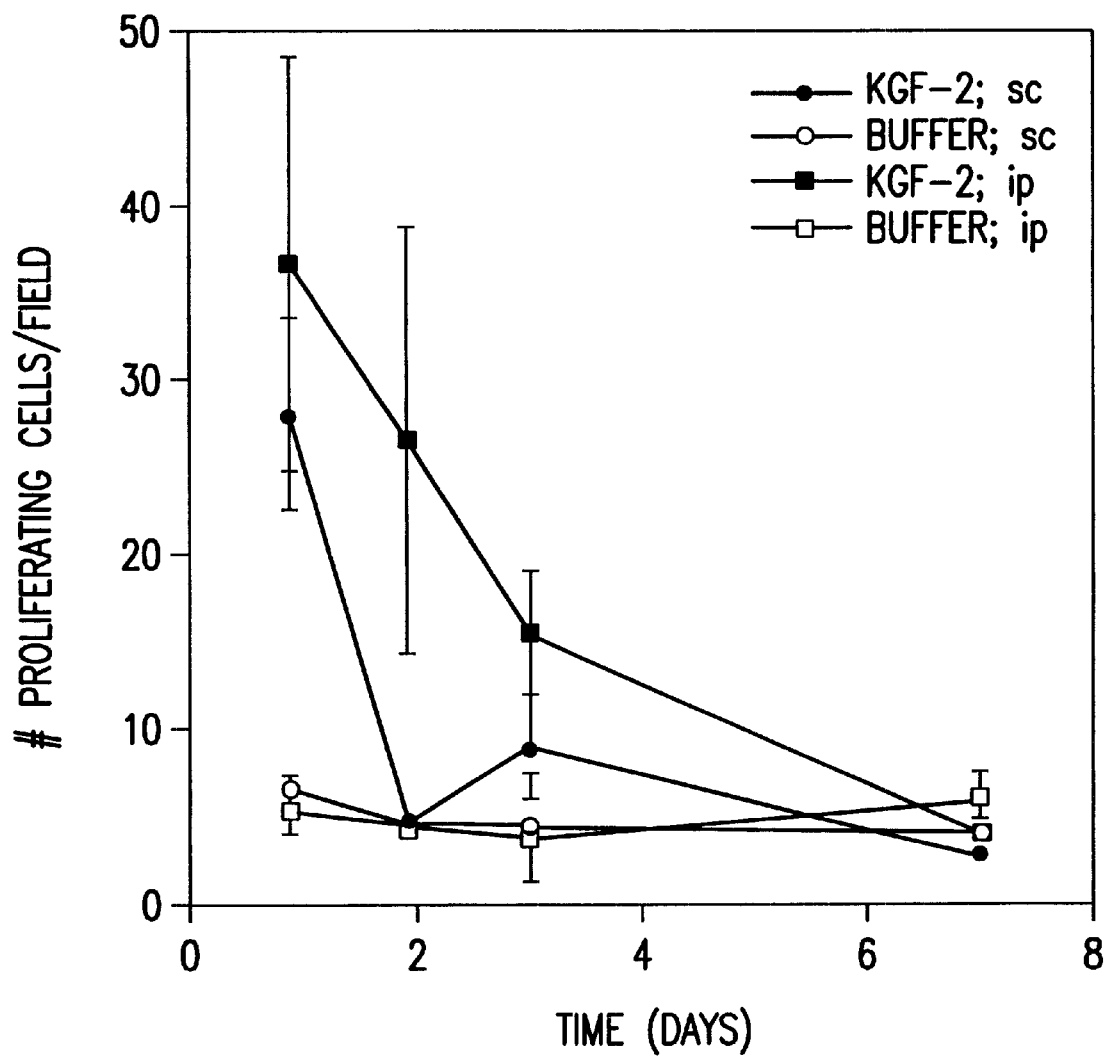
FIG. 28. Normal Sprague Dawley rats were injected daily with KGF-2 Δ33 (5 mg/kg; HG03411-E2) or buffer and sacrificed one day after the final injection. A blinded observer counted the proliferating cells in ten randomly chosen fields per animals at a 10×magnification. SC administration of KGF-2 Δ33 elicited a significant proliferation after one day which then returned to normal by 2 days. KGF-2 Δ33 given ip stimulated proliferation from 1–3 days but only the results from days 1 and 3 were statistically significant.

When administered ip, KGF-2 Δ33 induced a rapid proliferation of hepatocytes (solid squares) (FIG. 28) after 1 injection and this augmented mitotic activity persisted for three days, returning to normal after 7 days of daily injections. In contrast to the dramatic effect ip administration of KGF-2 exerted on the liver, when given sc (solid circle, FIG. 28) this growth factor demonstrated minor effects. Proliferation was elevated after one day of treatment but returned to normal values after two daily injections.

Pancreas

Figure 29:
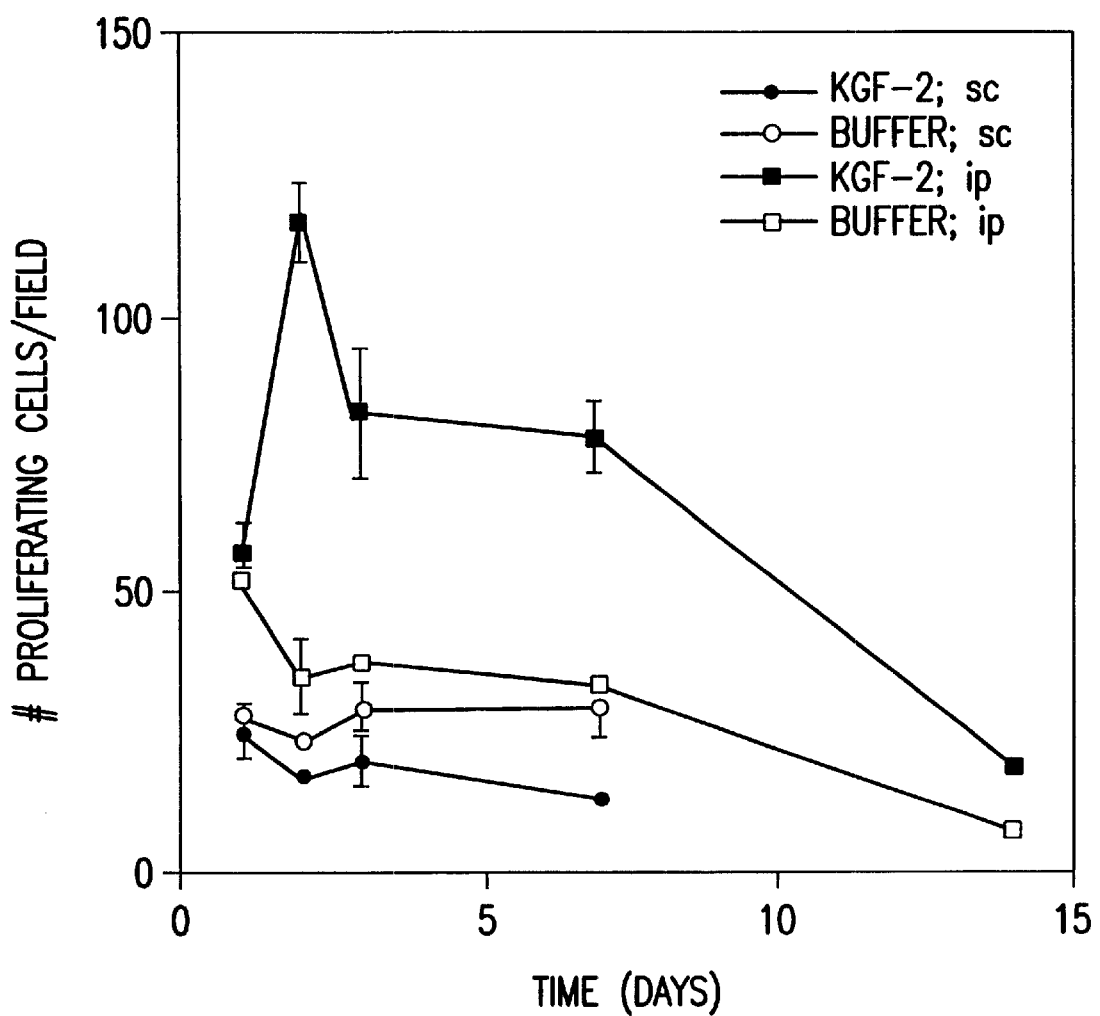
FIG. 29. Normal Sprague Dawley rats were injected daily with KGF-2 Δ33 (5 mg/kg; HG03411-E2) or buffer and sacrificed one day after the final injection. A blinded observer counted the proliferating cells in ten randomly chosen fields per animal at a 10×magnification. KGF-2 Δ33 given ip stimulated proliferation over the entire study period while sc administration of KGF-2 Δ33 did not increase the proliferation at any time point.

In contrast to the quickly reversible effects of ip administered KGF-2 Δ33 on the liver, such injections induced proliferation of the pancreas which continued over the 14 day study period (solid squares, FIG. 29). Surprisingly, subcutaneous administration of KGF-2 Δ33 (solid circles) failed to induce proliferation at any time point.

Kidney and Bladder

Figure 30:
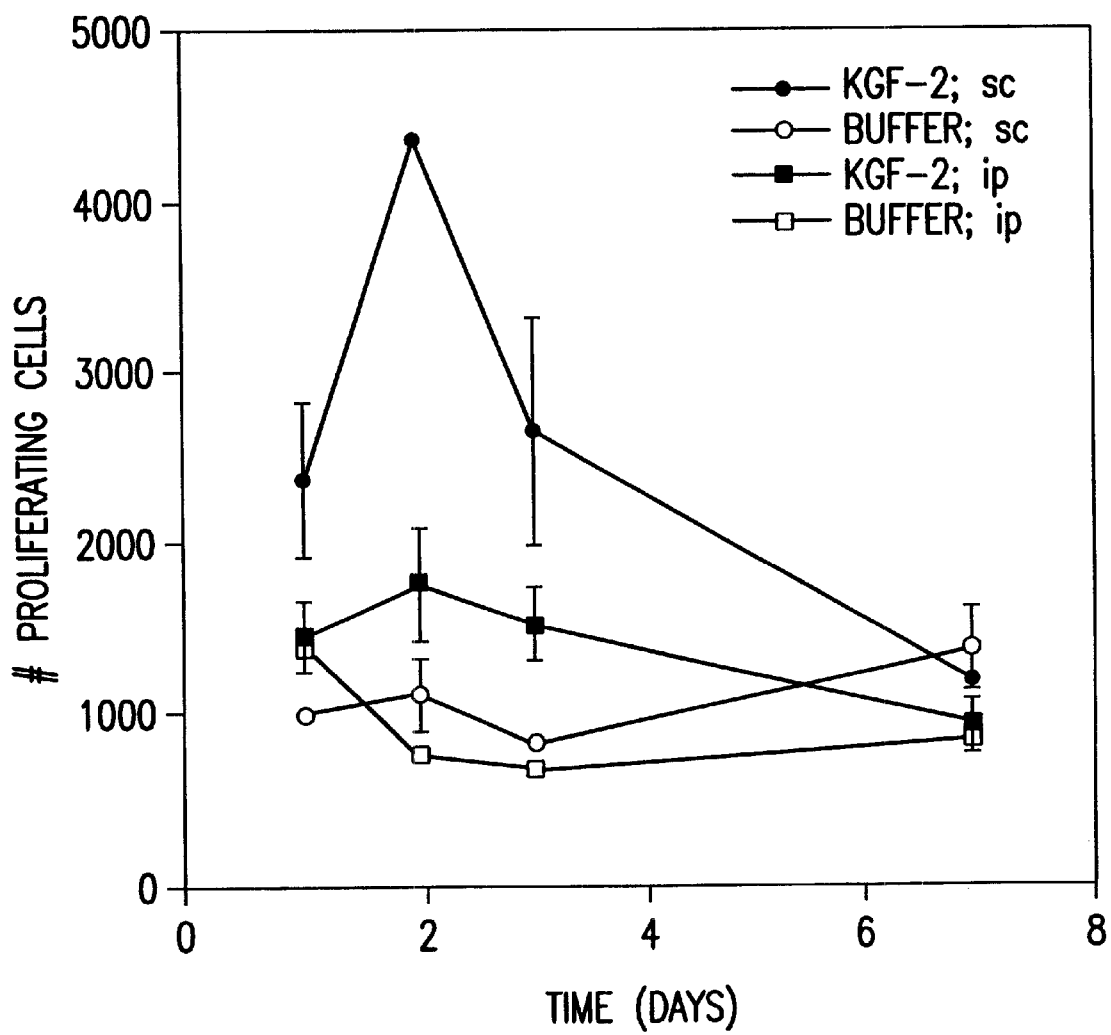
FIG. 30. Normal Sprague Dawley rats were injected daily with KGF-2 Δ33 (5 mg/kg; HG03411-E2) or buffer and sacrificed one day after the final injection. A blinded observer counted the proliferating cells in one cross-section per animal at a 10×magnification. KGF-2 Δ33 given sc elicited a significant increase in proliferation after 1, 2, and 3 days of daily administration. When KGF-2 Δ33 was given ip, proliferation was seen after 2 and 3 days only.

KGF-2 Δ33 induced proliferation of renal epithelia when given either by the sc or ip route but the former induced a greater effect. SC administration induced a rapid increase in proliferation (solid circles) that peaked after 2 days which then returned to normal after 7 daily treatments (FIG. 30). When KGF-2 Δ33 was given ip (solid squares, FIG. 30), there was a modest, but significant increase in proliferation seen at days 2 and 3 only. Intraperitoneal injection of KGF-2 Δ33 also induced proliferation of bladder epithelial cells over the 7 day study period (solid squares, FIG. 23). Subcutaneous administration elicited a small increase in proliferation but this failed to achieve statistical significance (solid circles, FIG. 23).

Prostate

Both sc and ip administration of KGF-2 Δ33 induced significant proliferation of the prostate (FIG. 24) but this normalized after two injections.

Esophagus

KGF-2 Δ33 given sc or ip elicited an early, short-lived increase in the proliferation of the esophageal cells (1 and 2 days, respectively) that rapidly returned to normal (results not shown).

Other Organs

Systemic administration of KGF-2 Δ33 by the ip and sc routes failed to elicit proliferation of the lung epithelia over a 7 day dosing period (results not shown).

Discussion

When administered in a sc route, stimulation of normal epithelial proliferation in some organs (liver, kidney, esophagus. and prostate) were observed but these effects, for the most part, were short-lived and all were reversible. The proliferation in these organs reversed even during daily sc administration of KGF-2.

The route of administration had dramatic effects on the observed proliferation. While daily ip administration increased the rate of liver proliferation over a 3 day period, animals given KGF-2 sc daily exhibited elevated rates after one day of treatment only. Even more surprising was the response of the pancreas. When animals were given KGF-2 ip, the pancreas exhibited a significantly elevated level of proliferation over the 14 day study period. However, sc administration of KGF-2 induced no increased mitotic activity in the pancreas. Likewise, ip, but not sc, treatment with KGF-2 elicited proliferation of the bladder mucosa.

IP administration of KGF-2 elicited a short-lived, small burst of proliferation in the kidney that was centered in the region containing collecting ducts. Daily sc treatment induced a prolonged, exaggerated proliferation in this area.

EXAMPLE 23

Effects of KGF-2 Δ33 on Lung Cellular Proliferation Following Intratracheal Administration This example demonstrates that KGF-2 Δ33 is capable of stimulating lung proliferation in normal rats following intratracheal administration (administration of KGF-2 Δ33 directly to the lung).

Methods

Male Lewis rats (220–270 g), (n=5/treatment group) were used in these studies. KGF-2 Δ33 or placebo (40 mM sodium acetate+150 mM NaCl at pH 6.5) was administered intratracheally at doses of 1 and 5 mg/kg in a volume of 0.6 mls followed by 3 mls of air. Treatments were administered on day 1 and day 2 of the experimental protocol.

On day 3, the day of sacrifice, rats were injected ip with 100 mg/kg of BrdU. Two hours later the rats were killed by C02 asphyxiation. Lungs were inflated with 10% buffered formalin via intratracheal catheter, and saggital sections of lung were paraffin embedded. To detect BrdU incorporation into replicating cells, five micron sections were subjected to immunohistochemical procedures using a mouse anti-BrdU monoclonal antibody and the ABC Elite detection system. The sections were lightly counterstained with hematoxylin.

Sections were read by two blinded observers. The number of proliferating cells was counted in 10 random fields per section at a 20× magnification. The results are expressed as the number of BrdU positive cells per field. Data are presented as mean±SEM. Statistical analyses (unpaired t-test) were performed with the Instat v2.0.1 and statistical significance is defined as p<0.05.

Results

Figure 31:
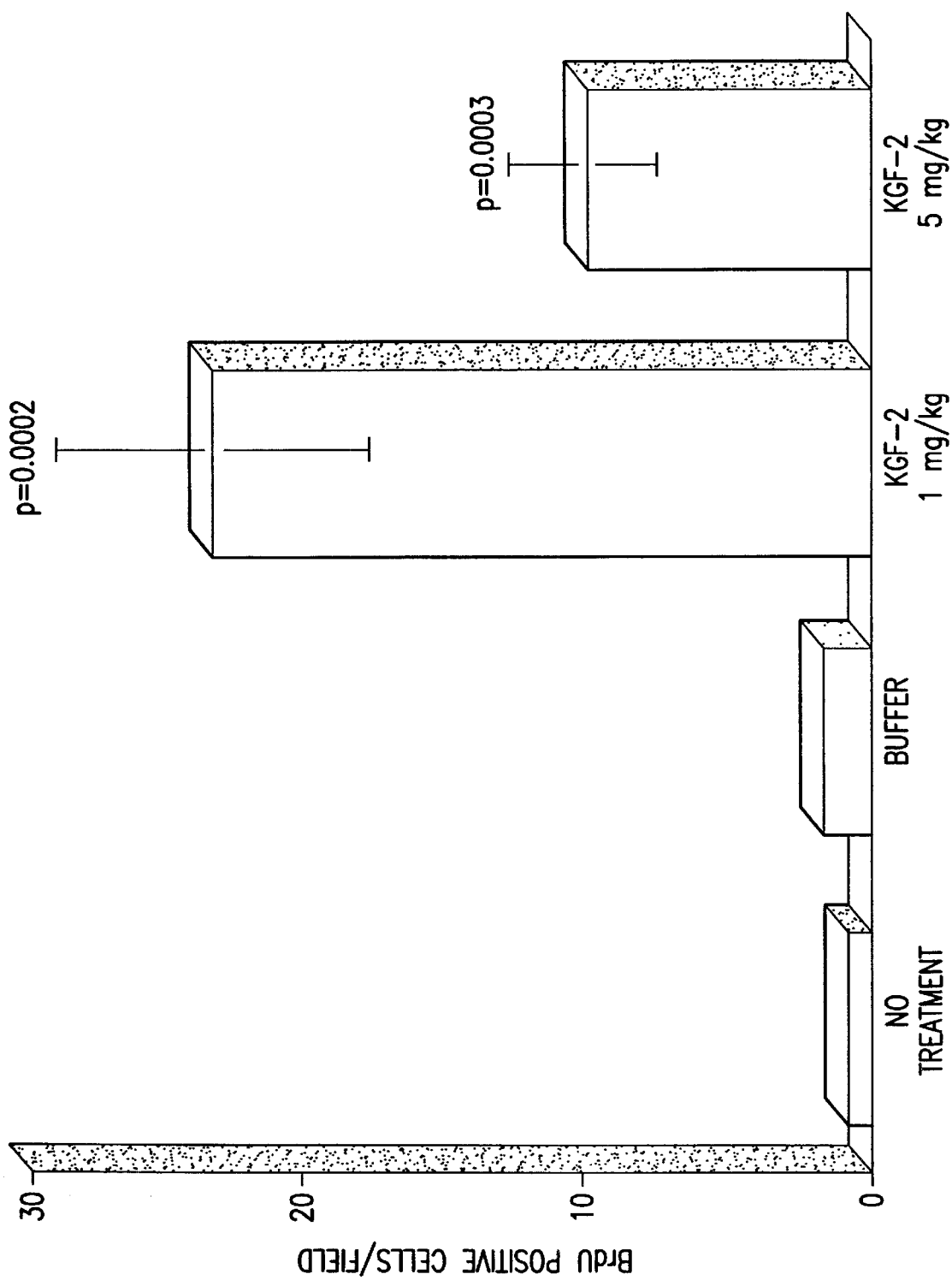
FIG. 31 demonstrates KGF-2 Δ33 induced proliferation in normal rat lung.

Intratracheal injection of KGF-2 Δ33 at 1 and 5 mg/kg resulted in an increase in proliferation of lung epithelial cells as shown in FIG. 31. KGF-2 Δ33 treatment resulted in statistically significant increases in the number of BrdU positive cells/field at 1 mg/kg 23.4 cells/field (p=0.0002) and at 5 mg/kg 10.3 cells/field (p=0.0003) relative to buffer controls of 1.58 cells per field.

EXAMPLE 24

KGF-2 Induces Proliferation of Normal Rat Salivary and Lacrimal Glands

Recombinant human KGF-2, a new member of the fibroblast growth factor (FGF) family was produced and purified. KGF-2 (FGF-10) has been shown to induce proliferation of mouse keratinocytes and rat prostate epithelial cells in vitro (Igarashi, M., et al., *J Biol. Chem.* 273:13230–13235 (1998); Emoto, H., et al., *J. Biol. Chem.* 272:23191–23194 (1997); and Lu, W., et al., *FASEB Journal* 12:A1463 (1998)). The effects of KGF-2 on the proliferative rate of salivary and lacrimal glands in normal rats were studied in this example. The lacrimal glands and two major salivary glands (parotid and submandibular) of normal rats that had been treated for 1–7 days with KGF-2 were examined and, as shown below, were found to have increased cellular proliferation.

Materials and Methods

Recombinant KGF-2

A bacterial expression vector (pHE4) encoding recombinant human KGF-2 was used to produce and purify KGF-2 Δ33 from an *E. coli* expression system as previously described. The purified protein was ≧95% pure as determined by SDS-PAGE and reverse-phase high performance liquid chromatography and had low endotoxin levels (≦0.5 EU/mg and ≦5 EU/ml).

Experimental Design

Male Sprague-Dawley rats were obtained from Harlan Sprague Dawley, Inc, Indianapolis, Ind. and weighed 166–243 g when used in these studies. The animals were maintained according to recommended standards (10) in microisolator cages with recycled paper bedding (Harlan Sprague Dawley, Inc) and provided with pelleted rodent diet (Harlan Sprague Dawley, Inc) and bottled drinking water on an ad libitum basis. The animal protocols used in this study were reviewed and approved by the Human Genome Sciences Institutional Animal Care and Use Committee.

Animals were used in groups of 6 and were injected with KGF-2Δ33 (formulated in 40 mM sodium acetate and 150 mM sodium chloride at pH 6.5) at a dose of 5 mg/kg or with buffer (40 mM sodium acetate and 150 mM sodium chloride at pH 6.5). Systemic treatments were administered by the intravenous route daily for a period of 1–7 days and rats were sacrificed 24 hours after the last treatment. To examine the reversibility of effects induced with KGF-2Δ33, additional animals were injected daily for 7 days with KGF-2Δ33 or buffer and sacrificed after a 7 day treatment-free period.

Histology

Two hours before sacrifice the rats were injected ip with 100 mg/kg of BrdU (Boehringer Mannheim Corp, Indianapolis, Ind.). The salivary glands were isolated, weighed, and fixed in 10% neutral buffered formalin for 24 hours. The eyes were removed intact and fixed. After fixation the tissues were paraffin embedded. To detect BrdU incorporation into replicating cells, five micron sections were subjected to immunohistochemical procedures using a mouse anti-BrdU monoclonal antibody (Boehringer Mannheim Corp) and the ABC Elite detection system (Vector Laboratories, Inc, Burlingame, Calif.). The sections were lightly counterstained with hematoxylin. Additional paraffin sections were stained with hematoxylin and eosin (H&E).

All sections used for quantitation were read by blinded observers. Three areas were randomly selected at a 10× magnification and the percent of positive cells per region of interest (% ROI) was assessed with the IPLab Spectrum software (version 3.1.1) from Signal Analytics Corp., Vienna, Va.

Statistical Analysis

Data are presented as mean±SEM. Statistical analyses were performed with the StatView Software Package (Abacus Concepts, Inc., Berkeley, Calif.). A factorial ANOVA with post hoc comparisons of Scheffe was used.

Results

After 5 to 6 daily intravenous injections with KGF-2Δ33 at a dose of 5 mg/kg, some of the rats had a wet muzzle. The effects of KGF-2Δ33 on the proliferation rate of the parotid and submandibular salivary glands were observed. Because both the salivary and lacrimal glands contain similar cells, and damage to both glands occurs in clinical settings, the lacrimal gland was examined as well.

Parotid Gland

Figure 32:
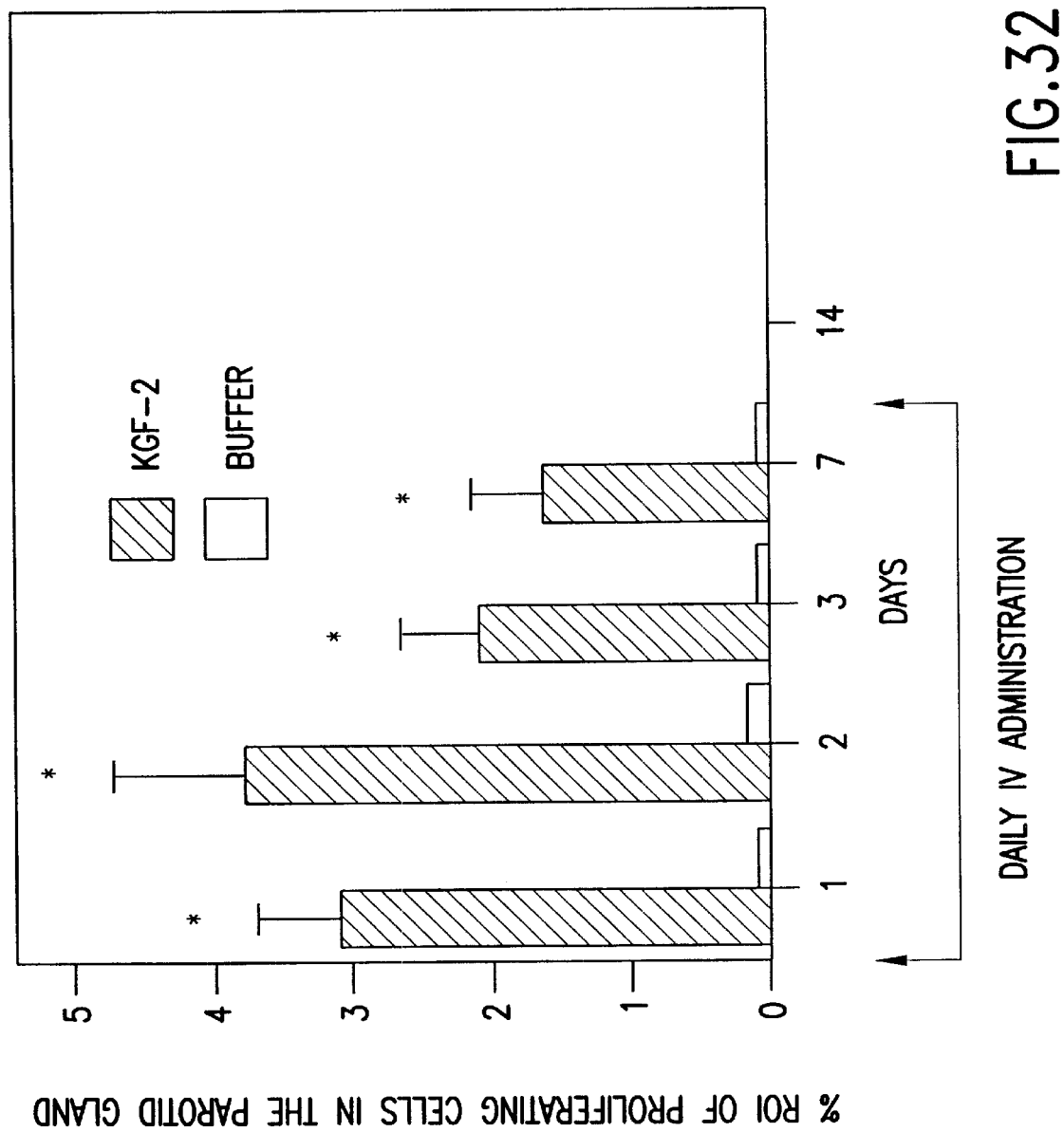
FIG. 32 shows a morphometric assessment of the number of BrdU positive cells in the parotid gland revealed dramatic proliferation over the seven day study period. Note that BrdU incorporation returned to normal after a seven day rest period. Measurements were performed in a blinded manner.
Figure 33:
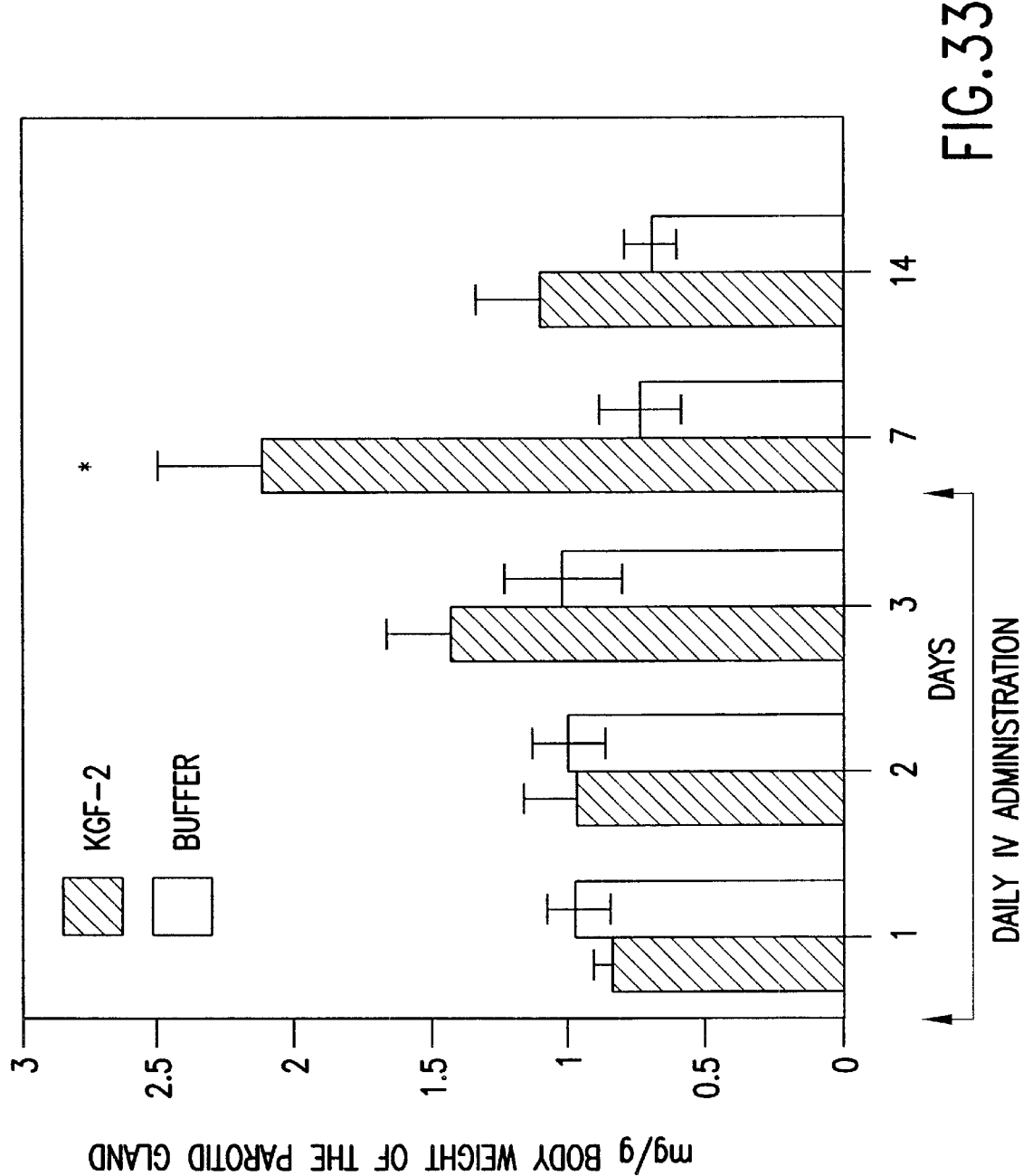
FIG. 33 shows the weight of the parotid glands from animals treated daily with KGF-2 or buffer are expressed as mg per g of body weight. Only after seven daily intravenous injections of KGF-2 did the organ weight significantly increase and this normalized after a seven day rest period.

KGF-2Δ33 at a dose of 5 mg/kg significantly increased proliferation of the serous secretory acini in the parotid gland after one injection. Quantitative analysis also showed significant proliferation. As can be seen in FIG. 32, one injection of KGF-2Δ33 induced a 40-fold increase in proliferation. Following seven daily injections the response had diminished somewhat to an 18-fold increase. Animals treated for seven days and then allowed to recover for seven days had no elevated proliferation demonstrating that this dramatic effect was reversible. This increased proliferation resulted in an increase in organ size. KGF-2Δ33 induced a three-fold increase in the weight of the parotid gland after seven daily injections but its size had returned to normal after a seven day recovery period (FIG. 33).

Submandibular Gland

Figure 34:
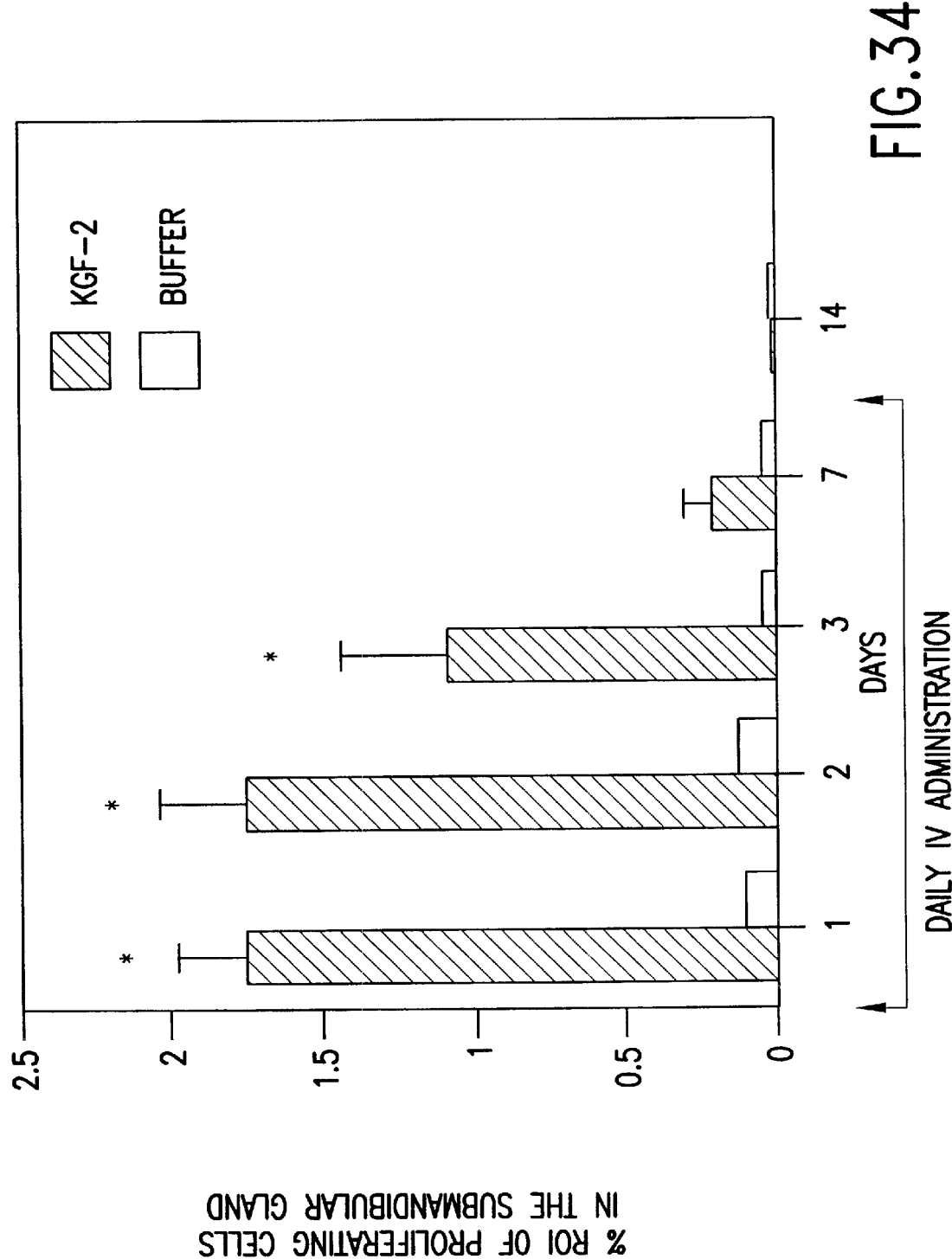
FIG. 34 shows the proliferative effect of KGF-2 on the submandibular gland was apparent after one injection (day 1). It remained active over three doses but after seven daily injections was no longer inducing a significant increase in proliferation. All measurements were performed in a blinded manner.
Figure 35:
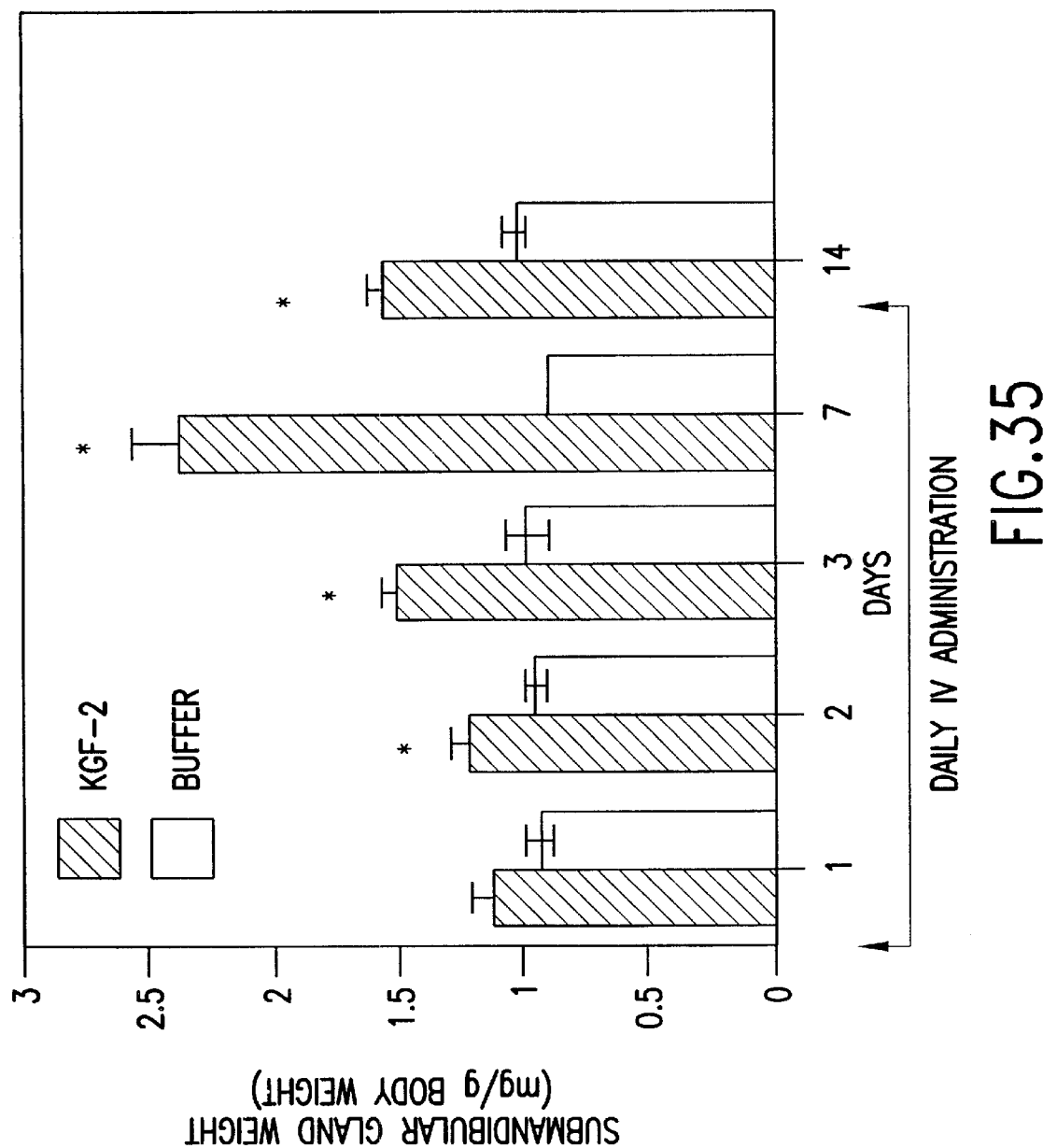
FIG. 35 shows the weight of the submandibular glands obtained from rats treated daily with KGF-2 showed a significant increase in size after two injections. This enlargement peaked after seven daily injections. After one week of recovery the weight of the submandibular gland from rats treated with KGF-2 had began to normalize but was still significant larger than tissue taken from buffer treated control rats.

KGF-2Δ33 treatment significantly increased proliferation of the submandibular gland. Both serous and mucous secretory cells are affected although the ducts appear to be resistant to the proliferation-enhancing action of KGF-2Δ33. The proliferation was quantitated and the results shown in FIG. 34. KGF-2Δ33 enhanced growth of cells after 1–3 daily treatments. After seven days there remained a slight elevation in proliferation but this did not attain statistical significance. Unlike the parotid gland, this increase in cellular proliferation was rapidly reflected in an increase in gland weight that started to normalize after treatment was withdrawn for 7 days (FIG. 35).

Discussion

Inhibition of saliva and tear production is a major clinical problem and currently the treatment for keratoconjunctivitis siccaalone costs the US over $100 million (Lemp, M. A, *Adv. Exp. Med. Biol.* 438:791–803 (1998)). The parotid gland is one of the three major salivary glands and is composed of serous cells that secrete a watery substance that contains enzymes such as amylase and lysozyme. The submandibular gland contains both serous and mucous secretory cells and secretes a thicker liquid (*Wheater's functional histology. A text and colour atlas*, New York: Churchill Livingstone, Ed. 3 (1993)).

KGF-2 induced a dramatic increase in the proliferation of the parotid and submandibular glands within 24 hours of the first intravenous injection. The augmented proliferation of the parotid gland remained over the seven day treatment period while the submandibular gland had normalized during seven days of daily administration of KGF-2. These proliferative changes were reflected in the organs by an increase in weight although there were spatial differences in the response.

Continuous infusions of epidermal growth factor (EGF) have been reported to increase proliferation of the parotid and submandibular salivary glands in rats and mice but its effect is more pronounced in the ductal epithelium. Ohlsson et al. reported an increase in both the serous and ductal cells following EGF administration in the mouse (Ohlsson, B., et al., *Pancreas* 14:94–98 (1997)). The proliferation occurred in the parotid and submandibular glands after three and seven days of continuous treatment, respectively. There was a higher index of labeling of the ductal rather than the serous cells in the parotid gland and the submandibular gland with 12 and 3 fold increases, respectively. The proliferation of the serous cells in the parotid and submandibular gland reached maximums of 5 and 2 fold, respectively. There was no change in organ weights. Breider et al., working in the rat, found continuous infusions of EGF for four weeks induced proliferation of the salivary gland ductular epithelium but no change of the acinar cells (Breider, M. A., et al., *Vet Pathol* 33:184 (1996)). As compared to EGF, KGF-2 induced a far more pronounced proliferation of the serous epithelium in both salivary glands.

Another growth factor has been reported to induce some changes in the salivary gland. KGF-1, which shares some homology with KGF-2, that has been reported to induce excessive salivation in transgenic mice within five days of birth (Guo, L., et al., *EMBO J.* 12:973–986 (1993)). The submandibular gland of these mice showed an undifferentiated morphology with few or no secretory granules. KGF-2, administered systemically in rats over a period of one week, did not induce such a change in these cells.

In summary, KGF-2 induced dramatic elevations in the proliferation of the saliva and tear producing cells of the salivary and lacrimal glands. It appeared to have little effect on the ductal cells in these organs although careful analysis of both cell types was not performed. These results suggest that KGF-2 may have clinically useful effects on salivary glands damaged as a result of radiation therapy, autoimmune diseases, or other medical conditions.

EXAMPLE 25

KGF-2Δ33 Induces Proliferation in the Extraorbital Lacrimal Gland

Since KGF-2Δ33 has shown proliferative effects on secretory tissues such as salivary glands and the pancreas, the effect of systemic administration of KGF-2Δ33 on the lacrimal glands was also investigated.

Materials and Methods

Normal male Sprague Dawley rats were injected intravenously daily with KGF-2Δ33 (HG03411-E6) or buffer. Two hours before sacrifice they received a systemic injection of BrdU so that proliferating cells could be detected immunohistologically. The lacrimal glands were excised and then fixed in 10% neutral buffered formalin for histological processing. Animals were used in groups of 6, and the proliferation of the tissue was assessed by a blinded observer using a computerized morphometry unit. The proliferation results are expressed as the percentage of a region of interest that has proliferating cells (% ROI). The error bars reflect the SEM. Statistical analysis was performed using StatView. A factorial ANOVA was performed followed by a Scheffe post-hoc test and statistical significant was defined as $p<0.05$.

Results

Figure 36:
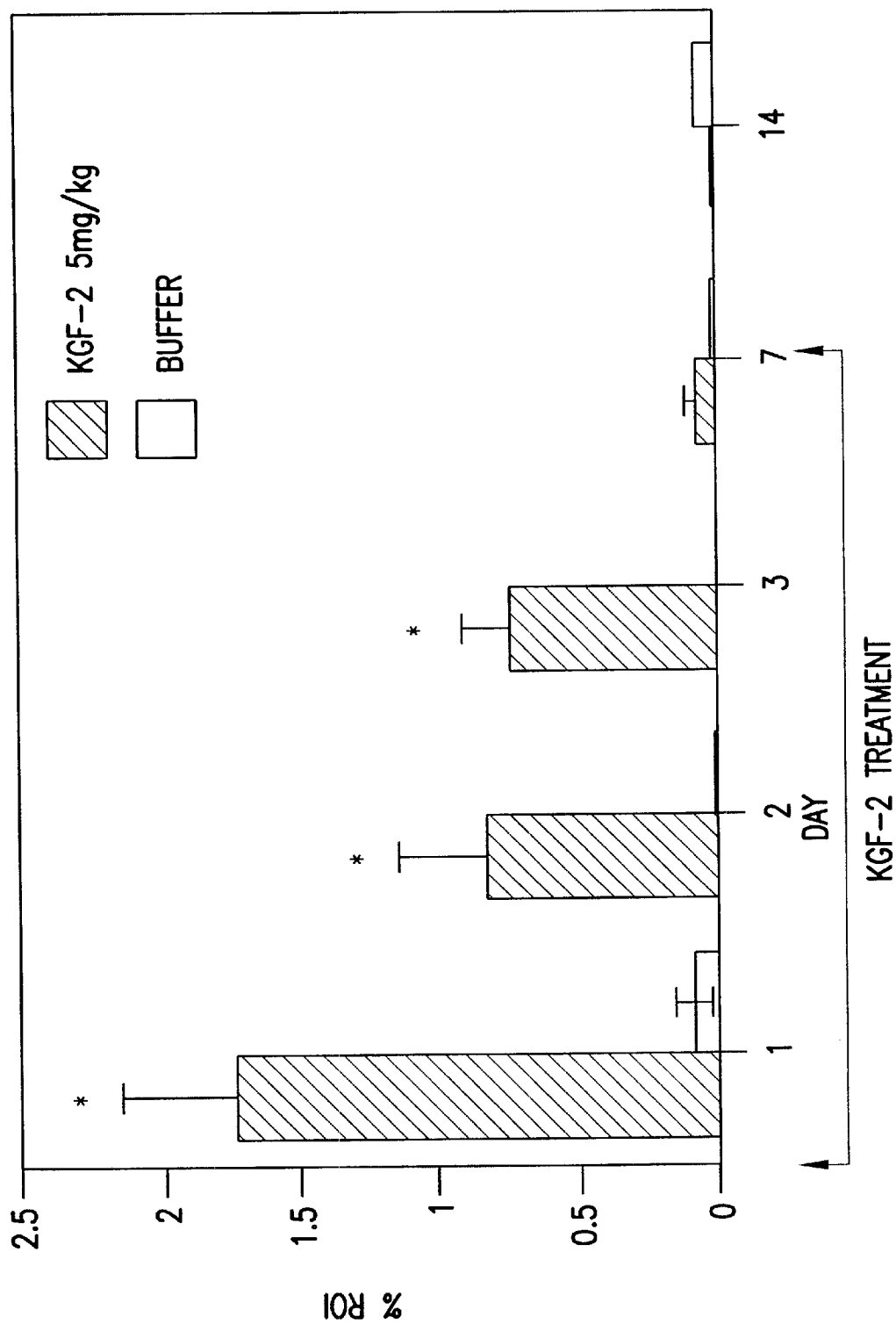
FIG. 36 shows the proliferation of the lacrimal gland after 1, 2 and 3 daily i.v. injections of KGF-2Δ33. Animals were used in groups of 6, and the proliferation of the tissue was assessed by a blinded observer using a computerized morphometry unit. The proliferation results are expressed as the percentage of a region of interest that has proliferating cells (% ROI). The error bars reflect the SEM. Statistical analysis was performed using StatView. A factorial ANOVA was performed followed by a Scheffé post-hoc test and statistical significant was defined as $p<0.05$.

As can be seen from FIG. 36, the lacrimal gland proliferates after 1, 2, and 3 daily i.v. treatments with KGF-2Δ33. However, the gland failed to demonstrate elevated proliferation after 7 daily administrations of this growth factor, a situation that has been observed in many organs and tissues. After 7 daily treatments, and then 7 days of rest, the buffer group displays a higher level of proliferation than the KGF-2 treated animals, possibly due to a down-regulation of KGF-2 receptors.

These results suggest that topical or systemic administration of KGF-2Δ33 may stimulate a therapeutic increase in the secretory capacity of the glands by its proliferative effect on lacrimal epithelial cells. These results also suggest that KGF-2 may have clinically useful effects on lacrimal glands damaged as a result Of radiation therapy, autoimmune diseases, or other medical conditions.

EXAMPLE 26

The Effect of KGF-2 on the Cornea and Conjunctiva

This experiment was performed to determine the effect of KGF-2 on the cornea and conjunctiva.

Experimental Design

KGF-2Δ33 was intravenously injected at 5 mg/kg on a daily basis in male SD rats. The animals were sacrificed at days 1, 2, 3 and 7. Another group of animals were injected for 7 days and allowed to rest for 7 before sacrifice. Two hours before sacrifice, the animals were injected with 100 mg/kg of BrdU. The eyes and the attached conjunctiva were removed. The number of replicating epithelial cells, which had incorporated BrdU, in the cornea and conjunctiva. The results express the replicating epithelia as number of cells per mm of tissue.

Results

Cornea

Figure 37:
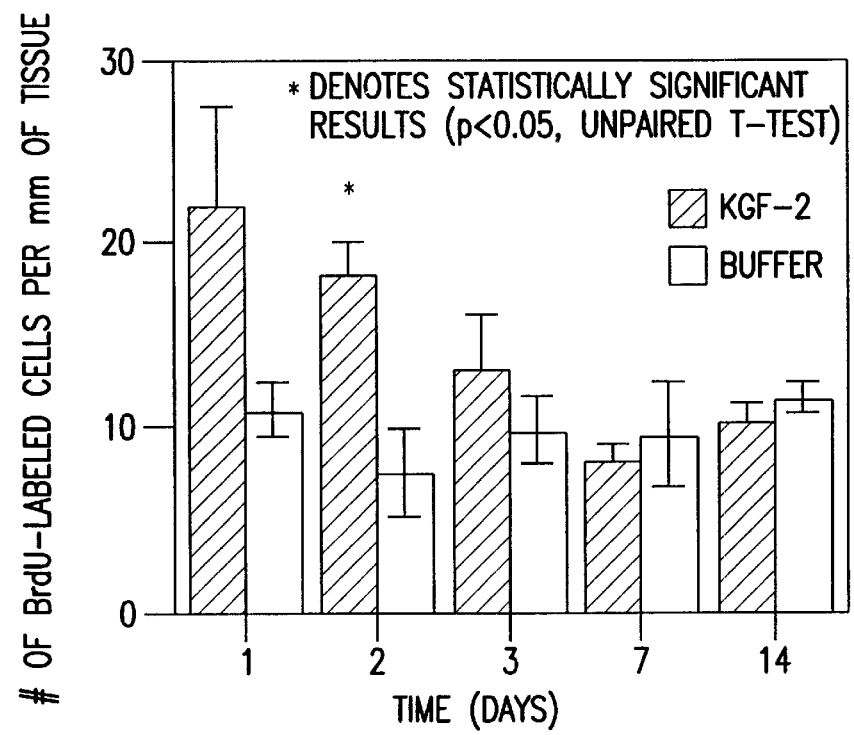
FIG. 37 shows the effectof KGF-2 intravenous injection at days 1, 2, 3 and 7 on the cornea. The results express the replicating epithelia as number of cells per mm of tissue. An increase in the number of proliferating cells following KGF-2 treatment on days 1 and 2 was observed. However, only the results from day 2 attained statistical significance.

As can be seen from FIG. 37, an increase in the number of proliferating cells following KGF-2Δ33 treatment on days 1 and 2 was observed. However, only the results from day 2 attained statistical significance. A factorial-ANOVA was performed on the results which revealed that there was no interaction between KGF-2Δ33 treatment and time. Therefore, KGF-2Δ33 does not appear to cause proliferation of epithelial cells in the cornea ($p=0.077$). However, as can be seen from the p value, the results approach significance.

Conjunctiva

Figure 38:
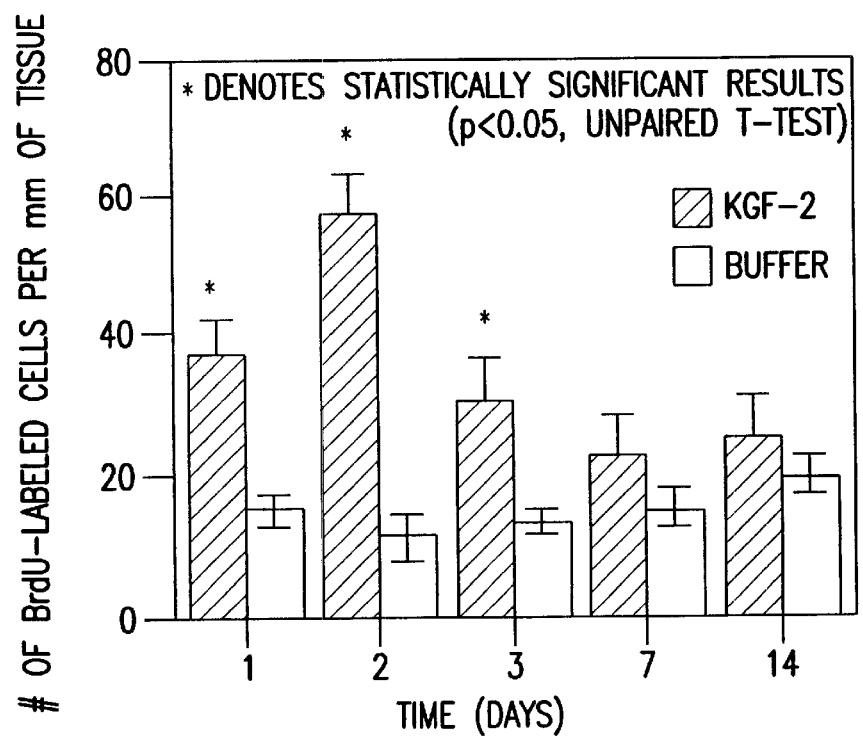
FIG. 38 shows the results of KGF-2 intravenous injection at days 1, 2, 3 and 7 on the conjunctiva. The results express the replicating epithelia as number of cells per mm of tissue. An increase in the number of proliferating cells following KGF-2 treatment on days 1, 2 and 3 was observed. These results were statistically significant.

As can be seen from FIG. 38, an increase in the number of proliferating cells following KGF-2Δ33 treatment on days 1, 2 and 3 was observed. However, the number of proliferating cells returned to normal values by the $7^{th}$ day of treatment. A factorial-ANOVA on the results revealed that KGF-2Δ33 causes proliferation of the epithelial cells in the conjunctiva ($p=0.0024$).

EXAMPLE 27

The Effect of KGF-2 on Pilocarpine-induced Salivation

Clinical syndromes of xerostomia (dry mouth) result from either radiation therapy to treat head and neck tumors or Sjorgen's Syndrome. Radiation therapy causes severe reduction in the saliva that is produced by a patient and can lead to problems such as difficulty eating and swallowing, mouth sores and lesions, and speech difficulties. Current treatments are sub-optimal. The most common treatment is oral administration of pilocarpine tablets to induce salivation.

Since KGF-2Δ33 exerts a proliferative effect on the cells of the salivary glands, it was interest to determine if KGF-2Δ33 injections also induced a functional difference in treating rats.

Materials and Methods

Normal male Sprague Dawley rats were injected intravenously daily with KGF-2Δ33 or buffer for 7 days. Animals were used in groups of 6. The results were analyzed using Student's t-test. Saliva was collected after 7 days of injections, by first anesthetizing the rats and then injecting them with pilocarpine HCl (2 mg/kg i.p.).

Results

Saliva was collected for 30 minutes directly from the mouth starting at the time of the pilocarpine injection. Saliva volume was calculated from weight and was then assayed for amylase content.

Figure 39A:
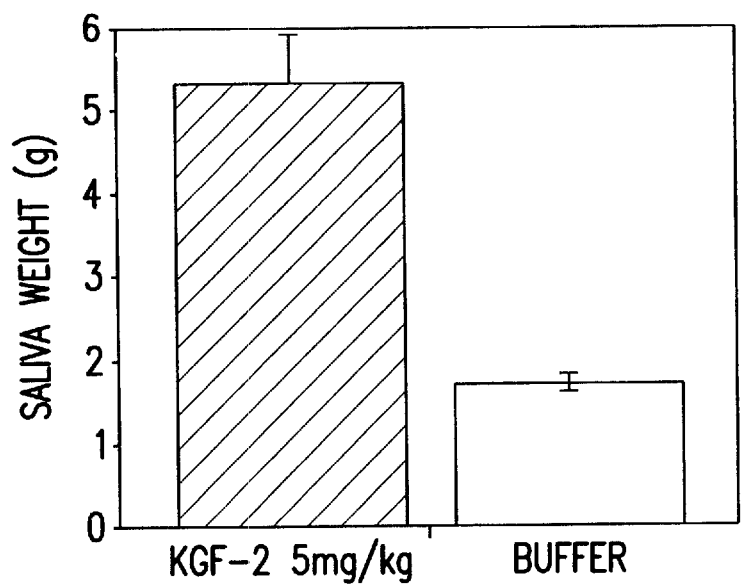
FIGS. 39(A) and (B) show the results of KGF-2Δ33 daily intravenous injections on pilocarpine-induced salivation.
Figure 39B:
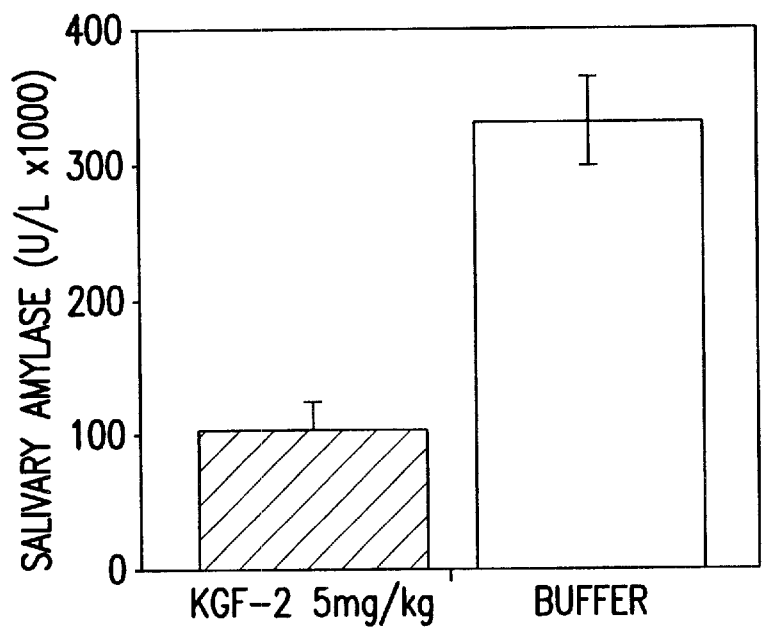
FIG. 39(B) shows that the concentration of arnylase in saliva is decreased following the daily KGF-2Δ33 injections.

As shown in FIG. 39 (A), KGF-2Δ33 treatment induces a large increase in saliva production in the treated animals. FIG. 39(B) shows that the concentration of amylase in saliva is decreased following the daily KGF-2Δ33 injections. Due to the massive proliferation brought on by KGF-2Δ33 treatment to the secretory acini of the parotid and submandibular salivary glands, it follows that there was an increase in saliva production. Thus, KGF-2 may be useful to treat xerostomia.

EXAMPLE 28

Effect of KGF-2 on Maxillary Sinus and Nasal Septum

KGF-2 Δ33 was administered to normal S.D. rats intravenously at a dose of 5 mg/kg. Animals were sacrificed 1, 2, 3 and 7 days following treatment. Additionally, one group of rats were injected daily with KGF-2Δ33 for 7 days and allowed to rest for 7 days (Day 14). Two hours prior to sacrifice, each animal was injected with 100 mg/kg of BrdU.

At the time of sacrifice, animals were decapitated and their nasal cavities were immediately flushed and fixed in neutral phosphate-buffered 10% formalin. The total number of labeled (BrdU) respiratory epithelial cells of both the nasal septum and maxillary sinus were counted and expressed per mm length of tissue.

Results

Maxillary Sinus

Figure 40:
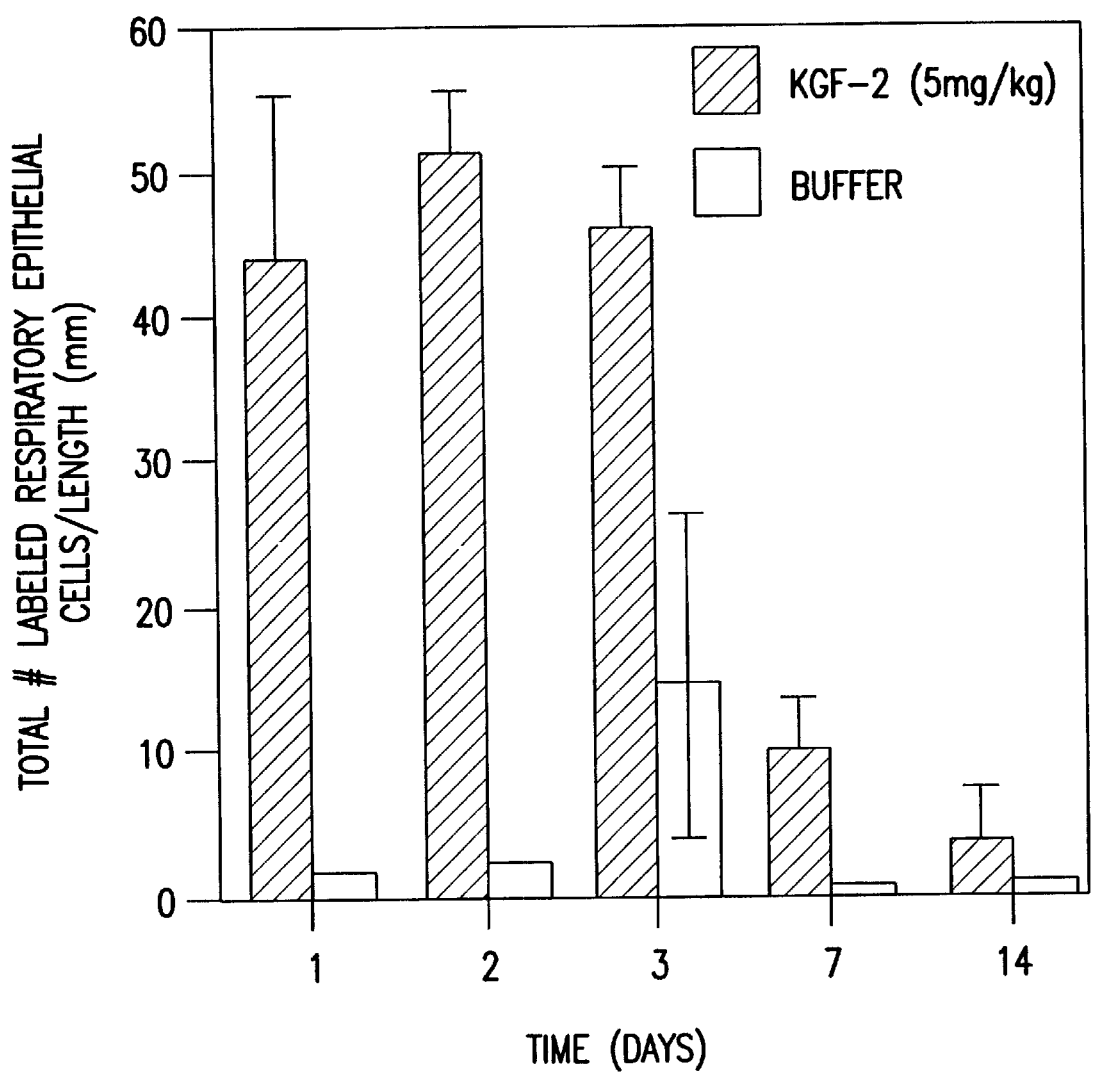
FIG. 40 shows the results of KGF-2 intravenous injection at days 1, 2, 3, 7 and 14 on the maxillary sinus in normal rats. There was an increase in the total number of proliferating cells following KGF-2 treatment on Days 1, 2, 3 and 7. All days, except Day 14, attained statistical significance. By day 14, the number of proliferating cells returned to normal.

As shown in FIG. 40, an increase was observed in the total number of proliferating cells following KGF-2Δ33 treatment on days 1, 2, 3 and 7, all of which attained statistical significance (Factorial-ANOVA: $p=0.0024, <0.0001, 0.0190$ and $0.0374$, respectively). The number of proliferating cells returned to normal by Day 14.

Nasal Septum

Figure 41:
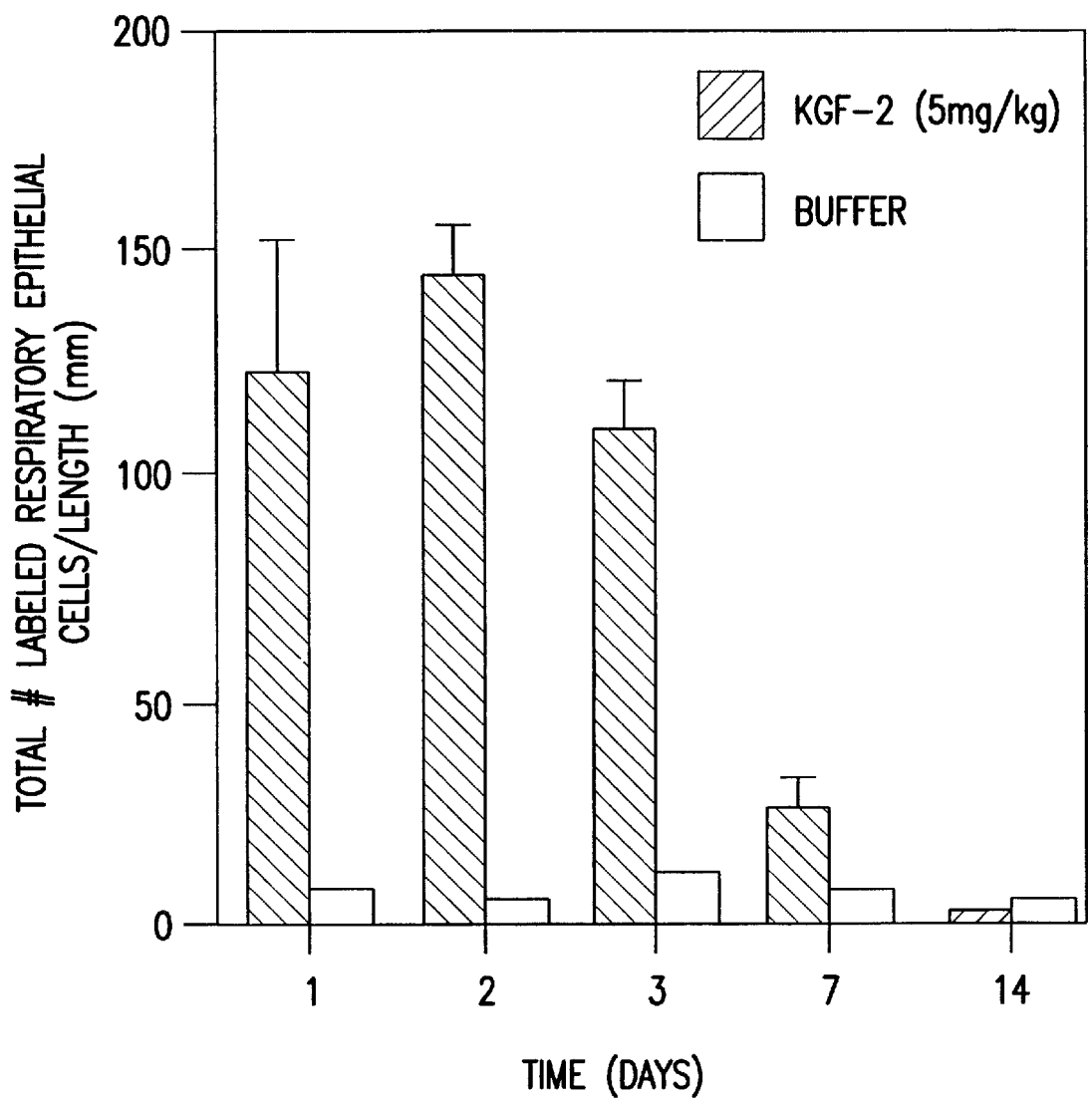
FIG. 41 shows the results of KGF-2Δ33 intravenous injection at days 1, 2, 3, 7 and 14 on the nasal septum in normal rats. There was an increase in the total number of proliferating cells following KGF-2 treatment on Days 1, 2, 3 and 7. All days, except Day 14, attained statistical significance. By day 14, the number of proliferating cells returned to normal.

As shown in FIG. 41, the trend seen in the respiratory epithelium of the maxillary sinus was also mirrored in that of the nasal septum. There was an increase in the total number of proliferating cells following KGF-2Δ33 treatment on Days 1, 2, 3 and 7. All days, except Day 14, attained statistical significance (Factorial-ANOVA: $p=0.0022, <0.0001, <0.0001$ and $0.0171$, respectively). By day 14, the number of proliferating cells returned to normal.

Conclusion

At a dose of 5 mg/kg, KGF-2Δ33 causes a significant increase in the total number of Brdu labeled epithelial cells of both the maxillary sinus and nasal septum. By Day 14, the proliferation returns to normal levels.

EXAMPLE 29

Effect of KGF-2 on Goblet Cells in the Conjunctiva

KGF-2Δ33 was administered to male SD rats intravenously at a dose of 5 mg/kg. The animals were sacrificed at days 1, 2, 3 and 7; additional rats were injected for 7 days and allowed to rest for 7 more days before sacrifice. The eyes and the attached conjunctiva were removed. The tissue was stained with PAS stain, and the number of PAS-positive cells (Goblet cells) in the conjunctiva was counted. The results are expressed as number of goblet cells per millimeter of tissue.

Results

Figure 42:
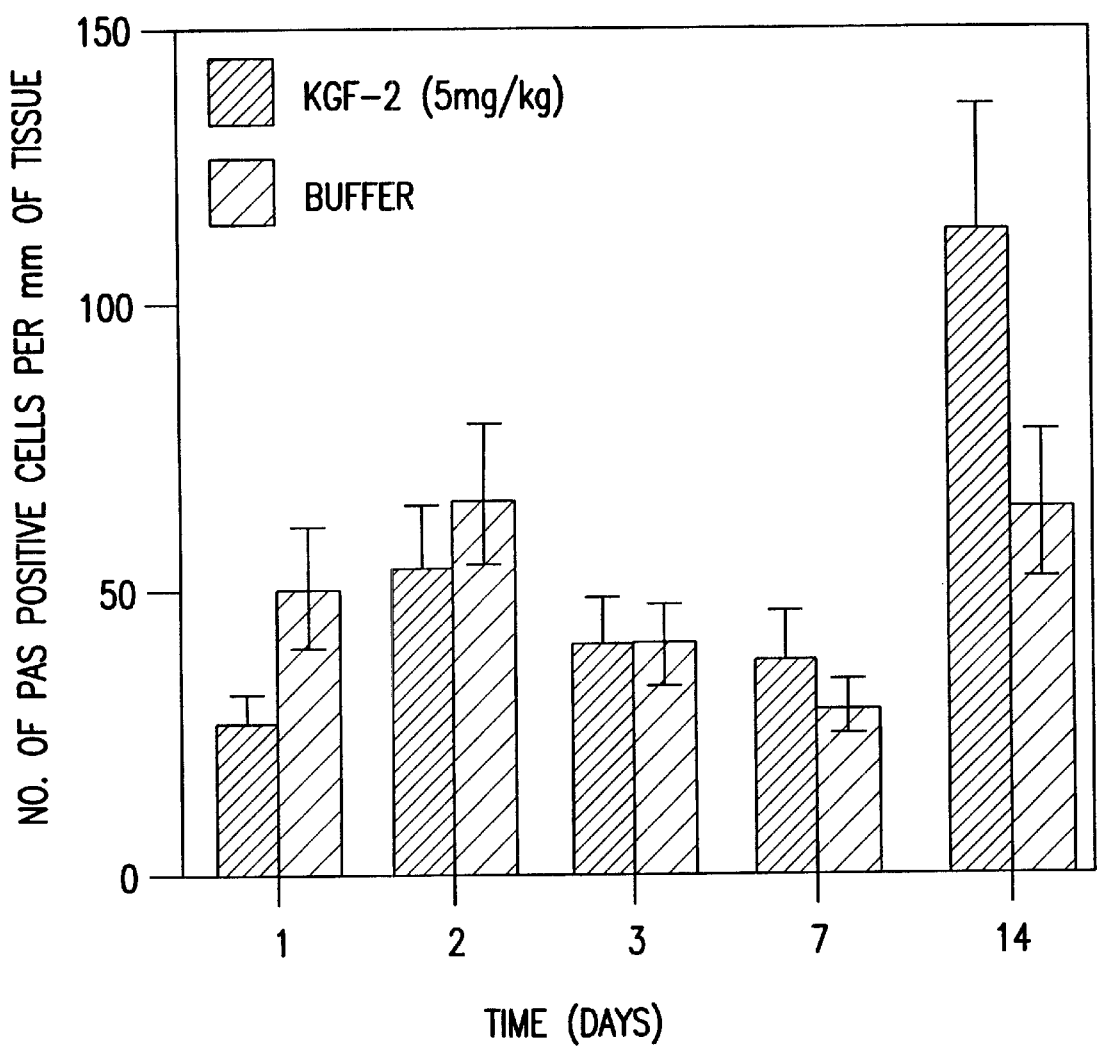
FIG. 42 shows the effect of KGF-2Δ33 on the number of goblet cells in the conjunctiva in male rats intravenously injected with either KGF-2Δ33 or buffer at days 1, 2, 3, and 7.

During the treatment period (days 1,2,3 and 7), there were no differences between the two treatment groups, KGF-2Δ33 and buffer. Animals that were treated for 7 days with KGF-2Δ33, and allowed to rest for 7 more days (Day 14 group on graph), had a higher number of goblet cells than those treated with buffer. This difference approached statistical significance (p=0.085, Scheffe's post-hoc test). The results are shown in FIG. 42.

EXAMPLE 30

Effect of KGF-2 on In Vivo Lung Proliferation

Methods

Male Sprague Dawley rats (approximately 200 g, n=5 per group) were anesthetized with isoflurane gas while in a supine position. Buffer or KGF-2 Δ33 (1 or 5 mg/kg) was administered intravenously (i.v.) via the tail vein in a volume of 0.5 ml. A single i.v. dose of KGF-2Δ33 or placebo was administered on experimental day 1. Animals were euthanized at 6, 24 or 48 hours following i.v. injection. On the day of euthanasia, the rats were injected i.p. with 100 mg/kg BrdU two hours prior to sacrifice. Euthanasia was carried out by anesthetizing with ketamine/xylazine followed by cervical dislocation.

Lung Tissue Harvest

A longitudinal skin incision was made from the sternal region to the chin. The left superior vena cava was clamped and the thoracic cavity was opened through the sternal borders and separated from the ribs. The lungs were released from the diaphragm and the pulmonary system was flushed of blood by injecting saline (10–15 mL) into the right ventricle. The blood/saline exited the pulmonary system via the left atrium. The left lobe was clamped at the main bronchus with artery forceps, while the right lung was inflated with 10–15 mL of 10% formalin via a slit hole in the trachea over the neck region, clamped and allowed to fix for about five minutes. The upper right lung and lower right was then removed, placed in a tissue cassette and immersed in 10% formalin for 24 hours. Lung tissue was placed in 70% alcohol and submitted for histopathological analysis. Tissue was embedded in paraffin, cross-sectioned and stained with H&E and a mouse anti-BrdU monoclonal antibody.

Histological Analysis

The number BrdU positive cells was counted under light microscopy at a magnification of 20x. 10 random fields were counted from each tissue sample. Counting was done by two independent observers who were blind to the treatment groups.

Statistical Analysis

All statistical analysis was accomplished using Instat v2.01. Experimental data was analyzed using an unpaired t test. A p value of <0.05 was considered significant. The data expressed as the mean±SEM.

Results

Figure 43:
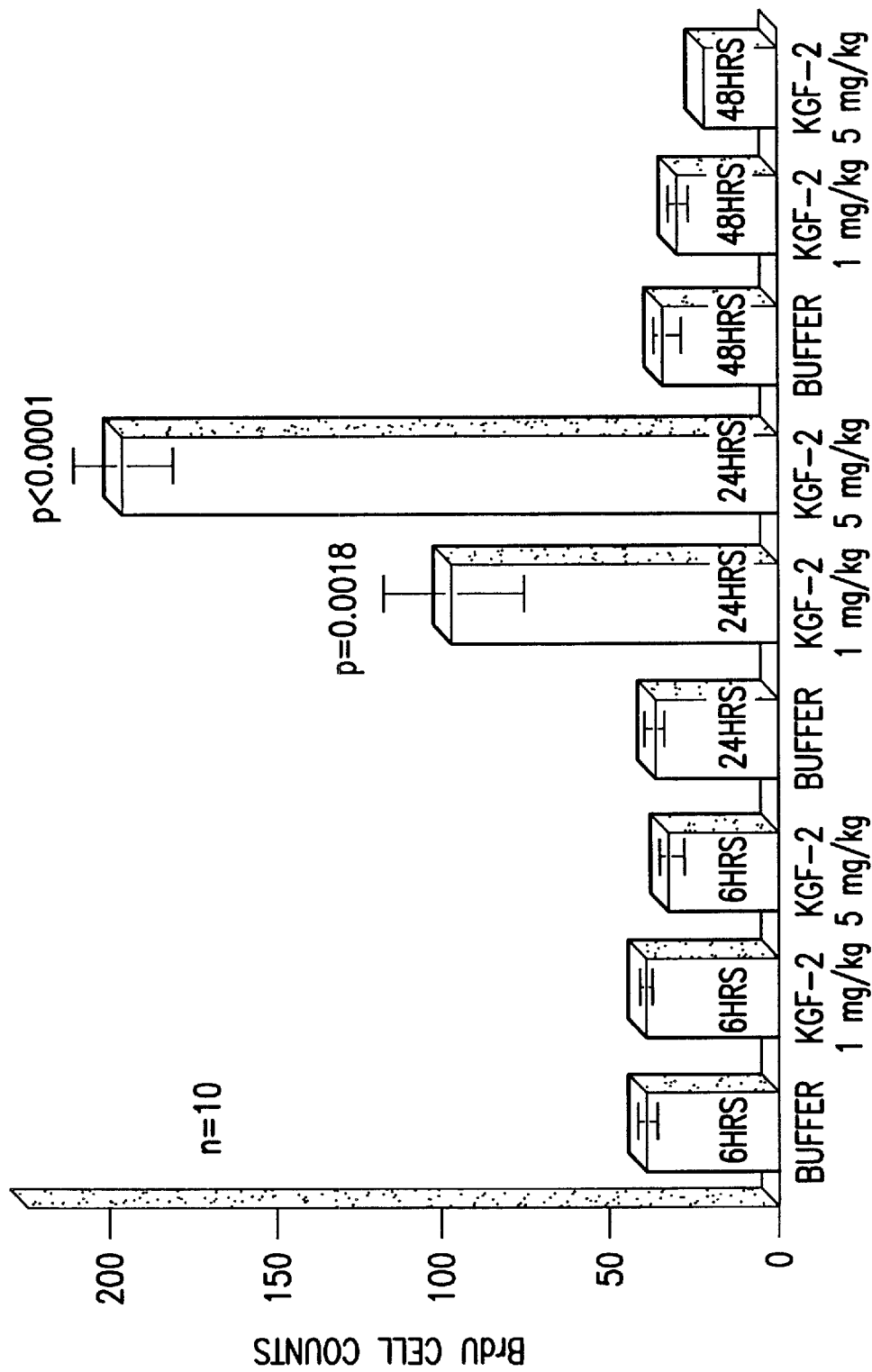
FIG. 43 shows the effect of intravenous KGF-2 on lung proliferation. Male SD rats received buffer or KGF-2Δ33 i.v. (1 or 5 mg/kg) on day 1. Animals were injected with BrdU (100 mg/kg, i.p.) 2 hours prior to euthanasia. Animals were sacrificed at 6, 24, or 48 hour time points. The average number of BrdU positive cells per field was counted in 5 random fields at 20×. Statistical significance is achieved using the unpaired t-test where $p<0.05$ when compared to the buffer control.

The results of the BrdU proliferation studies are shown in FIG. 43. In rats receiving buffer, there were approximately 36 BrdU positive cells per field under 20x magnification. At 24 hours after a single i.v. treatment of 1 mg/kg KGF-2Δ33, 97 BrdU positive cells per field were observed; an increase that was significant (p=0.0118) relative to the KGF-2 buffer control group. Rats receiving 5 mg/kg KGF-2Δ33 exhibited a significant increase in BrdU positive cells per field (197 cell per field; p<0.0001) when compared to the buffer control (37 cells per field). At the 6 and 48 hour time points, there were no differences observed between the groups with regard to the number of BrdU positive cells.

Conclusion

At 6 hours after i.v. injection of KGF-2 Δ33, no increase in proliferation was observed by BrdU immunostaining.

A single i.v. administration of KGF-2 Δ33 at 5 mg/kg resulted in a significant increase in BrdU immunostaining in the lung relative to buffer controls in both experiments.

In one of two experiments performed, an i.v. dose of 1 mg/kg KGF-2 Δ33 resulted in a significant increase in BrdU immunostaining relative to buffer control.

At 48 hours after i.v. administration of KGF-2 Δ33, there was no observed difference in proliferation of lung cells among the groups.

EXAMPLE 31

Effect of Nebulized KGF-2 on In Vivo Lung Proliferation

Methods

Male Lewis or SD rats (250–350 g, n=5 per group) were anesthetized with intramuscular ketamine/xylazine to immobilize them during the exposure period. A Pari-Proneb LC Jet+nebulizer was used to nebulize buffer or KGF-2Δ33 This nebulizer delivers a range of particle sizes whereby 74% of the particles are <5 $\mu$m in size and 24% of the particles are <2$\mu$ in size. Rats inhaled nebulized buffer of KGF-2Δ33 (6 or 12 mg/rat) over a period of 45 to 60 minutes. Twenty-four hours after the exposure period, (Day 2), the rats were injected i.p. with 100 mg/kg BrdU two hours prior to sacrifice. Euthanasia was carried out by $CO_2$ asphyxiation for tissue harvesting.

Lung Tissue Harvest

A longitudinal skin incision was made from the sternum region to the chin. The left superior vena cava was clamped and the thoracic cavity was opened through the sternal borders and separated from the ribs. The lungs were released from the diaphragm. The pulmonary system was flushed of blood by injecting saline (10–15 mL) into the right ventricle. The blood/saline exited the pulmonary system via left auricle. The left lobe was clamped at the main bronchus with artery forceps, removed and snap frozen in liquid nitrogen for collagen content assay. The right lung was insufflated with 10–15 mL of 10% formalin via a slit hole in the trachea over the neck region, clamped and allowed to fix for about five minutes. The upper right lung and lower right was then removed, placed in a tissue cassette and immersed in 10% formalin for 24 hours. Lung tissue was placed in 70% alcohol and submitted for hisopathological analysis. Tissue was embedded in paraffin, cross-sectioned and stained with H&E and a mouse anti-BrdU monoclonal antibody.

Histological Analysis

The number BrdU positive cells was counted under light microscopy at a magnification of 20x. Ten random fields were counted from each tissue sample. Counting was done by two independent observers who were blind to the treatment groups.

Statistical Analysis

All statistical analysis was accomplished using Instat v2.01. Experimental data was analyzed using an unpaired t test. A p value of <0.05 was considered significant. The data was expressed as the mean±SEM.

Nebulizer Design

Five animals treated simultaneously on one nebulizer unit.

Results

Microscopic Observations

Figure 44:
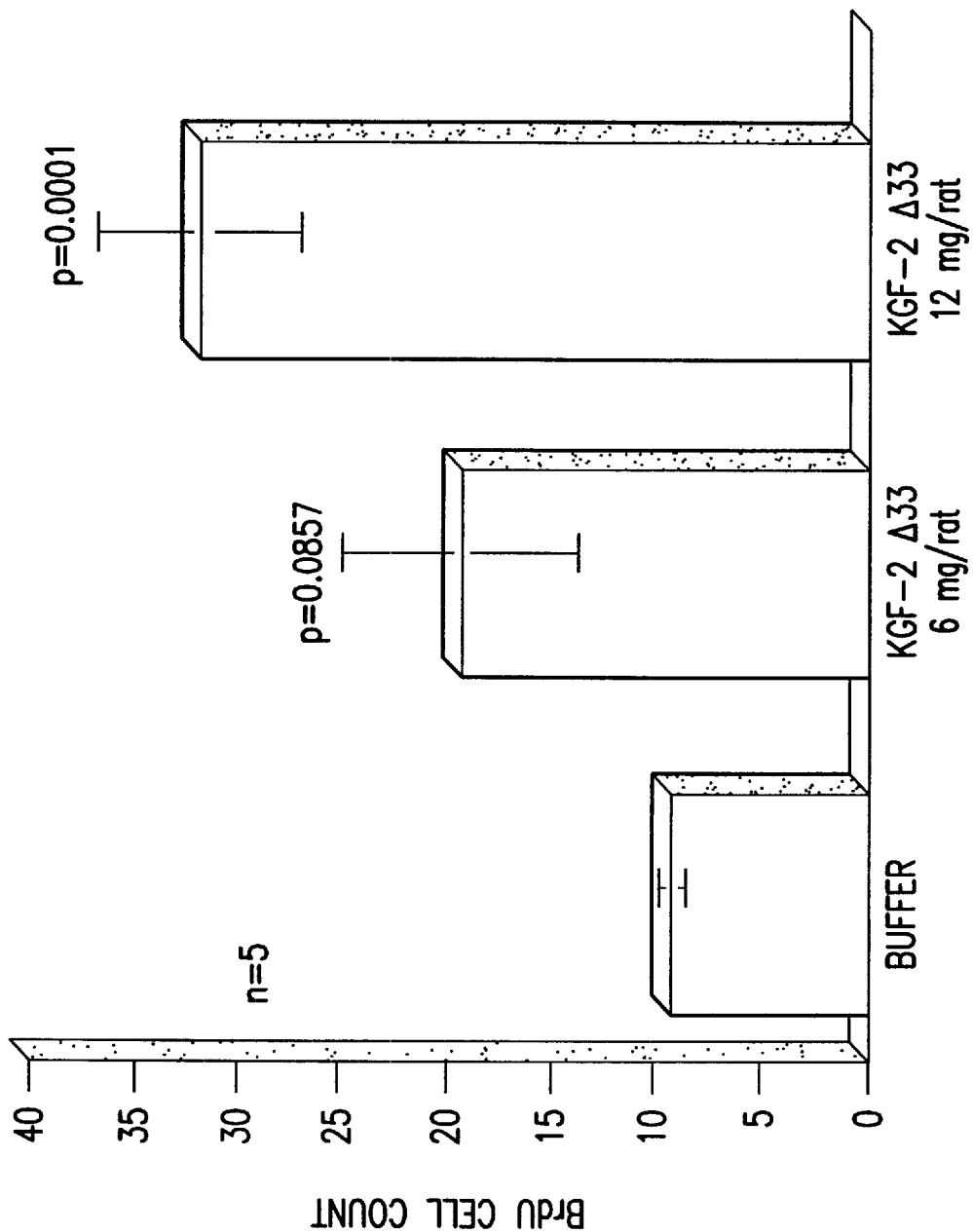
FIG. 44 shows the effect of nebulized KGF-2 on proliferation in normal rat lungs. Male Lewis rats inhaled nebulized buffer or KGF-2Δ33 (56 or 12 mg/rat). Twenty four hours post-nebulization, animals received BrdU (100 mg/kg, i.p.) 2 hours prior to euthanasia. The average number of positively stained cells in 5 random microscopic fields (20×) per lobe was the BrdU cell count.

Upon histological observation of the BrdU cell counts, rats treated with KGF-2Δ33 buffer (n=5) had an average of 9 BrdU positive cells per field. Treatment with KGF-2Δ33 at 6 mg/rat (n=5) produced a not quite significant increase to 20 BrdU positive cells per field (p=0.0857) when compared to the buffer control. Treatment KGF-2Δ33 at 12 mg/rat (n=5) resulted in a significant increase in BrdU positive cells per field (32 cells per field; p=0.001) when compared to the buffer control. The results are shown in FIG. 44.

EXAMPLE 32

Prophylactic KGF-2 Δ33 in Bleomycin Lung Damage

The purpose of this example was to examine the effect of KGF-2Δ33 in the bleomycin-induced rat model of lung injury. Bleomycin causes fibrosis of the lung. KGF-2Δ33 was tested for its prophylactic (protective) effect in the lungs. Parameters that were evaluated include body weight, histology, lung collagen content.

Methods

Male Lewis rats (200–250 g, n=5 to 8 per group) were anesthetized with isoflurane gas and while in a supine position. A pharyngo-laryngo fiberscope was used to locate the pharynx and a metal feeding tube (20 gauge) attached to a 5 ml syringe was inserted into the trachea. Buffer or KGF-2 Δ33 (0.5, 1 or 5 mg/kg) was administered intratracheally (i.t.) into the lungs in a volume of 0.6 ml followed by 4 cc of air on days 1 and 2 of the experiment. The air was then used to drive the liquid into the lungs. The rats were quickly placed in a recumbent position and allowed to recover. Resuscitation was done if necessary. On day 3 of the experiment, bleomycin (5 units/0.5 ml) was administered intratracheally to all the animals except for the no treatment group. Clinical observations were made daily (e.g. weight loss, death etc.) On the last day of the experiment (Day 14), the rats were injected i.p. with 100 mg/kg BrdU two hours prior to sacrifice. Euthanasia was carried out by $CO_2$ asphyxiation for tissue harvesting, histopathological analysis and lung collagen content assay.

Lung Tissue Harvest

A longitudinal skin incision was made from the xiphisternal region to the neck region. The thoracic cavity was opened through the sternal borders and separated from the ribs. The lungs were released from the diaphragm and the left lobe was clamped at the main bronchus with artery forceps, removed and snap frozen in liquid nitrogen for collagen content assay. The right lung was inflated with 10% formalin via a slit hole in the trachea over the neck region, clamped and allowed to fix for about five minutes. The right lung was then removed, placed in a tissue cassette and immersed in 10% formalin for 24 hours. Lung tissue was placed in 70% alcohol and submitted for histopathological analysis. Tissue was embedded in paraffin, cross-sectioned and stained with H&E and mouse anti-BrdU monoclonal antibody.

Histological Analysis

The number of BrdU positive cells was counted under light microscopy at a magnification of 20×. Ten random fields were counted from each tissue sample. Counting was performed by two independent observers who were blinded to the treatment groups.

Statistical Analysis

All statistical analysis was accomplished using Instat v2.01. Experimental data was analyzed using an unpaired t test. A p value of <0.05 was considered significant. The data was expressed as the mean±SEM.

Results

Body Weight

Figure 45:
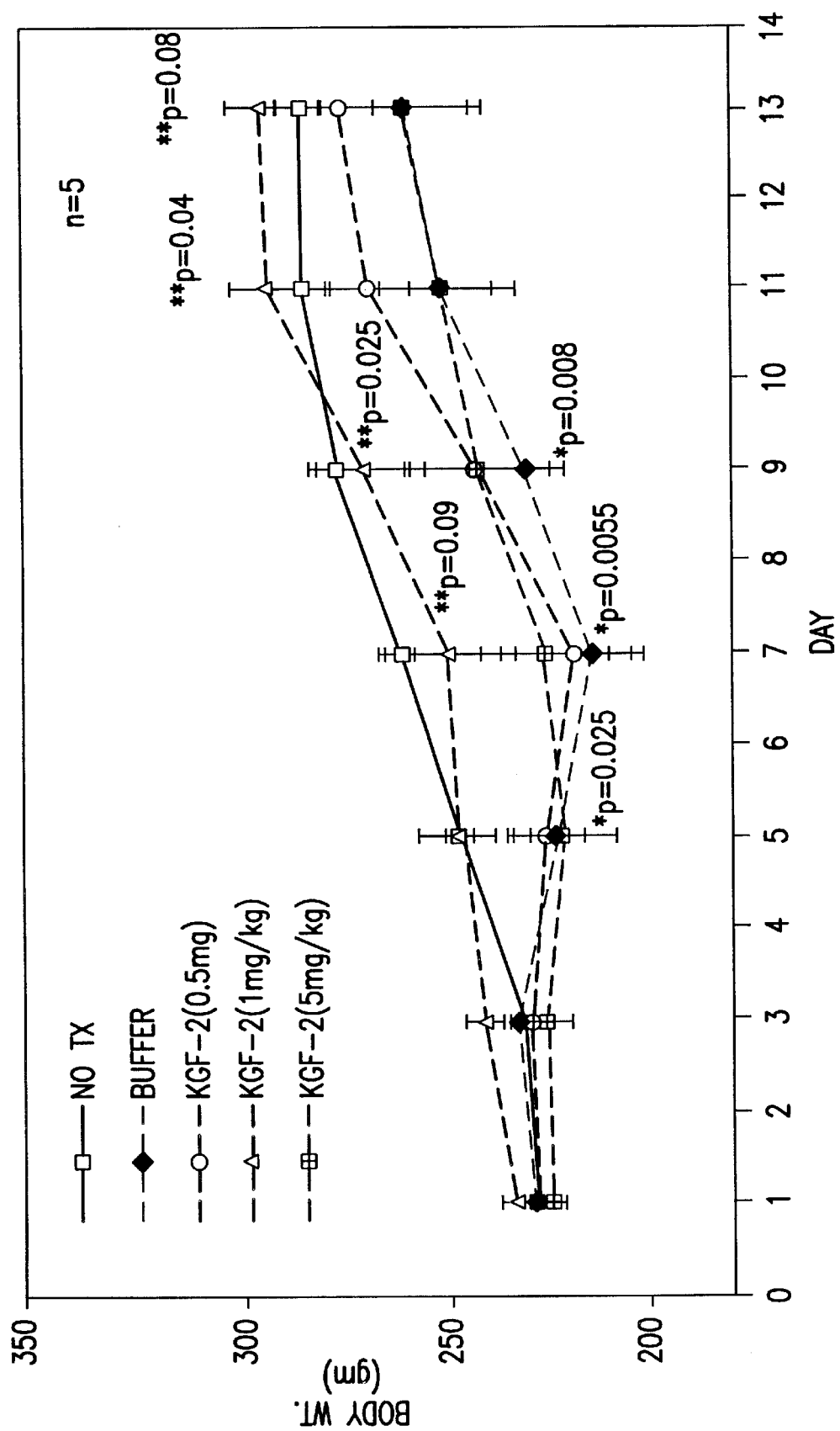
FIG. 45 shows the of prophylactic KGF-2Δ33 on body weights in a bleomycin-induced lung injury rat model. Male rats were given intratracheal doses of KGF-2Δ33 (0.5, 1 and 5 mg/kg) of buffer. Treatments were given on day 0 and day 1. Bleomycin was given on day 3. Animals were weighed on alternate days until the $14^{th}$ day. Statistical analysis was done using an unpaired t-test. *compared with the no treatment group; **compared to the KGF-2 buffer group.

FIG. 45 shows the body weights of the animals during this experiment. Animals in the "no treatment" group continued to increase in weight throughout the experiment. Animals receiving bleomycin and KGF-2 buffer lost weight during the experiment until day 7. Following day 7, these animals began to gain weight. In the treatment groups, KGF-2 Δ33 at a dose of 1 mg/kg, was able to prevent the weight loss observed in the other groups receiving bleomycin. This difference in body weight was seen on days 5, 7 and 9 relative to the buffer placebo group. Animals receiving 0.5 or 5 mg/kg KGF-2 Δ33 had body weights that were similar to the KGF-2 buffer controls.

Microscopic Observations

Figure 46:
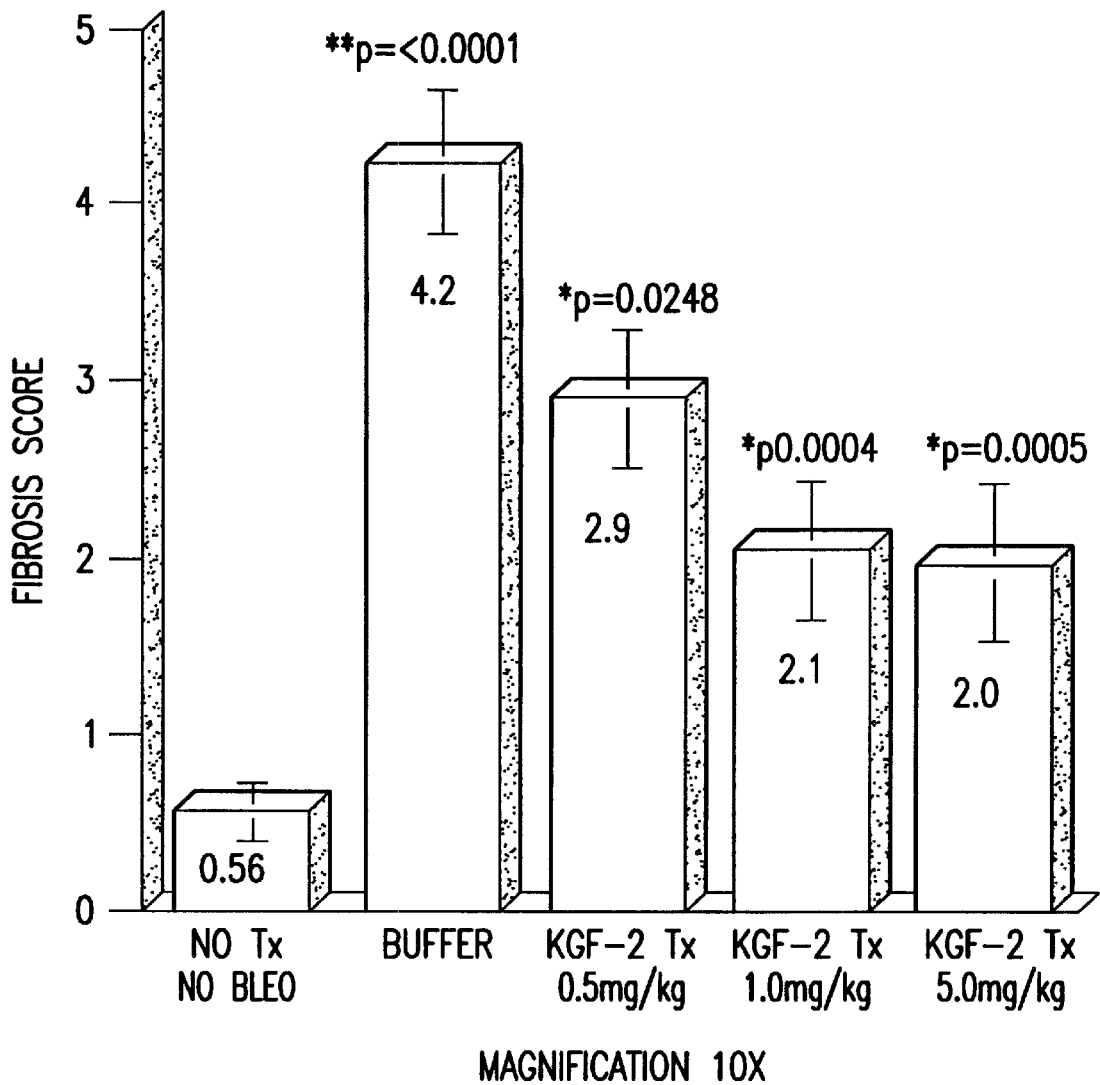
FIG. 46 shows the effect of prophylactic KGF-2Δ33 on fibrosis score in bleomycin-induced lung injury rat model. Male Lewis rats (n=5) were given intratracheal doses of of KGF-2Δ33 0.5 mg/ml, 1 mg/ml, 5 mg/ml or buffer while under anesthesia. Treatments were given on day 0 and day 1. Bleomycin was administered on day 3. On the final day of the experiment (day 14), animals were injected with BrdU (100 mg/kg, i.p.) 2 hours prior to euthanasia. The scoring was graded 0=normal, 1–3=mild, 4–6=moderate, and 7–9= severe at 10x. Statistical analysis was performed with a student's paired t-test. *compared to buffer treatment group, ** compared to no treatment group.

No architectural damage was observed in H&E stained sections of the lung parenchyma of the "no treatment" group animals. Fibrosis scoring was done using a scale ranging from 0–9, (0=normal, 1–3=mild, 4–6=moderate, 7–9= severe). Animals in the no treatment groups had a mean score of 0.56. Architectural damage was observed in all other treatment groups (groups receiving bleomycin). As shown in FIG. 46, rats treated with bleomycin and KGF-2 buffer had a mean fibrosis score of 4.24 (**p=<0.0001) a significant change relative to the no 20 treatment group. Animals receiving KGF-2 Δ33 displayed significant reductions in fibrosis scores at 0.5 mg/kg KGF-2 Δ33 (2.91, *p=0.0248), 1 mg/kg KGF-2 Δ33 (2.07, p=0.0004) and 5 mg/kg KGF-2 Δ33 (1.98, p=0.0005) when compared to the KGF-2 buffer placebo group.

Figure 47:
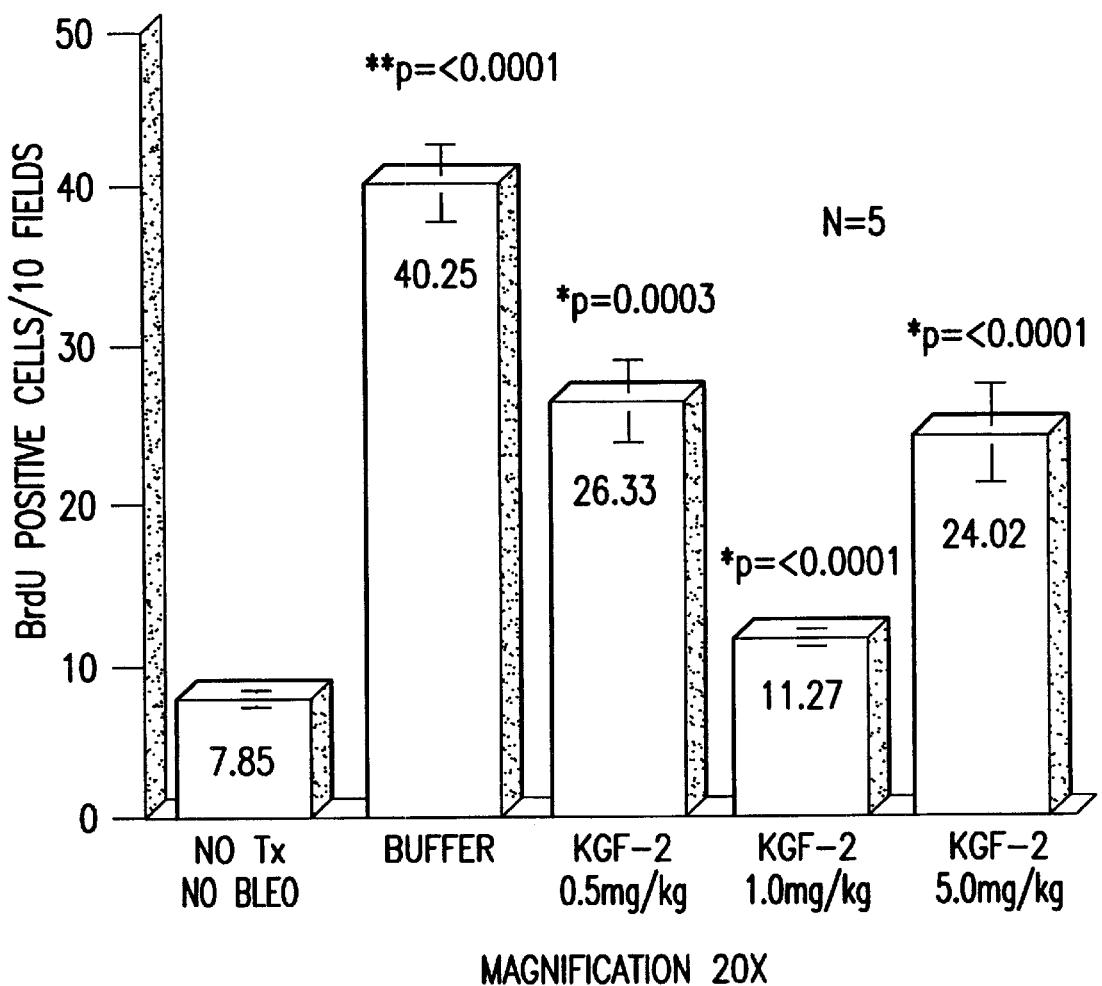
FIG. 47 shows the effect of prophylactic KGF-2 Δ33 on bleomycin-induced lung injury rat model. Male Lewis rats (n=5) were given intratracheal doses of of KGF-2 0.5 mg/ml, 1 mg/ml, 5 mg/ml or buffer while under anesthesia. Treatments were given on day 0 and day 1. Bleomycin was administered on day 3. On the final day of the experiment (day 14), animals were injected with BrdU (100 mg/kg, i.p.) 2 hours prior to euthanasia. The number of BrdU positive cells per field was counted in 10 random fields at 20x. Statistical analysis was performed with a student's paired t-test. *compared to Buffer treatment group **compared to no treatment group.

Cell proliferation, shown in FIG. 47, was assessed by counting the number of BrdU positive cells per field. In a normal rat the lungs have an average of 7 BrdU positive cells per field illustrating the low level of cell proliferation occurring under normal physiological conditions. When rats were treated with KGF-2 buffer and bleomycin, there was a significant increase in the number of cells per field, 40 (p=<0.0001) when compared to the no treatment group. Rats receiving KGF-2Δ33 displayed a significantly lower number of BrdU positive cells at doses of 0.5 mg/kg (26, p=0.0003) positive 1 mg/kg (11, p=<0.0001) and at 5 mg/kg (24, p=<0.0001) when compared to the KGF-2 buffer controls.

These results suggest that KGF-2 may have clinically useful effects on lung fibrosis.

EXAMPLE 33

Effect of KGF-2 Δ33 on Bladder Capacity in a Cyclophosphamide-Induced Cystitis Rat Model Experimental Design Male SD rats (200 g) received KGF-2Δ33 in doses of 0.1 mg/kg, 0.3 mg/kg, 1.0 mg/kg or 3.0 mg/kg intravenously. On day 1, 200 mg/kg of cyclophosphamide (CP) was administered i.p. Animals were sacrificed on day 4. Six animals were used in each experimental group. Experimental groups included a saline control group, a CP only control (200 mg/kg) group, a buffer+CP (200 mg/kg) group a KGF-2Δ33 (1.0 mg/kg)+CP (200 mg/kg), and a KGF-2Δ33 (3.0 mg/kg)+CP (200 mg/kg) group.

Two additional parameters were performed at the time of sacrifice. These measurements included bladder capacity and bladder wet weight. Bladder capacity was defined as the amount of formalin (in milliliter quantity) injected into the bladder until one drop of formalin is visible exiting from the urethra. Prior to filling the bladder is emptied of all urine by gently squeezing the bladder and forcing the urine out through the urethra. The bladder is allowed to fix several minutes. Once fixed the bladder is removed, drained and weighed providing a measure of wet weight. (* compared to CP only control; 554 compared to buffer control).

Results

Microscopic Observations

Figure 48:
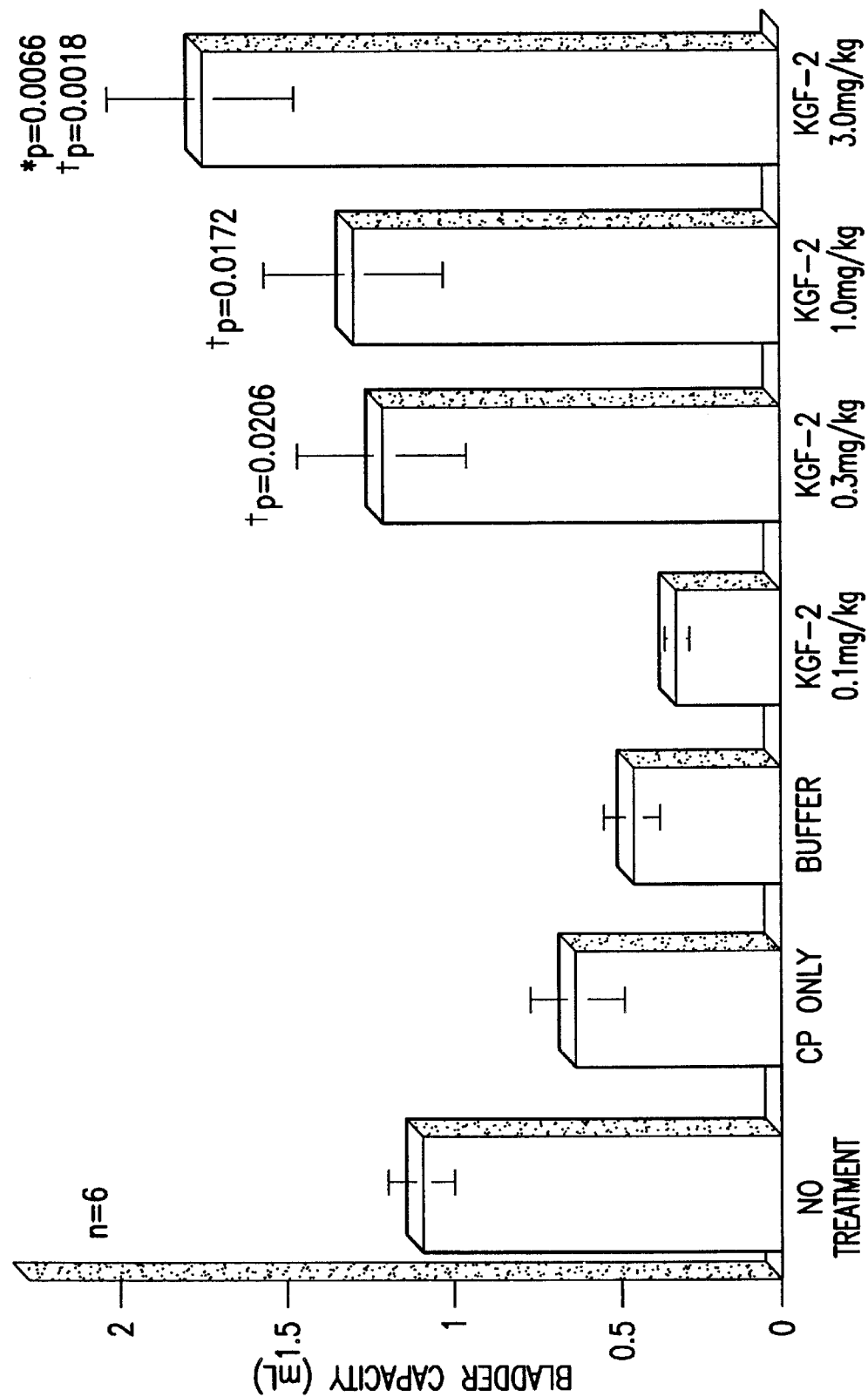
FIG. 48 shows the effect of KGF-2Δ33 on bladder capacity in cyclophosphamide-induced cystitis rat model. Male SD rats (200 g) received KGF-2Δ33 in doses of 0.1 mg/kg, 0.3 mg/kg, 1.0 mg/kg or 3.0 mg/kg intravenously. On day 1, 200 mg/kg of cyclophosphamide (CP) was administered i.p. Animals were sacrificed on day 4. After urine was removed from the bladder, it was filled with formalin until it leaked out of the urethra. The volume of formalin injected into the bladders was recorded as the bladder capacity. (* compared to CP only control; † compared to buffer control).

The bladder capacity of the saline control group was 1.10±0.1 ml. The CP only group was significantly reduced to 0.62±0.15 ml and the buffer control group was 0.45±0.01 ml. The bladder capacity of the KGF-2Δ33 groups treated with 0.3 mg/kg and 1.0 mg/kg (1.20±0.25 ml, p=0.0206;

1.28±0.27, p=0.0172, respectively) were significantly increased compared to the buffer control The bladder capacity of the KGF-2Δ33 at 3.0 mg/kg (1.72±0.28, p=0.28 ml) was significantly increased compared to the CP only control (p=0.0066) and the buffer-treated control (p=0.0018). The results are shown in FIG. 48.

Figure 49:
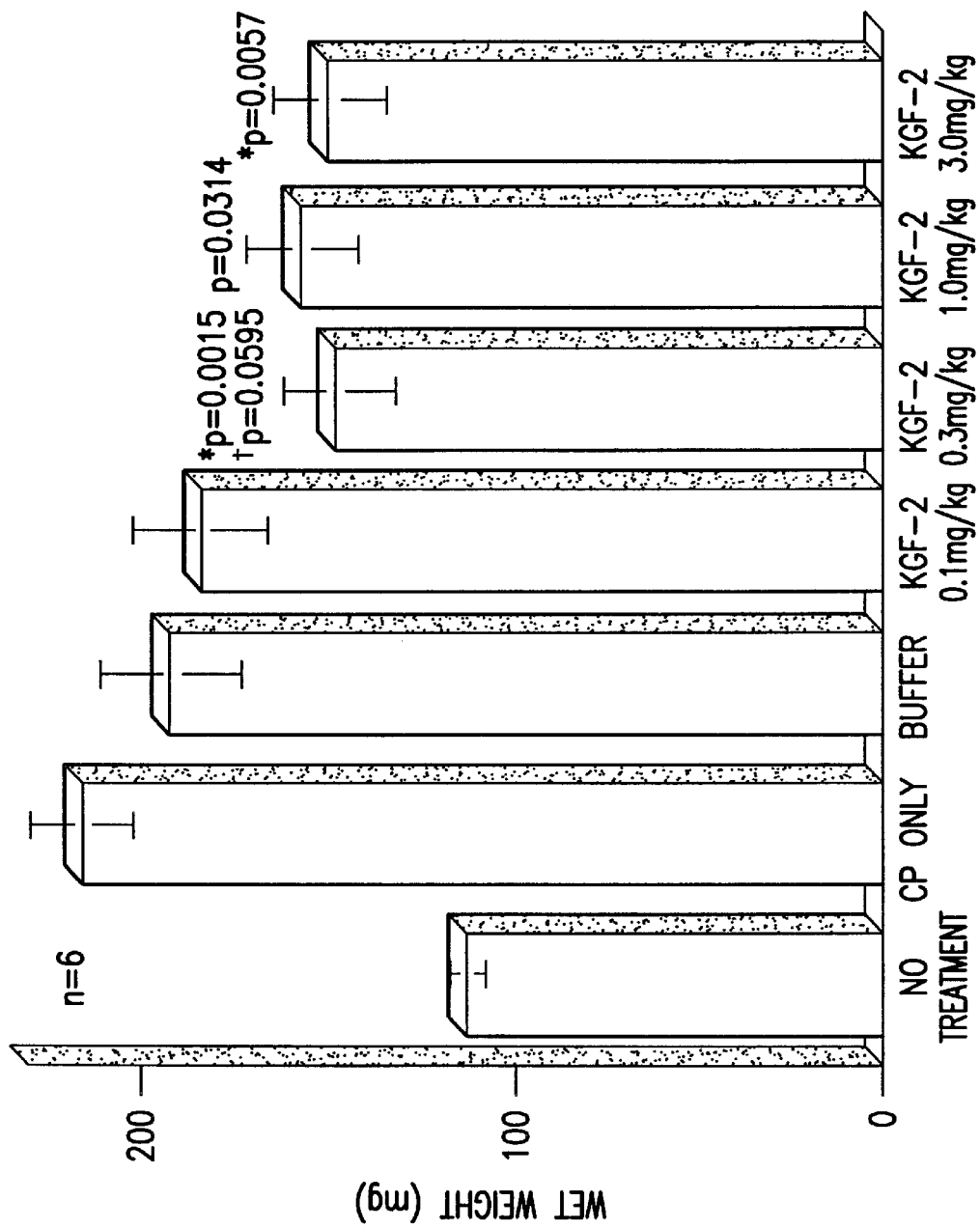
FIG. 49 shows the effect of KGF-2Δ33 on bladder wet weight in cyclophosphamide-induced cystitis rat model. Male SD rats (200 g) received KGF-2Δ33 in doses of 0.1 mg/kg, 0.3 mg/kg, 1.0 mg/kg or 3.0 mg/kg intravenously. On day 1, 200 mg/kg of cyclophosphamide (CP) was administered i.p. Animals were sacrificed on day 4. Bladders were fixed in formalin, harvested, weighed and then placed in tissue cassettes for histological analysis. (* compared to CP only control; † compared to buffer control).

The bladder wet weight of the saline control group was 0.11 mg. The wet weight of the CP only group was 0.22±0.01 mg and that of buffer control was 0.19±0.01 mg. The KGF-2Δ33 group (0.3 mg/kg) wet weight (0.15±0.007 mg) was significantly reduced compared to the CP only control (p=0.0015) and almost significantly reduced compared to the buffer-treated control (p=0.0595) group. The KGF-2Δ33 groups treated with 1.0 mg/kg (0.15±0.02 mg; p=0.0314) and 3.0 mg/kg (0.149±0.01 mg, p=0.0057) were significantly reduced in bladder wet weight compared to the buffer-treated control. These results are shown in FIG. 49.

EXAMPLE 34
Effect of KGF-2 Δ33 and Mesna in Cyclophosphamide-Induced Cystitis The effect of KGF-2Δ33 and mesna on bladder wall thickness, bladder ulceration and urothelium was examined in the cyclophosphamide-induced cystitis rat model. Mesna is currently used as a prophylactic agent for the prevention of hemorrhagic cystitis induced by cyclophosphamide or structural analogs.

Experimental Method and Design

Male SD rats (300–400 g) received either buffer or 5.0 mg/kg KGF-2Δ33 intravenously via the tail vein on day 0. On day 1, 200 mg/kg of cyclophosphamide (CP) i.p and Mesna (20 μg/g or 40 μg/g,), i.v. via the tail vein. One group of animals was injected i.p. with saline as a CP control. Five animals were used in each experimental group. Experimental groups included saline control group, a CP only control group (200 mg/kg), a Mesna (20 mg/kg)+CP (200 mg/kg) group, a Mesna (40 mg/kg)+CP (200 mg/kg) group, a buffer+CP (200 mg/kg) group, and a KGF-2Δ33 (5 mg/kg)+CP (200 mg/kg) group.

Animals were sacrificed on day 3,48 hours after CP injection the animals were injected with 100 mg/kg of BrdU. Two hour later the animals were euthanized by $CO_2$ asphyxiation. The bladders were fixed for histological processing by direct injection of 10% formalin into the lumen of the bladder and rinsing of the exterior of the bladder with formalin. After 5 minutes, the bladders were harvested. The uninary bladders were parafinn embedded, cross-sectioned and stained with H&E and a mouse anti-BrdU monoclonal antibody.

The extent of urothelial damage was assessed using the following scoring system: Urothelial damage (ulceration) was scored as 0–100% (in units of 10) loss of the urothelium. The amount of normal urothelium was assessed and scored as 0–100% (in increments of 10%). Normal urothelium was defined as a dense stratified epithelium containing at least a thickness a single layer of cells appearing as tall columnar or cuboidal cells with round nuceli. In addition, the thickness of the bladder wall was measured at 10 random sites per section and expressed in μm. This measurement included the distance from the urothelium through the smooth muscle layers to serosal surface. All histology measurements were performed by blinded observers. Statistical analysis was performed using the students unpaired t-test on Instat 2.01 where significance is found if p ≦0.05.

Results

Microscopic Observations

Figure 50:
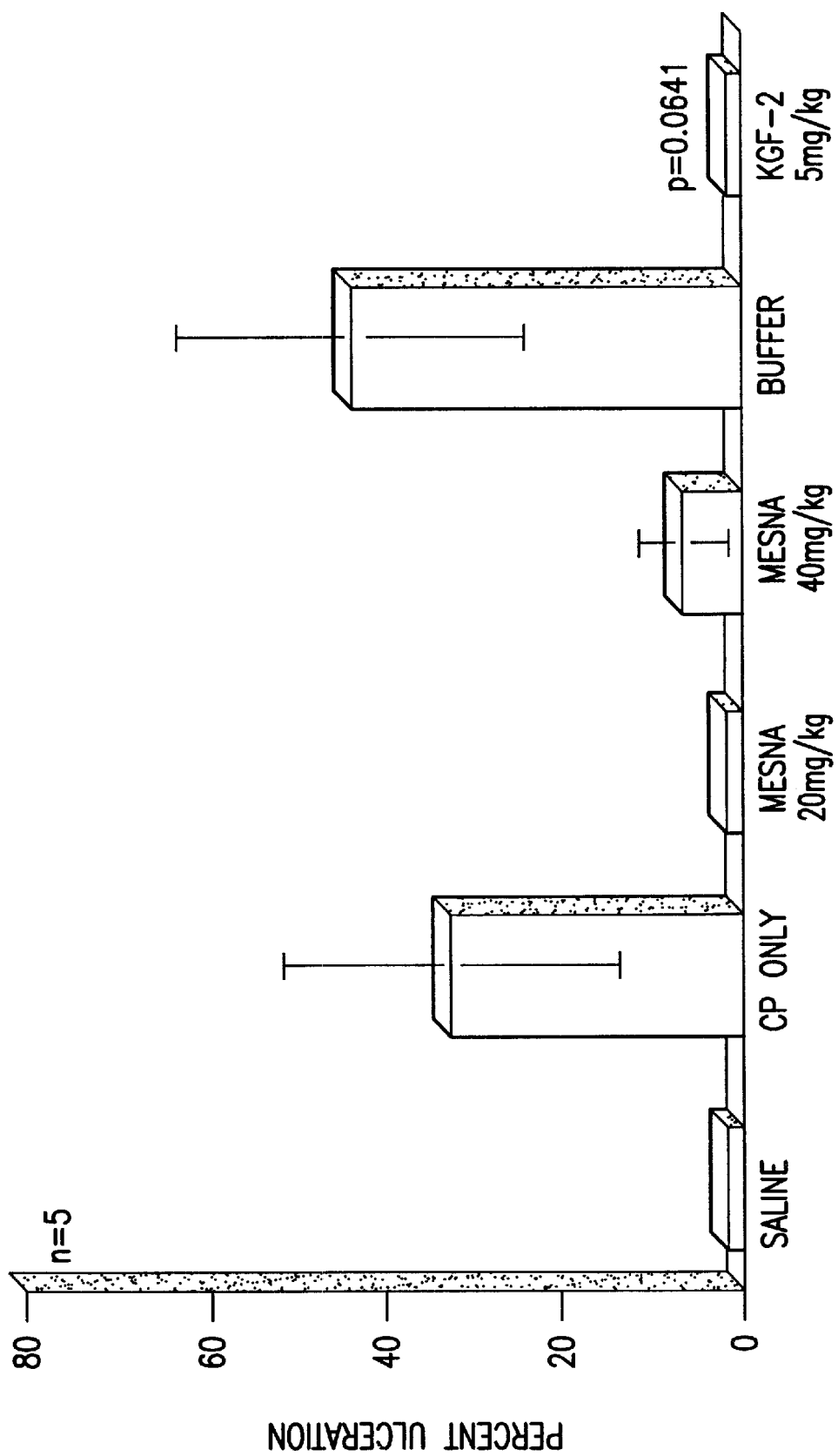
FIG. 50 shows the effect of KGF-2Δ33 and mesnaon bladder ulceration of cyclophosphamide-induced cystitis. Male S.D. rats (200 g) received either buffer or 5.0 mg/kg KGF-2Δ33 intravenously on day 0. On day 1, 200 mg/kg of cyclophosphamide (CP) i.p and Mesna (20 μg/g or 40 μg/g, i.v.). Animals were sacrificed on day 3 and bladders were fixed internally with formalin before tissue harvest. Saline was used as a normal control. Statistical analysis was performed using the unpaired t-test where significance is found if p≦0.05. *Compared to CP only; **compared to buffer.

In normal rats treated i.p. with saline (CP vehicle control), the bladder wall was not enlarged and no ulceration of the urothelium was observed. Pretreatment with buffer placebo 24 hours prior to i.p. administration of CP (200 mg/kg) resulted in 43%±19 ulceration of the total bladder epithelial area. Administration of KGF-2 Δ33 24 hours prior to CP resulted in a reduction in the extent of ulceration (1.4%±0.24; p=0.0641) when compared to placebo treated animals receiving CP. Administration of Mesna at 20 or 40 mg/kg resulted in a reduction of ulceration to 1.4%±0.24 or 6.2%±4.7, respectively however these values were not statistically significant relative to the control. These results are shown in FIG. 50.

Figure 51:
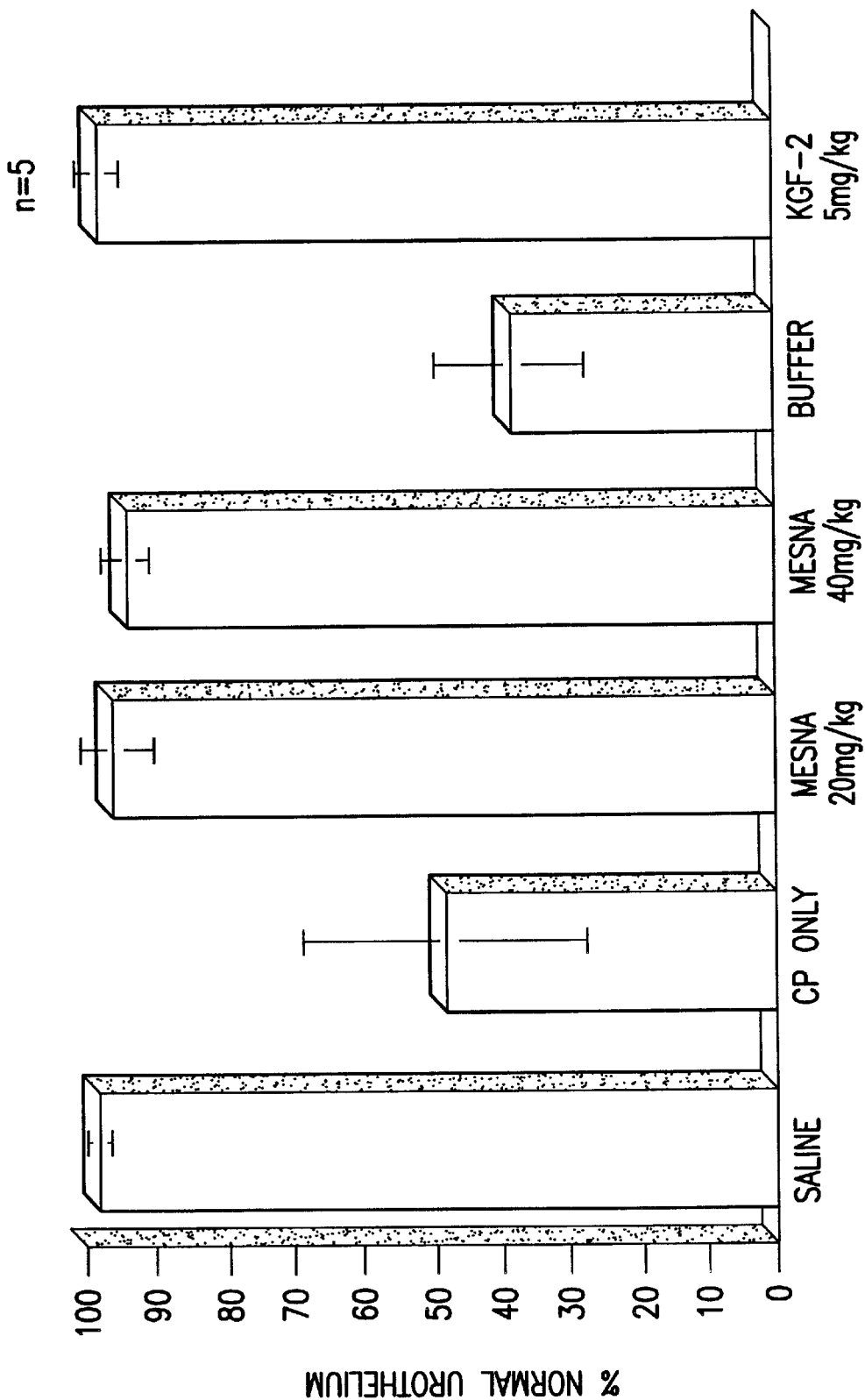
FIG. 51 shows the effect of KGF-2Δ33 and mesna on percent normal urothelium of cyclophosphamide-induced cystitis. Male S.D. rats (200 g) received either buffer or 5.0 mg/kg KGF-2Δ33 intravenously on day 0. On day 1, 200 mg/kg of cyclophosphamide (CP) i.p and Mesna (20 μg/g or 40 μg/g, i.v.). Animals were sacrificed on day 3 and bladders were fixed internally with formalin before tissue harvest. Saline was used as a normal control. Statistical analysis was performed using the unpaired t-test where significance is found if p≦0.05. *Compared to CP only; **compared to buffer.

In some cases the urothelial lining may not exhibit ulceration but may still be abnormal in appearance. Thus, the "percent normal urothelial" was established as a measure of the amount of urothelium with columnar or cuboidal morphology, rounded nuclei, and possessing at least 1 cell layer in thickness. Groups treated with KGF-2Δ33 24 hours prior to CP administration had 97%±3normal urothelium (p=0.0574) and 93%±3 (p=0.0625) normal urothelium respectively. These values were considered to be not quite significant when compared to the CP only group. These results are shown in FIG. 51.

Figure 52:
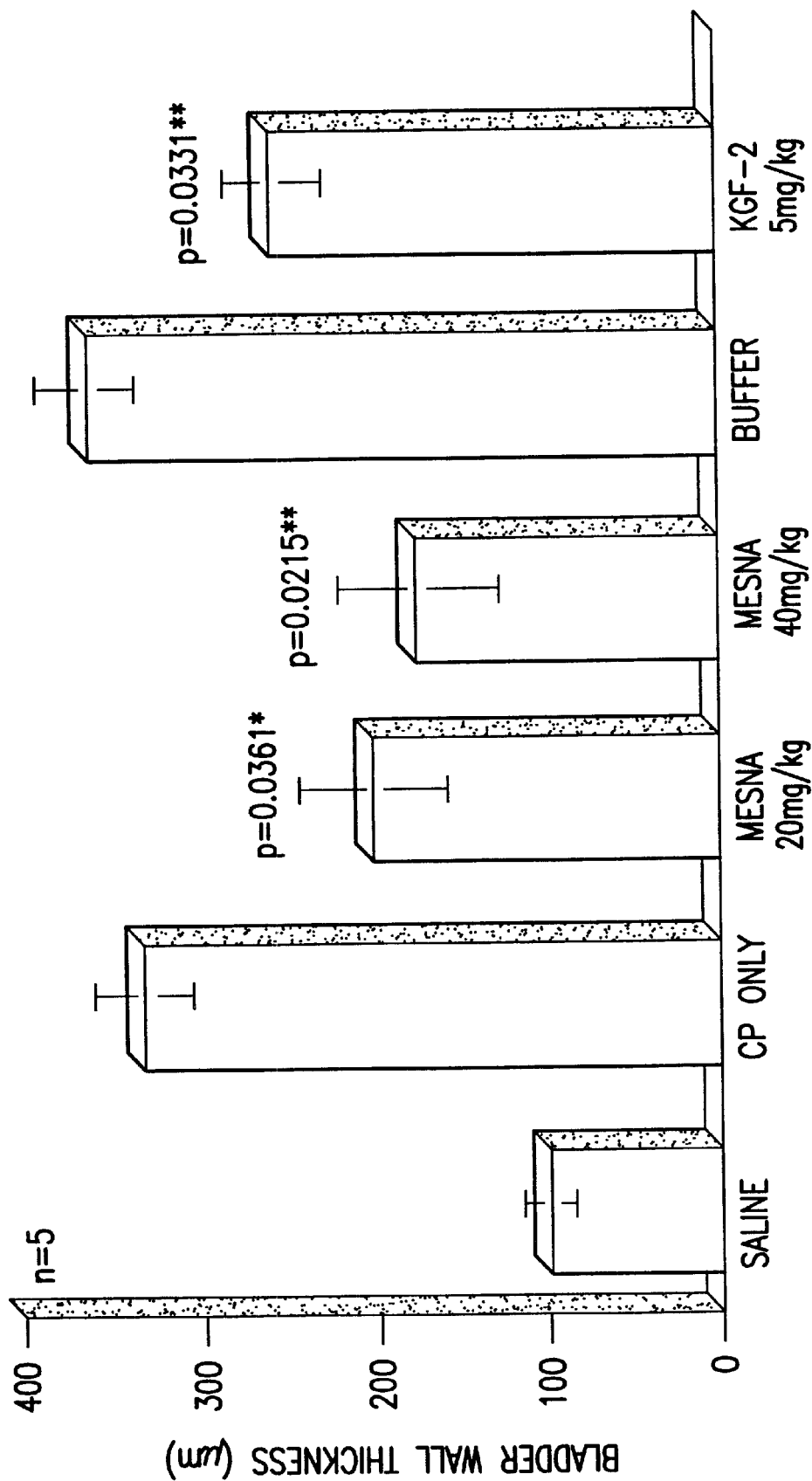
FIG. 52 shows the effect of KGF-2Δ33 and mesna on bladder wall thickness of cyclophosphamide-induced cystitis. Male S.D. rats (200 g) received either buffer or 5.0 mg/kg KGF-2Δ33 intravenously on day 0. On day 1, 200 mg/kg of cyclophosphamide (CP) i.p and Mesna (20 μg/g or 40 μg/g, i.v.). Animals were sacrificed on day 3 and bladders were fixed internally with formalin before tissue harvest. Saline was used as a normal control. Statistical analysis was performed using the unpaired t-test where significance is found if p≦0.05. *Compared to CP only; **compared to buffer.

The thickness of the urinary bladder wall was also evaluated as an additional measure of CP damage. Bladder wall thickness was measured from the epithelium through smooth muscle layers to the serosal surface. In groups treated with saline (CP vehicle control) alone, the thickness of the bladder wall is approximately 100 μm±16. KGF-2 Δ33 pretreatment (252 μm±30; p=0.0331±29). Mesna treatment also resulted in significant decreases in bladder wall thickness at 20 mg/kg (198 μm±34; p=0.0361) and 40 mg/kg (172 μm±46; p=0.0215) when compared to the CP only group. These results are shown in FIG. 52.

EXAMPLE 35
Synergistic Effect of KGF-2 Δ33 and Mesna in Cyclophosphamide-Induced Cystitis The synergistic effect of KGF-2Δ33 and mesna on bladder capacity and bladder wet weight in cyclophosphamide-induced cystitis rat model was examined.

Experimental Design

Male SD rats (350–400 g) (n=7) received, on day 0, either buffer or 5.0 mg/kg KGF-2Δ33 intravenously and on day 1, Mesna (40 μg/g, i.v.) or both treatments on the respective administration days. Cyclophosphamide (300 mg/kg, i.p.) was administered on day 1 to all treatment groups with the exception of the saline control. One group was added as a CP control with no treatment. On day 3, animals received BrdU (100 mg/kg, i.p.) 2 hours prior to euthanasia. After urine was removed from the bladder, it was filled with formalin until it leaked out of the urethra. The volume of formalin injected into the bladder was recorded as the bladder capacity. Bladders were fixed with 10% neutral-buffered formalin, weighed and placed in tissue cassettes for histological analysis.

The experimental groups consisted of six animals per group. The following experimental groups were used: a saline control group, a CP only control (300 mg/kg) group, a buffer+CP (300 mg/kg) group, a KGF-2 Δ33 (3.0 mg/kg)+a CP (300 mg/kg) group, a Mesna (40 mg/kg)+CP (300 mg/kg) group, and a KGF-2 Δ33 (3.0 mg/kg)+CP (300 mg/kg)+Mesna (40 mg/kg).

Results

Figure 53:
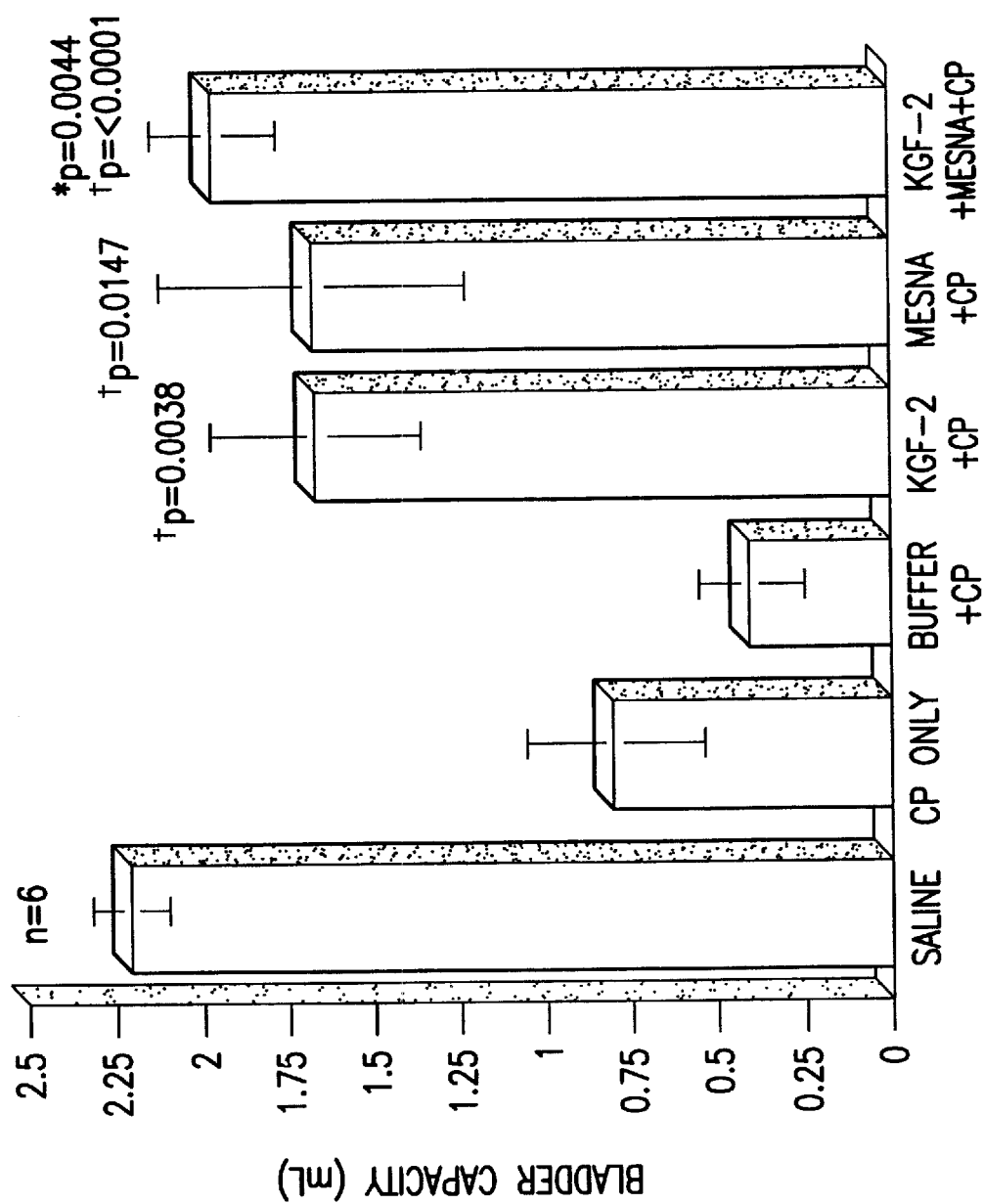
FIG. 53 shows the synergistic effect of KGF-2Δ33 and mesna on bladder capacity of cyclophosphamide-induced cystitis. Male SD rats (350–400 g) (n=7) received, on day 0, either buffer or 5.0 mg/kg KGF-2Δ33 intravenously and on day 1, Mesna (40 μg/g, i.v.) or both treatments on the respective administration days. Cyclophosphamide (300 mg/kg, i.p.) was administered on day 1 to all treatment groups with the exception of the saline control. One group was added as a CP control with no treatment. On day 3, animals received BrdU (100 mg/kg, i.p.) 2 hours prior to euthanasia. After urine was removed from the bladder, it was filled with formalin until it leaked out of the urethra. The volume of formalin injected into the bladder was recorded as the bladder capacity. *Compared to CP only control; † compared to buffer control.

The bladder capacity of the saline control group was 2.21±0.1 ml. The group receiving CP only had a significantly reduced bladder capacity of 0.80±0.27 ml while the buffer control was 0.40±0.15 ml. The bladder capacity of the KGF-2 Δ33 treated group (1.66±0.31 ml, p=0.0038) was significantly increased when compared to the buffer control. Likewise, the Mesna (40 mg/kg) group (1.67±0.44 ml, p=0.0147) was significantly increased in comparison to the buffer control. The animals treated with both KGF-2 Δ33 and Mesna (1.96±0.19 ml) also displayed a significant increase in capacity when compared to CP only control (p=0.0044) and the buffer control group (p<0.0001). These results are shown in FIG. 53.

The bladder wet weight of the saline control group was 0.16 mg. The wet weight of the CP only control was 0.30±0.01 mg. The KGF-2 Δ33 group (0.33±0.3 mg) and the Mesna group (0.28±0.03 mg) were no significantly different from the control groups. However, animals treated with both KGF-2 Δ33 and Mesna exhibited a significant reduction in bladder wet weight (0.19±0.08 mg) when compared to the CP only group (p=0.193) and the buffer control (p=0.0099). These results are shown in FIG. 54.

EXAMPLE 36
KGF-2 Δ33 Induced Changes in Buccal Mucosa and Tongue

In cynomolgus monkeys, daily intravascular injections of KGF-2Δ33 at 300 μg/kg resulted in grossly visible thickening of the oral (buccal) and esophageal mucosa. Microscopically, hyperkeratosis of the buccal mucosa, tongue and esophagus were noted in monkeys treated both daily and every other day with KGF-2Δ33. The buccal and esophageal mucosa hyperkeratosis correlated with the grossly visible thickening of the buccal and esophageal mucosa.

EXAMPLE 37
KGF-2 Δ33 Induced Goblet Cell Changes

In male Sprague Dawley rats, daily intravenous injections of KGF-2Δ33 at 5 mg/kg resulted in goblet cell hyperplasia in the respiratory epithelium of the nasal air passage way. This was characterized by a minimal to mild goblet cell hyperplasia after 7 consecutive days of KGF-2Δ33 treatment followed by a 7 day treatment-free period.

It will be clear that the invention may be practiced otherwise than as particularly described in the foregoing description and examples.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

SEQUENCE LISTING

<160> NUMBER OF SEQ ID NOS: 148

<210> SEQ ID NO 1
<211> LENGTH: 627
<212> TYPE: DNA
<213> ORGANISM: Homo sapiens
<220> FEATURE:
<221> NAME/KEY: CDS
<222> LOCATION: (1)..(624)

<400> SEQUENCE: 1

```
atg tgg aaa tgg ata ctg aca cat tgt gcc tca gcc ttt ccc cac ctg      48
Met Trp Lys Trp Ile Leu Thr His Cys Ala Ser Ala Phe Pro His Leu
 1               5                  10                  15 ccc ggc tgc tgc tgc tgc ttt ttg ttg ctg ttc ttg gtg tct tcc          96
Pro Gly Cys Cys Cys Cys Phe Leu Leu Leu Phe Leu Val Ser Ser
             20                  25                  30 gtc cct gtc acc tgc caa gcc ctt ggt cag gac atg gtg tca cca gag     144
Val Pro Val Thr Cys Gln Ala Leu Gly Gln Asp Met Val Ser Pro Glu
         35                  40                  45 gcc acc aac tct tct tcc tcc tcc ttc tcc tct cct tcc agc gcg gga     192
Ala Thr Asn Ser Ser Ser Ser Ser Phe Ser Ser Pro Ser Ser Ala Gly
     50                  55                  60 agg cat gtg cgg agc tac aat cac ctt caa gga gat gtc cgc tgg aga     240
Arg His Val Arg Ser Tyr Asn His Leu Gln Gly Asp Val Arg Trp Arg
 65                  70                  75                  80 aag cta ttc tct ttc acc aag tac ttt ctc aag att gag aag aac ggg     288
Lys Leu Phe Ser Phe Thr Lys Tyr Phe Leu Lys Ile Glu Lys Asn Gly
                 85                  90                  95 aag gtc agc ggg acc aag aag gag aac tgc ccg tac agc atc ctg gag     336
Lys Val Ser Gly Thr Lys Lys Glu Asn Cys Pro Tyr Ser Ile Leu Glu
            100                 105                 110 ata aca tca gta gaa atc gga gtt gtt gcc gtc aaa gcc att aac agc     384
Ile Thr Ser Val Glu Ile Gly Val Val Ala Val Lys Ala Ile Asn Ser
        115                 120                 125
```

-continued

```
aac tat tac tta gcc atg aac aag aag ggg aaa ctc tat ggc tca aaa    432
Asn Tyr Tyr Leu Ala Met Asn Lys Lys Gly Lys Leu Tyr Gly Ser Lys
    130                 135                 140 gaa ttt aac aat gac tgt aag ctg aag gag agg ata gag gaa aat gga    480
Glu Phe Asn Asn Asp Cys Lys Leu Lys Glu Arg Ile Glu Glu Asn Gly
145                 150                 155                 160 tac aat acc tat gca tca ttt aac tgg cag cat aat ggg agg caa atg    528
Tyr Asn Thr Tyr Ala Ser Phe Asn Trp Gln His Asn Gly Arg Gln Met
                165                 170                 175 tat gtg gca ttg aat gga aaa gga gct cca agg aga gga cag aaa aca    576
Tyr Val Ala Leu Asn Gly Lys Gly Ala Pro Arg Arg Gly Gln Lys Thr
            180                 185                 190 cga agg aaa aac acc tct gct cac ttt ctt cca atg gtg gta cac tca    624
Arg Arg Lys Asn Thr Ser Ala His Phe Leu Pro Met Val Val His Ser
        195                 200                 205 tag                                                                627
```

<210> SEQ ID NO 2
<211> LENGTH: 208
<212> TYPE: PRT
<213> ORGANISM: Homo sapiens

<400> SEQUENCE: 2

```
Met Trp Lys Trp Ile Leu Thr His Cys Ala Ser Ala Phe Pro His Leu
 1               5                  10                  15

Pro Gly Cys Cys Cys Cys Cys Phe Leu Leu Leu Phe Leu Val Ser Ser
                20                  25                  30

Val Pro Val Thr Cys Gln Ala Leu Gly Gln Asp Met Val Ser Pro Glu
            35                  40                  45

Ala Thr Asn Ser Ser Ser Ser Ser Phe Ser Ser Pro Ser Ser Ala Gly
        50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205
```

<210> SEQ ID NO 3
<211> LENGTH: 36
<212> TYPE: DNA
<213> ORGANISM: Homo sapiens

<400> SEQUENCE: 3
ccccacatgt ggaaatggat actgacacat tgtgcc                            36

```
<210> SEQ ID NO 4
<211> LENGTH: 35
<212> TYPE: DNA
<213> ORGANISM: Homo sapiens

<400> SEQUENCE: 4
cccaagcttc cacaaacgtt gccttcctct atgag                          35

<210> SEQ ID NO 5
<211> LENGTH: 36
<212> TYPE: DNA
<213> ORGANISM: Homo sapiens

<400> SEQUENCE: 5
catgccatgg cgtgccaagc ccttggtcag gacatg                         36

<210> SEQ ID NO 6
<211> LENGTH: 35
<212> TYPE: DNA
<213> ORGANISM: Homo sapiens

<400> SEQUENCE: 6
cccaagcttc cacaaacgtt gccttcctct atgag                          35

<210> SEQ ID NO 7
<211> LENGTH: 35
<212> TYPE: DNA
<213> ORGANISM: Homo sapiens

<400> SEQUENCE: 7
gcgggatccg ccatcatgtg gaaatggata ctcac                          35

<210> SEQ ID NO 8
<211> LENGTH: 27
<212> TYPE: DNA
<213> ORGANISM: Homo sapiens

<400> SEQUENCE: 8
gcgcggtacc acaaacgttg ccttcct                                   27

<210> SEQ ID NO 9
<211> LENGTH: 40
<212> TYPE: DNA
<213> ORGANISM: Homo sapiens

<400> SEQUENCE: 9
taacgaggat ccgccatcat gtggaaatgg atactgacac                     40

<210> SEQ ID NO 10
<211> LENGTH: 38
<212> TYPE: DNA
<213> ORGANISM: Homo sapiens

<400> SEQUENCE: 10
taagcactcg agtgagtgta ccaccattgg aagaaatg                       38

<210> SEQ ID NO 11
<211> LENGTH: 54
<212> TYPE: DNA
<213> ORGANISM: Homo sapiens

<400> SEQUENCE: 11
attaaccctc actaaaggga ggccatgtgg aaatggatac tgacacattg tgcc     54
```

<210> SEQ ID NO 12
<211> LENGTH: 35
<212> TYPE: DNA
<213> ORGANISM: Homo sapiens

<400> SEQUENCE: 12
cccaagcttc cacaaacgtt gccttcctct atgag                              35

<210> SEQ ID NO 13
<211> LENGTH: 206
<212> TYPE: PRT
<213> ORGANISM: Homo sapiens

<400> SEQUENCE: 13

```
Met Ser Gly Pro Gly Thr Ala Ala Val Ala Leu Leu Pro Ala Val Leu
  1               5                  10                  15

Leu Ala Leu Ala Pro Trp Ala Gly Arg Gly Ala Ala Ala Pro
             20                  25                  30

Thr Ala Pro Asn Gly Thr Leu Glu Ala Glu Leu Glu Arg Arg Trp Glu
             35                  40                  45

Ser Leu Val Ala Leu Ser Leu Ala Arg Leu Pro Val Ala Ala Gln Pro
 50                  55                  60

Lys Glu Ala Ala Val Gln Ser Gly Ala Gly Asp Tyr Leu Leu Gly Ile
 65                  70                  75                  80

Lys Arg Leu Arg Arg Leu Tyr Cys Asn Val Gly Ile Gly Phe His Leu
                 85                  90                  95

Gln Ala Leu Pro Asp Gly Arg Ile Gly Gly Ala His Ala Asp Thr Arg
                100                 105                 110

Asp Ser Leu Leu Glu Leu Ser Pro Val Glu Arg Gly Val Val Ser Ile
                115                 120                 125

Phe Gly Val Ala Ser Arg Phe Phe Val Ala Met Ser Ser Lys Gly Lys
130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
                180                 185                 190

Val Ser Pro Thr Met Lys Val Thr His Phe Leu Pro Arg Leu
                195                 200                 205
```

<210> SEQ ID NO 14
<211> LENGTH: 198
<212> TYPE: PRT
<213> ORGANISM: Homo sapiens

<400> SEQUENCE: 14

```
Met Ser Arg Gly Ala Gly Arg Leu Gln Gly Thr Leu Trp Ala Leu Val
  1               5                  10                  15

Phe Leu Gly Ile Leu Val Gly Met Val Val Pro Ser Pro Ala Gly Thr
             20                  25                  30

Arg Ala Asn Asn Thr Leu Leu Asp Ser Arg Gly Trp Gly Thr Leu Leu
             35                  40                  45

Ser Arg Ser Arg Ala Gly Leu Ala Gly Glu Ile Ala Gly Val Asn Trp
 50                  55                  60

Glu Ser Gly Tyr Leu Val Gly Ile Lys Arg Gln Arg Arg Leu Tyr Cys
```

```
                65                  70                  75                  80
Asn Val Gly Ile Gly Phe His Leu Gln Val Leu Pro Asp Gly Arg Ile
                        85                  90                  95

Ser Gly Thr His Glu Glu Asn Pro Tyr Ser Leu Leu Glu Ile Ser Thr
                100                 105                 110

Val Glu Arg Gly Val Val Ser Leu Phe Gly Val Arg Ser Ala Leu Phe
                115                 120                 125

Val Ala Met Asn Ser Lys Gly Arg Leu Tyr Ala Thr Pro Ser Phe Gln
            130                 135                 140

Glu Glu Cys Lys Phe Arg Glu Thr Leu Leu Pro Asn Asn Tyr Asn Ala
145                 150                 155                 160

Tyr Glu Ser Asp Leu Tyr Gln Gly Thr Tyr Ile Ala Leu Ser Lys Tyr
                165                 170                 175

Gly Arg Val Lys Arg Gly Ser Lys Val Ser Pro Ile Met Thr Val Thr
                180                 185                 190

His Phe Leu Pro Arg Ile
            195

<210> SEQ ID NO 15
<211> LENGTH: 268
<212> TYPE: PRT
<213> ORGANISM: Homo sapiens

<400> SEQUENCE: 15

Met Ser Leu Ser Phe Leu Leu Leu Leu Phe Phe Ser His Leu Ile Leu
 1               5                  10                  15

Ser Ala Trp Ala His Gly Glu Lys Arg Leu Ala Pro Lys Gly Gln Pro
                20                  25                  30

Gly Pro Ala Ala Thr Asp Arg Asn Pro Arg Gly Ser Ser Ser Arg Gln
            35                  40                  45

Ser Ser Ser Ser Ala Met Ser Ser Ser Ala Ser Ser Pro Ala
 50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
                100                 105                 110

His Glu Ala Asn Met Leu Ser Val Leu Glu Ile Phe Ala Val Ser Gln
            115                 120                 125

Gly Ile Val Gly Ile Arg Gly Val Phe Ser Asn Lys Phe Leu Ala Met
130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
                180                 185                 190

Asn Lys Arg Gly Lys Ala Lys Arg Gly Cys Ser Pro Arg Val Lys Pro
            195                 200                 205

Gln His Ile Ser Thr His Phe Leu Pro Arg Phe Lys Gln Ser Glu Gln
        210                 215                 220

Pro Glu Leu Ser Phe Thr Val Thr Val Pro Glu Lys Lys Asn Pro Pro
225                 230                 235                 240
```

```
Ser Pro Ile Lys Ser Lys Ile Pro Leu Ser Ala Pro Arg Lys Asn Thr
                245                 250                 255

Asn Ser Val Lys Tyr Arg Leu Lys Phe Arg Phe Gly
            260                 265
```

<210> SEQ ID NO 16
<211> LENGTH: 155
<212> TYPE: PRT
<213> ORGANISM: Homo sapiens

<400> SEQUENCE: 16

```
Met Ala Glu Gly Glu Ile Thr Thr Phe Thr Ala Leu Thr Glu Lys Phe
  1               5                  10                  15

Asn Leu Pro Pro Gly Asn Tyr Lys Lys Pro Lys Leu Leu Tyr Cys Ser
             20                  25                  30

Asn Gly Gly His Phe Leu Arg Ile Leu Pro Asp Gly Thr Val Asp Gly
         35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 17
<211> LENGTH: 155
<212> TYPE: PRT
<213> ORGANISM: Homo sapiens

<400> SEQUENCE: 17

```
Met Ala Ala Gly Ser Ile Thr Thr Leu Pro Ala Leu Pro Glu Asp Gly
  1               5                  10                  15

Gly Ser Gly Ala Phe Pro Pro Gly His Phe Lys Asp Pro Lys Arg Leu
             20                  25                  30

Tyr Cys Lys Asn Gly Gly Phe Phe Leu Arg Ile His Pro Asp Gly Arg
         35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140
```

```
Ala Ile Leu Phe Leu Pro Met Ser Ala Lys Ser
145                 150                 155
```

<210> SEQ ID NO 18
<211> LENGTH: 208
<212> TYPE: PRT
<213> ORGANISM: Homo sapiens

<400> SEQUENCE: 18

```
Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
        50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205
```

<210> SEQ ID NO 19
<211> LENGTH: 194
<212> TYPE: PRT
<213> ORGANISM: Homo sapiens

<400> SEQUENCE: 19

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110
```

Val Glu Ser Glu Phe Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
                180                 185                 190

Ile Thr

<210> SEQ ID NO 20
<211> LENGTH: 208
<212> TYPE: PRT
<213> ORGANISM: Homo sapiens

<400> SEQUENCE: 20

Met Trp Lys Trp Ile Leu Thr His Cys Ala Ser Ala Phe Pro His Leu
1               5                   10                  15

Pro Gly Cys Cys Cys Cys Cys Phe Leu Leu Phe Leu Val Ser Ser
                20                  25                  30

Val Pro Val Thr Cys Gln Ala Leu Gly Gln Asp Met Val Ser Pro Glu
            35                  40                  45

Ala Thr Asn Ser Ser Ser Ser Phe Ser Ser Pro Ser Ser Ala Gly
    50                  55                  60

Arg His Val Arg Ser Tyr Asn His Leu Gln Gly Asp Val Arg Trp Arg
65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
                100                 105                 110

Ile Thr Ser Val Glu Ile Gly Val Val Ala Val Lys Ala Ile Asn Ser
            115                 120                 125

Asn Tyr Tyr Leu Ala Met Asn Lys Lys Gly Lys Leu Tyr Gly Ser Lys
130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
                180                 185                 190

Arg Arg Lys Asn Thr Ser Ala His Phe Leu Pro Met Val Val His Ser
            195                 200                 205

<210> SEQ ID NO 21
<211> LENGTH: 239
<212> TYPE: PRT
<213> ORGANISM: Homo sapiens

<400> SEQUENCE: 21

Met Gly Leu Ile Trp Leu Leu Leu Leu Ser Leu Leu Glu Pro Gly Trp
1               5                   10                  15

Pro Ala Ala Gly Pro Gly Ala Arg Leu Arg Arg Asp Ala Gly Gly Arg
                20                  25                  30

Gly Gly Val Tyr Glu His Leu Gly Gly Ala Pro Arg Arg Arg Lys Leu

-continued

```
                35                  40                  45
Tyr Cys Ala Thr Lys Tyr His Leu Gln Leu His Pro Ser Gly Arg Val
         50                  55                  60
Asn Gly Ser Leu Glu Asn Ser Ala Tyr Ser Ile Leu Glu Ile Thr Ala
 65                  70                  75                  80
Val Glu Val Gly Ile Val Ala Ile Arg Gly Leu Phe Ser Gly Arg Tyr
                 85                  90                  95
Leu Ala Met Asn Lys Arg Gly Arg Leu Tyr Ala Ser Glu His Tyr Ser
                100                 105                 110
Ala Glu Cys Glu Phe Val Glu Arg Ile His Glu Leu Gly Tyr Asn Thr
            115                 120                 125
Tyr Ala Ser Arg Leu Tyr Arg Thr Val Ser Ser Thr Pro Gly Ala Arg
130                 135                 140
Arg Gln Pro Ser Ala Glu Arg Leu Trp Tyr Val Ser Val Asn Gly Lys
145                 150                 155                 160
Gly Arg Pro Arg Arg Gly Phe Lys Thr Arg Thr Gln Lys Ser Ser
                165                 170                 175
Leu Phe Leu Pro Arg Val Leu Asp His Arg Asp His Glu Met Val Arg
                180                 185                 190
Gln Leu Gln Ser Gly Leu Pro Arg Pro Pro Gly Lys Gly Val Gln Pro
            195                 200                 205
Arg Arg Arg Arg Gln Lys Gln Ser Pro Asp Asn Leu Glu Pro Ser His
210                 215                 220
Val Gln Ala Ser Arg Leu Gly Ser Gln Leu Glu Ala Ser Ala His
225                 230                 235

<210> SEQ ID NO 22
<211> LENGTH: 268
<212> TYPE: PRT
<213> ORGANISM: Homo sapiens

<400> SEQUENCE: 22

Met Gly Ser Pro Arg Ser Ala Leu Ser Cys Leu Leu Leu His Leu Leu
  1               5                  10                  15
Val Leu Cys Leu Gln Ala Gln Val Arg Ser Ala Ala Gln Lys Arg Gly
                 20                  25                  30
Pro Gly Ala Gly Asn Pro Ala Asp Thr Leu Gly Gln Gly His Glu Asp
             35                  40                  45
Arg Pro Phe Gly Gln Arg Ser Arg Ala Gly Lys Asn Phe Thr Asn Pro
         50                  55                  60
Ala Pro Asn Tyr Pro Glu Glu Gly Ser Lys Glu Gln Arg Asp Ser Val
 65                  70                  75                  80
Leu Pro Lys Val Thr Gln Arg His Val Arg Glu Gln Ser Leu Val Thr
                 85                  90                  95
Asp Gln Leu Ser Arg Arg Leu Ile Arg Thr Tyr Gln Leu Tyr Ser Arg
                100                 105                 110
Thr Ser Gly Lys His Val Gln Val Leu Ala Asn Lys Arg Ile Asn Ala
            115                 120                 125
Met Ala Glu Asp Gly Asp Pro Phe Ala Lys Leu Ile Val Glu Thr Asp
130                 135                 140
Thr Phe Gly Ser Arg Val Arg Val Arg Gly Ala Glu Thr Gly Leu Tyr
145                 150                 155                 160
Ile Cys Met Asn Lys Lys Gly Lys Leu Ile Ala Lys Ser Asn Gly Lys
                165                 170                 175
```

-continued

```
Gly Lys Asp Cys Val Phe Thr Glu Ile Val Leu Glu Asn Asn Tyr Thr
            180                 185                 190

Ala Leu Gln Asn Ala Lys Tyr Glu Gly Trp Tyr Met Ala Phe Thr Arg
        195                 200                 205

Lys Gly Arg Pro Arg Lys Gly Ser Lys Thr Arg Gln His Gln Arg Glu
    210                 215                 220

Val His Phe Met Lys Arg Leu Pro Arg Gly His His Thr Thr Glu Gln
225                 230                 235                 240

Ser Leu Arg Phe Glu Phe Leu Asn Tyr Pro Pro Phe Thr Arg Ser Leu
                245                 250                 255

Arg Gly Ser Gln Arg Thr Trp Ala Pro Glu Pro Arg
            260                 265

<210> SEQ ID NO 23
<211> LENGTH: 4177
<212> TYPE: DNA
<213> ORGANISM: Homo sapiens
<220> FEATURE:
<221> NAME/KEY: CDS
<222> LOCATION: (593)..(1216)

<400> SEQUENCE: 23
ggaattccgg gaagagaggg aagaaaacaa cggcgactgg gcagctgcct ccacttctga     60
caactccaaa gggatatact tgtagaagtg gctcgcaggc tggggctccg cagagagaga    120
ccagaaggtg ccaaccgcag aggggtgcag atatctcccc ctattcccca ccccacctcc    180
cttgggtttt gttcaccgtg ctgtcatctg ttttcagac cttttttggca tctaacatgg    240 tgaagaaagg agtaaagaag agaacaaagt aactcctggg ggagcgaaga gcgctggtga    300
ccaacaccac caacgccacc accagctcct gctgctgcgg ccacccacgt ccaccattta    360
ccgggaggct ccagaggcgt aggcagcgga tccgagaaag gagcgagggg agtcagccgg    420
cttttccgag gagttatgga tgttggtgca ttcacttctg gccagatccg cgcccagagg    480
gagctaacca gcagccacca cctcgagctc tctccttgcc ttgcatcggg tcttacccct    540
ccagtatgtt ccttctgatg agacaatttc cagtgccgag agtttcagta ca atg tgg   598
                                                        Met Trp
                                                          1 aaa tgg ata ctg aca cat tgt gcc tca gcc ttt ccc cac ctg ccc ggc      646
Lys Trp Ile Leu Thr His Cys Ala Ser Ala Phe Pro His Leu Pro Gly
      5                  10                 15 tgc tgc tgc tgc ttt ttg ttg ctg ttc ttg gtg tct tcc gtc cct           694
Cys Cys Cys Cys Phe Leu Leu Leu Phe Leu Val Ser Ser Val Pro
 20                  25                  30 gtc acc tgc caa gcc ctt ggt cag gac atg gtg tca cca gag gcc acc       742
Val Thr Cys Gln Ala Leu Gly Gln Asp Met Val Ser Pro Glu Ala Thr
 35                  40                  45                  50 aac tct tct tcc tcc tcc ttc tcc tct cct tcc agc gcg gga agg cat       790
Asn Ser Ser Ser Ser Ser Phe Ser Ser Pro Ser Ser Ala Gly Arg His
                 55                  60                  65 gtg cgg agc tac aat cac ctt caa gga gat gtc cgc tgg aga aag cta       838
Val Arg Ser Tyr Asn His Leu Gln Gly Asp Val Arg Trp Arg Lys Leu
             70                  75                  80 ttc tct ttc acc aag tac ttt ctc aag att gag aag aac ggg aag gtc       886
Phe Ser Phe Thr Lys Tyr Phe Leu Lys Ile Glu Lys Asn Gly Lys Val
         85                  90                  95 agc ggg acc aag aag gag aac tgc ccg tac agc atc ctg gag ata aca       934
Ser Gly Thr Lys Lys Glu Asn Cys Pro Tyr Ser Ile Leu Glu Ile Thr
    100                 105                 110
```

-continued

| | |
|---|---|
| tca gta gaa atc gga gtt gtt gcc gtc aaa gcc att aac agc aac tat<br>Ser Val Glu Ile Gly Val Val Ala Val Lys Ala Ile Asn Ser Asn Tyr<br>115                              120                        125                        130 | 982 |
| tac tta gcc atg aac aag aag ggg aaa ctc tat ggc tca aaa gaa ttt<br>Tyr Leu Ala Met Asn Lys Lys Gly Lys Leu Tyr Gly Ser Lys Glu Phe<br>                         135                        140                        145 | 1030 |
| aac aat gac tgt aag ctg aag gag agg ata gag gaa aat gga tac aat<br>Asn Asn Asp Cys Lys Leu Lys Glu Arg Ile Glu Glu Asn Gly Tyr Asn<br>              150                        155                        160 | 1078 |
| acc tat gca tca ttt aac tgg cag cat aat ggg agg caa atg tat gtg<br>Thr Tyr Ala Ser Phe Asn Trp Gln His Asn Gly Arg Gln Met Tyr Val<br>         165                        170                        175 | 1126 |
| gca ttg aat gga aaa gga gct cca agg aga gga cag aaa aca cga agg<br>Ala Leu Asn Gly Lys Gly Ala Pro Arg Arg Gly Gln Lys Thr Arg Arg<br>180                              185                        190 | 1174 |
| aaa aac acc tct gct cac ttt ctt cca atg gtg gta cac tca<br>Lys Asn Thr Ser Ala His Phe Leu Pro Met Val Val His Ser<br>195                              200                        205 | 1216 |
| tagaggaagg caacgtttgt ggatgcagta aaaccaatgg ctcttttgcc aagaatagtg | 1276 |
| gatattcttc atgaagacag tagattgaaa ggcaaagaca cgttgcagat gtctgcttgc | 1336 |
| ttaaaagaaa gccagccttt gaaggttttt gtattcactg ctgacatatg atgttctttt | 1396 |
| aattagttct gtgtcatgtc ttataatcaa gatataggca gatcgaatgg gatagaagtt | 1456 |
| attcccaagt gaaaaacatt gtggctgggt tttttgttgt tgttgtcaag ttttgttttt | 1516 |
| taaacctctg agatagaact taaggacat agaacaatct gttgaaagaa cgatcttcgg | 1576 |
| gaaagttatt tatggaatac gaactccatat caaagacttc attgctcatt caagcctaat | 1636 |
| gaatcaatga acagtaatac gtgcaagcat ttactggaaa gcacttgggt catatcatat | 1696 |
| gcacaaccaa aggagttctg gatgtggtct catggaataa ttgaatagaa tttaaaaata | 1756 |
| taaacatgtt agtgtgaaac tgttctaaca atacaaatag tatggtatgc ttgtgcattc | 1816 |
| tgccttcatc cctttctatt tctttctaag ttatttattt aataggatgt taaatatctt | 1876 |
| ttggggtttt aaagagtatc tcagcagctg tcttctgatt tatctttct ttttattcag | 1936 |
| cacaccacat gcatgttcac gacaaagtgt ttttaaaact tggcgaacac ttcaaaaata | 1996 |
| ggagttggga ttagggaagc agtatgagtg cccgtgtgct atcagttgac ttaatttgca | 2056 |
| cttctgcagt aataaccatc aacaataaat atggcaatgc tgtgccatgg cttgagtgag | 2116 |
| agatgtctgc tatcatttga aaacatatat tactctcgag gcttcctgtc tcaagaaata | 2176 |
| gaccagaagg ccaaattctt ctctttcaat acatcagttt gcctccaaga atatactaaa | 2236 |
| aaaaggaaaa ttaattgcta aatacatta aatagcctag cctcattatt tactcatgat | 2296 |
| ttcttgccaa atgtcatggc ggtaaagagg ctgtccacat ctctaaaaac cctctgtaaa | 2356 |
| ttccacataa tgcatctttc ccaaggaac tataaagaat ttggtatgaa gcgcaactct | 2416 |
| cccagggct taaactgagc aaatcaaata tatactggta tatgtgtaac catatacaaa | 2476 |
| aacctgttct agctgtatga tctagtcttt acaaaaccaa ataaaacttg ttttctgtaa | 2536 |
| atttaaagag ctttacaagg ttccataatg taaccatatc aaaattcatt ttgttagagc | 2596 |
| acgtatagaa aagagtacat aagagtttac caatcatcat cacattgtat tccactaaat | 2656 |
| aaatacataa gccttatttg cagtgtctgt agtgatttta aaaatgtaga aaatactat | 2716 |
| ttgttctaaa tacttttaag caataactat aatagtatat tgatgctgca gttttatctt | 2776 |
| catatttctt gttttgaaaa agcatttat tgtttggaca cagtatttg gtacaaaaaa | 2836 |
| aaagactcac taaatgtgtc ttactaaagt ttaacctttg gaaatgctgg cgttctgtga | 2896 |

-continued

```
ttctccaaca aacttatttg tgtcaatact taaccagcac ttccagttaa tctgttattt    2956
ttaaaaattg ctttattaag aaattttttg tataatccca taaaaggtca tattttcccc   3016
attcttcaaa aaaactgtat ttcagaagaa acacatttga ggcactgtct tttggcttat   3076
agtttaaatt gcatttcatc atactttgct tccaacttgc tttttggcaa atgagattat   3136
aaaaatgttt aattttttgtg gttggaatct ggatgttaaa atttaattgg taactcagtc  3196
tgtgagctat aatgtaatgc attcctatcc aaactaggta tcttttttc ctttatgttg    3256 aaataataat ggcacctgac acatagacat agaccaccca caacctaaat taaatgtttg   3316
gtaagacaaa tacacattgg atgaccacag taacagcaaa cagggcacaa actggattct   3376
tatttcacat agacatttag attactaaag agggctatgt gtaaacagtc atcattatag   3436
tactcaagac actaaaacag cttctagcca aatatattaa agcttgcaga ggccaaaaat   3496
agaaaacatc tcccctgtct ctcccacatt tccctcacag aaagacaaaa aacctgcctg   3556
gtgcagtagc tcacacctgt aatcccagca gtttgggaga ctgtgggaag atggcttgag   3616
tccaggagtt ctagacaggc ctgagaaacc tagtgagaca tccttctctt aaacaaaaca   3676
aaacaaaaca aatgtagcca tgcgtggtgg catataccctg tggtcccaac tactcaggag   3736
gctgaaacgg aaggatctct tgggccccag gagtttgagg ctgcagtgag ctataatctt   3796
gccattgcac tccagcctgg gtgaaaaaga gccagaaaga aaggaaagag agaaaagaga   3856
aaagaaagag agaaaagaca gaaagacagg aaggaaggaa ggaaggaagg aaggaaggaa   3916
ggaagcaagg aaagaaggaa ggaaggaaag aagggaggga aggaaggaga gagaaagaaa   3976
gattgtttgg taaggagtaa tgacattctc ttgcatttaa aagtggcata tttgcttgaa   4036
atggaaatag aattctggtc ccttttgcaa ctactgaaga aaaaaaaaag cagtttcagc   4096
cctgaatgtt gtagatttga aaaaaaaaaa aaaaaactc gagggggggc ccgtacccaa    4156
ttcgccctat agtgagtcgt a                                              4177
```

<210> SEQ ID NO 24
<211> LENGTH: 208
<212> TYPE: PRT
<213> ORGANISM: Homo sapiens

<400> SEQUENCE: 24

```
Met Trp Lys Trp Ile Leu Thr His Cys Ala Ser Ala Phe Pro His Leu
  1               5                  10                  15

Pro Gly Cys Cys Cys Cys Phe Leu Leu Leu Phe Leu Val Ser Ser
             20                  25                  30

Val Pro Val Thr Cys Gln Ala Leu Gly Gln Asp Met Val Ser Pro Glu
         35                  40                  45

Ala Thr Asn Ser Ser Ser Ser Phe Ser Ser Pro Ser Ser Ala Gly
     50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140
```

```
Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
                180                 185                 190

Arg Arg Lys Asn Thr Ser Ala His Phe Leu Pro Met Val Val His Ser
            195                 200                 205
```

<210> SEQ ID NO 25
<211> LENGTH: 31
<212> TYPE: PRT
<213> ORGANISM: Homo sapiens

<400> SEQUENCE: 25

```
Gly Gln Asp Met Val Ser Pro Glu Ala Thr Asn Ser Ser Ser Ser Ser
1               5                   10                  15

Phe Ser Ser Pro Ser Ser Ala Gly Arg His Val Arg Ser Tyr Asn
            20                  25                  30
```

<210> SEQ ID NO 26
<211> LENGTH: 19
<212> TYPE: PRT
<213> ORGANISM: Homo sapiens

<400> SEQUENCE: 26

```
Lys Ile Glu Lys Asn Gly Lys Val Ser Gly Thr Lys Lys Glu Asn Cys
1               5                   10                  15

Pro Tyr Ser
```

<210> SEQ ID NO 27
<211> LENGTH: 30
<212> TYPE: PRT
<213> ORGANISM: Homo sapiens

<400> SEQUENCE: 27

```
Asn Lys Lys Gly Lys Leu Tyr Gly Ser Lys Glu Phe Asn Asn Asp Cys
1               5                   10                  15

Lys Leu Lys Glu Arg Ile Glu Glu Asn Gly Tyr Asn Thr Tyr
                20                  25                  30
```

<210> SEQ ID NO 28
<211> LENGTH: 19
<212> TYPE: PRT
<213> ORGANISM: Homo sapiens

<400> SEQUENCE: 28

```
Asn Gly Lys Gly Ala Pro Arg Arg Gly Gln Lys Thr Arg Arg Lys Asn
1               5                   10                  15

Thr Ser Ala
```

<210> SEQ ID NO 29
<211> LENGTH: 555
<212> TYPE: DNA
<213> ORGANISM: Homo sapiens
<220> FEATURE:
<221> NAME/KEY: CDS
<222> LOCATION: (1)..(552)

<400> SEQUENCE: 29

```
atg aga gga tcg cat cac cat cac cat cac gga tcc tgc cag gct ctg        48
```

```
Met Arg Gly Ser His His His His His Gly Ser Cys Gln Ala Leu
 1               5                  10                  15 ggt cag gac atg gtt tct ccg gaa gct acc aac tct tcc tct tcc tct       96
Gly Gln Asp Met Val Ser Pro Glu Ala Thr Asn Ser Ser Ser Ser Ser
             20                  25                  30 ttc tct tcc ccg tct tcc gct ggt cgt cac gtt cgt tct tac aac cac      144
Phe Ser Ser Pro Ser Ser Ala Gly Arg His Val Arg Ser Tyr Asn His
         35                  40                  45 ctg cag ggt gac gtt cgt tgg cgt aaa ctg ttc tct ttc acc aaa tac      192
Leu Gln Gly Asp Val Arg Trp Arg Lys Leu Phe Ser Phe Thr Lys Tyr
 50                  55                  60 ttc ctg aaa atc gaa aaa aac ggt aaa gtt tct ggg acc aag aag gag      240
Phe Leu Lys Ile Glu Lys Asn Gly Lys Val Ser Gly Thr Lys Lys Glu
 65                  70                  75                  80 aac tgc ccg tac agc atc ctg gag ata aca tca gta gaa atc gga gtt      288
Asn Cys Pro Tyr Ser Ile Leu Glu Ile Thr Ser Val Glu Ile Gly Val
             85                  90                  95 gtt gcc gtc aaa gcc att aac agc aac tat tac tta gcc atg aac aag      336
Val Ala Val Lys Ala Ile Asn Ser Asn Tyr Tyr Leu Ala Met Asn Lys
         100                 105                 110 aag ggg aaa ctc tat ggc tca aaa gaa ttt aac aat gac tgt aag ctg      384
Lys Gly Lys Leu Tyr Gly Ser Lys Glu Phe Asn Asn Asp Cys Lys Leu
     115                 120                 125 aag gag agg ata gag gaa aat gga tac aat acc tat gca tca ttt aac      432
Lys Glu Arg Ile Glu Glu Asn Gly Tyr Asn Thr Tyr Ala Ser Phe Asn
 130                 135                 140 tgg cag cat aat ggg agg caa atg tat gtg gca ttg aat gga aaa gga      480
Trp Gln His Asn Gly Arg Gln Met Tyr Val Ala Leu Asn Gly Lys Gly
145                 150                 155                 160 gct cca agg aga gga cag aaa aca cga agg aaa aac acc tct gct cac      528
Ala Pro Arg Arg Gly Gln Lys Thr Arg Arg Lys Asn Thr Ser Ala His
                 165                 170                 175 ttt ctt cca atg gtg gta cac tca tag                                  555
Phe Leu Pro Met Val Val His Ser
             180
```

<210> SEQ ID NO 30
<211> LENGTH: 184
<212> TYPE: PRT
<213> ORGANISM: Homo sapiens

<400> SEQUENCE: 30

```
Met Arg Gly Ser His His His His His Gly Ser Cys Gln Ala Leu
 1               5                  10                  15

Gly Gln Asp Met Val Ser Pro Glu Ala Thr Asn Ser Ser Ser Ser Ser
             20                  25                  30

Phe Ser Ser Pro Ser Ser Ala Gly Arg His Val Arg Ser Tyr Asn His
         35                  40                  45

Leu Gln Gly Asp Val Arg Trp Arg Lys Leu Phe Ser Phe Thr Lys Tyr
 50                  55                  60

Phe Leu Lys Ile Glu Lys Asn Gly Lys Val Ser Gly Thr Lys Lys Glu
 65                  70                  75                  80

Asn Cys Pro Tyr Ser Ile Leu Glu Ile Thr Ser Val Glu Ile Gly Val
             85                  90                  95

Val Ala Val Lys Ala Ile Asn Ser Asn Tyr Tyr Leu Ala Met Asn Lys
         100                 105                 110

Lys Gly Lys Leu Tyr Gly Ser Lys Glu Phe Asn Asn Asp Cys Lys Leu
     115                 120                 125
```

```
Lys Glu Arg Ile Glu Glu Asn Gly Tyr Asn Thr Tyr Ala Ser Phe Asn
    130                 135                 140

Trp Gln His Asn Gly Arg Gln Met Tyr Val Ala Leu Asn Gly Lys Gly
145             150                 155                 160

Ala Pro Arg Arg Gly Gln Lys Thr Arg Arg Lys Asn Thr Ser Ala His
                165                 170                 175

Phe Leu Pro Met Val Val His Ser
            180

<210> SEQ ID NO 31
<211> LENGTH: 84
<212> TYPE: DNA
<213> ORGANISM: Homo sapiens

<400> SEQUENCE: 31
atgtggaaat ggatactgac ccactgcgct tctgctttcc cgcacctgcc gggttgctgc    60
tgctgctgct tcctgctgct gttc                                          84

<210> SEQ ID NO 32
<211> LENGTH: 82
<212> TYPE: DNA
<213> ORGANISM: Homo sapiens

<400> SEQUENCE: 32
ccggagaaac catgtcctga cccagagcct ggcaggtaac cggaacagaa gaaaccagga    60
acagcagcag gaagcagcag ca                                            82

<210> SEQ ID NO 33
<211> LENGTH: 80
<212> TYPE: DNA
<213> ORGANISM: Homo sapiens

<400> SEQUENCE: 33
gggtcaggac atggtttctc cggaagctac caactcttct tcttcttctt tctcttctcc    60
gtcttctgct ggtcgtcacg                                               80

<210> SEQ ID NO 34
<211> LENGTH: 81
<212> TYPE: DNA
<213> ORGANISM: Homo sapiens

<400> SEQUENCE: 34
ggtgaaagag aacagtttac gccaacgaac gtcaccctgc aggtggttgt aagaacgaac    60
gtgacgacca gcagaagacg g                                             81

<210> SEQ ID NO 35
<211> LENGTH: 75
<212> TYPE: DNA
<213> ORGANISM: Homo sapiens

<400> SEQUENCE: 35
cgttggcgta aactgttctc tttcaccaaa tacttcctga aaatcgaaaa aaacggtaaa    60
gtttctggga ccaaa                                                    75

<210> SEQ ID NO 36
<211> LENGTH: 39
<212> TYPE: DNA
<213> ORGANISM: Homo sapiens

<400> SEQUENCE: 36
```

```
tttggtccca gaaactttac cgttttttc gattttcag                                    39
```

<210> SEQ ID NO 37
<211> LENGTH: 36
<212> TYPE: DNA
<213> ORGANISM: Homo sapiens

<400> SEQUENCE: 37

```
aaaggatcca tgtggaaatg gatactgacc cactgc                                      36
```

<210> SEQ ID NO 38
<211> LENGTH: 627
<212> TYPE: DNA
<213> ORGANISM: Homo sapiens
<220> FEATURE:
<221> NAME/KEY: CDS
<222> LOCATION: (1)..(624)

<400> SEQUENCE: 38

| atg | tgg | aaa | tgg | ata | ctg | acc | cac | tgc | gct | tct | gct | ttc | ccg | cac | ctg | 48 |
| Met | Trp | Lys | Trp | Ile | Leu | Thr | His | Cys | Ala | Ser | Ala | Phe | Pro | His | Leu | |
| 1 | | | | 5 | | | | | 10 | | | | | 15 | | |

| ccg | ggt | tgc | tgc | tgc | tgc | ttc | ctg | ctg | ctg | ttc | ctg | gtt | tct | tct | | 96 |
| Pro | Gly | Cys | Cys | Cys | Cys | Phe | Leu | Leu | Leu | Phe | Leu | Val | Ser | Ser | | |
| | | | 20 | | | | | 25 | | | | | 30 | | | |

| gtt | ccg | gtt | acc | tgc | cag | gct | ctg | ggt | cag | gac | atg | gtt | tct | ccg | gaa | 144 |
| Val | Pro | Val | Thr | Cys | Gln | Ala | Leu | Gly | Gln | Asp | Met | Val | Ser | Pro | Glu | |
| | | | 35 | | | | | 40 | | | | | 45 | | | |

| gct | acc | aac | tct | tcc | tct | tcc | tct | ttc | tct | tcc | ccg | act | tcc | gct | ggt | 192 |
| Ala | Thr | Asn | Ser | Ser | Ser | Ser | Ser | Phe | Ser | Ser | Pro | Thr | Ser | Ala | Gly | |
| | | 50 | | | | | 55 | | | | | 60 | | | | |

| cgt | cac | gtt | cgt | tct | tac | aac | cac | ctg | cag | ggt | gac | gtt | cgt | tgg | cgt | 240 |
| Arg | His | Val | Arg | Ser | Tyr | Asn | His | Leu | Gln | Gly | Asp | Val | Arg | Trp | Arg | |
| 65 | | | | 70 | | | | | 75 | | | | | 80 | | |

| aaa | ctg | ttc | tct | ttc | acc | aaa | tac | ttc | ctg | aaa | atc | gaa | aaa | aac | ggt | 288 |
| Lys | Leu | Phe | Ser | Phe | Thr | Lys | Tyr | Phe | Leu | Lys | Ile | Glu | Lys | Asn | Gly | |
| | | | | 85 | | | | | 90 | | | | | 95 | | |

| aaa | gtt | tct | ggg | acc | aag | aag | gag | aac | tgc | ccg | tac | agc | atc | ctg | gag | 336 |
| Lys | Val | Ser | Gly | Thr | Lys | Lys | Glu | Asn | Cys | Pro | Tyr | Ser | Ile | Leu | Glu | |
| | | | 100 | | | | | 105 | | | | | 110 | | | |

| ata | aca | tca | gta | gaa | atc | gga | gtt | gtt | gcc | gtc | aaa | gcc | att | aac | agc | 384 |
| Ile | Thr | Ser | Val | Glu | Ile | Gly | Val | Val | Ala | Val | Lys | Ala | Ile | Asn | Ser | |
| | | 115 | | | | | 120 | | | | | 125 | | | | |

| aac | tat | tac | tta | gcc | atg | aac | aag | aag | ggg | aaa | ctc | tat | ggc | tca | aaa | 432 |
| Asn | Tyr | Tyr | Leu | Ala | Met | Asn | Lys | Lys | Gly | Lys | Leu | Tyr | Gly | Ser | Lys | |
| | 130 | | | | | 135 | | | | | 140 | | | | | |

| gaa | ttt | aac | aat | gac | tgt | aag | ctg | aag | gag | agg | ata | gag | gaa | aat | gga | 480 |
| Glu | Phe | Asn | Asn | Asp | Cys | Lys | Leu | Lys | Glu | Arg | Ile | Glu | Glu | Asn | Gly | |
| 145 | | | | | 150 | | | | | 155 | | | | | 160 | |

| tac | aat | acc | tat | gca | tca | ttt | aac | tgg | cag | cat | aat | ggg | agg | caa | atg | 528 |
| Tyr | Asn | Thr | Tyr | Ala | Ser | Phe | Asn | Trp | Gln | His | Asn | Gly | Arg | Gln | Met | |
| | | | | 165 | | | | | 170 | | | | | 175 | | |

| tat | gtg | gca | ttg | aat | gga | aaa | gga | gct | cca | agg | aga | gga | cag | aaa | aca | 576 |
| Tyr | Val | Ala | Leu | Asn | Gly | Lys | Gly | Ala | Pro | Arg | Arg | Gly | Gln | Lys | Thr | |
| | | | 180 | | | | | 185 | | | | | 190 | | | |

| cga | agg | aaa | aac | acc | tct | gct | cac | ttt | ctt | cca | atg | gtg | gta | cac | tca | 624 |
| Arg | Arg | Lys | Asn | Thr | Ser | Ala | His | Phe | Leu | Pro | Met | Val | Val | His | Ser | |
| | | 195 | | | | | 200 | | | | | 205 | | | | |

```
tag                                                                           627
```

<210> SEQ ID NO 39
<211> LENGTH: 208
<212> TYPE: PRT
<213> ORGANISM: Homo sapiens

<400> SEQUENCE: 39

```
Met Trp Lys Trp Ile Leu Thr His Cys Ala Ser Ala Phe Pro His Leu
  1               5                  10                  15

Pro Gly Cys Cys Cys Cys Phe Leu Leu Leu Phe Leu Val Ser Ser
             20                  25                  30

Val Pro Val Thr Cys Gln Ala Leu Gly Gln Asp Met Val Ser Pro Glu
         35                  40                  45

Ala Thr Asn Ser Ser Ser Ser Phe Ser Ser Pro Thr Ser Ala Gly
     50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205
```

<210> SEQ ID NO 40
<211> LENGTH: 38
<212> TYPE: DNA
<213> ORGANISM: Homo sapiens

<400> SEQUENCE: 40
tttcatgact tgtcaagctc tgggtcaaga tatggttc                    38

<210> SEQ ID NO 41
<211> LENGTH: 28
<212> TYPE: DNA
<213> ORGANISM: Homo sapiens

<400> SEQUENCE: 41
gcccaagctt ccacaaacgt tgccttcc                              28

<210> SEQ ID NO 42
<211> LENGTH: 525
<212> TYPE: DNA
<213> ORGANISM: Homo sapiens
<220> FEATURE:
<221> NAME/KEY: CDS
<222> LOCATION: (1)..(522)

<400> SEQUENCE: 42

```
atg acc tgc cag gct ctg ggt cag gac atg gtt tct ccg gaa gct acc    48
Met Thr Cys Gln Ala Leu Gly Gln Asp Met Val Ser Pro Glu Ala Thr
```

```
                1               5                    10                   15
aac tct tcc tct tcc tct ttc tct tcc ccg tct tcc gct ggt cgt cac      96
Asn Ser Ser Ser Ser Ser Phe Ser Ser Pro Ser Ser Ala Gly Arg His
                        20                  25                  30 gtt cgt tct tac aac cac ctg cag ggt gac gtt cgt tgg cgt aaa ctg      144
Val Arg Ser Tyr Asn His Leu Gln Gly Asp Val Arg Trp Arg Lys Leu
                35                  40                  45 ttc tct ttc acc aaa tac ttc ctg aaa atc gaa aaa aac ggt aaa gtt      192
Phe Ser Phe Thr Lys Tyr Phe Leu Lys Ile Glu Lys Asn Gly Lys Val
         50                  55                  60 tct ggg acc aag aag gag aac tgc ccg tac agc atc ctg gag ata aca      240
Ser Gly Thr Lys Lys Glu Asn Cys Pro Tyr Ser Ile Leu Glu Ile Thr
 65                  70                  75                  80 tca gta gaa atc gga gtt gtt gcc gtc aaa gcc att aac agc aac tat      288
Ser Val Glu Ile Gly Val Val Ala Val Lys Ala Ile Asn Ser Asn Tyr
                         85                  90                  95 tac tta gcc atg aac aag aag ggg aaa ctc tat ggc tca aaa gaa ttt      336
Tyr Leu Ala Met Asn Lys Lys Gly Lys Leu Tyr Gly Ser Lys Glu Phe
                100                 105                 110 aac aat gac tgt aag ctg aag gag agg ata gag gaa aat gga tac aat      384
Asn Asn Asp Cys Lys Leu Lys Glu Arg Ile Glu Glu Asn Gly Tyr Asn
                115                 120                 125 acc tat gca tca ttt aac tgg cag cat aat ggg agg caa atg tat gtg      432
Thr Tyr Ala Ser Phe Asn Trp Gln His Asn Gly Arg Gln Met Tyr Val
        130                 135                 140 gca ttg aat gga aaa gga gct cca agg aga gga cag aaa aca cga agg      480
Ala Leu Asn Gly Lys Gly Ala Pro Arg Arg Gly Gln Lys Thr Arg Arg
145                 150                 155                 160 aaa aac acc tct gct cac ttt ctt cca atg gtg gta cac tca tag         525
Lys Asn Thr Ser Ala His Phe Leu Pro Met Val Val His Ser
                165                 170

<210> SEQ ID NO 43
<211> LENGTH: 174
<212> TYPE: PRT
<213> ORGANISM: Homo sapiens

<400> SEQUENCE: 43

Met Thr Cys Gln Ala Leu Gly Gln Asp Met Val Ser Pro Glu Ala Thr
 1               5                  10                  15

Asn Ser Ser Ser Ser Phe Ser Ser Pro Ser Ser Ala Gly Arg His
                20                  25                  30

Val Arg Ser Tyr Asn His Leu Gln Gly Asp Val Arg Trp Arg Lys Leu
            35                  40                  45

Phe Ser Phe Thr Lys Tyr Phe Leu Lys Ile Glu Lys Asn Gly Lys Val
     50                  55                  60

Ser Gly Thr Lys Lys Glu Asn Cys Pro Tyr Ser Ile Leu Glu Ile Thr
 65                  70                  75                  80

Ser Val Glu Ile Gly Val Val Ala Val Lys Ala Ile Asn Ser Asn Tyr
                 85                  90                  95

Tyr Leu Ala Met Asn Lys Lys Gly Lys Leu Tyr Gly Ser Lys Glu Phe
                100                 105                 110

Asn Asn Asp Cys Lys Leu Lys Glu Arg Ile Glu Glu Asn Gly Tyr Asn
            115                 120                 125

Thr Tyr Ala Ser Phe Asn Trp Gln His Asn Gly Arg Gln Met Tyr Val
        130                 135                 140

Ala Leu Asn Gly Lys Gly Ala Pro Arg Arg Gly Gln Lys Thr Arg Arg
145                 150                 155                 160
```

```
Lys Asn Thr Ser Ala His Phe Leu Pro Met Val Val His Ser
            165                 170
```

<210> SEQ ID NO 44
<211> LENGTH: 45
<212> TYPE: DNA
<213> ORGANISM: Homo sapiens

<400> SEQUENCE: 44
tcagtgaatt cattaaagag gagaaattaa tcatgacttg ccagg          45

<210> SEQ ID NO 45
<211> LENGTH: 48
<212> TYPE: DNA
<213> ORGANISM: Homo sapiens

<400> SEQUENCE: 45
tcatgacttg ccaggcactg ggtcaagaca tggtttcccc ggaagcta       48

<210> SEQ ID NO 46
<211> LENGTH: 48
<212> TYPE: DNA
<213> ORGANISM: Homo sapiens

<400> SEQUENCE: 46
gcttcagcag cccatctagc gcaggtcgtc acgttcgctc ttacaacc       48

<210> SEQ ID NO 47
<211> LENGTH: 48
<212> TYPE: DNA
<213> ORGANISM: Homo sapiens

<400> SEQUENCE: 47
gttcgttggc gcaaactgtt cagctttacc aagtacttcc tgaaaatc       48

<210> SEQ ID NO 48
<211> LENGTH: 28
<212> TYPE: DNA
<213> ORGANISM: Homo sapiens

<400> SEQUENCE: 48
tcgaaaaaaa cggtaaagtt tctgggac                             28

<210> SEQ ID NO 49
<211> LENGTH: 48
<212> TYPE: DNA
<213> ORGANISM: Homo sapiens

<400> SEQUENCE: 49
gatgggctgc tgaagctaga gctggagctg ttggtagctt ccggggaa       48

<210> SEQ ID NO 50
<211> LENGTH: 45
<212> TYPE: DNA
<213> ORGANISM: Homo sapiens

<400> SEQUENCE: 50
aacagtttgc gccaacgaac atcaccctgt aagtggttgt aagag          45

<210> SEQ ID NO 51
<211> LENGTH: 47
<212> TYPE: DNA
<213> ORGANISM: Homo sapiens

<400> SEQUENCE: 51
ttcttggtcc cagaaacttt accgtttttt tcgattttca ggaagta 47

<210> SEQ ID NO 52
<211> LENGTH: 24
<212> TYPE: DNA
<213> ORGANISM: Homo sapiens

<400> SEQUENCE: 52
ttcttggtcc cagaaacttt accg 24

<210> SEQ ID NO 53
<211> LENGTH: 45
<212> TYPE: DNA
<213> ORGANISM: Homo sapiens

<400> SEQUENCE: 53
agatcaggct tctattatta tgagtgtacc accattggaa gaaag 45

<210> SEQ ID NO 54
<211> LENGTH: 525
<212> TYPE: DNA
<213> ORGANISM: Homo sapiens
<220> FEATURE:
<221> NAME/KEY: CDS
<222> LOCATION: (1)..(522)

<400> SEQUENCE: 54

```
atg act tgc cag gca ctg ggt caa gac atg gtt tcc ccg gaa gct acc      48
Met Thr Cys Gln Ala Leu Gly Gln Asp Met Val Ser Pro Glu Ala Thr
 1               5                  10                  15 aac agc tcc agc tct agc ttc agc agc cca tct agc gca ggt cgt cac      96
Asn Ser Ser Ser Ser Ser Phe Ser Ser Pro Ser Ser Ala Gly Arg His
             20                  25                  30 gtt cgc tct tac aac cac tta cag ggt gat gtt cgt tgg cgc aaa ctg     144
Val Arg Ser Tyr Asn His Leu Gln Gly Asp Val Arg Trp Arg Lys Leu
         35                  40                  45 ttc agc ttt acc aag tac ttc ctg aaa atc gaa aaa aac ggt aaa gtt     192
Phe Ser Phe Thr Lys Tyr Phe Leu Lys Ile Glu Lys Asn Gly Lys Val
     50                  55                  60 tct ggg acc aag aag gag aac tgc ccg tac agc atc ctg gag ata aca     240
Ser Gly Thr Lys Lys Glu Asn Cys Pro Tyr Ser Ile Leu Glu Ile Thr
 65                  70                  75                  80 tca gta gaa atc gga gtt gtt gcc gtc aaa gcc att aac agc aac tat     288
Ser Val Glu Ile Gly Val Val Ala Val Lys Ala Ile Asn Ser Asn Tyr
                 85                  90                  95 tac tta gcc atg aac aag aag ggg aaa ctc tat ggc tca aaa gaa ttt     336
Tyr Leu Ala Met Asn Lys Lys Gly Lys Leu Tyr Gly Ser Lys Glu Phe
            100                 105                 110 aac aat gac tgt aag ctg aag gag agg ata gag gaa aat gga tac aat     384
Asn Asn Asp Cys Lys Leu Lys Glu Arg Ile Glu Glu Asn Gly Tyr Asn
        115                 120                 125 acc tat gca tca ttt aac tgg cag cat aat ggg agg caa atg tat gtg     432
Thr Tyr Ala Ser Phe Asn Trp Gln His Asn Gly Arg Gln Met Tyr Val
    130                 135                 140 gca ttg aat gga aaa gga gct cca agg aga gga cag aaa aca cga agg     480
Ala Leu Asn Gly Lys Gly Ala Pro Arg Arg Gly Gln Lys Thr Arg Arg
145                 150                 155                 160 aaa aac acc tct gct cac ttt cca atg gtg gta cac tca tag             525
Lys Asn Thr Ser Ala His Phe Pro Met Val Val His Ser
                165                 170
```

<210> SEQ ID NO 55
<211> LENGTH: 174
<212> TYPE: PRT
<213> ORGANISM: Homo sapiens

<400> SEQUENCE: 55

Met Thr Cys Gln Ala Leu Gly Gln Asp Met Val Ser Pro Glu Ala Thr
1               5                   10                  15

Asn Ser Ser Ser Ser Phe Ser Ser Pro Ser Ser Ala Gly Arg His
            20                  25                  30

Val Arg Ser Tyr Asn His Leu Gln Gly Asp Val Arg Trp Arg Lys Leu
        35                  40                  45

Phe Ser Phe Thr Lys Tyr Phe Leu Lys Ile Glu Lys Asn Gly Lys Val
    50                  55                  60

Ser Gly Thr Lys Lys Glu Asn Cys Pro Tyr Ser Ile Leu Glu Ile Thr
65                  70                  75                  80

Ser Val Glu Ile Gly Val Val Ala Val Lys Ala Ile Asn Ser Asn Tyr
                85                  90                  95

Tyr Leu Ala Met Asn Lys Lys Gly Lys Leu Tyr Gly Ser Lys Glu Phe
            100                 105                 110

Asn Asn Asp Cys Lys Leu Lys Glu Arg Ile Glu Glu Asn Gly Tyr Asn
        115                 120                 125

Thr Tyr Ala Ser Phe Asn Trp Gln His Asn Gly Arg Gln Met Tyr Val
    130                 135                 140

Ala Leu Asn Gly Lys Gly Ala Pro Arg Arg Gly Gln Lys Thr Arg Arg
145                 150                 155                 160

Lys Asn Thr Ser Ala His Phe Leu Pro Met Val Val His Ser
                165                 170

<210> SEQ ID NO 56
<211> LENGTH: 35
<212> TYPE: DNA
<213> ORGANISM: Homo sapiens

<400> SEQUENCE: 56
ggaccctcat gacctgccag gctctgggtc aggac                                35

<210> SEQ ID NO 57
<211> LENGTH: 28
<212> TYPE: DNA
<213> ORGANISM: Homo sapiens

<400> SEQUENCE: 57
ggacagccat ggctggtcgt cacgttcg                                        28

<210> SEQ ID NO 58
<211> LENGTH: 29
<212> TYPE: DNA
<213> ORGANISM: Homo sapiens

<400> SEQUENCE: 58
ggacagccat ggttcgttgg cgtaaactg                                       29

<210> SEQ ID NO 59
<211> LENGTH: 31
<212> TYPE: DNA
<213> ORGANISM: Homo sapiens

<400> SEQUENCE: 59

```
ggacagccat ggaaaaaaac ggtaaagttt c                                    31
```

<210> SEQ ID NO 60
<211> LENGTH: 29
<212> TYPE: DNA
<213> ORGANISM: Homo sapiens

<400> SEQUENCE: 60

```
ggaccccat ggagaactgc ccgtagagc                                        29
```

<210> SEQ ID NO 61
<211> LENGTH: 32
<212> TYPE: DNA
<213> ORGANISM: Homo sapiens

<400> SEQUENCE: 61

```
ggaccccat ggtcaaagcc attaacagca ac                                    32
```

<210> SEQ ID NO 62
<211> LENGTH: 33
<212> TYPE: DNA
<213> ORGANISM: Homo sapiens

<400> SEQUENCE: 62

```
ggaccccat ggggaaactc tatggctcaa aag                                   33
```

<210> SEQ ID NO 63
<211> LENGTH: 37
<212> TYPE: DNA
<213> ORGANISM: Homo sapiens

<400> SEQUENCE: 63

```
ctgcccaagc ttattatgag tgtaccacca ttggaag                              37
```

<210> SEQ ID NO 64
<211> LENGTH: 36
<212> TYPE: DNA
<213> ORGANISM: Homo sapiens

<400> SEQUENCE: 64

```
ctgcccaagc ttattacttc agcttacagt cattgt                               36
```

<210> SEQ ID NO 65
<211> LENGTH: 525
<212> TYPE: DNA
<213> ORGANISM: Homo sapiens
<220> FEATURE:
<221> NAME/KEY: CDS
<222> LOCATION: (1)..(522)

<400> SEQUENCE: 65

```
atg acc tgc cag gct ctg ggt cag gac atg gtt tct ccg gaa gct acc       48
Met Thr Cys Gln Ala Leu Gly Gln Asp Met Val Ser Pro Glu Ala Thr
  1               5                  10                  15 aac tct tcc tct tcc tct ttc tct tcc ccg tct tcc gct ggt cgt cac       96
Asn Ser Ser Ser Ser Ser Phe Ser Ser Pro Ser Ser Ala Gly Arg His
                 20                  25                  30 gtt cgt tct tac aac cac ctg cag ggt gac gtt cgt tgg cgt aaa ctg      144
Val Arg Ser Tyr Asn His Leu Gln Gly Asp Val Arg Trp Arg Lys Leu
             35                  40                  45 ttc tct ttc acc aaa tac ttc ctg aaa atc gaa aaa aac ggt aaa gtt      192
Phe Ser Phe Thr Lys Tyr Phe Leu Lys Ile Glu Lys Asn Gly Lys Val
         50                  55                  60
```

```
tct ggg acc aag aag gag aac tgc ccg tac agc atc ctg gag ata aca      240
Ser Gly Thr Lys Lys Glu Asn Cys Pro Tyr Ser Ile Leu Glu Ile Thr
 65                  70                  75                  80 tca gta gaa atc gga gtt gtt gcc gtc aaa gcc att aac agc aac tat      288
Ser Val Glu Ile Gly Val Val Ala Val Lys Ala Ile Asn Ser Asn Tyr
                 85                  90                  95 tac tta gcc atg aac aag aag ggg aaa ctc tat ggc tca aaa gaa ttt      336
Tyr Leu Ala Met Asn Lys Lys Gly Lys Leu Tyr Gly Ser Lys Glu Phe
            100                 105                 110 aac aat gac tgt aag ctg aag gag agg ata gag gaa aat gga tac aat      384
Asn Asn Asp Cys Lys Leu Lys Glu Arg Ile Glu Glu Asn Gly Tyr Asn
        115                 120                 125 acc tat gca tca ttt aac tgg cag cat aat ggg agg caa atg tat gtg      432
Thr Tyr Ala Ser Phe Asn Trp Gln His Asn Gly Arg Gln Met Tyr Val
    130                 135                 140 gca ttg aat gga aaa gga gct cca agg aga gga cag aaa aca cga agg      480
Ala Leu Asn Gly Lys Gly Ala Pro Arg Arg Gly Gln Lys Thr Arg Arg
145                 150                 155                 160 aaa aac acc tct gct cac ttt ctt cca atg gtg gta cac tca tag          525
Lys Asn Thr Ser Ala His Phe Leu Pro Met Val Val His Ser
                165                 170

<210> SEQ ID NO 66
<211> LENGTH: 174
<212> TYPE: PRT
<213> ORGANISM: Homo sapiens

<400> SEQUENCE: 66

Met Thr Cys Gln Ala Leu Gly Gln Asp Met Val Ser Pro Glu Ala Thr
 1               5                  10                  15

Asn Ser Ser Ser Ser Phe Ser Ser Pro Ser Ser Ala Gly Arg His
            20                  25                  30

Val Arg Ser Tyr Asn His Leu Gln Gly Asp Val Arg Trp Arg Lys Leu
        35                  40                  45

Phe Ser Phe Thr Lys Tyr Phe Leu Lys Ile Glu Lys Asn Gly Lys Val
    50                  55                  60

Ser Gly Thr Lys Lys Glu Asn Cys Pro Tyr Ser Ile Leu Glu Ile Thr
 65                  70                  75                  80

Ser Val Glu Ile Gly Val Val Ala Val Lys Ala Ile Asn Ser Asn Tyr
                 85                  90                  95

Tyr Leu Ala Met Asn Lys Lys Gly Lys Leu Tyr Gly Ser Lys Glu Phe
            100                 105                 110

Asn Asn Asp Cys Lys Leu Lys Glu Arg Ile Glu Glu Asn Gly Tyr Asn
        115                 120                 125

Thr Tyr Ala Ser Phe Asn Trp Gln His Asn Gly Arg Gln Met Tyr Val
    130                 135                 140

Ala Leu Asn Gly Lys Gly Ala Pro Arg Arg Gly Gln Lys Thr Arg Arg
145                 150                 155                 160

Lys Asn Thr Ser Ala His Phe Leu Pro Met Val Val His Ser
                165                 170

<210> SEQ ID NO 67
<211> LENGTH: 444
<212> TYPE: DNA
<213> ORGANISM: Homo sapiens
<220> FEATURE:
<221> NAME/KEY: CDS
<222> LOCATION: (1)..(441)
```

```
<400> SEQUENCE: 67 atg gct ggt cgt cac gtt cgt tct tac aac cac ctg cag ggt gac gtt    48
Met Ala Gly Arg His Val Arg Ser Tyr Asn His Leu Gln Gly Asp Val
 1               5                  10                  15 cgt tgg cgt aaa ctg ttc tct ttc acc aaa tac ttc ctg aaa atc gaa    96
Arg Trp Arg Lys Leu Phe Ser Phe Thr Lys Tyr Phe Leu Lys Ile Glu
                 20                  25                  30 aaa aac ggt aaa gtt tct ggg acc aag aag gag aac tgc ccg tac agc   144
Lys Asn Gly Lys Val Ser Gly Thr Lys Lys Glu Asn Cys Pro Tyr Ser
             35                  40                  45 atc ctg gag ata aca tca gta gaa atc gga gtt gtt gcc gtc aaa gcc   192
Ile Leu Glu Ile Thr Ser Val Glu Ile Gly Val Val Ala Val Lys Ala
         50                  55                  60 att aac agc aac tat tac tta gcc atg aac aag aag ggg aaa ctc tat   240
Ile Asn Ser Asn Tyr Tyr Leu Ala Met Asn Lys Lys Gly Lys Leu Tyr
     65                  70                  75                  80 ggc tca aaa gaa ttt aac aat gac tgt aag ctg aag gag agg ata gag   288
Gly Ser Lys Glu Phe Asn Asn Asp Cys Lys Leu Lys Glu Arg Ile Glu
                 85                  90                  95 gaa aat gga tac aat acc tat gca tca ttt aac tgg cag cat aat ggg   336
Glu Asn Gly Tyr Asn Thr Tyr Ala Ser Phe Asn Trp Gln His Asn Gly
            100                 105                 110 agg caa atg tat gtg gca ttg aat gga aaa gga gct cca agg aga gga   384
Arg Gln Met Tyr Val Ala Leu Asn Gly Lys Gly Ala Pro Arg Arg Gly
        115                 120                 125 cag aaa aca cga agg aaa aac acc tct gct cac ttt ctt cca atg gtg   432
Gln Lys Thr Arg Arg Lys Asn Thr Ser Ala His Phe Leu Pro Met Val
    130                 135                 140 gta cac tca tag                                                   444
Val His Ser
145

<210> SEQ ID NO 68
<211> LENGTH: 147
<212> TYPE: PRT
<213> ORGANISM: Homo sapiens

<400> SEQUENCE: 68

Met Ala Gly Arg His Val Arg Ser Tyr Asn His Leu Gln Gly Asp Val
 1               5                  10                  15

Arg Trp Arg Lys Leu Phe Ser Phe Thr Lys Tyr Phe Leu Lys Ile Glu
                 20                  25                  30

Lys Asn Gly Lys Val Ser Gly Thr Lys Lys Glu Asn Cys Pro Tyr Ser
             35                  40                  45

Ile Leu Glu Ile Thr Ser Val Glu Ile Gly Val Val Ala Val Lys Ala
         50                  55                  60

Ile Asn Ser Asn Tyr Tyr Leu Ala Met Asn Lys Lys Gly Lys Leu Tyr
     65                  70                  75                  80

Gly Ser Lys Glu Phe Asn Asn Asp Cys Lys Leu Lys Glu Arg Ile Glu
                 85                  90                  95

Glu Asn Gly Tyr Asn Thr Tyr Ala Ser Phe Asn Trp Gln His Asn Gly
            100                 105                 110

Arg Gln Met Tyr Val Ala Leu Asn Gly Lys Gly Ala Pro Arg Arg Gly
        115                 120                 125

Gln Lys Thr Arg Arg Lys Asn Thr Ser Ala His Phe Leu Pro Met Val
    130                 135                 140

Val His Ser
145
```

<210> SEQ ID NO 69
<211> LENGTH: 402
<212> TYPE: DNA
<213> ORGANISM: Homo sapiens
<220> FEATURE:
<221> NAME/KEY: CDS
<222> LOCATION: (1)..(399)

<400> SEQUENCE: 69

| atg gtt cgt tgg cgt aaa ctg ttc tct ttc acc aaa tac ttc ctg aaa | 48 |
| Met Val Arg Trp Arg Lys Leu Phe Ser Phe Thr Lys Tyr Phe Leu Lys | |
| 1               5                   10                  15      | |

| atc gaa aaa aac ggt aaa gtt tct ggg acc aag aag gag aac tgc ccg | 96 |
| Ile Glu Lys Asn Gly Lys Val Ser Gly Thr Lys Lys Glu Asn Cys Pro | |
|         20                  25                  30              | |

| tac agc atc ctg gag ata aca tca gta gaa atc gga gtt gtt gcc gtc | 144 |
| Tyr Ser Ile Leu Glu Ile Thr Ser Val Glu Ile Gly Val Val Ala Val | |
|     35                  40                  45                  | |

| aaa gcc att aac agc aac tat tac tta gcc atg aac aag aag ggg aaa | 192 |
| Lys Ala Ile Asn Ser Asn Tyr Tyr Leu Ala Met Asn Lys Lys Gly Lys | |
| 50                  55                  60                      | |

| ctc tat ggc tca aaa gaa ttt aac aat gac tgt aag ctg aag gag agg | 240 |
| Leu Tyr Gly Ser Lys Glu Phe Asn Asn Asp Cys Lys Leu Lys Glu Arg | |
| 65              70                  75                  80      | |

| ata gag gaa aat gga tac aat acc tat gca tca ttt aac tgg cag cat | 288 |
| Ile Glu Glu Asn Gly Tyr Asn Thr Tyr Ala Ser Phe Asn Trp Gln His | |
|             85                  90                  95          | |

| aat ggg agg caa atg tat gtg gca ttg aat gga aaa gga gct cca agg | 336 |
| Asn Gly Arg Gln Met Tyr Val Ala Leu Asn Gly Lys Gly Ala Pro Arg | |
|         100                 105                 110             | |

| aga gga cag aaa aca cga agg aaa aac acc tct gct cac ttt ctt cca | 384 |
| Arg Gly Gln Lys Thr Arg Arg Lys Asn Thr Ser Ala His Phe Leu Pro | |
|     115                 120                 125                 | |

| atg gtg gta cac tca tag | 402 |
| Met Val Val His Ser     | |
|     130                 | |

<210> SEQ ID NO 70
<211> LENGTH: 133
<212> TYPE: PRT
<213> ORGANISM: Homo sapiens

<400> SEQUENCE: 70

Met Val Arg Trp Arg Lys Leu Phe Ser Phe Thr Lys Tyr Phe Leu Lys
1               5                   10                  15

Ile Glu Lys Asn Gly Lys Val Ser Gly Thr Lys Lys Glu Asn Cys Pro
            20                  25                  30

Tyr Ser Ile Leu Glu Ile Thr Ser Val Glu Ile Gly Val Val Ala Val
        35                  40                  45

Lys Ala Ile Asn Ser Asn Tyr Tyr Leu Ala Met Asn Lys Lys Gly Lys
    50                  55                  60

Leu Tyr Gly Ser Lys Glu Phe Asn Asn Asp Cys Lys Leu Lys Glu Arg
65                  70                  75                  80

Ile Glu Glu Asn Gly Tyr Asn Thr Tyr Ala Ser Phe Asn Trp Gln His
                85                  90                  95

Asn Gly Arg Gln Met Tyr Val Ala Leu Asn Gly Lys Gly Ala Pro Arg
            100                 105                 110

Arg Gly Gln Lys Thr Arg Arg Lys Asn Thr Ser Ala His Phe Leu Pro
        115                 120                 125

```
Met Val Val His Ser
    130

<210> SEQ ID NO 71
<211> LENGTH: 354
<212> TYPE: DNA
<213> ORGANISM: Homo sapiens
<220> FEATURE:
<221> NAME/KEY: CDS
<222> LOCATION: (1)..(351)

<400> SEQUENCE: 71 atg gaa aaa aac ggt aaa gtt tct ggg acc aag aag gag aac tgc ccg      48
Met Glu Lys Asn Gly Lys Val Ser Gly Thr Lys Lys Glu Asn Cys Pro
 1               5                  10                  15 tac agc atc ctg gag ata aca tca gta gaa atc gga gtt gtt gcc gtc      96
Tyr Ser Ile Leu Glu Ile Thr Ser Val Glu Ile Gly Val Val Ala Val
             20                  25                  30 aaa gcc att aac agc aac tat tac tta gcc atg aac aag aag ggg aaa     144
Lys Ala Ile Asn Ser Asn Tyr Tyr Leu Ala Met Asn Lys Lys Gly Lys
         35                  40                  45 ctc tat ggc tca aaa gaa ttt aac aat gac tgt aag ctg aag gag agg     192
Leu Tyr Gly Ser Lys Glu Phe Asn Asn Asp Cys Lys Leu Lys Glu Arg
     50                  55                  60 ata gag gaa aat gga tac aat acc tat gca tca ttt aac tgg cag cat     240
Ile Glu Glu Asn Gly Tyr Asn Thr Tyr Ala Ser Phe Asn Trp Gln His
 65                  70                  75                  80 aat ggg agg caa atg tat gtg gca ttg aat gga aaa gga gct cca agg     288
Asn Gly Arg Gln Met Tyr Val Ala Leu Asn Gly Lys Gly Ala Pro Arg
                 85                  90                  95 aga gga cag aaa aca cga agg aaa aac acc tct gct cac ttt ctt cca     336
Arg Gly Gln Lys Thr Arg Arg Lys Asn Thr Ser Ala His Phe Leu Pro
            100                 105                 110 atg gtg gta cac tca tag                                             354
Met Val Val His Ser
            115

<210> SEQ ID NO 72
<211> LENGTH: 117
<212> TYPE: PRT
<213> ORGANISM: Homo sapiens

<400> SEQUENCE: 72

Met Glu Lys Asn Gly Lys Val Ser Gly Thr Lys Lys Glu Asn Cys Pro
 1               5                  10                  15

Tyr Ser Ile Leu Glu Ile Thr Ser Val Glu Ile Gly Val Val Ala Val
             20                  25                  30

Lys Ala Ile Asn Ser Asn Tyr Tyr Leu Ala Met Asn Lys Lys Gly Lys
         35                  40                  45

Leu Tyr Gly Ser Lys Glu Phe Asn Asn Asp Cys Lys Leu Lys Glu Arg
     50                  55                  60

Ile Glu Glu Asn Gly Tyr Asn Thr Tyr Ala Ser Phe Asn Trp Gln His
 65                  70                  75                  80

Asn Gly Arg Gln Met Tyr Val Ala Leu Asn Gly Lys Gly Ala Pro Arg
                 85                  90                  95

Arg Gly Gln Lys Thr Arg Arg Lys Asn Thr Ser Ala His Phe Leu Pro
            100                 105                 110

Met Val Val His Ser
            115
```

<210> SEQ ID NO 73
<211> LENGTH: 321
<212> TYPE: DNA
<213> ORGANISM: Homo sapiens
<220> FEATURE:
<221> NAME/KEY: CDS
<222> LOCATION: (1)..(318)

<400> SEQUENCE: 73

```
atg gag aac tgc ccg tac agc atc ctg gag ata aca tca gta gaa atc      48
Met Glu Asn Cys Pro Tyr Ser Ile Leu Glu Ile Thr Ser Val Glu Ile
 1               5                  10                  15 gga gtt gtt gcc gtc aaa gcc att aac agc aac tat tac tta gcc atg      96
Gly Val Val Ala Val Lys Ala Ile Asn Ser Asn Tyr Tyr Leu Ala Met
             20                  25                  30 aac aag aag ggg aaa ctc tat ggc tca aaa gaa ttt aac aat gac tgt     144
Asn Lys Lys Gly Lys Leu Tyr Gly Ser Lys Glu Phe Asn Asn Asp Cys
         35                  40                  45 aag ctg aag gag agg ata gag gaa aat gga tac aat acc tat gca tca     192
Lys Leu Lys Glu Arg Ile Glu Glu Asn Gly Tyr Asn Thr Tyr Ala Ser
     50                  55                  60 ttt aac tgg cag cat aat ggg agg caa atg tat gtg gca ttg aat gga     240
Phe Asn Trp Gln His Asn Gly Arg Gln Met Tyr Val Ala Leu Asn Gly
 65                  70                  75                  80 aaa gga gct cca agg aga gga cag aaa aca cga agg aaa aac acc tct     288
Lys Gly Ala Pro Arg Arg Gly Gln Lys Thr Arg Arg Lys Asn Thr Ser
                 85                  90                  95 gct cac ttt ctt cca atg gtg gta cac tca tag                         321
Ala His Phe Leu Pro Met Val Val His Ser
                100                 105
```

<210> SEQ ID NO 74
<211> LENGTH: 106
<212> TYPE: PRT
<213> ORGANISM: Homo sapiens

<400> SEQUENCE: 74

```
Met Glu Asn Cys Pro Tyr Ser Ile Leu Glu Ile Thr Ser Val Glu Ile
 1               5                  10                  15

Gly Val Val Ala Val Lys Ala Ile Asn Ser Asn Tyr Tyr Leu Ala Met
             20                  25                  30

Asn Lys Lys Gly Lys Leu Tyr Gly Ser Lys Glu Phe Asn Asn Asp Cys
         35                  40                  45

Lys Leu Lys Glu Arg Ile Glu Glu Asn Gly Tyr Asn Thr Tyr Ala Ser
     50                  55                  60

Phe Asn Trp Gln His Asn Gly Arg Gln Met Tyr Val Ala Leu Asn Gly
 65                  70                  75                  80

Lys Gly Ala Pro Arg Arg Gly Gln Lys Thr Arg Arg Lys Asn Thr Ser
                 85                  90                  95

Ala His Phe Leu Pro Met Val Val His Ser
                100                 105
```

<210> SEQ ID NO 75
<211> LENGTH: 264
<212> TYPE: DNA
<213> ORGANISM: Homo sapiens
<220> FEATURE:
<221> NAME/KEY: CDS
<222> LOCATION: (1)..(261)

<400> SEQUENCE: 75

```
atg gtc aaa gcc att aac agc aac tat tac tta gcc atg aac aag aag     48
Met Val Lys Ala Ile Asn Ser Asn Tyr Tyr Leu Ala Met Asn Lys Lys
 1               5                  10                  15 ggg aaa ctc tat ggc tca aaa gaa ttt aac aat gac tgt aag ctg aag     96
Gly Lys Leu Tyr Gly Ser Lys Glu Phe Asn Asn Asp Cys Lys Leu Lys
             20                  25                  30 gag agg ata gag gaa aat gga tac aat acc tat gca tca ttt aac tgg   144
Glu Arg Ile Glu Glu Asn Gly Tyr Asn Thr Tyr Ala Ser Phe Asn Trp
         35                  40                  45 cag cat aat ggg agg caa atg tat gtg gca ttg aat gga aaa gga gct   192
Gln His Asn Gly Arg Gln Met Tyr Val Ala Leu Asn Gly Lys Gly Ala
     50                  55                  60 cca agg aga gga cag aaa aca cga agg aaa aac acc tct gct cac ttt   240
Pro Arg Arg Gly Gln Lys Thr Arg Arg Lys Asn Thr Ser Ala His Phe
 65                  70                  75                  80 ctt cca atg gtg gta cac tca tag                                   264
Leu Pro Met Val Val His Ser
                 85

<210> SEQ ID NO 76
<211> LENGTH: 87
<212> TYPE: PRT
<213> ORGANISM: Homo sapiens

<400> SEQUENCE: 76

Met Val Lys Ala Ile Asn Ser Asn Tyr Tyr Leu Ala Met Asn Lys Lys
 1               5                  10                  15

Gly Lys Leu Tyr Gly Ser Lys Glu Phe Asn Asn Asp Cys Lys Leu Lys
             20                  25                  30

Glu Arg Ile Glu Glu Asn Gly Tyr Asn Thr Tyr Ala Ser Phe Asn Trp
         35                  40                  45

Gln His Asn Gly Arg Gln Met Tyr Val Ala Leu Asn Gly Lys Gly Ala
     50                  55                  60

Pro Arg Arg Gly Gln Lys Thr Arg Arg Lys Asn Thr Ser Ala His Phe
 65                  70                  75                  80

Leu Pro Met Val Val His Ser
                 85

<210> SEQ ID NO 77
<211> LENGTH: 219
<212> TYPE: DNA
<213> ORGANISM: Homo sapiens
<220> FEATURE:
<221> NAME/KEY: CDS
<222> LOCATION: (1)..(216)

<400> SEQUENCE: 77 atg ggg aaa ctc tat ggc tca aaa gaa ttt aac aat gac tgt aag ctg     48
Met Gly Lys Leu Tyr Gly Ser Lys Glu Phe Asn Asn Asp Cys Lys Leu
 1               5                  10                  15 aag gag agg ata gag gaa aat gga tac aat acc tat gca tca ttt aac     96
Lys Glu Arg Ile Glu Glu Asn Gly Tyr Asn Thr Tyr Ala Ser Phe Asn
             20                  25                  30 tgg cag cat aat ggg agg caa atg tat gtg gca ttg aat gga aaa gga   144
Trp Gln His Asn Gly Arg Gln Met Tyr Val Ala Leu Asn Gly Lys Gly
         35                  40                  45 gct cca agg aga gga cag aaa aca cga agg aaa aac acc tct gct cac   192
Ala Pro Arg Arg Gly Gln Lys Thr Arg Arg Lys Asn Thr Ser Ala His
     50                  55                  60 ttt ctt cca atg gtg gta cac tca tag                               219
Phe Leu Pro Met Val Val His Ser
```

-continued

```
<210> SEQ ID NO 78
<211> LENGTH: 72
<212> TYPE: PRT
<213> ORGANISM: Homo sapiens

<400> SEQUENCE: 78

Met Gly Lys Leu Tyr Gly Ser Lys Glu Phe Asn Asp Cys Lys Leu
 1               5                  10                  15

Lys Glu Arg Ile Glu Glu Asn Gly Tyr Asn Thr Tyr Ala Ser Phe Asn
                20                  25                  30

Trp Gln His Asn Gly Arg Gln Met Tyr Val Ala Leu Asn Gly Lys Gly
             35                  40                  45

Ala Pro Arg Arg Gly Gln Lys Thr Arg Arg Lys Asn Thr Ser Ala His
         50                  55                  60

Phe Leu Pro Met Val Val His Ser
 65                  70

<210> SEQ ID NO 79
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 79 atg acc tgc cag gct ctg ggt cag gac atg gtt tct ccg gaa gct acc      48
Met Thr Cys Gln Ala Leu Gly Gln Asp Met Val Ser Pro Glu Ala Thr
 1               5                  10                  15 aac tct tcc tct tcc tct ttc tct tcc ccg tct tcc gct ggt cgt cac      96
Asn Ser Ser Ser Ser Ser Phe Ser Ser Pro Ser Ser Ala Gly Arg His
                20                  25                  30 gtt cgt tct tac aac cac ctg cag ggt gac gtt cgt tgg cgt aaa ctg     144
Val Arg Ser Tyr Asn His Leu Gln Gly Asp Val Arg Trp Arg Lys Leu
             35                  40                  45 ttc tct ttc acc aaa tac ttc ctg aaa atc gaa aaa aac ggt aaa gtt     192
Phe Ser Phe Thr Lys Tyr Phe Leu Lys Ile Glu Lys Asn Gly Lys Val
         50                  55                  60 tct ggg acc aag aag gag aac tgc ccg tac agc atc ctg gag ata aca     240
Ser Gly Thr Lys Lys Glu Asn Cys Pro Tyr Ser Ile Leu Glu Ile Thr
 65                  70                  75                  80 tca gta gaa atc gga gtt gtt gcc gtc aaa gcc att aac agc aac tat     288
Ser Val Glu Ile Gly Val Val Ala Val Lys Ala Ile Asn Ser Asn Tyr
                 85                  90                  95 tac tta gcc atg aac aag aag ggg aaa ctc tat ggc tca aaa gaa ttt     336
Tyr Leu Ala Met Asn Lys Lys Gly Lys Leu Tyr Gly Ser Lys Glu Phe
            100                 105                 110 aac aat gac tgt aag ctg aag                                          357
Asn Asn Asp Cys Lys Leu Lys
            115

<210> SEQ ID NO 80
<211> LENGTH: 119
<212> TYPE: PRT
<213> ORGANISM: Homo sapiens

<400> SEQUENCE: 80

Met Thr Cys Gln Ala Leu Gly Gln Asp Met Val Ser Pro Glu Ala Thr
 1               5                  10                  15
```

-continued

```
Asn Ser Ser Ser Ser Phe Ser Ser Pro Ser Ser Ala Gly Arg His
             20                  25                  30

Val Arg Ser Tyr Asn His Leu Gln Gly Asp Val Arg Trp Arg Lys Leu
         35                  40                  45

Phe Ser Phe Thr Lys Tyr Phe Leu Lys Ile Glu Lys Asn Gly Lys Val
     50                  55                  60

Ser Gly Thr Lys Lys Glu Asn Cys Pro Tyr Ser Ile Leu Glu Ile Thr
 65                  70                  75                  80

Ser Val Glu Ile Gly Val Val Ala Val Lys Ala Ile Asn Ser Asn Tyr
                 85                  90                  95

Tyr Leu Ala Met Asn Lys Lys Gly Lys Leu Tyr Gly Ser Lys Glu Phe
            100                 105                 110

Asn Asn Asp Cys Lys Leu Lys
            115
```

<210> SEQ ID NO 81
<211> LENGTH: 276
<212> TYPE: DNA
<213> ORGANISM: Homo sapiens
<220> FEATURE:
<221> NAME/KEY: CDS
<222> LOCATION: (1)..(276)

<400> SEQUENCE: 81

```
atg gct ggt cgt cac gtt cgt tct tac aac cac ctg cag ggt gac gtt    48
Met Ala Gly Arg His Val Arg Ser Tyr Asn His Leu Gln Gly Asp Val
  1               5                  10                  15 cgt tgg cgt aaa ctg ttc tct ttc acc aaa tac ttc ctg aaa atc gaa    96
Arg Trp Arg Lys Leu Phe Ser Phe Thr Lys Tyr Phe Leu Lys Ile Glu
                 20                  25                  30 aaa aac ggt aaa gtt tct ggg acc aag aag gag aac tgc ccg tac agc   144
Lys Asn Gly Lys Val Ser Gly Thr Lys Lys Glu Asn Cys Pro Tyr Ser
             35                  40                  45 atc ctg gag ata aca tca gta gaa atc gga gtt gtt gcc gtc aaa gcc   192
Ile Leu Glu Ile Thr Ser Val Glu Ile Gly Val Val Ala Val Lys Ala
         50                  55                  60 att aac agc aac tat tac tta gcc atg aac aag aag ggg aaa ctc tat   240
Ile Asn Ser Asn Tyr Tyr Leu Ala Met Asn Lys Lys Gly Lys Leu Tyr
 65                  70                  75                  80 ggc tca aaa gaa ttt aac aat gac tgt aag ctg aag                   276
Gly Ser Lys Glu Phe Asn Asn Asp Cys Lys Leu Lys
                 85                  90
```

<210> SEQ ID NO 82
<211> LENGTH: 92
<212> TYPE: PRT
<213> ORGANISM: Homo sapiens

<400> SEQUENCE: 82

```
Met Ala Gly Arg His Val Arg Ser Tyr Asn His Leu Gln Gly Asp Val
  1               5                  10                  15

Arg Trp Arg Lys Leu Phe Ser Phe Thr Lys Tyr Phe Leu Lys Ile Glu
                 20                  25                  30

Lys Asn Gly Lys Val Ser Gly Thr Lys Lys Glu Asn Cys Pro Tyr Ser
             35                  40                  45

Ile Leu Glu Ile Thr Ser Val Glu Ile Gly Val Val Ala Val Lys Ala
         50                  55                  60

Ile Asn Ser Asn Tyr Tyr Leu Ala Met Asn Lys Lys Gly Lys Leu Tyr
 65                  70                  75                  80
```

Gly Ser Lys Glu Phe Asn Asn Asp Cys Lys Leu Lys
            85                  90

<210> SEQ ID NO 83
<211> LENGTH: 525
<212> TYPE: DNA
<213> ORGANISM: Homo sapiens

<400> SEQUENCE: 83

| | | | | | |
|---|---|---|---|---|---|
| atgacctctc | aggctctggg | tcaggacatg | gtttctccgg | aagctaccaa | ctcttcctct | 60 |
| tcctctttct | cttccccgtc | ttccgctggt | cgtcacgttc | gttcttacaa | ccacctgcag | 120 |
| ggtgacgttc | gttggcgtaa | actgttctct | ttcaccaaat | acttcctgaa | aatcgaaaaa | 180 |
| aacggtaaag | tttctgggac | caagaaggag | aactctccgt | acagcatcct | ggagataaca | 240 |
| tcagtagaaa | tcggagttgt | tgccgtcaaa | gccattaaca | gcaactatta | cttagccatg | 300 |
| aacaagaagg | ggaaactcta | tggctcaaaa | gaatttaaca | atgactgtaa | gctgaaggag | 360 |
| aggatagagg | aaaatggata | caatacctat | gcatcattta | actggcagca | taatgggagg | 420 |
| caaatgtatg | tggcattgaa | tggaaaagga | gctccaagga | gaggacagaa | aacacgaagg | 480 |
| aaaaacacct | ctgctcactt | tcttccaatg | gtggtacact | catag | | 525 |

<210> SEQ ID NO 84
<211> LENGTH: 525
<212> TYPE: DNA
<213> ORGANISM: Homo sapiens

<400> SEQUENCE: 84

| | | | | | |
|---|---|---|---|---|---|
| atgacctgcc | aggctctggg | tcaggacatg | gtttctccgg | aagctaccaa | ctcttcctct | 60 |
| tcctctttct | cttccccgtc | ttccgctggt | cgtcacgttc | gttcttacaa | ccacctgcag | 120 |
| ggtgacgttc | gttggcgtaa | actgttctct | ttcaccaaat | acttcctgaa | aatcgaaaaa | 180 |
| aacggtaaag | tttctgggac | caagaaggag | aactctccgt | acagcatcct | ggagataaca | 240 |
| tcagtagaaa | tcggagttgt | tgccgtcaaa | gccattaaca | gcaactatta | cttagccatg | 300 |
| aacaagaagg | ggaaactcta | tggctcaaaa | gaatttaaca | atgactgtaa | gctgaaggag | 360 |
| aggatagagg | aaaatggata | caatacctat | gcatcattta | actggcagca | taatgggagg | 420 |
| caaatgtatg | tggcattgaa | tggaaaagga | gctccaagga | gaggacagaa | aacacgaagg | 480 |
| aaaaacacct | ctgctcactt | tcttccaatg | gtggtacact | catag | | 525 |

<210> SEQ ID NO 85
<211> LENGTH: 29
<212> TYPE: DNA
<213> ORGANISM: Homo sapiens

<400> SEQUENCE: 85
ggaccctcat gacctctcag gctctgggt                                    29

<210> SEQ ID NO 86
<211> LENGTH: 21
<212> TYPE: DNA
<213> ORGANISM: Homo sapiens

<400> SEQUENCE: 86
aaggagaact ctccgtacag c                                            21

<210> SEQ ID NO 87
<211> LENGTH: 21
<212> TYPE: DNA

<213> ORGANISM: Homo sapiens

<400> SEQUENCE: 87
gctgtacggt ctgttctcct t					21

<210> SEQ ID NO 88
<211> LENGTH: 35
<212> TYPE: DNA
<213> ORGANISM: Homo sapiens

<400> SEQUENCE: 88
ggaccctcat gacctgccag gctctgggtc aggac					35

<210> SEQ ID NO 89
<211> LENGTH: 37
<212> TYPE: DNA
<213> ORGANISM: Homo sapiens

<400> SEQUENCE: 89
ctgcccaagc ttattatgag tgtaccacca ttggaag					37

<210> SEQ ID NO 90
<211> LENGTH: 33
<212> TYPE: DNA
<213> ORGANISM: Homo sapiens

<400> SEQUENCE: 90
aaaggatcct gccaggctct gggtcaggac atg					33

<210> SEQ ID NO 91
<211> LENGTH: 32
<212> TYPE: DNA
<213> ORGANISM: Homo sapiens

<400> SEQUENCE: 91
gcggcacatg tcttacaacc acctgcaggg tg					32

<210> SEQ ID NO 92
<211> LENGTH: 28
<212> TYPE: DNA
<213> ORGANISM: Homo sapiens

<400> SEQUENCE: 92
gggcccaagc ttatgagtgt accaccat					28

<210> SEQ ID NO 93
<211> LENGTH: 36
<212> TYPE: DNA
<213> ORGANISM: Homo sapiens

<400> SEQUENCE: 93
ccggcggatc ccatatgtct acaaccacc tgcagg					36

<210> SEQ ID NO 94
<211> LENGTH: 35
<212> TYPE: DNA
<213> ORGANISM: Homo sapiens

<400> SEQUENCE: 94
ccggcggtac cttattatga gtgtaccacc attgg					35

<210> SEQ ID NO 95
<211> LENGTH: 426

```
<212> TYPE: DNA
<213> ORGANISM: Homo sapiens

<400> SEQUENCE: 95
atgtcttaca accacctgca gggtgacgtt cgttggcgta aactgttctc tttcaccaaa      60
tacttcctga aaatcgaaaa aaacggtaaa gtttctggga ccaagaagga gaactgcccg     120
tacagcatcc tggagataac atcagtagaa atcggagttg ttgccgtcaa agccattaac    180
agcaactatt acttagccat gaacaagaag gggaaactct atggctcaaa agaatttaac    240
aatgactgta agctgaagga gaggatagag gaaaatggat acaataccta tgcatcattt    300
aactggcagc ataatgggag gcaaatgtat gtggcattga atggaaaagg agctccaagg    360
agaggacaga aaacacgaag gaaaaacacc tctgctcact tcttccaat ggtggtacac     420 tcataa                                                               426

<210> SEQ ID NO 96
<211> LENGTH: 141
<212> TYPE: PRT
<213> ORGANISM: Homo sapiens

<400> SEQUENCE: 96

Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
                20                  25                  30

Gly Thr Lys Lys Glu Asn Cys Pro Tyr Ser Ile Leu Glu Ile Thr Ser
            35                  40                  45

Val Glu Ile Gly Val Val Ala Val Lys Ala Ile Asn Ser Asn Tyr Tyr
        50                  55                  60

Leu Ala Met Asn Lys Lys Gly Lys Leu Tyr Gly Ser Lys Glu Phe Asn
    65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
               100                 105                 110

Leu Asn Gly Lys Gly Ala Pro Arg Arg Gly Gln Lys Thr Arg Arg Lys
           115                 120                 125

Asn Thr Ser Ala His Phe Leu Pro Met Val Val His Ser
       130                 135                 140

<210> SEQ ID NO 97
<211> LENGTH: 20
<212> TYPE: DNA
<213> ORGANISM: Homo sapiens

<400> SEQUENCE: 97
caaccacctg cagggtgacg                                                 20

<210> SEQ ID NO 98
<211> LENGTH: 78
<212> TYPE: DNA
<213> ORGANISM: Homo sapiens

<400> SEQUENCE: 98
aacggtcgac aaatgtatgt ggcactgaac ggtaaaggtg ctccacgtcg tggtcagaaa     60
acccgtcgta aaaacacc                                                   78
```

```
<210> SEQ ID NO 99
<211> LENGTH: 76
<212> TYPE: DNA
<213> ORGANISM: Homo sapiens

<400> SEQUENCE: 99
gggcccaagc ttaagagtgt accaccattg gcagaaagtg agcagaggtg tttttacgac      60
gggttttctg accacg                                                     76

<210> SEQ ID NO 100
<211> LENGTH: 23
<212> TYPE: DNA
<213> ORGANISM: Homo sapiens

<400> SEQUENCE: 100
gccacataca tttgtcgacc gtt                                             23

<210> SEQ ID NO 101
<211> LENGTH: 19
<212> TYPE: DNA
<213> ORGANISM: Homo sapiens

<400> SEQUENCE: 101
gggcccaagc ttaagagtg                                                  19

<210> SEQ ID NO 102
<211> LENGTH: 23
<212> TYPE: DNA
<213> ORGANISM: Homo sapiens

<400> SEQUENCE: 102
gccacataca tttgtcgacc gtt                                             23

<210> SEQ ID NO 103
<211> LENGTH: 90
<212> TYPE: DNA
<213> ORGANISM: Homo sapiens

<400> SEQUENCE: 103
ctgcagggtg acgttcgttg gcgtaaactg ttctccttca ccaaatactt cctgaaaatc      60
gaaaaaaacg gtaaagtttc tggtaccaag                                      90

<210> SEQ ID NO 104
<211> LENGTH: 90
<212> TYPE: DNA
<213> ORGANISM: Homo sapiens

<400> SEQUENCE: 104
agctttaaca gcaacaacac cgatttcaac ggaggtgatt tccaggatgg agtacgggca      60
gttttctttc ttggtaccag aaactttacc                                      90

<210> SEQ ID NO 105
<211> LENGTH: 90
<212> TYPE: DNA
<213> ORGANISM: Homo sapiens

<400> SEQUENCE: 105
ggtgttgttg ctgttaaagc tatcaactcc aactactacc tggctatgaa caagaaaggt      60
aaactgtacg gttccaaaga atttaacaac                                      90

<210> SEQ ID NO 106
```

```
<211> LENGTH: 100
<212> TYPE: DNA
<213> ORGANISM: Homo sapiens

<400> SEQUENCE: 106
gtcgaccgtt gtgctgccag ttgaaggaag cgtaggtgtt gtaaccgttt tcttcgatac      60
gttctttcag tttacagtcg ttgttaaatt ctttggaacc                           100

<210> SEQ ID NO 107
<211> LENGTH: 25
<212> TYPE: DNA
<213> ORGANISM: Homo sapiens

<400> SEQUENCE: 107
gcggcgtcga ccgttgtgct gccag                                           25

<210> SEQ ID NO 108
<211> LENGTH: 26
<212> TYPE: DNA
<213> ORGANISM: Homo sapiens

<400> SEQUENCE: 108
gcggcctgca gggtgacgtt cgttgg                                          26

<210> SEQ ID NO 109
<211> LENGTH: 36
<212> TYPE: DNA
<213> ORGANISM: Homo sapiens

<400> SEQUENCE: 109
ccggcggatc ccatatgtct tacaaccacc tgcagg                               36

<210> SEQ ID NO 110
<211> LENGTH: 34
<212> TYPE: DNA
<213> ORGANISM: Homo sapiens

<400> SEQUENCE: 110
cgcgcgatat cttattaaga gtgtaccacc attg                                 34

<210> SEQ ID NO 111
<211> LENGTH: 426
<212> TYPE: DNA
<213> ORGANISM: Homo sapiens

<400> SEQUENCE: 111
atgtcttaca accacctgca gggtgacgtt cgttggcgta aactgttctc cttcaccaaa     60
tacttcctga aaatcgaaaa aacggtaaa gtttctggta ccaagaaaga aaactgcccg     120
tactccatcc tggaaatcac ctccgttgaa atcggtgttg ttgctgttaa agctatcaac    180
tccaactact acctggctat gaacaagaaa ggtaaactgt acggttccaa agaatttaac    240
aacgactgta aactgaaaga acgtatcgaa gaaaacggtt acaacaccta cgcttccttc    300
aactggcagc acaacggtcg acaaatgtat gtggcactga acgtaaaggg tgctccacgt    360
cgtggtcaga aacccgtcg taaaaacacc tctgctcact ttctgccaat ggtggtacac    420
tcttaa                                                              426

<210> SEQ ID NO 112
<211> LENGTH: 141
<212> TYPE: PRT
<213> ORGANISM: Homo sapiens
```

<400> SEQUENCE: 112

| Met | Ser | Tyr | Asn | His | Leu | Gln | Gly | Asp | Val | Arg | Trp | Arg | Lys | Leu | Phe |
|---|---|---|---|---|---|---|---|---|---|---|---|---|---|---|---|
| 1 | | | | 5 | | | | | 10 | | | | | 15 | |

| Ser | Phe | Thr | Lys | Tyr | Phe | Leu | Lys | Ile | Glu | Lys | Asn | Gly | Lys | Val | Ser |
| | | | 20 | | | | | 25 | | | | | 30 | | |

| Gly | Thr | Lys | Glu | Asn | Cys | Pro | Tyr | Ser | Ile | Leu | Glu | Ile | Thr | Ser |
| | | 35 | | | | 40 | | | | | 45 | | | |

| Val | Glu | Ile | Gly | Val | Val | Ala | Val | Lys | Ala | Ile | Asn | Ser | Asn | Tyr | Tyr |
| | 50 | | | | 55 | | | | | 60 | | | | | |

| Leu | Ala | Met | Asn | Lys | Lys | Gly | Lys | Leu | Tyr | Gly | Ser | Lys | Glu | Phe | Asn |
| 65 | | | | | 70 | | | | | 75 | | | | | 80 |

| Asn | Asp | Cys | Lys | Leu | Lys | Glu | Arg | Ile | Glu | Glu | Asn | Gly | Tyr | Asn | Thr |
| | | | | 85 | | | | | 90 | | | | | 95 | |

| Tyr | Ala | Ser | Phe | Asn | Trp | Gln | His | Asn | Gly | Arg | Gln | Met | Tyr | Val | Ala |
| | | | 100 | | | | | 105 | | | | | 110 | | |

| Leu | Asn | Gly | Lys | Gly | Ala | Pro | Arg | Arg | Gly | Gln | Lys | Thr | Arg | Arg | Lys |
| | | | 115 | | | | | 120 | | | | | 125 | | |

| Asn | Thr | Ser | Ala | His | Phe | Leu | Pro | Met | Val | Val | His | Ser |
| | 130 | | | | | 135 | | | | | 140 | |

<210> SEQ ID NO 113
<211> LENGTH: 28
<212> TYPE: DNA
<213> ORGANISM: Homo sapiens

<400> SEQUENCE: 113
cgcggccatg gctctgggtc aggacatg                      28

<210> SEQ ID NO 114
<211> LENGTH: 28
<212> TYPE: DNA
<213> ORGANISM: Homo sapiens

<400> SEQUENCE: 114
gggcccaagc ttatgagtgt accaccat                      28

<210> SEQ ID NO 115
<211> LENGTH: 516
<212> TYPE: DNA
<213> ORGANISM: Homo sapiens

<400> SEQUENCE: 115
atggctctgg gtcaagatat ggtttctccg gaagctacca actcttcctc ttcctctttc    60
tcttccccgt cttccgctgg tcgtcacgtt cgttcttaca accacctgca gggtgacgtt   120
cgttggcgta aactgttctc tttccaccaaa tacttcctga aaatcgaaaa aaacggtaaa   180
gtttctggga ccaagaagga gaactgcccg tacagcatcc tggagataac atcagtagaa   240
atcggagttg ttgccgtcaa agccattaac agcaactatt acttagccat gaacaagaag   300
gggaaactct atggctcaaa agaatttaac aatgactgta agctgaagga gaggatagag   360
gaaaatggat acaataccta tgcatcattt aactggcagc ataatgggag gcaaatgtat   420
gtggcattga atggaaaagg agctccaagg agaggacaga aaacacgaag gaaaaacacc   480
tctgctcact tcttccaat ggtggtacac tcataa                              516

<210> SEQ ID NO 116
<211> LENGTH: 171

<212> TYPE: PRT
<213> ORGANISM: Homo sapiens

<400> SEQUENCE: 116

```
Met Ala Leu Gly Gln Asp Met Val Ser Pro Glu Ala Thr Asn Ser Ser
 1               5                  10                  15

Ser Ser Ser Phe Ser Ser Pro Ser Ser Ala Gly Arg His Val Arg Ser
            20                  25                  30

Tyr Asn His Leu Gln Gly Asp Val Arg Trp Arg Lys Leu Phe Ser Phe
        35                  40                  45

Thr Lys Tyr Phe Leu Lys Ile Glu Lys Asn Gly Lys Val Ser Gly Thr
    50                  55                  60

Lys Lys Glu Asn Cys Pro Tyr Ser Ile Leu Glu Ile Thr Ser Val Glu
65                  70                  75                  80

Ile Gly Val Val Ala Val Lys Ala Ile Asn Ser Asn Tyr Tyr Leu Ala
                85                  90                  95

Met Asn Lys Lys Gly Lys Leu Tyr Gly Ser Lys Glu Phe Asn Asn Asp
            100                 105                 110

Cys Lys Leu Lys Glu Arg Ile Glu Glu Asn Gly Tyr Asn Thr Tyr Ala
        115                 120                 125

Ser Phe Asn Trp Gln His Asn Gly Arg Gln Met Tyr Val Ala Leu Asn
    130                 135                 140

Gly Lys Gly Ala Pro Arg Arg Gly Gln Lys Thr Arg Arg Lys Asn Thr
145                 150                 155                 160

Ser Ala His Phe Leu Pro Met Val Val His Ser
                165                 170
```

<210> SEQ ID NO 117
<211> LENGTH: 32
<212> TYPE: DNA
<213> ORGANISM: Homo sapiens

<400> SEQUENCE: 117
gcggcacatg tcttacaacc acctgcaggg tg                              32

<210> SEQ ID NO 118
<211> LENGTH: 75
<212> TYPE: DNA
<213> ORGANISM: Homo sapiens

<400> SEQUENCE: 118
ctgcccaagc ttttatgagt gtaccaccat tggaagaaag tgagcagagg tgtttttttc    60
tcgtgttttc tgtcc                                                    75

<210> SEQ ID NO 119
<211> LENGTH: 426
<212> TYPE: DNA
<213> ORGANISM: Homo sapiens

<400> SEQUENCE: 119
atgtcttaca accacctgca gggtgacgtt cgttggcgta aactgttctc tttcaccaaa    60
tacttcctga aaatcgaaaa aaacggtaaa gtttctggga ccaagaagga gaactgcccg   120
tacagcatcc tggagataac atcagtagaa atcggagttg ttgccgtcaa agccattaac   180
agcaactatt acttagccat gaacaagaag gggaaactct atggctcaaa agaatttaac   240
aatgactgta agctgaagga gaggatagag gaaaatggat acaataccta tgcatcattt   300
aactggcagc ataatgggag gcaaatgtat gtggcattga atggaaaagg agctccaagg   360

```
agaggacaga aaacacgaga aaaaaacacc tctgctcact ttcttccaat ggtggtacac    420
tcatag                                                               426
```

```
<210> SEQ ID NO 120
<211> LENGTH: 141
<212> TYPE: PRT
<213> ORGANISM: Homo sapiens

<400> SEQUENCE: 120
```

| Met | Ser | Tyr | Asn | His | Leu | Gln | Gly | Asp | Val | Arg | Trp | Arg | Lys | Leu | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Phe | Thr | Lys | Tyr | Phe | Leu | Lys | Ile | Glu | Lys | Asn | Gly | Lys | Val | Ser |
|     |     |     | 20  |     |     |     |     | 25  |     |     |     |     | 30  |     |     |

| Gly | Thr | Lys | Lys | Glu | Asn | Cys | Pro | Tyr | Ser | Ile | Leu | Glu | Ile | Thr | Ser |
|     |     | 35  |     |     |     |     | 40  |     |     |     |     | 45  |     |     |     |

| Val | Glu | Ile | Gly | Val | Val | Ala | Val | Lys | Ala | Ile | Ser | Asn | Tyr | Tyr |
| 50  |     |     |     |     | 55  |     |     |     |     | 60  |     |     |     |     |

| Leu | Ala | Met | Asn | Lys | Lys | Gly | Lys | Leu | Tyr | Gly | Ser | Lys | Glu | Phe | Asn |
| 65  |     |     |     |     | 70  |     |     |     |     | 75  |     |     |     |     | 80  |

| Asn | Asp | Cys | Lys | Leu | Lys | Glu | Arg | Ile | Glu | Glu | Asn | Gly | Tyr | Asn | Thr |
|     |     |     |     | 85  |     |     |     |     | 90  |     |     |     |     | 95  |     |

| Tyr | Ala | Ser | Phe | Asn | Trp | Gln | His | Asn | Gly | Arg | Gln | Met | Tyr | Val | Ala |
|     |     |     |     | 100 |     |     |     |     | 105 |     |     |     |     | 110 |     |

| Leu | Asn | Gly | Lys | Gly | Ala | Pro | Arg | Arg | Gly | Gln | Lys | Thr | Arg | Glu | Lys |
|     |     |     | 115 |     |     |     |     | 120 |     |     |     |     | 125 |     |     |

| Asn | Thr | Ser | Ala | His | Phe | Leu | Pro | Met | Val | Val | His | Ser |
|     |     | 130 |     |     |     |     | 135 |     |     |     |     | 140 |

```
<210> SEQ ID NO 121
<211> LENGTH: 32
<212> TYPE: DNA
<213> ORGANISM: Homo sapiens

<400> SEQUENCE: 121
gcggcacatg tcttacaacc acctgcaggg tg                                  32

<210> SEQ ID NO 122
<211> LENGTH: 75
<212> TYPE: DNA
<213> ORGANISM: Homo sapiens

<400> SEQUENCE: 122
ctgcccaagc ttttatgagt gtaccaccat tggaagaaag tgagcagagg tgttttctg    60 tcgtgttttc tgtcc                                                     75

<210> SEQ ID NO 123
<211> LENGTH: 426
<212> TYPE: DNA
<213> ORGANISM: Homo sapiens

<400> SEQUENCE: 123
atgtcttaca accacctgca gggtgacgtt cgttggcgta aactgttctc tttcaccaaa    60
tacttcctga aaatcgaaaa aaacggtaaa gtttctggga ccaagaagga gaactgcccg   120
tacagcatcc tggagataac atcagtagaa atcggagttg ttgccgtcaa agccattaac   180
agcaactatt acttagccat gaacaagaag gggaaactct atggctcaaa agaatttaac   240
aatgactgta gctgaagga gaggatagag gaaaatggat acaataccta tgcatcattt   300
```

```
aactggcagc ataatgggag gcaaatgtat gtggcattga atggaaaagg agctccaagg    360
agaggacaga aaacacgaca gaaaaacacc tctgctcact ttcttccaat ggtggtacac    420
tcatag                                                                426
```

<210> SEQ ID NO 124
<211> LENGTH: 141
<212> TYPE: PRT
<213> ORGANISM: Homo sapiens

<400> SEQUENCE: 124

```
Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
    50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Gln Lys
        115                 120                 125

Asn Thr Ser Ala His Phe Leu Pro Met Val Val His Ser
    130                 135                 140
```

<210> SEQ ID NO 125
<211> LENGTH: 32
<212> TYPE: DNA
<213> ORGANISM: Homo sapiens

<400> SEQUENCE: 125

```
gcggcacatg tcttacaacc acctgcaggg tg                                    32
```

<210> SEQ ID NO 126
<211> LENGTH: 84
<212> TYPE: DNA
<213> ORGANISM: Homo sapiens

<400> SEQUENCE: 126

```
ctgcccaagc ttttatgagt gtaccaccat tggaagaaag tgagcagagg tgttttttcct    60 tcgtgtttcc tgtcctctcc ttgg                                             84
```

<210> SEQ ID NO 127
<211> LENGTH: 426
<212> TYPE: DNA
<213> ORGANISM: Homo sapiens

<400> SEQUENCE: 127

```
atgtcttaca accacctgca gggtgacgtt cgttggcgta aactgttctc tttcaccaaa     60
tacttcctga aaatcgaaaa aaacggtaaa gtttctggga ccaagaagga gaactgcccg    120
tacagcatcc tggagataac atcagtagaa atcggagttg ttgccgtcaa agccattaac    180
agcaactatt acttagccat gaacaagaag gggaaactct atggctcaaa agaatttaac    240
```

```
aatgactgta agctgaagga gaggatagag gaaaatggat acaatacccta tgcatcattt    300 aactggcagc ataatgggag gcaaatgtat gtggcattga atggaaaagg agctccaagg    360
agaggacagg aaacacgaag gaaaaacacc tctgctcact ttcttccaat ggtggtacac    420
tcatag                                                               426
```

<210> SEQ ID NO 128
<211> LENGTH: 141
<212> TYPE: PRT
<213> ORGANISM: Homo sapiens

<400> SEQUENCE: 128

```
Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Glu Thr Arg Arg Lys
        115                 120                 125

Asn Thr Ser Ala His Phe Leu Pro Met Val Val His Ser
    130                 135                 140
```

<210> SEQ ID NO 129
<211> LENGTH: 32
<212> TYPE: DNA
<213> ORGANISM: Homo sapiens

<400> SEQUENCE: 129

```
gcggcacatg tcttacaacc acctgcaggg tg                                   32
```

<210> SEQ ID NO 130
<211> LENGTH: 84
<212> TYPE: DNA
<213> ORGANISM: Homo sapiens

<400> SEQUENCE: 130

```
ctgcccaagc ttttatgagt gtaccaccat tggaagaaag tgagcagagg tgttttttcct   60 tcgtgtctgc tgtcctctcc ttgg                                            84
```

<210> SEQ ID NO 131
<211> LENGTH: 426
<212> TYPE: DNA
<213> ORGANISM: Homo sapiens

<400> SEQUENCE: 131

```
atgtcttaca accaccctgca gggtgacgtt cgttggcgta aactgttctc tttcaccaaa    60
tacttcctga aaatcgaaaa aaacggtaaa gtttctggga ccaagaagga gaactgcccg    120
tacagcatcc tggagataac atcagtagaa atcggagttg ttgccgtcaa agccattaac    180
```

```
agcaactatt acttagccat gaacaagaag gggaaactct atggctcaaa agaatttaac      240
aatgactgta agctgaagga gaggatagag gaaaatggat acaataccta tgcatcattt      300
aactggcagc ataatgggag gcaaatgtat gtggcattga atggaaaagg agctccaagg      360
agaggacagc agacacgaag gaaaaacacc tctgctcact ttcttccaat ggtggtacac      420
tcatag                                                                 426

<210> SEQ ID NO 132
<211> LENGTH: 141
<212> TYPE: PRT
<213> ORGANISM: Homo sapiens

<400> SEQUENCE: 132

Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Gln Thr Arg Arg Lys
        115                 120                 125

Asn Thr Ser Ala His Phe Leu Pro Met Val Val His Ser
    130                 135                 140
```

```
<210> SEQ ID NO 133
<211> LENGTH: 32
<212> TYPE: DNA
<213> ORGANISM: Homo sapiens

<400> SEQUENCE: 133
gcggcacatg tcttacaacc acctgcaggg tg                                     32

<210> SEQ ID NO 134
<211> LENGTH: 93
<212> TYPE: DNA
<213> ORGANISM: Homo sapiens

<400> SEQUENCE: 134
ctgcccaagc ttttatgagt gtaccaccat tggaagaaag tgagcagagg tgttttttcct     60 tcgtgttttc tgtccttccc ttggagctcc ttt                                    93

<210> SEQ ID NO 135
<211> LENGTH: 426
<212> TYPE: DNA
<213> ORGANISM: Homo sapiens

<400> SEQUENCE: 135
atgtcttaca accacctgca gggtgacgtt cgttggcgta aactgttctc tttcaccaaa       60
tacttcctga aatcgaaaa aaacggtaaa gtttctggga ccaagaagga gaactgcccg      120
```

```
tacagcatcc tgagataac atcagtagaa atcggagttg ttgccgtcaa agccattaac      180
agcaactatt acttagccat gaacaagaag gggaaactct atggctcaaa agaatttaac      240
aatgactgta agctgaagga gaggatagag gaaaatggat acaataccta tgcatcattt      300
aactggcagc ataatgggag gcaaatgtat gtggcattga atggaaaagg agctccaagg      360
gaaggacaga aaacacgaag gaaaaacacc tctgctcact tcttccaat ggtggtacac       420 tcatag                                                                426
```

<210> SEQ ID NO 136
<211> LENGTH: 140
<212> TYPE: PRT
<213> ORGANISM: Homo sapiens

<400> SEQUENCE: 136

```
Met Tyr Asn His Leu Gln Gly Asp Val Arg Trp Arg Lys Leu Phe Ser
  1               5                  10                  15

Phe Thr Lys Tyr Phe Leu Lys Ile Glu Lys Asn Gly Lys Val Ser Gly
             20                  25                  30

Thr Lys Lys Glu Asn Cys Pro Tyr Ser Ile Leu Glu Ile Thr Ser Val
         35                  40                  45

Glu Ile Gly Val Val Ala Val Lys Ala Ile Asn Ser Asn Tyr Tyr Leu
     50                  55                  60

Ala Met Asn Lys Lys Gly Lys Leu Tyr Gly Ser Lys Glu Phe Asn Asn
 65                  70                  75                  80

Asp Cys Lys Leu Lys Glu Arg Ile Glu Glu Asn Gly Tyr Asn Thr Tyr
                 85                  90                  95

Ala Ser Phe Asn Trp Gln His Asn Gly Arg Gln Met Tyr Val Ala Leu
            100                 105                 110

Asn Gly Lys Gly Ala Pro Arg Glu Gly Gln Lys Thr Arg Arg Lys Asn
        115                 120                 125

Thr Ser Ala His Phe Leu Pro Met Val Val His Ser
    130                 135                 140
```

<210> SEQ ID NO 137
<211> LENGTH: 32
<212> TYPE: DNA
<213> ORGANISM: Homo sapiens

<400> SEQUENCE: 137

```
gcggcacatg tcttacaacc acctgcaggg tg                                    32
```

<210> SEQ ID NO 138
<211> LENGTH: 93
<212> TYPE: DNA
<213> ORGANISM: Homo sapiens

<400> SEQUENCE: 138

```
ctgcccaagc ttttatgagt gtaccaccat tggaagaaag tgagcagagg tgttttttcct     60 tcgtgttttc tgtccctgcc ttggagctcc ttt                                   93
```

<210> SEQ ID NO 139
<211> LENGTH: 426
<212> TYPE: DNA
<213> ORGANISM: Homo sapiens

<400> SEQUENCE: 139

```
atgtcttaca accacctgca gggtgacgtt cgttggcgta aactgttctc tttcaccaaa      60
```

-continued

```
tacttcctga aaatcgaaaa aaacggtaaa gtttctggga ccaagaagga gaactgcccg      120
tacagcatcc tggagataac atcagtagaa atcggagttg ttgccgtcaa agccattaac      180
agcaactatt acttagccat gaacaagaag gggaaactct atggctcaaa agaatttaac      240
aatgactgta agctgaagga gaggatagag gaaaatggat acaataccta tgcatcattt      300
aactggcagc ataatgggag gcaaatgtat gtggcattga atggaaaagg agctccaagg      360
cagggacaga aaacacgaag gaaaaacacc tctgctcact tcttccaatg gtggtacac       420 tcatag                                                                 426
```

<210> SEQ ID NO 140
<211> LENGTH: 141
<212> TYPE: PRT
<213> ORGANISM: Homo sapiens

<400> SEQUENCE: 140

```
Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Lys Gly Ala Pro Arg Gln Gly Gln Lys Thr Arg Arg Lys
        115                 120                 125

Asn Thr Ser Ala His Phe Leu Pro Met Val Val His Ser
    130                 135                 140
```

<210> SEQ ID NO 141
<211> LENGTH: 32
<212> TYPE: DNA
<213> ORGANISM: Homo sapiens

<400> SEQUENCE: 141

```
gcggcacatg tcttacaacc acctgcaggg tg                                     32
```

<210> SEQ ID NO 142
<211> LENGTH: 21
<212> TYPE: DNA
<213> ORGANISM: Homo sapiens

<400> SEQUENCE: 142

```
ttgaatggag aaggagctcc a                                                 21
```

<210> SEQ ID NO 143
<211> LENGTH: 21
<212> TYPE: DNA
<213> ORGANISM: Homo sapiens

<400> SEQUENCE: 143

```
tggagctcct tctccattca a                                                 21
```

<210> SEQ ID NO 144
<211> LENGTH: 33
<212> TYPE: DNA
<213> ORGANISM: Homo sapiens

<400> SEQUENCE: 144

```
ctgcccaagc ttttatgagt gtaccaccat tgg                                    33
```

<210> SEQ ID NO 145
<211> LENGTH: 426
<212> TYPE: DNA
<213> ORGANISM: Homo sapiens

<400> SEQUENCE: 145

```
atgtcttaca accacctgca gggtgacgtt cgttggcgta aactgttctc tttcaccaaa       60
tacttcctga aaatcgaaaa aaacggtaaa gtttctggga ccaagaagga gaactgcccg      120
tacagcatcc tggagataac atcagtagaa atcggagttg ttgccgtcaa agccattaac     180
agcaactatt acttagccat gaacaagaag gggaaactct atggctcaaa agaatttaac     240
aatgactgta agctgaagga gaggatagag gaaaatggat acaataccta tgcatcattt     300
aactggcagc ataatgggag gcaaatgtat gtggcattga atggagaagg agctccaagg     360
agaggacaga aaacacgaag gaaaaacacc tctgctcact ttcttccaat ggtggtacac     420
tcatag                                                                426
```

<210> SEQ ID NO 146
<211> LENGTH: 141
<212> TYPE: PRT
<213> ORGANISM: Homo sapiens

<400> SEQUENCE: 146

```
Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Glu Gly Ala Pro Arg Arg Gly Gln Lys Thr Arg Arg Lys
        115                 120                 125

Asn Thr Ser Ala His Phe Leu Pro Met Val Val His Ser
    130                 135                 140
```

<210> SEQ ID NO 147
<211> LENGTH: 3974
<212> TYPE: DNA
<213> ORGANISM: Homo sapiens

<400> SEQUENCE: 147

```
ggtacctaag tgagtagggc gtccgatcga cggacgcctt tttttgaat tcgtaatcat        60
```

```
ggtcatagct gtttcctgtg tgaaattgtt atccgctcac aattccacac aacatacgag    120
ccggaagcat aaagtgtaaa gcctggggtg cctaatgagt gagctaactc acattaattg    180
cgttgcgctc actgcccgct ttccagtcgg gaaacctgtc gtgccagctg cattaatgaa    240
tcggccaacg cgcggggaga ggcggttttgc gtattgggcg ctcttccgct tcctcgctca    300
ctgactcgct gcgctcggtc gttcggctgc ggcgagcggt atcagctcac tcaaaggcgg    360
taatacggtt atccacagaa tcaggggata cgcaggaaa gaacatgtga gcaaaaggcc    420
agcaaaaggc caggaaccgt aaaaaggccg cgttgctggc gtttttccat aggctccgcc    480
cccctgacga gcatcacaaa aatcgacgct caagtcagag gtggcgaaac ccgacaggac    540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaagaacagt atttggtatc tgcgctctgc tgaagccagt taccttcgga aaaagagttg    960
gtagctcttg atccggcaaa caaaccaccg ctggtagcgg tggttttttt gtttgcaagc    1020
agcagattac gcgcagaaaa aaaggatctc aagaagatcc tttgatcttt tctacggggt    1080
ctgacgctca gtggaacgaa aactcacgtt aagggatttt ggtcatgaga ttatcgtcga    1140
caattcgcgc gcgaaggcga agcggcatgc atttacgttg acaccatcga atggtgcaaa    1200
acctttcgcg gtatggcatg atagcgcccg gaagagagtc aattcagggt ggtgaatgtg    1260
aaaccagtaa cgttatacga tgtcgcagag tatgccggtg tctcttatca gaccgttcc    1320 cgcgtggtga accaggccag ccacgtttct gcgaaaacgc gggaaaaagt ggaagcggcg    1380
atggcggagc tgaattacat tcccaaccgc gtggcacaac aactggcggg caaacagtcg    1440
ttgctgattg gcgttgccac ctccagtctg gccctgcacg cgccgtcgca aattgtcgcg    1500
gcgattaaat ctcgcgccga tcaactgggt gccagcgtgg tggtgtcgat ggtagaacga    1560
agcggcgtcg aagcctgtaa agcggcggtg cacaatcttc tcgcgcaacg cgtcagtggg    1620
ctgatcatta actatccgct ggatgaccag gatgccattg ctgtggaagc tgcctgcact    1680
aatgttccgg cgttatttct tgatgtctct gaccagacac ccatcaacag tattattttc    1740
tcccatgaag acgtacgcg actgggcgtg gagcatctgg tcgcattggg tcaccagcaa    1800
atcgcgctgt tagcgggccc attaagttct gtctcggcgc gtctgcgtct ggctggctgg    1860
cataaatatc tcactcgcaa tcaaattcag ccgatagcgg aacgggaagg cgactggagt    1920
gccatgtccg gttttcaaca aaccatgcaa atgctgaatg agggcatcgt tcccactgcg    1980
atgctggttg ccaacgatca gatggcgctg ggcgcaatgc gcgccattac cgagtccggg    2040
ctgcgcgttg gtgcggatat ctcggtagtg ggatacgacg ataccgaaga cagctcatgt    2100
tatatcccgc cgttaaccac catcaaacag gattttcgcc tgctggggca accagcgtg    2160 gaccgcttgc tgcaactctc tcaggccag gcggtgaagg gcaatcagct gttgcccgtc    2220
tcactggtga aagaaaaac caccctggcg cccaatacgc aaaccgcctc tccccgcgcg    2280
ttggccgatt cattaatgca gctggcacga caggtttccc gactggaaag cgggcagtga    2340
gcgcaacgca attaatgtaa gttagcgcga attgtcgacc aaagcggcca tcgtgcctcc    2400
```

-continued

```
ccactcctgc agttcggggg catggatgcg cggatagccg ctgctggttt cctggatgcc      2460
gacggatttg cactgccggt agaactccgc gaggtcgtcc agcctcaggc agcagctgaa      2520
ccaactcgcg aggggatcga gcccggggtg ggcgaagaac tccagcatga gatccccgcg      2580
ctggaggatc atccagccgg cgtcccggaa aacgattccg aagcccaacc tttcatagaa      2640
ggcggcggtg gaatcgaaat ctcgtgatgg caggttgggc gtcgcttggt cggtcatttc      2700 gaacccccaga gtcccgctca aagaactcg tcaagaaggc gatagaaggc gatgcgctgc      2760
gaatcgggag cggcgatacc gtaaagcacg aggaagcggt cagcccattc gccgccaagc      2820
tcttcagcaa tatcacgggt agccaacgct atgtcctgat agcggtccgc cacacccagc      2880
cggccacagt cgatgaatcc agaaaagcgg ccatttttcca ccatgatatt cggcaagcag      2940
gcatcgccat gggtcacgac gagatcctcg ccgtcgggca tgcgcgcctt gagcctggcg      3000
aacagttcgg ctggcgcgag cccctgatgc tcttcgtcca gatcatcctg atcgacaaga      3060
ccggcttcca tccgagtacg tgctcgctcg atgcgatgtt tcgcttggtg gtcgaatggg      3120
caggtagccg gatcaagcgt atgcagccgc cgcattgcat cagccatgat ggatactttc      3180
tcggcaggag caaggtgaga tgacaggaga tcctgccccg gcacttcgcc caatagcagc      3240
cagtcccttc ccgcttcagt gacaacgtcg agcacagctg cgcaaggaac gcccgtcgtg      3300
gccagccacg atagccgcgc tgcctcgtcc tgcagttcat tcagggcacc ggacaggtcg      3360
gtcttgacaa aaagaaccgg gcgcccctgc gctgacagcc ggaacacggc ggcatcagag      3420
cagccgattg tctgttgtgc ccagtcatag ccgaatagcc tctccaccca agcggccgga      3480
gaacctgcgt gcaatccatc ttgttcaatc atgcgaaacg atcctcatcc tgtctcttga      3540
tcagatcttg atccctgcg ccatcagatc cttggcggca agaaagccat ccagtttact      3600
ttgcagggct tcccaacctt accagagggc gccccagctg gcaattccgg ttcgcttgct      3660
gtccataaaa ccgcccagtc tagctatcgc catgtaagcc cactgcaagc tacctgcttt      3720
ctctttgcgc ttgcgttttc ccttgtccag atagcccagt agctgacatt catccggggt      3780
cagcaccgtt tctgcggact ggctttctac gtgttccgct tcctttagca gcccttgcgc      3840
cctgagtgct tgcggcagcg tgaagcttaa aaaactgcaa aaaatagttt gacttgtgag      3900
cggataacaa ttaagatgta cccaattgtg agcggataac aatttcacac attaaagagg      3960
agaaattaca tatg                                                       3974
```

<210> SEQ ID NO 148
<211> LENGTH: 112
<212> TYPE: DNA
<213> ORGANISM: Homo sapiens

<400> SEQUENCE: 148

```
aagcttaaaa aactgcaaaa aatagtttga cttgtgagcg gataacaatt aagatgtacc       60
caattgtgag cggataacaa tttcacacat taaagaggag aaattacata tg              112
```

What is claimed is:

1. A method of stimulating proliferation of Goblet cells comprising administering to an individual a polypeptide comprising amino acids 69 to 208 of SEQ ID NO:2, wherein said polypeptide is administered in an amount effective to stimulate proliferation of Goblet cells.

2. The method of claim 1, wherein said Goblet cells are in the respiratory epithelium of the nasal air passage way.

3. The method of claim 1, wherein said Goblet cells are in the conjunctiva.

4. The method of claim 1, wherein said polypeptide comprises amino acids 63 to 208 of SEQ ID NO:2.

5. The method of claim 4, wherein said Goblet cells are in the respiratory epithelium of the nasal air passage way.

6. The method of claim 4, wherein said Goblet cells are in the conjunctiva.

7. The method of claim 4, wherein said polypeptide is administered with a pharmaceutically acceptable carrier or excipient.

8. The method of claim 1, wherein said polypeptide is administered with a pharmaceutically acceptable carrier or excipient.

* * * * *

UNITED STATES PATENT AND TRADEMARK OFFICE
CERTIFICATE OF CORRECTION

PATENT NO. : 6,599,879 B1
DATED : July 29, 2003
INVENTOR(S) : Jimenez et al.

It is certified that error appears in the above-identified patent and that said Letters Patent is hereby corrected as shown below:

<u>Title page,</u>
Item [56], References Cited, please insert the following:
-- U.S. PATENT DOCUMENTS

| | | |
|---|---|---|
| 5,194,596 | 03/16/1993 | Tischer et al. |
| 5,350,836 | 09/27/1994 | Kopchick et al. |
| 5,580,856 | 12/03/1996 | Prestrelski et al. |
| 5,677,278 | 10/14/1997 | Gospodarowicz et al. |
| 5,703,047 | 12/30/1997 | Wilson, S.E. |
| 5,731,170 | 03/24/1998 | Rubin et al. |
| 5,773,586 | 06/30/1998 | Gospodarowicz et al. |
| 5,814,605 | 09/29/1998 | Pierce et al. |
| 5,824,643 | 10/20/1998 | Pierce et al. |
| 5,843,883 | 12/01/1998 | Gospodarowicz et al. |
| 5,863,767 | 01/12/1999 | Gospodarowicz et al. |

FOREIGN PATENT DOCUMENTS

| | | |
|---|---|---|
| WO | WO 90/08771 | 08/09/1990 |
| WO | WO 92/14480 | 09/03/1992 |
| WO | WO 92/22304 | 12/23/1992 |
| WO | WO 93/21908 | 11/11/1993 |
| WO | WO 94/22427 | 10/13/1994 |
| WO | WO 94/23032 | 10/13/1994 |
| WO | WO 95/01434 | 01/12/1995 |
| WO | WO 95/03831 | 02/09/1995 |
| WO | WO 95/24928 | 09/21/1995 |
| JP | 7-345689 | 12/07/1995 |
| JP | 8-103240 | 03/28/1996 |
| WO | WO 96/11949 | 04/25/1996 |
| WO | WO 96/11950 | 04/25/1996 |
| WO | WO 96/11951 | 04/25/1996 |
| WO | WO 96/11952 | 04/25/1996 |
| JP | 8-214378 | 07/24/1996 |
| WO | WO 96/22369 | 07/25/1996 |
| WO | WO 96/25422 | 08/22/1996 |
| WO | WO 97/20929 | 12/06/1997 |
| WO | WO 98/06844 | 02/19/1998 |
| WO | WO 98/16642 | 04/23/1998 |
| WO | WO 98/16243 | 04/23/1998 |
| GB | 2 321 852 A | 08/12/1998 |
| JP | 10-330283 | 12/15/1998 |
| JP | 10-330284 | 12/15/1998 |
| JP | 10-330285 | 12/15/1998 |

UNITED STATES PATENT AND TRADEMARK OFFICE
CERTIFICATE OF CORRECTION

PATENT NO. : 6,599,879 B1
DATED : July 29, 2003
INVENTOR(S) : Jimenez et al.

It is certified that error appears in the above-identified patent and that said Letters Patent is hereby corrected as shown below:

Title page (cont'd),
OTHER PUBLICATIONS

Finch, P. W. et al., "Human KGF Is FGF-Related with Properties of a Paracrine Effector of Epithelial Cell Growth," *Science* 245:752-755, American Association for the Advancement of Science (1989).

Hartung, H. et al., "Murine FGF-12 and FGF-13: expression in embryonic nervous sytem, connective tissue and heart," *Mech. Develop.* 64:31-39, Elsevier Science Ireland Ltd. (June 1997).

Hartung, H. et al., "Assignment[a] of *Fgf12* to mouse chromosome bands 16B1→B3 in situ hybridization," *Cytogenet. Cell Genet.* 76:185-186 (April 1997).

Jimenez, P. et al., "Effect of Topical Keratinocyte Growth Factor-2 on Wound healting in a Glucocorticoid-Impaired Model," *J. Cutan. Pathol.* 245:105 (February 1997).

Jimenez, P.A. et al., "Effect of Keratinocyte Growth Factor-2 on Cell Proliferation *In Vivo*," *FASEB J.* 11:A523, Abstract No. 3025, Federation of American Societies for Experimental Biology (April 1997).

Kelley, M. J. et al., "Emergence of the keratinocyte growth factor multigene family during the great ape radiation," *Proc. Natl. Acad. Sci. USA* 89:9287-9291, National Academy of Sciences of the USA (1992).

Mason, I.J. et al., "FGF-7 (keratinocyte growth factor) expression during mouse development suggests roles in myogenesis, forebrain regionalisation and epithelial-mesenchymal interactions," *Mech. Dev.* 45:15-30, Elsevier Science Ireland Ltd. (January 1994).

Miyamoto, M. et al., "Molecular Cloning of a Novel Cytokine cDNA Encoding the Ninth Member of the Fibroblast Growth Factor Family, Which Has a Unique Secretion Property," *Mol. Cell. Biol.* 13(7):4251-4259, American Society for Microbiology (1993).

Ron, D. et al., "Expression of Biologically Active Recombinant Keratinocyte Growth Factor," *J. Biol. Chem.* 268(4):2984-2988, American Society for Biochemistry and Molecular Biology, Inc. (1993).

Yamasaki, M. et al., "Structure and Expression of the Rat mRNA Encoding a Novel Member of the Fibroblast Growth Factor Family," *J. Biol. Chem.* 271:15918-15921, The American Society for Biochemistry and Molecular Biology, Inc. (July 1996).

Yan, G. et al., "Sequence of Rat Keratinocyte Growth Factor (Heparin-Binding Growth Factor Type 7)," *In Vitro Cell. Dev. Biol.* 27A:437-438, Tissue Culture Association (1991).

NCBI Entrez, GenBank Report with Revision History, Accession No. M79878, McCombie, W.R. et al. (1992).

NCBI Entrez, GenBank Report with Revision History, Accession No. T52063, Hillier, L. et al. (February 1995).

NCBI Entrez, GenBank Report with Revision History, Accession No. D46201, Sasaki, T. et al. (August 1995).

NCBI Entrez, GenBank Report with Revision History, Accession No. D46420, Sasaki, T. et al. (August 1995).

NCBI Entrez, GenBank Report with Revision History, Accession No. D54216, Fujiwara, T. et al. (September 1995).

NCBI Entrez, GenBank Report with Revision History, Accession No. D68729, Kohara, Y. et al. (December 1995).

UNITED STATES PATENT AND TRADEMARK OFFICE
CERTIFICATE OF CORRECTION

PATENT NO. : 6,599,879 B1
DATED : July 29, 2003
INVENTOR(S) : Jimenez et al.

It is certified that error appears in the above-identified patent and that said Letters Patent is hereby corrected as shown below:

Title page (cont'd),

NCBI Entrez, GenBank Report with Revision History, Accession No. D69248, Kohara, Y. et al. (December 1995).

NCBI Entrez, GenBank Report with Revision History, Accession No. D65627, Kohara, Y. et al. (December 1995).

NCBI Entrez, GenBank Report with Revision History, Accession No. D66221, Kohara, Y. et al. (December 1995).

NCBI Entrez, GenBank Report with Revision History, Accession No. C02000, Okubo, K. (July 1996).

NCBI Entrez, GenBank Report with Revision History, Accession No. W29377, Marra, M. et al. (September 1996).

NCBI Entrez, GenBank Report with Revision History, Accession No. W32720, Hillier, L. et al. (October 1996).

NCBI Entrez, GenBank Report with Revision History, Accession No. W60824, Hillier, L. et al. (October 1996).

NCBI Entrez, GenBank Report with Revision History, Accession No. T70682, Shen, B. et al. (October 1996).

NCBI Entrez, GenBank Report with Revision History, Accession No. AA094753, Liew, C.C. (October 1996).

NCBI Entrez, GenBank Report with Revision History, Accession No. AA133331, Hillier, L. et al. (November 1996).

NCBI Entrez, GenBank Report with Revision History, Accession No. AA190058, Marra, M. et al. (January 1997).

NCBI Entrez, GenBank Report with Revision History, Accession No. AA018953, Hillier, L. et al. (January 1997).

NCBI Entrez, GenBank Report with Revision History, Accession No. AA240978, Marra, M. et al. (March 1997).

NCBI Entrez, GenBank Report with Revision History, Accession No. AA289560, Marra, M. et al. (April 1997).

NCBI Entrez, GenBank Report with Revision History, Accession No. AA296993, Adams, M.D. et al. (April 1997).

NCBI Entrez, GenBank Report with Revision History, Accession No. AA298937, Adams, M.D. et al. (April 1997).

NCBI Entrez, GenBank Report with Revision History, Accession No. AA312184, Adams, M.D. et al. (April 1997).

NCBI Entrez, GenBank Report with Revision History, Accession No. AA312483, Adams, M.D. et al. (April 1997).

NCBI Entrez, GenBank Report with Revision History, Accession No. AA356781, Adams, M.D. et al. (April 1997).

NCBI Entrez, GenBank Report with Revision History, Accession No. AA412789, Marra, M. et al. (May 1997).

NCBI Entrez, GenBank Report with Revision History, Accession No. AA472256, Marra, M. et al. (June 1997).

UNITED STATES PATENT AND TRADEMARK OFFICE
CERTIFICATE OF CORRECTION

PATENT NO. : 6,599,879 B1
DATED : July 29, 2003
INVENTOR(S) : Jimenez et al.

It is certified that error appears in the above-identified patent and that said Letters Patent is hereby corrected as shown below:

Title page (cont'd),

NCBI Entrez, GenBank Report with Revision History, Accession No. C38464, Kohara, Y. *et al.* (September 1997).

NCBI Entrez, GenBank Report with Revision History, Accession No. C56505, Kohara, Y. *et al.* (September 1997).

NCBI Entrez, GenBank Report with Revision History, Accession No. C57074, Kohara, Y. *et al.* (September 1997).

NCBI Entrez, GenBank Report with Revision History, Accession No. C58558, Kohara, Y. *et al.* (September 1997).

NCBI Entrez, GenBank Report with Revision History, Accession No. C58846, Kohara, Y. *et al.* (September 1997).

NCBI Entrez, GenBank Report with Revision History, Accession No. C59317, Kohara, Y. *et al.* (September 1997).

NCBI Entrez, GenBank Report with Revision History, Accession No. C59311, Kohara, Y. *et al.* (September 1997).

NCBI Entrez, GenBank Report with Revision History, Accession No. AA605609, Clark, M. *et al.* (September 1997). --

Column 48,
Line 57, change "physiologcially" to -- physiologically --

Column 59,
Line 12, change "th" to -- the --

Column 63,
Line 36, change "th" to -- the --
Line 38, change "wequence" to -- sequence --

Column 65,
Line 54, change "apporximately" to -- approximately --

Column 66,
Line 12, change "CAalif." to -- CA. --

Column 68,
Line 59, change "sythetic" to -- synthetic --

Column 72,
Line 52, change "containing containing" to -- containing --

UNITED STATES PATENT AND TRADEMARK OFFICE
CERTIFICATE OF CORRECTION

PATENT NO.    : 6,599,879 B1
DATED         : July 29, 2003
INVENTOR(S)   : Jimenez et al.

It is certified that error appears in the above-identified patent and that said Letters Patent is hereby corrected as shown below:

Column 73,
Line 18, change "haparin" to -- heparin --
Line 22, change "solubilty" to -- solubility --

Column 76,
Line 43, change "expresssion" to -- expression --

Column 83,
Line 55, change "demostrate" to -- demonstrate --

Signed and Sealed this

Twenty-third Day of December, 2003

JAMES E. ROGAN
*Director of the United States Patent and Trademark Office*